United States Patent
Li et al.

(10) Patent No.: US 12,281,335 B2
(45) Date of Patent: Apr. 22, 2025

(54) METHODS AND COMPOSITIONS FOR DELIVERY OF VIRAL VECTORS ACROSS THE BLOOD-BRAIN BARRIER

(71) Applicant: The University of North Carolina at Chapel Hill, Chapel Hill, NC (US)

(72) Inventors: Chengwen Li, Chapel Hill, NC (US); Richard Jude Samulski, Chapel Hill, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 18/518,000

(22) Filed: Nov. 22, 2023

(65) Prior Publication Data

US 2024/0158762 A1 May 16, 2024

Related U.S. Application Data

(62) Division of application No. 16/956,306, filed as application No. PCT/US2018/066551 on Dec. 19, 2018, now Pat. No. 11,905,533.

(60) Provisional application No. 62/607,662, filed on Dec. 19, 2017.

(51) Int. Cl.
*C12N 7/00* (2006.01)
*C07K 14/005* (2006.01)
*C12N 15/86* (2006.01)

(52) U.S. Cl.
CPC .............. *C12N 7/00* (2013.01); *C07K 14/005* (2013.01); *C12N 15/86* (2013.01); *C12N 2750/14122* (2013.01); *C12N 2750/14123* (2013.01); *C12N 2750/14143* (2013.01)

(58) Field of Classification Search
None
See application file for complete search history.

(56) References Cited

U.S. PATENT DOCUMENTS

| 11,905,533 B2 * | 2/2024 | Li .......................... C12N 7/00 |
| 2006/0127358 A1 | 6/2006 | Muzyczka et al. |
| 2014/0219974 A1 | 8/2014 | Pan |
| 2015/0079038 A1 | 3/2015 | Deverman et al. |
| 2017/0253643 A1 | 9/2017 | Yamashita et al. |

FOREIGN PATENT DOCUMENTS

| WO | 2004099423 A1 | 11/2004 |
| WO | 2013123503 A1 | 8/2013 |
| WO | 2013158879 A1 | 10/2013 |
| WO | 2016035820 A1 | 3/2016 |
| WO | 2016054554 A1 | 4/2016 |
| WO | 2017136536 A1 | 8/2017 |
| WO | 2017176651 A1 | 10/2017 |

OTHER PUBLICATIONS

Zhang et al. "Customized blood-brain barrier shuttle peptide to increase AAV9 vector crossing the BBB and augment transduction in the brain" Biomaterials 281:121340. (Year: 2022).*
Frieden, et al., "A mechanism for lipid binding to apoE and the role of intrinsically disordered regions coupled to domain-domain interactions", PNAS, 114(24):6292-6297 (2017).
Arbetman et al. "Novel Caprine Adeno-Associated Virus (AAV) Capsid (AAV-Go.1) Is Closely Related to the Primate AAV-5 and Has Unique Tropism and Neutralization Properties" Journal of Virology, 79(24):15238-15245 (2005).
Asokan et al. "Reengineering a receptor footprint of adeno-associated virus enables selective and systemic gene transfer to muscle" Nature Biotechnology, 28(1):79-82 (2010).
Asuri et al. "Directed Evolution of Adeno-associated Virus for Enhanced Gene Delivery and Gene Targeting in Human Pluripotent Stem Cells" Molecular Therapy, 20(2):329-338 (2012).
Banks, William A. "Characteristics of compounds that cross the blood-brain barrier" BMC Neurology, 9(Suppl 1):S3 (2009).
Bello et al. "Novel Adeno-associated Viruses Derived From Pig Tissues Transduce Most Major Organs in Mice" Scientific Reports, 4:6644 (pp. 1-11) (2014).
Bennett et al. "AAV2 Gene Therapy Readministration in Three Adults with Congenital Blindness" Gene Therapy, 4 (120ra115) (pp. 1-10) (2012).
Bossis et al. "Cloning of an Avian Adeno-Associated Virus (AAAV) and Generation of Recombinant AAAV Particles" Journal of Virology, 77(12):6799-6810 (2003).
Bowles et al. "Phase 1 Gene Therapy for Duchenne Muscular Dystrophy Using a Translational Optimized AAV Vector" Molecular Therapy, 20(2):443-455 (2012).
Carlon et al. "Efficient Gene Transfer Into the Mouse Lung by Fetal Intratracheal Injection of rAAV2/6.2" Molecular Therapy, 18(12):2130-2138 (2010).
Cearley et al. "Transduction Characteristics of Adeno-associated Virus Vectors Expressing Cap Serotypes 7, 8, 9, and Rh10 in the Mouse Brain" 13(3):528-537 (2006).
Chai et al. "Application of polyploid adeno-associated virus vectors for transduction enhancement and neutralizing antibody evasion" Journal of Controlled Release, 262:348-356 (2017).
Choudhury et al. "Widespread Central Nervous System Gene Transfer and Silencing After Systemic Delivery of Novel AAV-AS Vector" Molecular Therapy, 24(4):726-735 (2016).

(Continued)

*Primary Examiner* — Sudhakar Katakam
*Assistant Examiner* — Zachary J Miknis
(74) *Attorney, Agent, or Firm* — Myers Bigel, P.A.

(57) ABSTRACT

Disclosed herein is an adeno-associated virus (AAV) particle comprising a surface-bound peptide that enhances transduction of cells across the blood-brain barrier (BBB). Also disclosed herein is a modified AAV capsid protein comprising an insertion of a polypeptide that enhances transduction of cells across the BBB, and an AAV particle comprising the modified AAV capsid protein. Specific peptides are provided. Pharmaceutical formulations and method of administering/delivering a nucleic acid to a cell of the brain and/or central nervous system are also disclosed.

11 Claims, 36 Drawing Sheets

Specification includes a Sequence Listing.

(56) References Cited

OTHER PUBLICATIONS

Cronin et al. "Efficient transduction and optogenetic stimulation of retinal bipolar cells by a synthetic adeno- associated virus capsid and promoter" EMBO Molecular Medicine, 6(9):1175-1190 (2014).
Dalkara et al. "In Vivo-Directed Evolution of a New Adeno-Associated Virus for Therapeutic Outer Retinal Gene Delivery from the Vitreous" Science Translational Medicine, 5(189):189ra76 (2013).
Davidoff et al. "Comparison of the Ability of Adeno-associated Viral Vectors Pseudotyped with Serotype 2, 5, and 8 Capsid Proteins to Mediate Efficient Transduction of the Liver in Murine and Nonhuman Primate Models" Molecular Therapy, 11(6):875-888 (2005).
Daya et al. "Gene Therapy Using Adeno-Associated Virus Vectors" Clinical Microbiology Reviews, 21(4):583-593 (2008).
Demeule et al. "Involvement of the low-density lipoprotein receptor-related protein in the transcytosis of the brain delivery vector angiopep-2" Journal of Neurochemistry, 106:1534-1544 (2008).
Deverman et al. "Cre-dependent selection yields AAV variants for widespread gene transfer to the adult brain" Nature Biotechnology, 34(2):204-209 (2016).
Dismuke et al. "Biosafety of recombinant adeno-associated virus vectors" Current Gene Therapy, 13(6):434-452 (2013) (Abstract only).
Dufes et al. "Transferrin and the transferrin receptor for the targeted delivery of therapeutic agents to the brain and cancer cells" Therapeutic Delivery, 4:629-640 (2013).
Erazo-Oliveras et al. "Improving the Endosomal Escape of Cell-Penetrating Peptides and Their Cargos: Strategies and Challenges" Pharmaceuticals, 5:1177-1209 (2012).
Excoffon et al. "Directed evolution of adeno-associated virus to an infectious respiratory virus" Proceedings of the National Academy of Sciences USA, 106(10):3865-3870 (2009).
Extended European Search Report corresponding to European Patent Application No. 18890295.1 (12 pages) (dated Sep. 2, 2021).
Fosgerau et al. "Peptide therapeutics: current status and future directions" Drug Discovery Today, 20(1):122-128 (2015).
Foust et al. "Intravascular AAV9 preferentially targets neonatal neurons and adult astrocytes" Nature Biotechnology, 27(1):59-65 (2009).
Gabriel et al. "Bioengineering of AAV2 Capsid at Specific Serine, Threonine, or Lysine Residues Improves Its Transduction Efficiency in Vitro and in Vivo" Human Gene Therapy Methods, 24(2):80-93 (2013).
Gaillard et al. "Enhanced brain delivery of liposomal methylprednisolone improved therapeutic efficacy in a model of neuroinflammation" Journal of Controlled Release, 164:364-369 (2012) (Abstract only).
Gao et al. "Clades of Adeno-Associated Viruses Are Widely Disseminated in Human Tissues" Journal of Virology, 78 (12):6381-6388 (2004).
Geoghegan et al. "Chondroitin Sulfate is the Primary Receptor for a Peptide-Modified AAV That Targets Brain Vascular Endothelium In Vivo" Molecular Therapy—Nucleic Acids, 3(e202) (pp. 1-13) (2014).
Girod et al. "Genetic capsid modifications allow efficient re-targeting of adeno-associated virus type 2" Nature Medicine, 5(9):1052-1056 (1999).
Gray et al. "Directed Evolution of a Novel Adeno-associated Virus (AAV) Vector That Crosses the Seizure-compromised Blood-Brain Barrier (BBB)" Molecular Therapy, 18(3):570-578 (2010).
Grifman et al. "Incorporation of Tumor-Targeting Peptides into Recombinant Adeno-associated Virus Capsids" Molecular Therapy, 3(6):964-975 (2001).
Grimm et al. "In Vitro and In Vivo Gene Therapy Vector Evolution via Multispecies Interbreeding and Retargeting of Adeno-Associated Viruses" Journal of Virology, 82(12):5887-5911 (2008).
Hastie et al. "Adeno-Associated Virus at 50: A Golden Anniversary of Discovery, Research, and Gene Therapy Success—A Personal Perspective" Human Gene Therapy, 26(5):257-265 (2015).
He et al. "Kinetics of Adeno-Associated Virus Serotype 2 (AAV2) and AAV8 Capsid Antigen Presentation In Vivo Are Identical" Human Gene Therapy, 24(5):545-553 (2013).
Hordeaux et al. "The Neurotropic Properties of AAV-PHP.B Are Limited to C57BL/6J Mice" Molecular Therapy, 26 (3):664-666 (2018).
Huang et al. "Genetic Manipulation of Brown Fat Via Oral Administration of an Engineered Recombinant Adeno-associated Viral Serotype Vector" Molecular Therapy, 24(6):1062-1069 (2016).
Iida et al. "Systemic Delivery of Tyrosine-Mutant AAV Vectors Results in Robust Transduction of Neurons in Adult Mice" BioMed Research International, 2013(974819):1-8 (2013).
International Preliminary Report on Patentability corresponding to International Patent Application No. PCT/US2018/066551 (6 pages) (dated Jul. 2, 2020).
Issa et al. "Assessment of Tropism and Effectiveness of New Primate-Derived Hybrid Recombinant AAV Serotypes in the Mouse and Primate Retina" PLoS One, 8(4):e60361 (2013).
Jacobson et al. "Improvement and Decline in Vision with Gene Therapy in Childhood Blindness" The New England Journal of Medicine, 372(20):1920-1926 (2015).
Jang et al. "An Evolved Adeno-associated Viral Variant Enhances Gene Delivery and Gene Targeting in Neural Stem Cells" Molecular Therapy, 19(4):667-675 (2011).
Jefferies et al. "Transferrin receptor on endothelium of brain capillaries" Nature, 312:162-163 (1984) (Abstract only).
Jones et al. "Blood-Brain Barrier Transport of Therapeutics via Receptor-Mediation" Pharmaceutical Research, 24 (9):1759-1771 (2007).
Kadam et al. "Potent Peptidic Fusion Inhibitors of Influenza Virus" Science, 358(6362):496-502 (2017).
Kannan et al. "Evidence for carrier-mediated transport of glutathione across the blood-brain barrier in the rat" The Journal of Clinical Investigation, 85(6):2009-2013 (1990).
Kaplitt et al. "Safety and tolerability of gene therapy with an adeno-associated virus (AAV) borne GAD gene for Parkinson's disease: an open label, phase I trial" Lancet, 369(9579):2097-2105 (2007) (Abstract only).
Kay, Mark A. "Selecting the Best AAV Capsid for Human Studies" Molecular Therapy, 23(12):1800-1801 (2015).
Khabou et al. "Insight into the mechanisms of enhanced retinal transduction by the engineered AAV2 capsid variant-7m8" Biotechnology and Bioengineering, 113(12):2712-2724 (2016).
Klimczak et al. "A Novel Adeno-Associated Viral Variant for Efficient and Selective Intravitreal Transduction of Rat Müller Cells" PLoS One, 4(10):e7467 (2009).
Koerber et al. "Molecular Evolution of Adeno-associated Virus for Enhanced Glial Gene Delivery" Molecular Therapy, 17(2):2088-2095 (2009).
Korbelin et al. "Pulmonary Targeting of Adeno-associated Viral Vectors by Next-generation Sequencing-guided Screening of Random Capsid Displayed Peptide Libraries" Molecular Therapy, 24(6):1050-1061 (2016).
Kotchey et al. "A Potential Role of Distinctively Delayed Blood Clearance of Recombinant Adeno-associated Virus Serotype 9 in Robust Cardiac Transduction" Molecular Therapy, 19(6):1079-1089 (2011).
Lawlor et al. "Efficient Gene Delivery and Selective Transduction of Glial Cells in the Mammalian Brain by AAV Serotypes Isolated From Nonhuman Primates" Molecular Therapy, 17(10):1692-1702 (2009).
Lee et al. "Receptor mediated uptake of peptides that bind the human transferrin receptor" European Journal of Biochemistry, 268:2004-2012 (2001).
Li et al. "Engineering and Selection of Shuffled AAV Genomes: A New Strategy for Producing Targeted Biological Nanoparticles" Molecular Therapy, 16(7):1252-1260 (2008).
Li et al. "Generation of Novel AAV Variants by Directed Evolution for Improved CFTR Delivery to Human Ciliated Airway Epithelium" Molecular Therapy, 17(12):2067-2077 (2009).
Li et al. "Single Amino Acid Modification of Adeno-Associated Virus Capsid Changes Transduction and Humoral Immune Profiles" Journal of Virology, 86(15):7752-7759 (2012).

(56) References Cited

OTHER PUBLICATIONS

Li et al. "Site-Directed Mutagenesis of Surface-Exposed Lysine Residues Leads to Improved Transduction by AAV2, But Not AAV8, Vectors in Murine Hepatocytes In Vivo" Human Gene Therapy Methods, 26(6):211-220 (2015).
Lisowski et al. "Selection and evaluation of clinically relevant AAV variants in a xenograft liver model" Nature, 506 (7488):382-386 (2014).
Liu et al. "Enhancing gene delivery of adeno-associated viruses by cell-permeable peptides" Molecular Therapy—Methods & Clinical Development, 1(12):1-13 (2014).
Lochrie et al. "Adeno-associated virus (AAV) capsid genes isolated from rat and mouse liver genomic DNA define two new AAV species distantly related to AAV-5" Virology, 353:68-82 (2006).
Maguire et al. "Directed evolution of adeno-associated virus for glioma cell transduction" Journal of Neuro-Oncology, 96(3):337-347 (2010).
Malakoutikhah et al. "Shuttle-mediated drug delivery to the brain" Angewandte Chemie, 50:7998-8014 (2011) (Abstract only).
Manno et al. "Successful transduction of liver in hemophilia by AAV-Factor IX and limitations imposed by the host immune response" Nature Medicine, 12(3):342-347 (2006).
Marks et al. "Safety and tolerability of intraputaminal delivery of CERE-120 (adeno-associated virus serotype 2-neurturin) to patients with idiopathic Parkinson's disease: an open-label, phase I trial" The Lancet Neurology, 7:400-408 (2008).
Marsic et al. "Vector design Tour de Force: Integrating Combinatorial and Rational Approaches to Derive Novel Adeno-associated Virus Variants" Molecular Therapy, 22(11):1900-1909 (2014).
Matsuzaki et al. "Intravenous administration of the adeno-associated virus-PHP.B capsid fails to upregulate transduction efficiency in the marmoset brain" Neuroscience Letters, 665:182-188 (2018) (Abstract only).
Meairs, Stephen "Facilitation of Drug Transport across the Blood-Brain Barrier with Ultrasound and Microbubbles" Pharmaceutics, 7:275-293 (2015).
Messina et al. "Adeno-Associated Viral Vectors Based on Serotype 3b Use Components of the Fibroblast Growth Factor Receptor Signaling Complex for Efficient Transduction" Human Gene Therapy, 23(10):1031-1042 (2012).
Michelfelder et al. "Peptide Ligands Incorporated into the Threefold Spike Capsid Domain to Re-Direct Gene Transduction of AAV8 and AAV9 In Vivo" PLoS One, 6(8):e23101 (2011).
Michelfelder et al. "Vectors selected from adeno-associated viral display peptide libraries for leukemia cell-targeted cytotoxic gene therapy" Experimental Hematology, 35(12):1766-1776 (2007) (Abstract only).
Muller et al. "Random peptide libraries displayed on adeno-associated virus to select for targeted gene therapy vectors" Nature Biotechnology, 21(9):1040-1046 (2003).
Naso et al. "Adeno-Associated Virus (AAV) as a Vector for Gene Therapy" BioDrugs, 31:317-334 (2017).
Nathwani et al. "Adenovirus-Associated Virus Vector-Mediated Gene Transfer in Hemophilia B" The New England Journal of Medicine, 365:2357-2365 (2011).
Oller-Salvia et al. "Blood-brain barrier shuttle peptides: an emerging paradigm for brain delivery" Chemical Society Reviews, 45(17):4690-4707 (2016).
Pei et al. "AAV8 virions hijack serum proteins to increase hepatocyte binding for transduction enhancement" Virology, 518:95-102 (2018).
Petrs-Silva et al. "High-efficiency Transduction of the Mouse Retina by Tyrosine-mutant AAV Serotype Vectors" Molecular Therapy, 17(3):463-471 (2009).
Powell et al. "Characterization of a novel adeno-associated viral vector with preferential oligodendrocyte tropism" Gene Therapy, 23(11):807-814 (2016).
Prades et al. "Delivery of gold nanoparticles to the brain by conjugation with a peptide that recognizes the transferrin receptor" Biomaterials, 33:7194-7205 (2012).
Pulicherla et al. "Engineering Liver-detargeted AAV9 Vectors for Cardiac and Musculoskeletal Gene Transfer" Molecular Therapy, 19(6):1070-1078 (2011).
Qian et al. "Targeted drug delivery via the transferrin receptor-mediated endocytosis pathway" Pharmacological Reviews, 54:561-587 (2002) (Abstract only).
Qiao et al. "Adeno-Associated Virus Serotype 6 Capsid Tyrosine-to-Phenylalanine Mutations Improve Gene Transfer to Skeletal Muscle" Human Gene Therapy, 21(10):1343-1348 (2010).
Ren et al. "The targeted delivery of anticancer drugs to brain glioma by PEGylated oxidized multi-walled carbon nanotubes modified with angiopep-2" Biomaterials, 33:3324-3333 (2012) (Abstract only).
Sallach et al. "Tropism-modified AAV Vectors Overcome Barriers to Successful Cutaneous Therapy" Molecular Therapy, 22(5):929-939 (2014).
Salmon et al. "Safety profile of recombinant adeno-associated viral vectors: focus on alipogene tiparvovec (Glybera)" Expert Review of Clinical Pharmacology, 7:53-65 (2014).
Schmidt et al. "Cloning and Characterization of a Bovine Adeno-Associated Virus" Journal of Virology, 78 (12):6509-6516 (2004).
Sellner et al. "Generation of efficient human blood progenitor-targeted recombinant adeno-associated viral vectors (AAV) by applying an AAV random peptide library on primary human hematopoietic progenitor cells" Exp Hem, 36:957-964 (2008) (Abstract only).
Sen et al. "Targeted Modifications in Adeno-Associated Virus Serotype 8 Capsid Improves Its Hepatic Gene Transfer Efficiency In Vivo" Human Gene Therapy Methods, 24(2):104-116 (2013).
Shen et al. "Engraftment of a Galactose Receptor Footprint onto Adeno-associated Viral Capsids Improves Transduction Efficiency" Journal of Biological Chemistry, 288(40):28814-28823 (2013).
Tenenbaum et al. "Evaluation of Risks Related to the Use of Adeno-Associated Virus-Based Vectors" Current Gene Therapy, 3(6):545-565 (2003).
Tervo et al. "A designer AAV variant permits efficient retrograde access to projection neurons" Neuron, 92 (2):372-382 (2016).
Varadi et al. "Novel random peptide libraries displayed on AAV serotype 9 for selection of endothelial cell-directed gene transfer vectors" Gene Therapy, 19(8):800-809 (2012).
Wang et al. "Direct Interaction of Human Serum Proteins with AAV Virions to Enhance AAV Transduction: Immediate Impact on Clinical Applications" Gene Therapy, 24(1):49-59 (2017).
Watakabe et al. "Comparative analyses of adeno-associated viral vector serotypes 1, 2, 5, 8 and 9 in marmoset, mouse and macaque cerebral cortex" Neuroscience, 93:144-157 (2015).
Wu et al. "Mutational Analysis of the Adeno-Associated Virus Type 2 (AAV2) Capsid Gene and Construction of AAV2 Vectors with Altered Tropism" Journal of Virology, 74(18):8635-8647 (2000).
Yang et al. "A myocardium tropic adeno-associated virus (AAV) evolved by DNA shuffling and in vivo selection" Proceedings of the National Academy of Sciences USA, 106(10):3946-3951 (2009).
Yu et al. "A muscle-targeting peptide displayed on AAV2 improves muscle tropism on systemic delivery" Gene Therapy, 16(8):953-962 (2009).
Yu et al. "Developing Therapeutic Antibodies for Neurodegenerative Disease" Neurotherapeutics, 10(3):459-472 (2013).
Zhang et al. "Blood-brain barrier shuttle peptides enhance AAV transduction in the brain after systemic administration" Biomaterials, 176:71-83 (2018).
Zhong et al. "Next generation of adeno-associated virus 2 vectors: point mutations in tyrosines lead to high-efficiency transduction at lower doses" Proceedings of the National Academy of Sciences USA, 105(22):7827-7832 (2008).
Zinn et al. "In Silico Reconstruction of the Viral Evolutionary Lineage Yields a Potent Gene Therapy Vector" Cell Reports, 12:1056-1068 (2015).
"International Search Report and the Written Opinion of the International Searching Authority corresponding to International Patent Application No. PCT/US2018/066551 (9 pages) (mailed Mar. 28, 2019)".

(56) References Cited

OTHER PUBLICATIONS

Chen, et al., ""Molecular Characterization of Adeno-Associated Viruses Infecting Children" Journal of Virology, 79 (23):14781-14792 (2005)".
Choudhury, et al., ""In Vivo Selection Yields AAV-B1 Capsid for Central Nervous System and Muscle Gene Therapy" Molecular Therapy, 24(7):1247-1257 (2016)".
Turanli-Yildiz, et al., ", "Protein Engineering Methods and Applications," Protein Engineering, Chapter 2, pp. 33-58, (2012)".
Vance, Melisa, et al., "AAV gene therapy for MPS1-associated corneal blindness", Scientific Reports, 6(1) (Feb. 22, 2016), 2016, 1-10.

\* cited by examiner

METHODS AND COMPOSITIONS FOR DELIVERY OF VIRAL VECTORS ACROSS THE BLOOD-BRAIN BARRIER

STATEMENT OF PRIORITY

This patent application is a divisional of U.S. patent application Ser. No. 16/956,306, filed Jun. 19, 2020 (allowed), which is a 35 U.S.C. § 371 national phase application of International Application Serial No. PCT/US2018/066551, filed Dec. 19, 2018, which claims the benefit, under 35 U.S.C. § 119(e), of U.S. Provisional Application No. 62/607,662, filed on Dec. 19, 2017, the entire contents of each of which are incorporated by reference herein.

STATEMENT REGARDING ELECTRONIC FILING OF A SEQUENCE LISTING

A Sequence Listing in XML format, entitled 5470-830DV_updated02052024_ST26.xml, 230,427 bytes in size, generated on Feb. 5, 2024, and filed herewith, is hereby incorporated by reference in its entirety for its disclosures.

FIELD OF THE INVENTION

This invention is directed to compositions and methods for delivering AAV vectors across the blood-brain barrier (BBB).

BACKGROUND OF THE INVENTION

Recombinant adeno-associated virus (rAAV) vector, one of the most promising vehicles of therapeutic gene delivery, has been employed and developed for several decades. Due to extensive preclinical studies, more and more clinical trials with rAAV vectors are ongoing and great success has been achieved in patients with blindness and hemophilia. rAAV vectors have also shown promise as a platform for neurological disorders. Upon intraparenchymal injection in rodents, some serotypes demonstrated the ability to efficiently transduce neurons including: AAV serotypes 7, 8, and 9 among the identified 12 AAV serotypes. It is worth noting that intraparenchymal injection, adopted by a majority of clinical trials, is able to successfully deliver AAV vectors to a local area of the brain, but most neurodegenerative disorders involve cell damage in multiple areas such as amyotrophic lateral sclerosis, frontotemporal dementia, Rett syndrome, and Huntington's disease. AAV9 possesses the remarkable ability to transduce parenchymal brain cells and portions of the blood-brain barrier (BBB) endothelium after intravenous injection. Systemic administration of AAV9 results in widespread neuron gene transfer in the neonatal brain, but much less neuron transduction efficacy in adults. Therefore, the BBB remains a major obstacle for AAV-mediated gene delivery to the central nervous system (CNS) via systemic administration.

The present invention overcomes previous shortcomings in the art by providing compositions and methods for delivery of viral vectors across the blood-brain barrier (BBB) and enhanced transduction of cells.

SUMMARY OF THE INVENTION

Aspects of the invention relate to an adeno-associated virus (AAV) particle comprising a surface-bound peptide, wherein the peptide bound to the surface of the AAV particle is Angiopep-2, GSH, HIV-1 TAT (48-60), ApoE (159-167)2, Leptin 30 (61-90), THR, PB5-3, PB5-5, PB5-14, or any combination thereof.

In various embodiments, the AAV is of a serotype or any combination of serotypes listed in Table 1.

In various embodiments, the AAV is AAV8, AAV9, AAV2, AAV2i8, AAV9.45 or any variant, mutant, or combination thereof.

In various embodiments, the protein bound to the surface of the AAV particle is present on the AAV particle surface in an amount ranging from about 2000 protein molecules per AAV particle to about $4 \times 10^7$ protein molecules per AAV particle.

In various embodiments, the particle comprises a heterologous nucleic acid molecule.

In various embodiments, the surface bound peptide has enhanced transduction activity across the blood brain barrier (BBB) relative to an AAV particle lacking the surface-bound protein.

In various embodiments, AAV particle comprising the surface-bound peptides has enhanced transduction activity of cells of the brain and/or central nervous system.

Another aspect of the invention relates to a pharmaceutical formulation comprising the AAV particle described above in a pharmaceutically acceptable carrier.

Another aspect of the invention relates to a method of delivering a nucleic acid to a cell of the brain and/or central nervous system. The method comprises contacting the cell, with the AAV particle described above, or the pharmaceutical formulation described above.

Another aspect of the invention relates to a method of administering a nucleic acid to a cell of the brain and/or central nervous system of a subject. The method comprises administering to the subject the AAV particle described above, or the pharmaceutical formulation described above. In embodiments, the AAV particle is administered systemically. In embodiments, the subject is a human subject.

Another aspect of the invention relates to a modified adeno-associated virus (AAV) capsid protein comprising an insertion of a polypeptide at a position between amino acids corresponding to amino acids 588 and 589 of AAV9. The polypeptide is Angiopep-2, GSH, HIV-1 TAT (48-60), ApoE (159-167)2, Leptin 30 (61-90), THR, PB5-3, PB5-5, or PB5-14.

In some embodiments, the inserted polypeptide further comprises a glycine at the N-terminus, the C-terminus, or both the N- and C-terminus.

In some embodiments, the AAV capsid protein is an AAV serotype or any combination of serotypes listed in Table 1.

In some embodiments, the modified AAV capsid protein is an AAV9 capsid protein.

Another aspect of the invention relates to a nucleic acid molecule encoding a modified AAV capsid protein of any one of the above modified AAV capsid proteins.

In some embodiments, the nucleic acid molecule is within a vector.

Another aspect of the invention relates to an AAV particle comprising the modified AAV capsid protein described above.

In some embodiments, the AAV particle is an AAV serotype or any combination of serotypes listed in Table 1.

In some embodiments, the AAV particle is AAV8, AAV9, AAV2, AAV2i8, AAV9.45 or any variant, mutant, or combination thereof.

In some embodiments, the AAV particle further comprises a heterologous nucleic acid molecule.

In some embodiments, the heterologous nucleic acid molecule encodes a therapeutic polypeptide.

In some embodiments, the AAV particle has enhanced transduction activity across the blood brain barrier (BBB) relative to a control AAV particle with a capsid lacking the inserted polypeptide.

In some embodiments, the AAV particle has enhanced transduction activity of cells of the brain and/or central nervous system relative to a control AAV particle with a capsid lacking the inserted polypeptide.

In some embodiments, the AAV particle has enhanced transduction to one or more of cortex, striatum, thalamus, cerebellum and spinal cord of a subject.

In some embodiments, the AAV particle has enhanced transduction to one or more of astrocytes, CC1+ oligodendrocytes, neuronal subtypes including NeuN+ cells throughout the brain, midbrain tyrosine hydroxylase (TH)+ dopaminergic neurons, Calbindin+ cerebellar Purkinje cells, interneuron populations and CD31+ endothelial cells of a subject.

Another aspect of the invention relates to a pharmaceutical formulation comprising the AAV particle that comprises the modified capsid protein described above, or to a pharmaceutical formulation comprising the modified capsid protein described above, in a pharmaceutically acceptable carrier.

Another aspect of the invention relates to a method of administering a nucleic acid to a cell of the brain and/or central nervous system, comprising contacting the cell with the AAV particle comprising a modified AAV capsid protein described above, or a pharmaceutical formulation comprising the same.

Another aspect of the invention relates to a method of delivering a nucleic acid to a cell of the brain and/or central nervous system of a subject, comprising administering to the subject the AAV particle comprising the modified AAV capsid protein described above, or a pharmaceutical formulation comprising the same.

In some embodiments of the methods, the AAV particle or pharmaceutical formulation is administered systemically. In some embodiments of the method, the subject is a human subject.

Another aspect of the invention relates to the AAV vector described above, the AAV particle, AAV virion and/or composition of this invention for use as a medicament in the beneficial treatment of a disorder or disease.

These and other aspects of the invention are addressed in more detail in the description of the invention set forth below.

BRIEF DESCRIPTION OF THE DRAWINGS

(FIG. 1A) The cell cytotoxicity of peptides was measured using the MTT assay. After that, the peptides with different concentrations were added into the cells for 48 h. (FIG. 1B) The transduction efficiency of different complexes of AAV8 with 10E+04 vg/cell and peptides were tested in the HEK293 and Huh7 cell lines. $*p<0.05$ when compared to the group of AAV8 transduction alone.

(FIG. 3A) On the $7^{th}$, day post administration of AAV8 or the complexes, imaging was taken for luminescence expression. (FIG. 3B) The average luciferase signal for liver and whole body, except liver, in different groups was calculated. At three weeks post-injection, mice were euthanized and the tissues were harvested for DNA extraction. Relative luciferase expression level (FIG. 3C) and vector copy numbers (FIG. 3D) in liver and brain were determined separately. The data represents the average and standard deviation from 5 mice. $*p<0.05$ when compared to control mice with AAV8 treatment only.

(FIG. 4A) On the $3^{rd}$ and $7^{th}$ day post administration of AAV8 or the different doses of complexes, imaging was taken for luminescence expression. (FIG. 4B) The average luciferase signal for liver and whole body, except liver, in mice treated with different doses of THR was calculated. (FIG. 4C) The gene copy numbers in liver, brain and spleen were determined separately. * $p<0.001$,  $p<0.01$, and $*p<0.05$ when compared to control mice with AAV8 treatment only.

(FIG. 5A) On the $3^{rd}$, $7^{th}$, $14^{th}$, and $21^{st}$ day post AAV8 or THR and AAV8 administration, imaging was taken for luminescence expression. (FIG. 5B) The average luciferase signal for liver in different groups was calculated. Relative luciferase expression level (FIG. 5C) and vector copy numbers (FIG. 5D) in brain were determined separately. The data represents the average and standard deviation from 5 mice. $*p<0.05$ when compared to control mice with AAV8 treatment only.

(FIG. 6A) HEK293 and Huh7 cells were transduced with 1E+08 AAV8/luc alone or the complex of AAV8 and THR at different concentrations. Luciferase expression was analyzed 48 h later. (FIG. 6B) The effect of THR on Nab titer. 1E+08 AAV8/luc in 50 ul was first incubated with THR at different concentrations at 4° C. for 2 h. Then, equal volumes of sera at different dilutions or PBS were added at 37° C. for 1 h, and then the mixture of AAV and peptide and serum were added into cells. Finally, cells were lysed for luciferase assay after 48 h post-transduction, and Nab titer was evaluated. The data represents an average of three separate infections, with the standard deviation indicated by an error bar.

(FIG. 7A, FIG. 7B) Mice were immunized with the incubated complex of 2E+11 vg AAV8/Luc and 0.1 mM THR peptide via retro-orbital injection. Luciferase expression was imaged on the $2^{nd}$ day and the $7^{th}$ day. (FIG. 7C) At the same time, blood was collected from the retro-orbital plexus at various time points after injection, and the viral titers were tested by qPCR.

(FIG. 8A) The binding ability of Huh7 cells with the AAV8 only or the complexes of AAV8 and transferrin or THR treatment was studied. The transduced cells were incubated at 4° C. for 1 h, then the genome copy number was measured and normalized to GAPDH. (FIG. 8B) hCMEC/D3 cells were cultured into monolayer formation and then incubated with either AAV8, AAV8 with THR separately, or AAV8-THR complex, then the media in the basal chamber was collected at different time points and the viral titer was analyzed by qPCR. All treatments were performed in triplicate. *$p<0.05$ when compared to cells with AAV8 treatment only.

(FIG. 10A) The membrane permeability assay of different treatments was conducted with FITC-dextran. No significant difference of permeability was observed. (FIG. 10B) Western blot showed similar expression levels of the major junction protein ZO-1 in hCMEC/D3 cells between the early and late time points in different groups. GAPDH is presented as a loading control for equal protein.

(FIG. 16A) representative imaging. (FIG. 16B) luciferase expression. (FIG. 16C) AAV genome copy number. The results represented the average and standard derivation from five mice.

DETAILED DESCRIPTION OF THE INVENTION

Figure 1A:
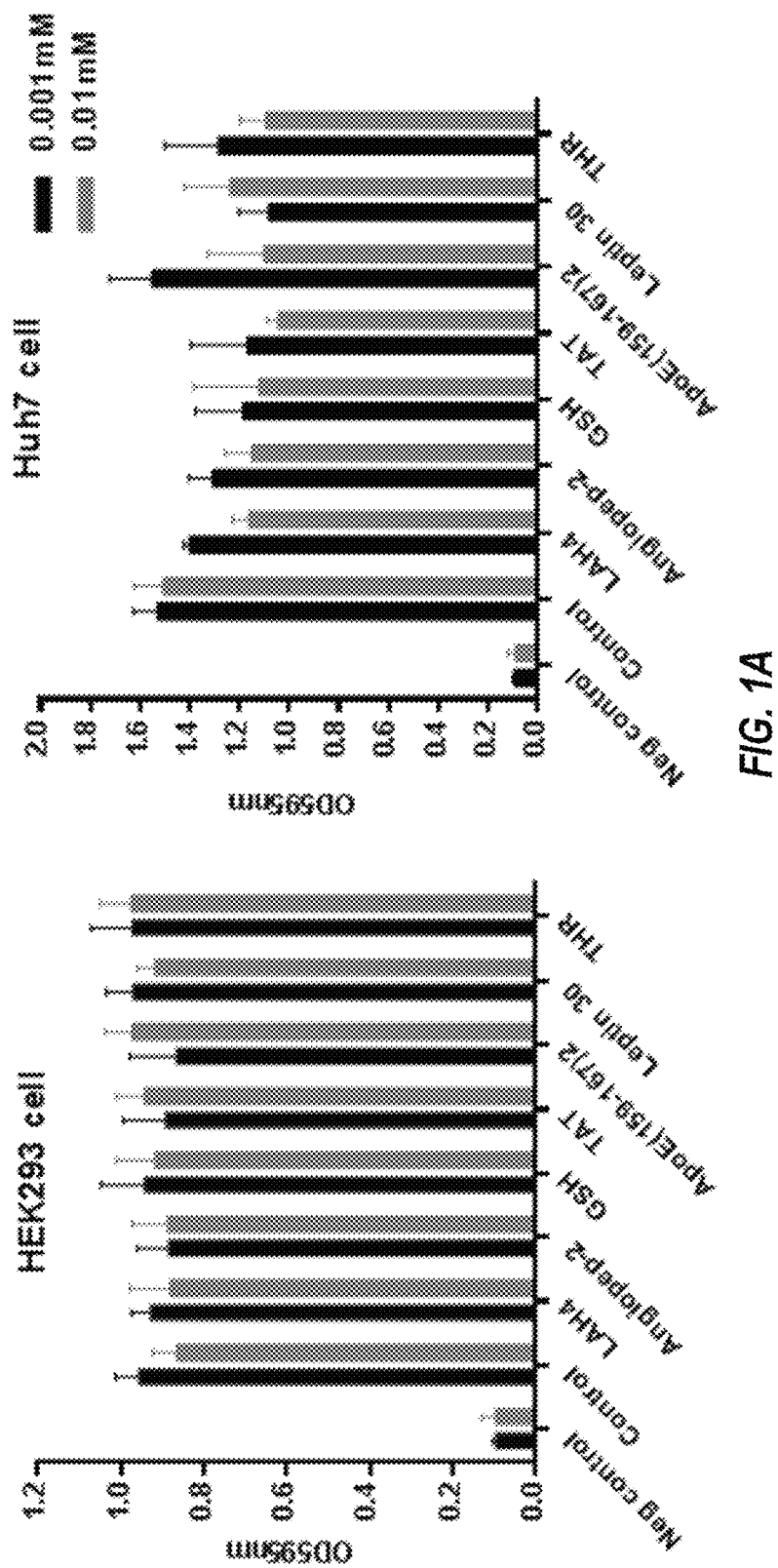
FIGS. 1A and 1B show screening peptides to enhance adeno-associated virus type 8 (AAV8) transduction without cytotoxicity in vitro.

The present invention will now be described with reference to the accompanying drawings, in which representative embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents, accession numbers and other references mentioned herein are incorporated by reference herein in their entirety.

The designation of all amino acid positions in the AAV capsid proteins in the description of the invention and the appended claims is with respect to VP1 capsid subunit numbering (native AAV2 VP1 capsid protein: GenBank Accession No. AAC03780 or YP680426). It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3).

Definitions

The following terms are used in the description herein and the appended claims:

The singular forms "a," "an" and "the" are intended to include the plural forms as well, unless the context clearly indicates otherwise.

Furthermore, the term "about," as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 USPQ 461, 463 (CCPA 1976) (emphasis in the original); see also MPEP § 2111.03. Thus, the term "consisting essentially of" when used in a claim of this invention is not intended to be interpreted to be equivalent to "comprising."

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate further, if, for example, the specification indicates that a particular amino acid can be selected from A, G, I, L and/or V, this language also indicates that the amino acid can be selected from any subset of these amino acid(s) for example A, G, I or L; A, G, I or V; A or G; only L; etc. as if each such subcombination is expressly set forth herein. Moreover, such language also indicates that one or more of the specified amino acids can be disclaimed (e.g., by negative proviso). For example, in particular embodiments the amino acid is not A, G or I; is not A; is not G or V; etc. as if each such possible disclaimer is expressly set forth herein.

As used herein, the terms "reduce," "reduces," "reduction" and similar terms mean a decrease of at least about 25%, 35%, 50%, 75%, 80%, 85%, 90%, 95%, 97% or more.

As used herein, the terms "enhance," "enhances," "enhancement" and similar terms indicate an increase of at least about 25%, 50%, 75%, 100%, 150%, 200%, 300%, 400%, 500% or more.

The term "parvovirus" as used herein encompasses the family Parvoviridae, including autonomously replicating parvoviruses and dependoviruses. The autonomous parvoviruses include members of the genera Parvovirus, Erythrovirus, Densovirus, Iteravirus, and Contravirus. Exemplary autonomous parvoviruses include, but are not limited to, minute virus of mouse, bovine parvovirus, canine parvovirus, chicken parvovirus, feline panleukopenia virus, feline parvovirus, goose parvovirus, H1 parvovirus, muscovy duck parvovirus, B19 virus, and any other autonomous parvovirus now known or later discovered. Other autonomous parvoviruses are known to those skilled in the art. See, e.g., BERNARD N. FIELDS et al., VIROLOGY, volume 2, chapter 69 (4th ed., Lippincott-Raven Publishers).

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known or later discovered. See, e.g., BERNARD N. FIELDS et al., VIROLOGY, volume 2, chapter 69 (4th ed., Lippincott-Raven Publishers). A number of relatively new AAV serotypes and clades have been identified (see, e.g., Gao et al., (2004) *J. Virology* 78:6381-6388; Moris et al., (2004) *Virology* 33-:375-383; and Table 1).

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC 001729, NC 001863, NC_001829, NC 001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC 001358, NC_001540, AF513851, AF513852, AY530579; the disclosures of which are incorporated by reference herein for teaching parvovirus and AAV nucleic acid and amino acid sequences. See also, e.g., Srivistava et al. (1983) *J. Virology* 45:555; Chiorini et al. (1998) *J. Virology* 71:6823; Chiorini et al., (1999) *J. Virology* 73:1309; Bantel-Schaal et al., (1999) *J. Virology* 73:939; Xiao et al., (1999) *J. Virology* 73:3994; Muramatsu et al., (1996) *Virology* 221:208; Shade et al., (1986) *J. Virol.* 58:921; Gao et al., (2002) *Proc. Nat. Acad. Sci.* USA 99:11854; Moris et al., (2004) *Virology* 33-:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 1.

The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) *Proc. Nat. Acad. Sci.* 99:10405-10), AAV4 (Padron et al., (2005) *J. Virol.* 79: 5047-58), AAV5 (Walters et al., (2004) *J. Virol.* 78: 3361-71) and CPV (Xie et al., (1996) *J. Mol. Biol.* 6:497-520 and Tsao et al., (1991) *Science* 251: 1456-64).

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

As used here, "systemic tropism" and "systemic transduction" (and equivalent terms) indicate that the virus capsid or virus vector of the invention exhibits tropism for and/or transduces tissues throughout the body (e.g., brain, lung, skeletal muscle, heart, liver, kidney and/or pancreas). In embodiments of the invention, systemic transduction of the central nervous system (e.g., brain, neuronal cells, etc.) is observed. In other embodiments, systemic transduction of cardiac muscle tissues is achieved.

As used herein, "selective tropism" or "specific tropism" means delivery of virus vectors to and/or specific transduction of certain target cells and/or certain tissues.

Unless indicated otherwise, "efficient transduction" or "efficient tropism," or similar terms, can be determined by reference to a suitable control (e.g., at least about 50%, 60%, 70%, 80%, 85%, 90%, 95%, 100%, 125%, 150%, 175%, 200%, 250%, 300%, 350%, 400%, 500% or more of the transduction or tropism, respectively, of the control). In particular embodiments, the virus vector efficiently transduces or has efficient tropism for neuronal cells and cardiomyocytes. Suitable controls will depend on a variety of factors including the desired tropism and/or transduction profile.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, transduction (e.g., undesirable transduction) of tissue(s) (e.g., liver) is 20% or less, 10% or less, 5% or less, 1% or less, 0.1% or less of the level of transduction of the desired target tissue(s) (e.g., skeletal muscle, diaphragm muscle, cardiac muscle and/or cells of the central nervous system).

In some embodiments of this invention, an AAV particle comprising a capsid of this invention can demonstrate multiple phenotypes of efficient transduction of certain tissues/cells and very low levels of transduction (e.g., reduced transduction) for certain tissues/cells, the transduction of which is not desirable.

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotides), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, 100-fold, 1000-fold, 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, 100-fold, 1000-fold, 10,000-fold or more as compared with the starting material.

An "isolated cell" refers to a cell that is separated from other components with which it is normally associated in its natural state. For example, an isolated cell can be a cell in culture medium and/or a cell in a pharmaceutically acceptable carrier of this invention. Thus, an isolated cell can be delivered to and/or introduced into a subject. In some embodiments, an isolated cell can be a cell that is removed from a subject and manipulated as described herein ex vivo and then returned to the subject.

As used herein, by "isolate" or "purify" (or grammatical equivalents) a virus vector or virus particle or population of virus particles, it is meant that the virus vector or virus particle or population of virus particles is at least partially separated from at least some of the other components in the starting material. In representative embodiments an "isolated" or "purified" virus vector or virus particle or population of virus particles is enriched by at least about 10-fold, 100-fold, 1000-fold, 10,000-fold or more as compared with the starting material.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability or induction of an immune response.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the invention. The prevention can be complete, e.g., the total absence of the disease, disorder and/or clinical symptom(s). The prevention can also be partial, such that the occurrence of the disease, disorder and/or clinical symptom(s) in the subject and/or the severity of onset is substantially less than what would occur in the absence of the present invention.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

A "prevention effective" amount as used herein is an amount that is sufficient to prevent and/or delay the onset of a disease, disorder and/or clinical symptoms in a subject and/or to reduce and/or delay the severity of the onset of a disease, disorder and/or clinical symptoms in a subject relative to what would occur in the absence of the methods of the invention. Those skilled in the art will appreciate that the level of prevention need not be complete, as long as some preventative benefit is provided to the subject.

The terms "heterologous nucleotide sequence" and "heterologous nucleic acid molecule" are used interchangeably herein and refer to a nucleic acid sequence that is not naturally occurring in the virus. Generally, the heterologous nucleic acid molecule or heterologous nucleotide sequence comprises an open reading frame that encodes a polypeptide and/or nontranslated RNA of interest (e.g., for delivery to a cell and/or subject).

As used herein, the terms "virus vector," "vector" or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "vector" may be used to refer to the vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans (Muzyczka, (1992) *Curr. Topics Microbiol. Immunol.* 158:97). Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the invention the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence" as described in U.S. Pat. No. 5,478,745 to Samulski et al.

An "AAV terminal repeat" or "AAV TR" may be from any AAV, including but not limited to serotypes 1, 2, 3, 4, 5, 6, 7, 8, 9, 10, 11 or 12 or any other AAV now known or later discovered (see, e.g., Table 1). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

AAV proteins VP1, VP2 and VP3 are capsid proteins that interact together to form an AAV capsid of an icosahedral symmetry. VP1.5 is an AAV capsid protein described in US Publication No. 2014/0037585.

The virus vectors of the invention can further be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al., (2000) *Molecular Therapy* 2:619.

The virus vectors of the invention can further be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

Further, the viral capsid or genomic elements can contain other modifications, including insertions, deletions and/or substitutions.

A "chimeric' capsid protein as used herein means an AAV capsid protein that has been modified by substitutions in one or more (e.g., 2, 3, 4, 5, 6, 7, 8, 9, 10, etc) amino acid residues in the amino acid sequence of the capsid protein relative to wild type, as well as insertions and/or deletions of one or more (e.g., 2, 3, 4, 5, 6, 7, 8, 9, 10, etc) amino acid residues in the amino acid sequence relative to wild type. In some embodiments, complete or partial domains, functional regions, epitopes, etc., from one AAV serotype can replace the corresponding wild type domain, functional region, epitope, etc. of a different AAV serotype, in any combination, to produce a chimeric capsid protein of this invention. Production of a chimeric capsid protein can be carried out according to protocols well known in the art and a large number of chimeric capsid proteins are described in the literature as well as herein that can be included in the capsid of this invention.

As used herein, the term "amino acid" encompasses any naturally occurring amino acid, modified forms thereof, and synthetic amino acids.

Naturally occurring, levorotatory (L-) amino acids are shown in Table 2.

Alternatively, the amino acid can be a modified amino acid residue (nonlimiting examples are shown in Table 4) and/or can be an amino acid that is modified by post-translation modification (e.g., acetylation, amidation, formylation, hydroxylation, methylation, phosphorylation or sulfatation).

Further, the non-naturally occurring amino acid can be an "unnatural" amino acid as described by Wang et al., *Annu Rev Biophys Biomol Struct.* 35:225-49 (2006)). These unnatural amino acids can advantageously be used to chemically link molecules of interest to the AAV capsid protein.

Virus Vectors with Surface Bound Peptide for Enhanced Transduction Across the Blood-Brain Barrier (BBB) and/or Enhanced Transduction of Cells of the Brain and/or Central Nervous System The present invention is based on the unexpected discovery that AAV virions with certain peptides bound to the surface have enhanced transduction properties and/or enhanced ability to cross the blood-brain barrier (BBB). Thus, in one embodiment, the present invention provides an adeno-associated virus (AAV) particle comprising a surface-bound peptide, wherein the peptide bound to the surface of the AAV particle is selected from the group consisting of: a) Angiopep-2; b) GSH; c) HIV-1 TAT (48-60); d) ApoE (159-167)2; e) Leptin 30 (61-90); f) THR; g) PB5-3; h) PB5-5; i) PB5-14; and j) any combination of (a)-(i) above. The amino acid sequence of each of these peptides is shown in Tables 5, 6, and 7 herein. In one embodiment, PB5-3 is bound to the surface of an AAV9 particle. In one embodiment PB5-5 is bound to the surface of an AAV9 particle. In one embodiment PB5-14 is bound to the surface of an AAV9 particle. In some embodiments, the peptide may be any known or later identified to enhance transduction properties and/or enhance the ability of AAV particles to cross the BBB. In some embodiments, the peptide may be selected (e.g., identified) from a phage display peptide library, for example, by methods described herein.

In some embodiments of this invention, an AAV particle can comprise one or more than one surface-bound peptide, which can be any peptide or combination of peptides as set forth in Tables 5, 6, and 7 herein. The peptides can be present in any combination and/or ratio relative to other peptides present.

In some embodiments, the peptide bound to the surface of the AAV particle can be present on the AAV particle surface in an amount ranging from about 2000 peptide molecules per AAV particle to about $4 \times 10^7$ peptide molecules per AAV particle, including any value within this range.

The AAV particle of this invention can be an AAV of a serotype or any combination of serotypes listed in Table 1.

In some embodiments, the AAV particle of this invention can be, singly or in any combination, AAV8, AAV9, AAV2, AAV2i8, AAV9.45, or any AAV mutant or variant described herein, now known or later identified. An AAV particle of this invention can be any "haploid" AAV particle as described, for example in U.S. Provisional Application No. 62/471,762, filed Mar. 15, 2017, the entire contents of which are incorporated by reference herein.

The AAV particles of the invention can, in some embodiments, be "targeted" virus vectors (e.g., having a directed tropism) and/or a "hybrid" parvovirus (i.e., in which the viral TRs and viral capsid are from different parvoviruses) as described in international patent publication WO 00/28004 and Chao et al. (2000) *Molecular Therapy* 2:619.

The AAV particles of the invention can, in some embodiments, be duplexed parvovirus particles as described in international patent publication WO 01/92551 (the disclosure of which is incorporated herein by reference in its entirety). Thus, in some embodiments, double stranded (duplex) genomes can be packaged into the virus capsids of the invention.

In some embodiments of the AAV particle of this invention, the peptide bound to the surface of the AAV particle can be present on the AAV particle surface in an amount in a range from about 2000 protein molecules per AAV particle to about $4 \times 10^7$ protein molecules per AAV particle (e.g., 2000, 3000, 4000, 5000, 6000, 7000, 8000, 9000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 60,000, 70,000, 80,000, 90,000, $1 \times 10^6$, $2 \times 10^6$, $3 \times 10^6$, $4 \times 10^6$, $5 \times 10^6$, $6 \times 10^6$, $7 \times 10^6$, $8 \times 10^6$, $9 \times 10^6$, $1 \times 10^7$, $2 \times 10^7$, $3 \times 10^7$, or $4 \times 10^7$, including any number in between 2000 and $4 \times 10^7$ not explicitly set forth herein). The number of peptide molecules per AAV particle can be determined according to protocols known in the art and as exemplified in the Examples section herein.

In some embodiments, the AAV particle comprising the surface-bound peptide has enhanced transduction activity across the blood-brain barrier and/or enhanced transduction activity in cells of the brain and/or central nervous system relative to an AAV particle lacking the surface-bound peptide. Accordingly, the number of peptide molecules attached to the AAV particle can be an amount that enhances transduction activity of the AAV particle across the blood-brain barrier and/or enhances transduction of cells of the brain and/or central nervous system relative to an AAV particle lacking the surface-bound peptide.

In some embodiments, the AAV particle of this invention can comprise a heterologous nucleic acid molecule.

In some embodiments, the AAV particle of this invention can be synthetic viral vector designed to display a range of desirable phenotypes that are suitable for different in vitro and in vivo applications. Thus, in one embodiment, the present invention provides an AAV particle comprising an adeno-associated virus (AAV) capsid, wherein the capsid comprises capsid protein VP1, wherein said capsid protein VP1 is from one or more than one first AAV serotype and capsid protein VP3, wherein said capsid protein VP3 is from one or more than one second AAV serotype and wherein at least one of said first AAV serotype is different from at least one of said second AAV serotype, in any combination.

In some embodiments, the AAV particle can comprise a capsid that comprises capsid protein VP2, wherein said capsid protein VP2 is from one or more than one third AAV serotype, wherein at least one of said one or more than one third AAV serotype is different from said first AAV serotype and/or said second AAV serotype, in any combination. In some embodiments, the AAV capsid described herein can comprise capsid protein VP1.5. VP1.5 is described in US Patent Publication No. 20140037585 and the amino acid sequence of VP1.5 is provided herein.

In some embodiments, the AAV particle of this invention can comprise a capsid that comprises capsid protein VP1.5, wherein said capsid protein VP1.5 is from one or more than one fourth AAV serotype, wherein at least one of said one or more than one fourth AAV serotype is different from said first AAV serotype and/or said second AAV serotype, in any combination. In some embodiments, the AAV capsid protein described herein can comprise capsid protein VP2.

The present invention also provides an AAV particle of this invention, comprising an AAV capsid wherein the capsid comprises capsid protein VP1, wherein said capsid protein VP1 is from one or more than one first AAV serotype and capsid protein VP2, wherein said capsid protein VP2 is from one or more than one second AAV serotype and wherein at least one of said first AAV serotype is different from at least one of said second AAV serotype, in any combination.

In some embodiments, the AAV particle of this invention can comprise a capsid that comprises capsid protein VP3, wherein said capsid protein VP3 is from one or more than one third AAV serotype, wherein at least one of said one or more than one third AAV serotype is different from said first AAV serotype and/or said second AAV serotype, in any combination. In some embodiments, the AAV capsid described herein can comprise capsid protein VP1.5.

The present invention further provides an AAV particle that comprises an adeno-associated virus (AAV) capsid, wherein the capsid comprises capsid protein VP1, wherein said capsid protein VP1 is from one or more than one first AAV serotype and capsid protein VP1.5, wherein said capsid protein VP1.5 is from one or more than one second AAV serotype and wherein at least one of said first AAV serotype is different from at least one of said second AAV serotype, in any combination.

In some embodiments, the AAV particle of this invention can comprise a capsid that comprises capsid protein VP3, wherein said capsid protein VP3 is from one or more than one third AAV serotype, wherein at least one of said one or more than one third AAV serotype is different from said first AAV serotype and/or said second AAV serotype, in any combination. In some embodiments, the AAV capsid protein described herein can comprise capsid protein VP2.

In some embodiments of the capsid of the AAV particle described herein, said one or more than one first AAV serotype, said one or more than one second AAV serotype, said one or more than one third AAV serotype and said one or more than one fourth AAV serotype are selected from the group consisting of the AAV serotypes listed in Table 1, in any combination.

In some embodiments of the AAV particle of this invention, the AAV capsid described herein lacks capsid protein VP2.

In some embodiments of the AAV particle of this invention, the capsid can comprise a chimeric capsid VP1 protein, a chimeric capsid VP2 protein, a chimeric capsid VP3 protein and/or a chimeric capsid VP1.5 protein.

In some embodiments of the AAV particle of this invention, the AAV capsid can be AAV AAV2/8/9, H-AAV82, H-AAV92, H-AAV82G9, AAV2/8 3:1, AAV2/8 1:1, AAV2/8 1:3, or AAV8/9.

Nonlimiting examples of AAV capsid proteins that can be included in the capsid of the AAV particle of this invention in any combination with other capsid proteins described herein and/or with other capsid proteins now known or later developed, include LK3, LK01-19, AAV-DJ, Olig001, rAAV2-retro, AAV-LiC, AAV0Kera1, AAV-Kera2, AAV-Kera3, AAV 7m8, AAV1,9, AAVr3.45, AAV clone 32, AAV clone 83, AAV-U87R7-C5, AAV ShH13, AAV ShH19, AAV L1-12, AAV HAE-1, AAV HAE-2, AAV variant ShH10, AAV2.5T, AAV LS1-4, AAV Lsm, AAV1289, AAVHSC 1-17, AAV2 Rec 1-4, AAV8BP2, AAV-B1, AAV-PHP.B, AAV9.45, AAV9.61, AAV9.47, AAVM41, AAV2 displayed peptides, AAV2-GMN, AAV9-peptide displayed, AAV8 and AAV9 peptide displayed, AAVpo2.1, AAVpo4, AAVpo5, AAVpo6, AAV rh, AAV Hu, AAV-Go.1, AAV-mo.1, BAAV, AAAV, AAV8 K137R, AAV Anc80L65, AAV2G9, AAV2 265 insertion-AAV2/265D, AAV2.5, AAV3 SASTG, AAV2i8, AAV8G9, AAV2 tyrosine mutants AAV2 Y-F, AAV8 Y-F, AAV9 Y-F, AAV6 Y-F, AAV6.2 and any combination thereof.

As a nonlimiting example, the AAV capsid proteins and virus capsids of the AAV particle of this invention can be chimeric in that they can comprise all or a portion of a capsid subunit from another virus, optionally another parvovirus or AAV, e.g., as described in international patent publication WO 00/28004.

The following publications describe chimeric or variant capsid proteins that can be incorporated into the capsid of the AAV particle of this invention in any combination with wild type capsid proteins and/or other chimeric or variant capsid proteins now known or later identified.

L Lisowski, A P Dane, K Chu, Y Zhang, S C Cunninghamm, E M Wilson, et al. Selection and evaluation of clinically relevant AAV variants in a xenograft liver model *Nature*, 506 (2014), pp. 382-386 (LK03 and others LK01-19)

Grimm D, Lee J S, Wang L, Desai T, Akache B, Storm T A, Kay M A. In vitro and in vivo gene therapy vector evolution via multispecies interbreeding and retargeting of adeno-associated viruses. *J Virol.* 2008 June; 82(12): 5887-911. (AAV-DJ)

Powell S K, Khan N, Parker C L, Samulski R J, Matsushima G, Gray S J, McCown T J. Characterization of a novel adeno-associated viral vector with preferential oligodendrocyte tropism. *Gene Ther.* 2016 November; 23(11):807-814. (Olig001)

Tervo D G, Hwang B Y, Viswanathan S, Gaj T, Lavzin M, Ritola K D, Lindo S, Michael S, Kuleshova E, Ojala D, Huang C C, Gerfen C R, Schiller J, Dudman J T, Hantman A W, Looger L L, Schaffer D V, Karpova A Y. A Designer AAV Variant Permits Efficient Retrograde Access to Projection Neurons. *Neuron.* 2016 Oct. 19; 92(2):372-382. (rAAV2-retro)

Marsic D, Govindasamy L, Currlin S, Markusic D M, Tseng Y S, Herzog R W, Agbandje-McKenna M, Zolotukhin S. Vector design Tour de Force: integrating combinatorial and rational approaches to derive novel adeno-associated virus variants. Mol Ther. 2014 November; 22(11):1900-9. (AAV-LiC)

Sallach J, Di Pasquale G, Larcher F, Niehoff N, Rubsam M, Huber A, Chiorini J, Almarza D, Eming S A, Ulus H, Nishimura S, Hacker U T, Hallek M, Niessen C M, Buning H. Tropism-modified AAV vectors overcome barriers to successful cutaneous therapy. Mol Ther. 2014 May; 22(5):929-39. (AAV-Kera1, AAV-Kera2, and AAV-Kera3)

Dalkara D, Byrne L C, Klimczak R R, Visel M, Yin L, Merigan W H, Flannery J G, Schaffer D V. In vivo-directed evolution of a new adeno-associated virus for therapeutic outer retinal gene delivery from the vitreous. Sci Transl Med. 2013 Jun. 12; 5(189):189ra76. (AAV 7m8)

Asuri P, Bartel M A, Vazin T, Jang J H, Wong T B, Schaffer D V. Directed evolution of adeno-associated virus for enhanced gene delivery and gene targeting in human pluripotent stem cells. Mol Ther. 2012 February; 20(2): 329-38. (AAV1.9)

Jang J H, Koerber J T, Kim J S, Asuri P, Vazin T, Bartel M, Keung A, Kwon I, Park K I, Schaffer D V. An evolved adeno-associated viral variant enhances gene delivery and gene targeting in neural stem cells. Mol Ther. 2011 April; 19(4):667-75. doi: 10.1038/mt.2010.287. (AAV r3.45)

Gray S J, Blake B L, Criswell H E, Nicolson S C, Samulski R J, McCown T J, Li W. Directed evolution of a novel adeno-associated virus (AAV) vector that crosses the seizure-compromised blood-brain barrier (BBB). Mol Ther. 2010 March; 18(3):570-8 (AAV clone 32 and 83)

Maguire C A, Gianni D, Meijer D H, Shaket L A, Wakimoto H, Rabkin S D, Gao G, Sena-Esteves M. Directed evolution of adeno-associated virus for glioma cell transduction. J Neurooncol. 2010 February; 96(3):337-47. (AAV-U87R7-C5)

Koerber J T, Klimczak R, Jang J H, Dalkara D, Flannery J G, Schaffer D V. Molecular evolution of adeno-associated virus for enhanced glial gene delivery. *Mol Ther.* 2009 December; 17(12):2088-95. (AAV ShH13, AAV ShH19, AAV L1-12)

Li W, Zhang L, Johnson J S, Zhijian W, Grieger J C, Ping-Jie X, Drouin L M, Agbandje-McKenna M, Pickles R J, Samulski R J. Generation of novel AAV variants by directed evolution for improved CFTR delivery to human ciliated airway epithelium. Mol Ther. 2009 December; 17(12):2067-77. (AAV HAE-1, AAV HAE-2)

Klimczak R R, Koerber J T, Dalkara D, Flannery J G, Schaffer D V. A novel adeno-associated viral variant for efficient and selective intravitreal transduction of rat Müller cells. PLoS One. 2009 Oct. 14; 4(10):e7467. (AAV variant ShH10)

Excoffon K J, Koerber J T, Dickey D D, Murtha M, Keshavjee S, Kaspar B K, Zabner J, Schaffer D V. Directed evolution of adeno-associated virus to an infectious respiratory virus. Proc Natl Acad Sci USA. 2009 Mar. 10; 106(10):3865-70. (AAV2.5T)

Sellner L, Stiefelhagen M, Kleinschmidt J A, Laufs S, Wenz F, Fruehauf S, Zeller W J, Veldwijk M R. Generation of efficient human blood progenitor-targeted recombinant adeno-associated viral vectors (AAV) by applying an AAV random peptide library on primary human hematopoietic progenitor cells. Exp Hematol. 2008 August; 36(8):957-64. (AAV LS1-4, AAV Lsm)

Li W, Asokan A, Wu Z, Van Dyke T, DiPrimio N, Johnson J S, Govindaswamy L, Agbandje-McKenna M, Leichtle S, Redmond D E Jr, McCown T J, Petermann K B, Sharpless N E, Samulski R J. Engineering and selection of shuffled AAV genomes: a new strategy for producing targeted biological nanoparticles. Mol Ther. 2008 July; 16(7):1252-60. (AAV1289)

Charbel Issa P, De Silva S R, Lipinski D M, Singh M S, Mouravlev A, You Q. Assessment of tropism and effectiveness of new primate-derived hybrid recombinant AAV serotypes in the mouse and primate retina. PLoS ONE. 2013; 8:e60361. (AAVHSC 1-17)

Huang W, McMurphy T, Liu X, Wang C, Cao L. Genetic Manipulation of Brown Fat Via Oral Administration of an Engineered Recombinant Adeno-associated Viral Serotype Vector. Mol Ther. 2016 June; 24(6):1062-9. (AAV2 Rec 1-4)

CroninT, Vandenberghe L H, Hantz P, et al. Efficient transduction and optogenetic stimulation of retinal bipolar cells by a synthetic adeno-associated virus capsid and promoter. EMBO Mol Med 2014; 6:1175-1190 (AAV8BP2)

Choudhury S R, Fitzpatrick Z, Harris A F, Maitland S A, Ferreira J S, Zhang Y, Ma S, Sharma R B, Gray-Edwards H L, Johnson J A, Johnson A K, Alonso L C, Punzo C, Wagner K R, Maguire C A, Kotin R M, Martin D R, Sena-Esteves M. In Vivo Selection Yields AAV-B1 Capsid for Central Nervous System and Muscle Gene Therapy. Mol Ther. 2016 August; 24(7):1247-57. (AAV-B1)

Deverman B E, Pravdo P L, Simpson B P, Kumar S R, Chan K Y, Banerjee A, Wu W L, Yang B, Huber N, Pasca S P, Gradinaru V. Cre-dependent selection yields AAV variants for widespread gene transfer to the adult brain. Nat Biotechnol. 2016 February; 34(2):204-9. doi: 10.1038/nbt.3440. (AAV-PHP.B)

Pulicherla N, Shen S, Yadav S, Debbink K, Govindasamy L, Agbandje-McKenna M, Asokan A. Engineering liver-detargeted AAV9 vectors for cardiac and musculoskeletal gene transfer. Mol Ther. 2011 June; 19(6):1070-8. (AAV9 derived mutants-AAV9.45, AAV9.61, AAV9.47)

Yang L, Jiang J, Drouin L M, Agbandje-McKenna M, Chen C, Qiao C, Pu D, Hu X, Wang D Z, Li J, Xiao X. A myocardium tropic adeno-associated virus (AAV) evolved by DNA shuffling and in vivo selection. Proc Natl Acad Sci USA. 2009 Mar. 10; 106(10):3946-51. (AAVM41)

Körbelin J, Sieber T, Michelfelder S, Lunding L, Spies E, Hunger A, Alawi M, Rapti K, Indenbirken D, Müller O J, Pasqualini R, Arap W, Kleinschmidt J A, Trepel M. Pulmonary Targeting of Adeno-associated Viral Vectors by Next-generation Sequencing-guided Screening of Random Capsid Displayed Peptide Libraries. *Mol Ther.* 2016 June; 24(6):1050-61. (AAV2 displayed peptides)

Geoghegan J C, Keiser N W, Okulist A, Martins I, Wilson M S, Davidson B L. Chondroitin Sulfate is the Primary Receptor for a Peptide-Modified AAV That Targets Brain Vascular Endothelium In Vivo. Mol Ther Nucleic Acids. 2014 Oct. 14; 3:e202. (AAV2-GMN)

Varadi K, Michelfelder S, Korff T, Hecker M, Trepel M, Katus H A, Kleinschmidt J A, Müller OJ. Novel random peptide libraries displayed on AAV serotype 9 for selection of endothelial cell-directed gene transfer vectors. Gene Ther. 2012 August; 19(8):800-9. (AAV9-peptide displayed)

Michelfelder S, Varadi K, Raupp C, Hunger A, Korbelin J, Pahrmann C, Schrepfer S, Müller O J, Kleinschmidt J A, Trepel M. Peptide ligands incorporated into the threefold spike capsid domain to re-direct gene transduction of AAV8 and AAV9 in vivo. *PLoS One.* 2011; 6(8):e23101. (AAV8 and AAV9 peptide displayed)

Yu C Y, Yuan Z, Cao Z, Wang B, Qiao C, Li J, Xiao X. A muscle-targeting peptide displayed on AAV2 improves muscle tropism on systemic delivery. Gene Ther. 2009 August; 16(8):953-62.

Michelfelder S, Lee M K, deLima-Hahn E, Wilmes T, Kaul F, Müller O, Kleinschmidt J A, Trepel M. Vectors selected from adeno-associated viral display peptide libraries for leukemia cell-targeted cytotoxic gene therapy. Exp Hematol. 2007 December; 35(12):1766-76.

Müller OJ, Kaul F, Weitzman M D, Pasqualini R, Arap W, Kleinschmidt J A, Trepel M. Random peptide libraries displayed on adeno-associated virus to select for targeted gene therapy vectors. Nat Biotechnol. 2003 September; 21(9):1040-6.

Grifman M, Trepel M, Speece P, Gilbert L B, Arap W, Pasqualini R, Weitzman M D. Incorporation of tumor-targeting peptides into recombinant adeno-associated virus capsids. Mol Ther. 2001 June; 3(6):964-75.

Anne Girod, Martin Ried, Christiane Wobus, Harald Lahm, Kristin Leike, Jurgen Kleinschmidt, Gilbert Deleage & Michael Hallek. Genetic capsid modifications allow efficient re-targeting of adeno-associated virus type 2. Nature Medicine, 1052-1056 (1999)

Bello A, Chand A, Aviles J, Soule G, Auricchio A, Kobinger G P. Novel adeno-associated viruses derived from pig tissues transduce most major organs in mice. *Sci Rep.* 2014 Oct. 22; 4:6644. (AAVpo2.1, -po4, -po5, and -po6).

Gao G, Vandenberghe L H, Alvira M R, Lu Y, Calcedo R, Zhou X, Wilson J M. Clades of Adeno-associated viruses are widely disseminated in human tissues. *J Virol.* 2004 June; 78(12):6381-8. (AAV rh and AAV Hu)

Arbetman A E, Lochrie M, Zhou S, Wellman J, Scallan C, Doroudchi M M, et al. Novel caprine adeno-associated virus (AAV) capsid (AAV-Go.1) is closely related to the primate AAV-5 and has unique tropism and neutralization properties. *J Virol.* 2005; 79:15238-15245. (AAV-Go.1)

Lochrie M A, Tatsuno G P, Arbetman A E, Jones K, Pater C, Smith P H, et al. Adeno-associated virus (AAV) capsid genes isolated from rat and mouse liver genomic DNA define two new AAV species distantly related to AAV-5. Virology 2006; 353:68-82. (AAV-mo.1)

Schmidt M, Katano H, Bossis I, Chiorini J A. Cloning and characterization of a bovine adeno-associated virus. J Virol. 2004; 78:6509-6516. (BAAV)

Bossis I, Chiorini J A. Cloning of an avian adeno-associated virus (AAAV) and generation of recombinant AAAV particles. *J Virol.* 2003; 77:6799-6810. (AAAV)

Chen C L, Jensen R L, Schnepp B C, Connell M J, Shell R, Sferra T J, Bartlett J S, Clark K R, Johnson P R. Molecular characterization of adeno-associated viruses infecting children. J Virol. 2005 December; 79(23):14781-92. (AAV variants)

Sen D, Gadkari R A, Sudha G, Gabriel N, Kumar Y S, Selot R, Samuel R, Rajalingam S, Ramya V, Nair S C, Srinivasan N, Srivastava A, Jayandharan G R. Targeted modifications in adeno-associated virus serotype 8 capsid improves its hepatic gene transfer efficiency in vivo. Hum Gene Ther Methods. 2013 April; 24(2):104-16. (AAV8 K137R)

Li B, Ma W, Ling C, Van Vliet K, Huang L Y, Agbandje-McKenna M, Srivastava A, Aslanidi G V. Site-Directed Mutagenesis of Surface-Exposed Lysine Residues Leads to Improved Transduction by AAV2, But Not AAV8, Vectors in Murine Hepatocytes In Vivo. Hum Gene Ther Methods. 2015 December; 26(6):211-20.

Gabriel N, Hareendran S, Sen D, Gadkari R A, Sudha G, Selot R, Hussain M, Dhaksnamoorthy R, Samuel R, Srinivasan N, et al. Bioengineering of AAV2 capsid at specific serine, threonine, or lysine residues improves its transduction efficiency in vitro and in vivo. Hum Gene Ther Methods. 2013 April; 24(2):80-93.

Zinn E, Pacouret S, Khaychuk V, Turunen H T, Carvalho L S, Andres-Mateos E, Shah S, Shelke R, Maurer A C, Plovie E, Xiao R, Vandenberghe L H. In Silico Reconstruction of the Viral Evolutionary Lineage Yields a Potent Gene Therapy Vector. Cell Rep. 2015 Aug. 11; 12(6):1056-68. (AAV Anc80L65)

Shen S, Horowitz E D, Troupes A N, Brown S M, Pulicherla N, Samulski R J, Agbandje-McKenna M, Asokan A. Engraftment of a galactose receptor footprint onto adeno-associated viral capsids improves transduction efficiency. J Biol Chem. 2013 Oct. 4; 288(40):28814-23. (AAV2G9)

Li C, Diprimio N, Bowles D E, Hirsch M L, Monahan P E, Asokan A, Rabinowitz J, Agbandje-McKenna M, Samulski R J. Single amino acid modification of adeno-associated virus capsid changes transduction and humoral immune profiles. J Virol. 2012 August; 86(15):7752-9. (AAV2 265 insertion-AAV2/265D)

Bowles D E, McPhee S W, Li C, Gray S J, Samulski J J, Camp A S, Li J, Wang B, Monahan P E, Rabinowitz J E, et al. Phase 1 gene therapy for Duchenne muscular dystrophy using a translational optimized AAV vector. Mol Ther. 2012 February; 20(2):443-55 (AAV2.5)

Messina E L, Nienaber J, Daneshmand M, Villamizar N, Samulski J, Milano C, Bowles D E. Adeno-associated viral vectors based on serotype 3b use components of the fibroblast growth factor receptor signaling complex for efficient transduction. Hum Gene Ther. 2012 October; 23(10):1031-42. (AAV3 SASTG)

Asokan A, Conway J C, Phillips J L, Li C, Hegge J, Sinnott R, Yadav S, DiPrimio N, Nam H J, Agbandje-McKenna M, McPhee S, Wolff J, Samulski R J. Reengineering a receptor footprint of adeno-associated virus enables selective and systemic gene transfer to muscle. Nat Biotechnol. 2010 January; 28(1):79-82. (AAV2i8)

Vance M, Llanga T, Bennett W, Woodard K, Murlidharan G, Chungfat N, Asokan A, Gilger B, Kurtzberg J, Samulski R J, Hirsch M L. AAV Gene Therapy for MPSI-associated Corneal Blindness. Sci Rep. 2016 Feb. 22; 6:22131. (AAV8G9)

Zhong L, Li B, Mah C S, Govindasamy L, Agbandje-McKenna M, Cooper M, Herzog R W, Zolotukhin I, Warrington K H Jr, Weigel-Van Aken K A, Hobbs J A, Zolotukhin S, Muzyczka N, Srivastava A. Next generation of adeno-associated virus 2 vectors: point mutations in tyrosines lead to high-efficiency transduction at lower doses. Proc Natl Acad Sci USA. 2008 Jun. 3; 105(22): 7827-32. (AAV2 tyrosine mutants AAV2 Y-F)

Petrs-Silva H, Dinculescu A, Li Q, Min S H, Chiodo V, Pang J J, Zhong L, Zolotukhin S, Srivastava A, Lewin A S, Hauswirth W W. High-efficiency transduction of the mouse retina by tyrosine-mutant AAV serotype vectors. Mol Ther. 2009 March; 17(3):463-71. (AAV8 Y-F and AAV9 Y-F)

Qiao C, Zhang W, Yuan Z, Shin J H, Li J, Jayandharan G R, Zhong L, Srivastava A, Xiao X, Duan D. Adeno-associated virus serotype 6 capsid tyrosine-to-phenylalanine mutations improve gene transfer to skeletal muscle. Hum Gene Ther. 2010 October; 21(10):1343-8 (AAV6 Y-F)

Carlon M, Toelen J, Van der Perren A, Vandenberghe L H, Reumers V, Sbragia L, Gijsbers R, Baekelandt V, Himmelreich U, Wilson J M, Deprest J, Debyser Z. Efficient gene transfer into the mouse lung by fetal intratracheal injection of rAAV2/6.2. Mol Ther. 2010 December; 18(12):2130-8. (AAV6.2)

PCT Publication No. WO2013158879A1 (lysine mutants)

It would be understood that any combination of VP1 and VP3, and when present, VP1.5 and VP2 from any combination of AAV serotypes can be employed to produce AAV particles comprising the AAV capsids described herein. For example, a VP1 protein from any combination of AAV serotypes can be combined with a VP3 protein from any combination of AAV serotypes and the respective VP1 proteins can be present in any ratio of different serotypes and the respective VP3 proteins can be present in any ratio of different serotypes and the VP1 and VP3 proteins can be present in any ratio of different serotypes. It would be further understood that, when present, a VP1.5 and/or VP2 protein from any combination of AAV serotypes can be combined with VP1 and VP3 protein from any combination of AAV serotypes and the respective VP1.5 proteins can be present in any ratio of different serotypes and the respective VP2 proteins can be present in any ratio of different serotypes and the respective VP1 proteins can be present in any ratio of different serotypes and the respective VP3 proteins can be present in any ratio of different serotypes and the VP1.5 and/or VP2 proteins can be present in combination with VP1 and VP3 proteins in any ratio of different serotypes.

For example, the respective viral proteins and/or the respective AAV serotypes can be combined in any ratio, which can be a ratio of A:B, A:B:C, A:B:C:D, A:B:C:D:E, A:B:C:D:E:F, A:B:C:D:E:F:G, A:B:C:D:E:F:G:H, A:B:C:D:E:F:G:H:I or A:B:C:D:E:F:G:H:I:J, wherein A can be 1, 2, 3, 4, 5, 6, 7, 8, 9, 10, 11, 12, 13, 14, 15, 20, 25, 30, 35, 40, 50, 60, 70, 80, 90, 100, etc.; B can be 1, 2, 3, 4, 5, 6, 7, 8, 9, 10, 11, 12, 13, 14, 15, 20, 25, 30, 35, 40, 50, 60, 70, 80, 90, 100, etc.; C can be 1, 2, 3, 4, 5, 6, 7, 8, 9, 10, 11, 12, 13, 14, 15, 20, 25, 30, 35, 40, 50, 60, 70, 80, 90, 100, etc.; D can be 1, 2, 3, 4, 5, 6, 7, 8, 9, 10, 11, 12, 13, 14, 15, 20, 25, 30, 35, 40, 50, 60, 70, 80, 90, 100, etc.; E can be 1, 2, 3, 4, 5, 6, 7, 8, 9, 10, 11, 12, 13, 14, 15, 20, 25, 30, 35, 40, 50, 60, 70, 80, 90, 100, etc.; F can be 1, 2, 3, 4, 5, 6, 7, 8, 9, 10, 11, 12, 13, 14, 15, 20, 25, 30, 35, 40, 50, 60, 70, 80, 90, 100, etc.; G can be 1, 2, 3, 4, 5, 6, 7, 8, 9, 10, 11, 12, 13, 14, 15, 20, 25, 30, 35, 40, 50, 60, 70, 80, 90, 100, etc.; H can be 1, 2, 3, 4, 5, 6, 7, 8, 9, 10, 11, 12, 13, 14, 15, 20, 25, 30, 35, 40, 50, 60, 70, 80, 90, 100, etc.; I can be 1, 2, 3, 4, 5, 6, 7, 8, 9, 10, 11, 12, 13, 14, 15, 20, 25, 30, 35, 40, 50, 60, 70, 80, 90, 100, etc.; and J can be 1, 2, 3, 4, 5, 6, 7, 8, 9, 10, 11, 12, 13, 14, 15, 20, 25, 30, 35, 40, 50, 60, 70, 80, 90, 100, etc.;

It would also be understood that any of the VP1, VP1.5, VP2 and/or VP3 capsid proteins can be present in a capsid of an AAV particle of this invention as a chimeric capsid protein, in any combination and ratio relative to the same protein type and/or relative to the different capsid proteins.

In some embodiments, the AAV particle of this invention can be a virus vector, which in certain embodiments can have systemic or selective tropism for cells of the brain and/or central nervous system. In some embodiments, the AAV particle of this invention can have reduced tropism for liver.

The present invention further provides a composition, which can be a pharmaceutical formulation comprising the virus vector or AAV particle of this invention and a pharmaceutically acceptable carrier.

In some nonlimiting examples, the present invention provides AAV particles comprising capsid proteins (VP1, VP1.5, VP2 and/or VP3) comprising a modification in the amino acid sequence in the three-fold axis loop 4 and virus capsids and virus vectors comprising the modified AAV capsid protein. The inventors have discovered that modifications in this loop can confer one or more desirable properties to virus vectors comprising the modified AAV capsid protein including without limitation (i) reduced transduction of liver, (ii) enhanced movement across endothelial cells, (iii) systemic transduction; (iv) enhanced transduction of muscle tissue (e.g., skeletal muscle, cardiac muscle and/or diaphragm muscle), and/or (v) increased transduction of brain tissues (e.g., neurons). Thus, the present invention addresses some of the limitations associated with conventional AAV vectors. For example, vectors based on AAV8 and rAAV9 vectors are attractive for systemic nucleic acid delivery because they readily cross the endothelial cell barrier; however, systemic administration of rAAV8 or rAAV9 results in most of the vector being delivered to the liver, thereby reducing transduction of other important target tissues such as skeletal muscle.

In embodiments of the invention, transduction by the AAV particles of this invention of cells of the brain and/or central nervous system is at least about five-fold, ten-fold, 50-fold, 100-fold, 1000-fold or higher than transduction levels by AAV particles that lack the surface bound peptides described herein.

In particular embodiments, the modified AAV capsid protein of the invention comprises one or more modifications in the amino acid sequence of the three-fold axis loop 4 (e.g., amino acid positions 575 to 600 [inclusive] of the native AAV2 VP1 capsid protein or the corresponding region of a capsid protein from another AAV). As used herein, a "modification" in an amino acid sequence includes substitutions, insertions and/or deletions, each of which can involve one, two, three, four, five, six, seven, eight, nine, ten or more amino acids. In particular embodiments, the modification is a substitution. For example, in particular embodiments, 1, 2, 3, 4, 5, 6, 7, 8, 9, 10, 11, 12, 13, 14, 15, 16, 17, 18, 19, 20, 21, 22, 23, 24, 25 or more amino acids from the three-fold axis loop 4 from one AAV can be substituted into amino acid positions 575-600 of the native AAV2 capsid protein or the corresponding positions of the capsid protein from another AAV. However, the modified virus capsids of the invention are not limited to AAV capsids in which amino acids from one AAV capsid are substituted into another AAV capsid, and the substituted and/or inserted amino acids can be from any source, and can further be naturally occurring or partially or completely synthetic.

As described herein, the nucleic acid and amino acid sequences of the capsid proteins from a number of AAV are known in the art. Thus, the amino acids "corresponding" to amino acid positions 575 to 600 (inclusive) or amino acid positions 585 to 590 (inclusive) of the native AAV2 capsid protein can be readily determined for any other AAV (e.g., by using sequence alignments).

In some embodiments, the invention contemplates that the modified capsid proteins of the invention can be produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV8, AAV9, AAV10, AAV11, or AAV12 capsid protein or any of the AAV shown in Table 1) but is not so limited. Those skilled in the art will understand that a variety of manipulations to the AAV capsid proteins are known in the art and the invention is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11 and/or AAV12 or any other AAV now known or later discovered). Such AAV capsid proteins are also within the scope of the present invention.

For example, in some embodiments, the AAV capsid protein to be modified can comprise an amino acid insertion directly following amino acid 264 of the native AAV2 capsid protein sequence (see, e.g., PCT Publication WO 2006/066066) and/or can be an AAV with an altered HI loop as described in PCT Publication WO 2009/108274 and/or can be an AAV that is modified to contain a poly-His sequence to facilitate purification. As another illustrative example, the AAV capsid protein can have a peptide targeting sequence incorporated therein as an insertion or substitution. Further, the AAV capsid protein can comprise a large domain from another AAV that has been substituted and/or inserted into the capsid protein.

Thus, in particular embodiments, the AAV capsid protein to be modified can be derived from a naturally occurring AAV but further comprise one or more foreign sequences (e.g., that are exogenous to the native virus) that are inserted and/or substituted into the capsid protein and/or has been altered by deletion of one or more amino acids.

Accordingly, when referring herein to a specific AAV capsid protein (e.g., an AAV2, AAV3, AAV4, AAV5, AAV6, AAV7, AAV8, AAV9, AAV10, AAV11 or AAV12 capsid protein or a capsid protein from any of the AAV shown in Table 1, etc.), it is intended to encompass the native capsid protein as well as capsid proteins that have alterations other than the modifications of the invention. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acids inserted therein (other than the insertions of the present invention) as compared with the native AAV capsid protein sequence. In embodiments of the invention, the capsid protein comprises 1, 2, 3, 4, 5, 6, 7, 8, 9, 10, 11, 12, 13, 14, 15, 16, 17, 18, 19 or 20, less than 20, less than 30, less than 40 less than 50, less than 60, or less than 70 amino acid substitutions (other than the amino acid substitutions according to the present invention) as compared with the native AAV capsid protein sequence. In embodiments of the invention, the capsid protein comprises a deletion of 1, 2, 3, 4, 5, 6, 7, 8, 9, 10, 11, 12, 13, 14, 15, 16, 17, 18, 19 or 20, more than 20, more than 30, more than 40, more than 50, more than 60, or more than 70 amino acids (other than the amino acid deletions of the invention) as compared with the native AAV capsid protein sequence.

Thus, for example, the term "AAV2 capsid protein" includes AAV capsid proteins having the native AAV2 capsid protein sequence (see GenBank Accession No. AAC03780) as well as those comprising substitutions, insertions and/or deletions (as described in the preceding paragraph) in the native AAV2 capsid protein sequence.

In particular embodiments, the AAV capsid protein has the native AAV capsid protein sequence or has an amino acid sequence that is at least about 70%, 75%, 80%, 85%, 90%, 95%, 97%, 98% or 99% similar or identical to a native AAV capsid protein sequence. For example, in particular embodiments, an "AAV2" capsid protein encompasses the native AAV2 capsid protein sequence as well as sequences that are at least about 75%, 80%<85%, 90%, 95%, 97%, 98% or 99% similar or identical to the native AAV2 capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, *Adv. Appl. Math.* 2, 482 (1981), by the sequence identity alignment algorithm of Needleman & Wunsch, *J. Mol. Biol.* 48,443 (1970), by the search for similarity method of Pearson & Lipman, *Proc. Natl. Acad. Sci.* USA 85,2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., *Nucl. Acid Res.* 12, 387-395 (1984), or by inspection.

Another suitable algorithm is the BLAST algorithm, described in Altschul et al., *J. Mol. Biol.* 215, 403-410, (1990) and Karlin et al., *Proc. Natl. Acad. Sci. USA* 90, 5873-5787 (1993). A particularly useful BLAST program is the WU-BLAST-2 program which was obtained from Altschul et al., *Methods in Enzymology,* 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al., (1997) *Nucleic Acids Res.* 25, 3389-3402.

In some embodiments of the invention, a modification can be made in the region of amino acid positions 585 to 590 (inclusive) of the native AAV2 capsid protein (using VP1 numbering) or the corresponding positions of other AAV (native AAV2 VP1 capsid protein: GenBank Accession No. AAC03780 or YP680426), i.e., at the amino acids corresponding to amino acid positions 585 to 590 (VP1 numbering) of the native AAV2 capsid protein. The amino acid positions in other AAV serotypes or modified AAV capsids that "correspond to" positions 585 to 590 of the native AAV2 capsid protein will be apparent to those skilled in the art and can be readily determined using sequence alignment techniques (see, e.g., FIG. 7 of WO 2006/066066) and/or crystal structure analysis (Padron et al., (2005) *J. Virol.* 79:5047-58).

To illustrate, the modification can be introduced into an AAV capsid protein that already contains insertions and/or deletions such that the position of all downstream sequences is shifted. In this situation, the amino acid positions corresponding to amino acid positions 585 to 590 in the AAV2 capsid protein would still be readily identifiable to those skilled in the art. To illustrate, the capsid protein can be an AAV2 capsid protein that contains an insertion following amino acid position 264 (see, e.g., WO 2006/066066). The amino acids found at positions 585 through 590 (e.g., RGNRQA (SEQ ID NO:1)) in the native AAV2 capsid protein) would now be at positions 586 through 591 but would still be identifiable to those skilled in the art.

In some embodiments, the AAV particle of this invention can comprise modified virus capsids that can be used as "capsid vehicles," as has been described, for example, in U.S. Pat. No. 5,863,541. Molecules that can be packaged by the modified virus capsid and transferred into a cell include heterologous DNA, RNA, polypeptides, small organic molecules, metals, or combinations of the same.

Heterologous molecules (e.g., nucleic acid, proteins, peptides, etc.) are defined as those that are not naturally found in an AAV infection, e.g., those not encoded by a wild-type AAV genome. Further, therapeutically useful molecules can be associated with the outside of the virus capsid for transfer of the molecules into host target cells. Such associated molecules can include DNA, RNA, small organic molecules, metals, carbohydrates, lipids and/or polypeptides. In one embodiment of the invention, the therapeutically useful molecule is covalently linked (i.e., conjugated or chemically coupled) to the capsid proteins. Methods of covalently linking molecules are known by those skilled in the art.

The modified virus capsids described herein also find use in raising antibodies against the novel capsid structures. As a further alternative, an exogenous amino acid sequence may be inserted into the modified virus capsid for antigen presentation to a cell, e.g., for administration to a subject to produce an immune response to the exogenous amino acid sequence.

In other embodiments, virus capsids can be administered to block certain cellular sites prior to and/or concurrently with (e.g., within minutes or hours of each other) administration of a virus vector of this invention delivering a nucleic acid encoding a polypeptide or functional RNA of interest. For example, the capsids can be delivered to block cellular receptors on liver cells and a delivery virus vector can be administered subsequently and/or concurrently, which may reduce transduction of liver cells, and enhance transduction of other targets (e.g., skeletal, cardiac and/or diaphragm muscle).

According to representative embodiments, modified virus capsids can be administered to a subject prior to and/or concurrently with a virus vector according to the present invention. Further, the invention provides compositions and pharmaceutical formulations comprising the inventive modified virus capsids and a virus vector of this invention.

In some embodiments of the AAV particles of this invention, modifications to the AAV capsid protein can be "selective" modifications. This approach is in contrast to previous work with whole subunit or large domain swaps between AAV serotypes (see, e.g., international patent publication WO 00/28004 and Hauck et al., (2003) *J. Virology* 77:2768-2774). In particular embodiments, a "selective" modification results in the insertion and/or substitution and/or deletion of less than about 20, 18, 15, 12, 10, 9, 8, 7, 6, 5, 4, 3 or 2 contiguous amino acids.

The modified capsid proteins and capsids can further comprise any other modification, now known or later identified.

The virus capsid can be a targeted virus capsid comprising a targeting sequence (e.g., substituted or inserted in the viral capsid) that directs the virus capsid to interact with cell-surface molecules present on a desired target tissue(s) (see, e.g., international patent publication WO 00/28004 and Hauck et al., (2003) *J Virology* 77:2768-2774); Shi et al., *Human Gene Therapy* 17:353-361 (2006) [describing insertion of the integrin receptor binding motif RGD at positions 520 and/or 584 of the AAV capsid subunit]; and U.S. Pat. No. 7,314,912 [describing insertion of the P1 peptide containing an RGD motif following amino acid positions 447, 534, 573 and 587 of the AAV2 capsid subunit]). Other positions within the AAV capsid subunit that tolerate insertions are known in the art (e.g., positions 449 and 588).

For example, some of the virus capsids of the AAV particles of the invention may have relatively inefficient tropism toward most target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another possibility one or more non-naturally occurring amino acids, as described by Wang et al. (*Annu Rev Biophys Biomol Struct.* 35:225-49 (2006)), can be incorporated into the AAV capsid subunit at an orthogonal site as a means of redirecting a low-transduction vector to a desired target tissue(s). These unnatural amino acids can advantageously be used to chemically link molecules of interest to the AAV capsid protein including without limitation: glycans (mannose—dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art (see, e.g., Greg T. Hermanson, *Bioconjugate Techniques,* 1$^{st}$ edition, Academic Press, 1996).

In representative embodiments, the targeting sequence may be a virus capsid sequence (e.g., an autonomous parvovirus capsid sequence, AAV capsid sequence, or any other viral capsid sequence) that directs infection to a particular cell type(s).

As another nonlimiting example, a heparin binding domain (e.g., the respiratory syncytial virus heparin binding domain) may be inserted or substituted into a capsid subunit that does not typically bind HS receptors (e.g., AAV 4, AAV5) to confer heparin binding to the resulting mutant.

B19 infects primary erythroid progenitor cells using globoside as its receptor. The structure of B19 has been determined to 8 Å resolution The region of the B19 capsid that binds to globoside has been mapped between amino acids 399-406, a looped out region between β-barrel structures E and F. Accordingly, the globoside receptor binding domain of the B19 capsid may be substituted into the AAV capsid protein to target a virus capsid or virus vector comprising the same to erythroid cells.

In representative embodiments, the exogenous targeting sequence may be any amino acid sequence encoding a peptide that alters the tropism of a virus capsid or virus vector comprising the modified AAV capsid protein. In particular embodiments, the targeting peptide or protein may be naturally occurring or, alternately, completely or partially synthetic. Exemplary targeting sequences include ligands and other peptides that bind to cell surface receptors and glycoproteins, such as RGD peptide sequences, bradykinin, hormones, peptide growth factors (e.g., epidermal growth factor, nerve growth factor, fibroblast growth factor, platelet-derived growth factor, insulin-like growth factors I and II, etc.), cytokines, melanocyte stimulating hormone (e.g., α, β or γ), neuropeptides and endorphins, and the like, and fragments thereof that retain the ability to target cells to their cognate receptors. Other illustrative peptides and proteins include substance P, keratinocyte growth factor, neuropeptide Y, gastrin releasing peptide, interleukin 2, hen egg white lysozyme, erythropoietin, gonadoliberin, corticostatin, β-endorphin, leu-enkephalin, rimorphin, α-neo-enkephalin, angiotensin, pneumadin, vasoactive intestinal peptide, neurotensin, motilin, and fragments thereof as described above. As yet a further alternative, the binding domain from a toxin (e.g., tetanus toxin or snake toxins, such as α-bungarotoxin, and the like) can be substituted into the capsid protein as a targeting sequence. In a yet further representative embodiment, the AAV capsid protein can be modified by substitution of a "nonclassical" import/export signal peptide (e.g., fibroblast growth factor-1 and -2, interleukin 1, HIV-1 Tat protein, herpes virus VP22 protein, and the like) as described by Cleves (*Current Biology* 7:R318 (1997)) into the AAV capsid protein. Also encompassed are peptide motifs that direct uptake by specific cells, e.g., a FVFLP (SEQ ID NO:2) peptide motif triggers uptake by liver cells. Phage display techniques, as well as other techniques known in the art, may be used to identify peptides that recognize any cell type of interest.

The targeting sequence may encode any peptide that targets to a cell surface binding site, including receptors (e.g., protein, carbohydrate, glycoprotein or proteoglycan). Examples of cell surface binding sites include, but are not limited to, heparan sulfate, chondroitin sulfate, and other glycosaminoglycans, sialic acid moieties found on mucins, glycoproteins, and gangliosides, MHC I glycoproteins, carbohydrate components found on membrane glycoproteins, including, mannose, N-acetyl-galactosamine, N-acetyl-glucosamine, fucose, galactose, and the like.

In particular embodiments, a heparan sulfate (HS) or heparin binding domain is substituted into the virus capsid (for example, in an AAV that otherwise does not bind to HS or heparin). It is known in the art that HS/heparin binding is mediated by a "basic patch" that is rich in arginines and/or lysines. In exemplary embodiments, a sequence following the motif BXXB (SEQ ID NO:3), where "B" is a basic residue and X is neutral and/or hydrophobic. As one nonlimiting example, BXXB is RGNR (SEQ ID NO:4). In particular embodiments, BXXB is substituted for amino acid positions 262 through 265 in the native AAV2 capsid protein or the corresponding position in the capsid protein of another AAV.

Other nonlimiting examples of suitable targeting sequences include the peptides targeting coronary artery endothelial cells identified by Müller et al., *Nature Biotechnology* 21:1040-1046 (2003) (consensus sequences NSVRDLG/S (SEQ ID NO:5), PRSVTVP (SEQ ID NO:6), NSVSSXS/A (SEQ ID NO:7)); tumor-targeting peptides as described by Grifman et al., *Molecular Therapy* 3:964-975 (2001) (e.g., NGR, NGRAHA (SEQ ID NO:8)); lung or brain targeting sequences as described by Work et al., *Molecular Therapy* 13:683-693 (2006) (QPEHSST (SEQ ID NO:9), VNTANST (SEQ ID NO:10), HGPMQKS (SEQ ID NO:11), PHKPPLA (SEQ ID NO:12), IKNNEMW (SEQ ID NO:13), RNLDTPM (SEQ ID NO:14), VDSHRQS (SEQ ID NO:15), YDSKTKT (SEQ ID NO:16), SQLPHQK (SEQ ID NO:17), STMQQNT (SEQ ID NO:18), TERYMTQ (SEQ ID NO:19), QPEHSST (SEQ ID NO:20), DASLSTS (SEQ ID NO:21), DLPNKKT (SEQ ID NO:22), DLTAARL (SEQ ID NO:23), EPHQFNY (SEQ ID NO:24), EPQSNHT (SEQ ID NO:25), MSSWPSQ (SEQ ID NO:26), NPKHNAT (SEQ ID NO:27), PDGMRTT (SEQ ID NO:28), PNNNKTT (SEQ ID NO:29), QSTTHDS (SEQ ID NO:30), TGSKQKQ (SEQ ID NO:31), SLKHQAL (SEQ ID NO:32) and SPIDGEQ (SEQ ID NO:33)); vascular targeting sequences described by Hajitou et al., TCM 16:80-88 (2006) (WIFPWIQL (SEQ ID NO:34), CDCRGDCFC (SEQ ID NO:35), CNGRC (SEQ ID NO:36), CPRECES (SEQ ID NO:37), GSL, CTTHWGFTLC (SEQ ID NO:38), CGRRAGGSC (SEQ ID NO:39), CKGGRAKDC (SEQ ID NO:40), and CVPEL- GHEC (SEQ ID NO:41)); targeting peptides as described by Koivunen et al., *J. Nucl. Med.* 40:883-888 (1999) (CRRETAWAK (SEQ ID NO:42), KGD, VSWFSHRYSPFAVS (SEQ ID NO:43), GYRDGYAGPILYN (SEQ ID NO:44), XXXY*XXX (SEQ ID NO:45) [where Y* is phospho-Tyr], Y*E/MNW (SEQ ID NO:46), RPLPPLP (SEQ ID NO:47), APPLPPR (SEQ ID NO:48), DVFYPYPYASGS (SEQ ID NO:49), MYWYPY (SEQ ID NO:50), DITWDQLWDLMK (SEQ ID NO:51), CWDDG/LWLC (SEQ ID NO:52), EWCEYLGGYLRCYA (SEQ ID NO:53), YXCXXGPXTWXCXP (SEQ ID NO:54), IEGPTLRQWLAARA (SEQ ID NO:55), LWXXY/W/F/H (SEQ ID NO:56), XFXXYLW (SEQ ID NO:57), SSIISHFRWGLCD (SEQ ID NO:58), MSRPACPPNDKYE (SEQ ID NO:59), CLRSGRGC (SEQ ID NO:60), CHWMFSPWC (SEQ ID NO:61), WXXF (SEQ ID NO:62), CSSRLDAC (SEQ ID NO:63), CLPVASC (SEQ ID NO:64), CGFECVRQCPERC (SEQ ID NO:65), CVALCREACGEGC (SEQ ID NO:66), SWCEPGWCR (SEQ ID NO:67), YSGKWGW (SEQ ID NO:68), GLSGGRS (SEQ ID NO:69), LMLPRAD (SEQ ID NO:70), CSCFRDVCC (SEQ ID NO:71), CRDVVSVIC (SEQ ID NO:72), CNGRC (SEQ ID NO:73), and GSL); and tumor targeting peptides as described by Newton & Deutscher, Phage Peptide Display in Handbook of Experimental Pharmacology, pages 145-163, Springer-Verlag, Berlin (2008) (MARSGL (SEQ ID NO:74), MARAKE (SEQ ID NO:75), MSRTMS (SEQ ID NO:76), KCCYSL (SEQ ID NO:77), WRR, WKR, WVR, WVK, WIK, WTR, WVL, WLL, WRT, WRG, WVS, WVA, MYWGDSHWLQYWYE (SEQ ID NO:78), MQLPLAT (SEQ ID NO:79), EWLS (SEQ ID NO:80), SNEW (SEQ ID NO:81), TNYL (SEQ ID NO:82), WIFPWIQL (SEQ ID NO:83), WDLAWMFRLPVG (SEQ ID NO:84), CTVALPGGYVRVC (SEQ ID NO:85), CVPELGHEC (SEQ ID NO:41), CGRRAGGSC (SEQ ID NO:39), CVAYCIEHHCWTC (SEQ ID NO:86), CVFAHNYDYLVC (SEQ ID NO:87), and CVFTSNYAFC (SEQ ID NO:88), VHSPNKK (SEQ ID NO:89), CDCRGDCFC (SEQ ID NO:35), CRGDWC (SEQ ID NO:90), XRGCDX (SEQ ID NO:91), PXXS/T (SEQ ID NO:92), CTTHWGFTLC (SEQ ID NO:38), SGKGPRQITAL (SEQ ID NO:93), A9A/Q)(N/A)(L/Y)(T/V/M/R)(R/K) (SEQ ID NO:94), VYMSPF (SEQ ID NO:95), MQLPLAT (SEQ ID NO:79), ATWLPPR (SEQ ID NO:96), HTMYYHHYQHHL (SEQ ID NO:97), SEVGCRAGPLQWLCEKYFG (SEQ ID NO:98), CGLLPVGRPDRNVWRWLC (SEQ ID NO:99), CKGQCDRFKGLPWEC (SEQ ID NO:100), SGRSA (SEQ ID NO:101), WGFP (SEQ ID NO:102), LWXXAr [Ar=Y, W, F, H](SEQ ID NO:103), XFXXYLW (SEQ ID NO:57), AEPMPHSLNFSQYLWYT (SEQ ID NO:104), WAY(W/F)SP (SEQ ID NO:105), IELLQAR (SEQ ID NO:106), DITWDQLWDLMK (SEQ ID NO:51), AYTKCSRQWRTCMTTH (SEQ ID NO:107), PQNSKIPGPTFLDPH (SEQ ID NO:108), SMEPALPDWWWKMFK (SEQ ID NO:109), ANTPCGPYTHDCPVKR (SEQ ID NO:110), TACHQHVRMVRP (SEQ ID NO:111), VPWMEPAYQRFL (SEQ ID NO:112), DPRATPGS (SEQ ID NO:113), FRPNRAQDYNTN (SEQ ID NO:114), CTKNSYLMC (SEQ ID NO: 115), C(R/Q)L/RT(G/N)XXG(A/V)GC (SEQ ID NO:116), CPIEDRPMC (SEQ ID NO:117), HEWSYLAPYPWF (SEQ ID NO:118), MCPKHPLGC (SEQ ID NO:119), RMWPSSTVNLSAGRR (SEQ ID NO:120), SAKTAVSQRVWLPSHRGGEP (SEQ ID NO:121), KSREHVNNSACPSKRITAAL (SEQ ID NO:122), EGFR (SEQ ID NO:123), RVS, AGS, AGLGVR (SEQ ID NO:124), GGR, GGL, GSV, GVS, GTRQGHTMRLGVSDG (SEQ ID NO:125), IAGLATPGWSHWLAL (SEQ ID NO:126), SMSIARL (SEQ ID NO:127), HTFEPGV (SEQ ID NO:128), NTSLKRISNKRIRRK (SEQ ID NO:129), LRIKRKRRKRKKTRK (SEQ ID NO:130), GGG, GFS, LWS, EGG, LLV, LSP, LBS, AGG, GRR, GGH and GTV).

As yet a further alternative, the targeting sequence may be a peptide that can be used for chemical coupling (e.g., can comprise arginine and/or lysine residues that can be chemically coupled through their R groups) to another molecule that targets entry into a cell.

As another option, the AAV capsid protein or virus capsid of the AAV particle of this invention can comprise a mutation as described in WO 2006/066066. For example, the capsid protein can comprise a selective amino acid substitution at amino acid position 263, 705, 708 and/or 716 of the native AAV2 capsid protein or a corresponding change(s) in a capsid protein from another AAV. Additionally, or alternatively, in representative embodiments, the capsid protein, virus capsid or vector comprises a selective amino acid insertion directly following amino acid position 264 of the AAV2 capsid protein or a corresponding change in the capsid protein from other AAV. By "directly following amino acid position X" it is intended that the insertion immediately follows the indicated amino acid position (for example, "following amino acid position 264" indicates a point insertion at position 265 or a larger insertion, e.g., from positions 265 to 268, etc.). The foregoing embodiments of the invention can be used to deliver a heterologous nucleic acid to a cell or subject as described herein. For example, the modified vector can be used to treat a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase) as described herein.

Those skilled in the art will appreciate that for some AAV capsid proteins the corresponding modification will be an insertion and/or a substitution, depending on whether the corresponding amino acid positions are partially or completely present in the virus or, alternatively, are completely absent. Likewise, when modifying AAV other than AAV2, the specific amino acid position(s) may be different than the position in AAV2 (see, e.g., Table 3). As discussed elsewhere herein, the corresponding amino acid position(s) will be readily apparent to those skilled in the art using well-known techniques.

In representative embodiments, the insertion and/or substitution and/or deletion in the capsid protein(s) results in the insertion, substitution and/or repositioning of an amino acid that (i) maintains the hydrophilic loop structure in that region; (ii) an amino acid that alters the configuration of the loop structure; (iii) a charged amino acid; and/or (iv) an amino acid that can be phosphorylated or sulfated or otherwise acquire a charge by post-translational modification (e.g., glycosylation) following 264 in an AAV2 capsid protein or a corresponding change in a capsid protein of another AAV. Suitable amino acids for insertion/substitution include aspartic acid, glutamic acid, valine, leucine, lysine, arginine, threonine, serine, tyrosine, glycine, alanine, proline, asparagine, phenylalanine, tyrosine or glutamine. In particular embodiments, a threonine is inserted or substituted into the capsid subunit. Nonlimiting examples of corresponding positions in a number of other AAV are shown in Table 3 (Position 2). In particular embodiments, the amino acid insertion or substitution is a threonine, aspartic acid, glutamic acid or phenylalanine (excepting AAV that have a threonine, glutamic acid or phenylalanine, respectively, at this position).

According to this aspect of the invention, in some embodiments the AAV particle of this invention can comprise a capsid protein that comprises an amino acid insertion following amino acid position 264 in an AAV2, AAV3a or AAV3b capsid protein(s) or in the corresponding position in an AAV2, AAV3a or AAV3b capsid protein that has been modified to comprise non-AAV2, AAV3a or AAV3b sequences, respectively, and/or has been modified by deletion of one or more amino acids (i.e., is derived from AAV2, AAV3a or AAV3b). The amino acid corresponding to position 264 in an AAV2 (or AAV3a or AAV3b) capsid subunit(s) will be readily identifiable in the starting virus that has been derived from AAV2 (or AAV3a or AAV3b), which can then be further modified according to the present invention. Suitable amino acids for insertion include aspartic acid, glutamic acid, valine, leucine, lysine, arginine, threonine, serine, tyrosine, glycine, alanine, proline, asparagine, phenylalanine, tyrosine or glutamine.

In other embodiments, the AAV capsid protein of the AAV particle of this invention can comprise an amino acid substitution at amino acid position 265 in an AAV1 capsid protein(s), at amino acid position 266 in an AAV8 capsid protein, or an amino acid substitution at amino acid position 265 in an AAV9 capsid protein or in the corresponding position in an AAV1, AAV8 or AAV9 capsid protein that has been modified to comprise non-AAV1, non-AAV8 or non-AAV9 sequences, respectively, and/or has been modified by deletion of one or more amino acids (i.e., is derived from AAV1, AAV8 or AAV9). The amino acid corresponding to position 265 in an AAV1 and AAV9 capsid subunit(s) and position 266 in the AAV8 capsid subunit(s) readily identifiable in the starting virus that has been derived from AAV1, AAV8 or AAV9, which can then be further modified according to the present invention. Suitable amino acids for insertion include aspartic acid, glutamic acid, valine, leucine, lysine, arginine, threonine, serine, tyrosine, glycine, alanine, proline, asparagine, phenylalanine, tyrosine or glutamine.

In representative embodiments of the AAV particle of this invention, the capsid protein can comprise a threonine, aspartic acid, glutamic acid, or phenylalanine following amino acid position 264 of the AAV2 capsid protein (i.e., an insertion) or the corresponding position of another capsid protein.

In other representative embodiments of the AAV particle of this invention, the modified capsid proteins or virus capsids can further comprise one or more mutations as described in WO 2007/089632 (e.g., an E4K mutation at amino acid position 531 of the AAV2 capsid protein or the corresponding position of the capsid protein from another AAV).

In further embodiments, the modified capsid protein or capsid can comprise a mutation as described in WO 2009/108274.

As another, possibility, the AAV capsid protein can comprise a mutation as described by Zhong et al. (*Virology* 381: 194-202 (2008); *Proc. Nat. Acad. Sci.* 105: 7827-32 (2008)). For example, the AAV capsid protein can comprise a Y→F mutation at amino acid position 730.

The modifications described above can be incorporated into the capsid proteins or capsids of the invention in combination with each other and/or with any other modification now known or later discovered.

In representative embodiments, the AAV particle or virus vector of this invention can comprise, consist essentially of or consist of: (a) a capsid, which can be a modified virus capsid (e.g., a modified AAV capsid) comprising a modified capsid protein; and (b) a nucleic acid comprising a terminal repeat sequence (e.g., an AAV TR), wherein the nucleic acid comprising the terminal repeat sequence is encapsidated by the virus capsid. The nucleic acid can optionally comprise two terminal repeats (e.g., two AAV TRs).

In representative embodiments, the virus vector of this invention is a recombinant virus vector comprising a heterologous nucleic acid encoding a polypeptide and/or a functional RNA of interest. Recombinant virus vectors are described in more detail below.

In some embodiments, the virus vectors of the invention (i) have reduced transduction of liver as compared with the level of transduction by a virus vector without the modified capsid proteins of this invention; (ii) exhibit enhanced systemic transduction by the virus vector in an animal subject as compared with the level observed by a virus vector without the modified capsid proteins of this invention; (iii) demonstrate enhanced movement across endothelial cells as compared with the level of movement by a virus vector without the modified capsid proteins of this invention, and/or (iv) exhibit a selective enhancement in transduction of muscle tissue (e.g., skeletal muscle, cardiac muscle and/or diaphragm muscle), and/or (v) increased transduction of brain tissues (e.g., neurons) as compared with the level of transduction by a virus vector without the modified capsid proteins of this invention. Further, in some embodiments of the invention, the virus vectors demonstrate efficient transduction or enhanced transduction of target tissues.

It will be understood by those skilled in the art that, in certain embodiments, the capsid proteins, virus capsids, virus vectors and AAV particles of the invention exclude those capsid proteins, capsids, virus vectors and AAV particles as they would be present or found in their native state.

Another aspect of the invention relates to an AAV capsid protein which comprises a modification of the amino acid sequence that is an insertion of a polypeptide at a position adjacent the threefold spike capsid domain of the AAV capsid. Specifically, the insertion site corresponds to amino acids 588 and 589 (the VP1 position) of AAV9. Such capsid proteins are referred to herein as "modified AAV capsid proteins." The inserted polypeptide is selected from PB5-3, PB5-5, PB5-14, Angiopep-2, GSH, HIV-1 TAT (48-60) ApoE (159-167)2, Leptin 30 (61-90), and THR, as described herein. In embodiments, a peptide linker of 1 or more amino acids is included at the N-terminus, the C-terminus, or both termini of the inserted polypeptide sequence. This provides flexibility at the junctions of the polypeptide insertion into the AAV capsid and ensures preservation of any structure necessary for these polypeptides to function at enhancing transduction activity of the vector. Linkers may be any amino acid(s) that serves as a spacer without affecting the tertiary structure, e.g., glycine, serine or a glycine-serine combination (e.g., GGG, GGS, GSS, GG, GS, SS, etc.).

The AAV capsid to be modified can be any AAV serotype or combination of serotypes (e.g. listed in Table 1). The AAV capsid can further be a chimeric capsid protein as described herein.

In addition to the insertions described above, the modified capsid may also contain further modifications (e.g., contain additional insertions, deletions or amino acid substitutions) as described herein. In embodiments, the modified capsid protein contains no additional insertions other than those required for appropriate transduction function of the inserted polypeptide. In embodiments, the modified capsid protein contains no deletions. In embodiments, the modified capsid protein contains no amino acid substitutions.

In another aspect of the invention, the modified capsid protein contains the polypeptide inserted, with or without the herein described linker(s), between amino acid 589 and 590 of AAV9 or the corresponding amino acid position of another AAV serotype for example as each is described in Michelfelder et al., (PLoS Volume 6, Issue 8, e23101 (2011)). In another aspect of the invention, the modified capsid protein contains the polypeptide inserted, with or without the herein described linker(s), between amino acid 590 and 591 of AAV8, or the corresponding amino acid position of another AAV serotype, for example as each is described in Michelfelder et al., (PLoS Volume 6, Issue 8, e23101 (2011)).

Another aspect of the invention relates to a nucleic acid molecule encoding a modified AAV capsid protein as described herein. The nucleic acid molecule can be contained within a vector (e.g., to facilitate manipulation or production). A variety of vectors are known in the art and provided herein.

Another aspect of the invention relates to an AAV particle, such as a recombinant AAV particle, that comprises a modified AAV capsid protein described herein. The AAV particle can be any AAV serotype or combination of AAV serotypes. Examples of such serotypes are provided in Table 1. In embodiments, the AAV particle is an AAV8, AAV9, AAV2, AAV2i8, AAV9.45 serotype. Variants and mutants and combinations thereof, are also contemplated.

In embodiments of the invention, transduction by the AAV particles of cells or tissues of the brain and/or central nervous system is at least about five-fold, ten-fold, 50-fold, 100-fold, 1000-fold or higher than transduction levels by an appropriate control (e.g., otherwise identical AAV particles that lack the capsid insert).

In embodiments of the invention, the AAV particle that comprises the modified AAV capsid protein has enhanced transduction activity across the blood brain barrier (BBB) of a subject (e.g., human) as conferred by the polypeptide insert. This activity is enhanced as compared to that of an appropriate control, such as an otherwise identical AAV particle without the polypeptide insert. In some embodiments, the AAV particle has enhanced transduction activity to cells of the brain and/or other central nervous system cells of a subject (e.g., human), relative to an appropriate control. In some embodiments, the AAV particle has enhanced transduction activity to the cortex, striatum, thalamus, cerebellum and/or spinal cord of a subject (e.g., a human subject), as compared to an appropriate control. In some embodiments, the AAV particle has enhanced transduction to astrocytes, CC1+ oligodendrocytes, neuronal subtypes including NeuN+ cells throughout the brain, midbrain tyrosine hydroxylase (TH)+ dopaminergic neurons, Calbindin+ cerebellar Purkinje cells, interneuron populations and/or CD31+ endothelial cells of a subject, as compared to an appropriate control.

In some embodiments, the AAV particle comprises a heterologous nucleic acid molecule (e.g., as described herein). In some embodiments, the heterologous nucleic acid molecule encodes a therapeutic polypeptide. Therapeutic polypeptides are known in the art with many exemplary therapeutic polypeptides being described herein.

Another aspect of the invention relates to a pharmaceutical formulation comprising the AAV particle, such as a recombinant AAV particle, that comprises a modified AAV capsid protein, as described herein. The AAV particle is comprised in a pharmaceutically acceptable carrier.

Another aspect of the invention relates to a method of administering or delivering a nucleic acid molecule to a cell of the brain and/or central nervous system. The method comprises contacting the cell with an AAV particle comprising the modified AAV capsid, described herein, which contains the nucleic acid molecule (e.g. as a heterologous nucleic acid molecule). The method may alternatively or also involve contacting the cell with a pharmaceutical formulation that contains the AAV particle having the modified AAV capsid and heterologous nucleic acid molecule. Administration can be to a subject such as a mammal, such as a human (e.g., by systemic administration).

Methods of Producing Virus Vectors

The present invention further provides methods of producing the AAV particles of this invention. Thus, the present invention provides a method of making an AAV particle, comprising: a) transfecting a host cell with one or more plasmids that provide, in combination all functions and genes needed to assemble AAV particles; b) introducing one or more nucleic acid constructs into a packaging cell line or producer cell line to provide, in combination, all functions and genes needed to assemble AAV particles; c) introducing into a host cell one or more recombinant baculovirus vectors that provide in combination all functions and genes needed to assemble AAV particles; and/or d) introducing into a host cell one or more recombinant herpesvirus vectors that provide in combination all functions and genes needed to assemble AAV particles. Nonlimiting examples of various methods of making the virus vectors of this invention are described in Clement and Greiger ("Manufacturing of recombinant adeno-associated viral vectors for clinical trials" *Mol. Ther. Methods Clin Dev.* 3:16002 (2016)) and in Greiger et al. ("Production of recombinant adeno-associated virus vectors using suspension HEK293 cells and continuous harvest of vector from the culture media for GMP FIX and FLT1 clinical vector" *Mol Ther* 24(2):287-297 (2016)), the entire contents of which are incorporated by reference herein.

In one representative embodiment, the present invention provides a method of producing an AAV particle, the method comprising providing to a cell: (a) a nucleic acid template comprising at least one TR sequence (e.g., AAV TR sequence), and (b) AAV sequences sufficient for replication of the nucleic acid template and encapsidation into AAV capsids (e.g., AAV rep sequences and AAV cap sequences encoding the AAV capsids of the invention). Optionally, the nucleic acid template further comprises at least one heterologous nucleic acid sequence. In particular embodiments, the nucleic acid template comprises two AAV ITR sequences, which are located 5' and 3' to the heterologous nucleic acid sequence (if present), although they need not be directly contiguous thereto.

The nucleic acid template and AAV rep and cap sequences are provided under conditions such that virus vector comprising the nucleic acid template packaged within the AAV capsid is produced in the cell. The method can further comprise the step of collecting the virus vector from the cell. The virus vector can be collected from the medium and/or by lysing the cells.

The cell can be a cell that is permissive for AAV viral replication. Any suitable cell known in the art may be employed. In particular embodiments, the cell is a mammalian cell. As another option, the cell can be a trans-complementing packaging cell line that provides functions deleted from a replication-defective helper virus, e.g., 293 cells or other E1a trans-complementing cells.

The AAV replication and capsid sequences may be provided by any method known in the art. Current protocols typically express the AAV rep/cap genes on a single plasmid. The AAV replication and packaging sequences need not be provided together, although it may be convenient to do so. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). Epstein Barr virus (EBV) vectors may also be employed to express the AAV cap and rep genes. One advantage of this method is that EBV vectors are episomal, yet will maintain a high copy number throughout successive cell divisions (i.e., are stably integrated into the cell as extra-chromosomal elements, designated as an "EBV based nuclear episome," see Margolski, (1992) *Curr. Top. Microbiol. Immun.* 158:67).

As a further alternative, the rep/cap sequences may be stably incorporated into a cell.

Typically the AAV rep/cap sequences will not be flanked by the TRs, to prevent rescue and/or packaging of these sequences.

The nucleic acid template can be provided to the cell using any method known in the art. For example, the template can be supplied by a non-viral (e.g., plasmid) or viral vector. In particular embodiments, the nucleic acid template is supplied by a herpesvirus or adenovirus vector (e.g., inserted into the E1a or E3 regions of a deleted adenovirus). As another illustration, Palombo et al., (1998) *J. Virology* 72:5025, describes a baculovirus vector carrying a reporter gene flanked by the AAV TRs. EBV vectors may also be employed to deliver the template, as described above with respect to the rep/cap genes.

In another representative embodiment, the nucleic acid template is provided by a replicating rAAV virus. In still other embodiments, an AAV provirus comprising the nucleic acid template is stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production as described by Ferrari et al., (1997) *Nature Med.* 3:1295, and U.S. Pat. Nos. 6,040,183 and 6,093,570.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

Those skilled in the art will appreciate that it may be advantageous to provide the AAV replication and capsid sequences and the helper virus sequences (e.g., adenovirus sequences) on a single helper construct. This helper construct may be a non-viral or viral construct. As one nonlimiting illustration, the helper construct can be a hybrid adenovirus or hybrid herpesvirus comprising the AAV rep/cap genes.

In one embodiment, the AAV rep/cap sequences and the adenovirus helper sequences are supplied by a single adenovirus helper vector. This vector further can further comprise the nucleic acid template. The AAV rep/cap sequences and/or the rAAV template can be inserted into a deleted region (e.g., the E1a or E3 regions) of the adenovirus.

In a further embodiment, the AAV rep/cap sequences and the adenovirus helper sequences are supplied by a single adenovirus helper vector. According to this embodiment, the rAAV template can be provided as a plasmid template.

In another illustrative embodiment, the AAV rep/cap sequences and adenovirus helper sequences are provided by a single adenovirus helper vector, and the rAAV template is integrated into the cell as a provirus. Alternatively, the rAAV template is provided by an EBV vector that is maintained within the cell as an extrachromosomal element (e.g., as an EBV based nuclear episome).

In a further exemplary embodiment, the AAV rep/cap sequences and adenovirus helper sequences are provided by a single adenovirus helper. The rAAV template can be provided as a separate replicating viral vector. For example, the rAAV template can be provided by a rAAV particle or a second recombinant adenovirus particle.

According to the foregoing methods, the hybrid adenovirus vector typically comprises the adenovirus 5' and 3' cis sequences sufficient for adenovirus replication and packaging (i.e., the adenovirus terminal repeats and PAC sequence). The AAV rep/cap sequences and if present the rAAV template are embedded in the adenovirus backbone and are flanked by the 5' and 3' cis sequences, so that these sequences may be packaged into adenovirus capsids. As described above, the adenovirus helper sequences and the AAV rep/cap sequences are generally not flanked by TRs so that these sequences are not packaged into the AAV virions.

Zhang et al. ((2001) *Gene Ther.* 18:704-12) describe a chimeric helper comprising both adenovirus and the AAV rep and cap genes.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) *Gene Therapy* 6:986 and WO 00/17377.

As a further alternative, the virus vectors of the invention can be produced in insect cells using baculovirus vectors to deliver the rep/cap genes and rAAV template as described, for example, by Urabe et al., (2002) *Human Gene Therapy* 13:1935-43.

AAV vector stocks free of contaminating helper virus may be obtained by any method known in the art. For example, AAV and helper virus may be readily differentiated based on size. AAV may also be separated away from helper virus based on affinity for a heparin substrate (Zolotukhin et al. (1999) *Gene Therapy* 6:973). Deleted replication-defective helper viruses can be used so that any contaminating helper virus is not replication competent. As a further alternative, an adenovirus helper lacking late gene expression may be employed, as only adenovirus early gene expression is required to mediate packaging of AAV virus. Adenovirus mutants defective for late gene expression are known in the art (e.g., ts100K and ts149 adenovirus mutants).

Recombinant Virus Vectors

The present invention provides a method of administering a nucleic acid molecule to a cell, the method comprising contacting the cell with the virus vector, the AAV particle, the composition and/or the pharmaceutical formulation of this invention.

The present invention further provides a method of delivering a nucleic acid to a subject, the method comprising administering to the subject the virus vector, the AAV particle, the composition and/or the pharmaceutical formulation of this invention.

The subject of this invention can be any animal and in some embodiments, the subject is a mammal and in some embodiments, the subject is a human. In some embodiments, the subject has or is at risk for a disorder that can be treated by immunotherapy and/or gene therapy protocols. Nonlimiting examples of such disorders include a muscular dystrophy including Duchenne or Becker muscular dystrophy, hemophilia A, hemophilia B, multiple sclerosis, diabetes mellitus, Gaucher disease, Fabry disease, Pompe disease, cancer, arthritis, muscle wasting, heart disease including congestive heart failure or peripheral artery disease, intimal hyperplasia, a neurological disorder including epilepsy, Huntington's disease, Parkinson's disease or Alzheimer's disease, an autoimmune disease, cystic fibrosis, thalassemia, Hurler's Syndrome, Sly syndrome, Scheie Syndrome, Hurler-Scheie Syndrome, Hunter's Syndrome, Sanfilippo Syndrome A, B, C, D, Morquio Syndrome, Maroteaux-Lamy Syndrome, Krabbe's disease, phenylketonuria, Batten's disease, spinal cerebral ataxia, LDL receptor deficiency, hyperammonemia, anemia, arthritis, a retinal degenerative disorder including macular degeneration, adenosine deaminase deficiency, a metabolic disorder, and cancer including tumor-forming cancers.

In the methods described herein, the virus vector, the AAV particle and/or the composition or pharmaceutical formulation of this invention can be administered/delivered to a subject of this invention via a systemic route (e.g., intravenously, intraarterially, intraperitoneally, etc.). In some embodiments, the virus vector and/or composition can be administered to the subject via an intracerebroventrical, intracisternal, intraparenchymal, intracranial and/or intrathecal route. In particular embodiments, the virus vector and/or pharmaceutical formulation of this invention is administered intravenously.

The virus vectors of the present invention are useful for the delivery of nucleic acid molecules to cells in vitro, ex vivo, and in vivo. In particular, the virus vectors can be advantageously employed to deliver or transfer nucleic acid molecules to animal cells, including mammalian cells.

Any heterologous nucleic acid sequence(s) of interest may be delivered in the virus vectors of the present invention. Nucleic acid molecules of interest include nucleic acid molecules encoding polypeptides, including therapeutic (e.g., for medical or veterinary uses) and/or immunogenic (e.g., for vaccines) polypeptides.

Therapeutic polypeptides include, but are not limited to, cystic fibrosis transmembrane regulator protein (CFTR), dystrophin (including mini- and micro-dystrophins, see, e.g, Vincent et al. (1993) *Nature Genetics* 5:130; U.S. Patent Publication No. 2003/017131; International publication WO/2008/088895, Wang et al. *Proc. Natl. Acad. Sci. USA* 97:13714-13719 (2000); and Gregorevic et al. *Mol. Ther.* 16:657-64 (2008)), myostatin propeptide, follistatin, activin type II soluble receptor, IGF-1, anti-inflammatory polypeptides such as the Ikappa B dominant mutant, sarcospan, utrophin (Tinsley et al. (1996) *Nature* 384:349), mini-utrophin, clotting factors (e.g., Factor VIII, Factor IX, Factor X, etc.), erythropoietin, angiostatin, endostatin, catalase, tyrosine hydroxylase, superoxide dismutase, leptin, the LDL receptor, lipoprotein lipase, ornithine transcarbamylase, β-globin, α-globin, spectrin, $\alpha_1$-antitrypsin, adenosine deaminase, hypoxanthine guanine phosphoribosyl transferase, β-glucocerebrosidase, sphingomyelinase, lysosomal hexosaminidase A, branched-chain keto acid dehydrogenase, RP65 protein, cytokines (e.g., α-interferon, β-interferon, interferon-γ, interleukin-2, interleukin-4, granulocyte-macrophage colony stimulating factor, lymphotoxin, and the like), peptide growth factors, neurotrophic factors and hormones (e.g., somatotropin, insulin, insulin-like growth factors 1 and 2, platelet derived growth factor, epidermal growth factor, fibroblast growth factor, nerve growth factor, neurotrophic factor-3 and -4, brain-derived neurotrophic factor, bone morphogenic proteins [including RANKL and VEGF], glial derived growth factor, transforming growth factor-α and -β, and the like), lysosomal acid α-glucosidase, α-galactosidase A, receptors (e.g., the tumor necrosis growth factora soluble receptor), S100A1, parvalbumin, adenylyl cyclase type 6, a molecule that modulates calcium handling (e.g., $SERCA_{2A}$, Inhibitor 1 of PP1 and fragments thereof [e.g., WO 2006/029319 and WO 2007/100465]), a molecule that effects G-protein coupled receptor kinase type 2 knockdown such as a truncated constitutively active bARKct, anti-inflammatory factors such as IRAP, anti-myostatin proteins, aspartoacylase, monoclonal antibodies (including single chain monoclonal antibodies; an exemplary Mab is the Herceptin® Mab), neuropeptides and fragments thereof (e.g., galanin, Neuropeptide Y (see, U.S. Pat. No. 7,071,172), angiogenesis inhibitors such as Vasohibins and other VEGF inhibitors (e.g., Vasohibin 2 [see, WO JP2006/073052]). Other illustrative heterologous nucleic acid sequences encode suicide gene products (e.g., thymidine kinase, cytosine deaminase, diphtheria toxin, and tumor necrosis factor), proteins conferring resistance to a drug used in cancer therapy, tumor suppressor gene products (e.g., p53, Rb, Wt-1), TRAIL, FAS-ligand, and any other polypeptide that has a therapeutic effect in a subject in need thereof. AAV vectors can also be used to deliver monoclonal antibodies and antibody fragments, for example, an antibody or antibody fragment directed against myostatin (see, e.g., Fang et al. *Nature Biotechnology* 23:584-590 (2005)).

Heterologous nucleic acid sequences encoding polypeptides include those encoding reporter polypeptides (e.g., an enzyme). Reporter polypeptides are known in the art and include, but are not limited to, Green Fluorescent Protein (GFP), luciferase, β-galactosidase, alkaline phosphatase, luciferase, and chloramphenicol acetyltransferase gene.

Optionally, the heterologous nucleic acid molecule encodes a secreted polypeptide (e.g., a polypeptide that is a secreted polypeptide in its native state or that has been engineered to be secreted, for example, by operable association with a secretory signal sequence as is known in the art).

Alternatively, in particular embodiments of this invention, the heterologous nucleic acid molecule may encode an antisense nucleic acid molecule, a ribozyme (e.g., as described in U.S. Pat. No. 5,877,022), RNAs that effect spliceosome-mediated trans-splicing (see, Puttaraju et al. (1999) *Nature Biotech.* 17:246; U.S. Pat. Nos. 6,013,487; 6,083,702), interfering RNAs (RNAi) including siRNA, shRNA or miRNA that mediate gene silencing (see, Sharp et al. (2000) *Science* 287:2431), and other non-translated RNAs, such as "guide" RNAs (Gorman et al. (1998) *Proc. Nat. Acad. Sci. USA* 95:4929; U.S. Pat. No. 5,869,248 to Yuan et al.), and the like. Exemplary untranslated RNAs include RNAi against a multiple drug resistance (MDR) gene product (e.g., to treat and/or prevent tumors and/or for administration to the heart to prevent damage by chemotherapy), RNAi against myostatin (e.g., for Duchenne muscular dystrophy), RNAi against VEGF (e.g., to treat and/or prevent tumors), RNAi against phospholamban (e.g., to treat cardiovascular disease, see, e.g., Andino et al. *J. Gene Med.* 10:132-142 (2008) and Li et al. *Acta Pharmacol Sin.* 26:51-55 (2005)); phospholamban inhibitory or dominant-negative molecules such as phospholamban S16E (e.g., to treat cardiovascular disease, see, e.g., Hoshijima et al. *Nat. Med* 8:864-871 (2002)), RNAi to adenosine kinase (e.g., for epilepsy), and RNAi directed against pathogenic organisms and viruses (e.g., hepatitis B and/or C virus, human immunodeficiency virus, CMV, herpes simplex virus, human papilloma virus, etc.).

Further, a nucleic acid sequence that directs alternative splicing can be delivered. To illustrate, an antisense sequence (or other inhibitory sequence) complementary to the 5' and/or 3' splice site of dystrophin exon 51 can be delivered in conjunction with a U1 or U7 small nuclear (sn) RNA promoter to induce skipping of this exon. For example, a DNA sequence comprising a U1 or U7 snRNA promoter located 5' to the antisense/inhibitory sequence(s) can be packaged and delivered in a modified capsid of the invention.

The virus vector may also comprise a heterologous nucleic acid molecule that shares homology with and recombines with a locus on a host cell chromosome. This approach can be utilized, for example, to correct a genetic defect in the host cell.

The present invention also provides virus vectors that express an immunogenic polypeptide, peptide and/or epitope, e.g., for vaccination. The nucleic acid molecule may encode any immunogen of interest known in the art including, but not limited to, immunogens from human immunodeficiency virus (HIV), simian immunodeficiency virus (SIV), influenza virus, HIV or SIV gag proteins, tumor antigens, cancer antigens, bacterial antigens, viral antigens, and the like.

The use of parvoviruses as vaccine vectors is known in the art (see, e.g., Miyamura et al. (1994) *Proc. Nat. Acad. Sci USA* 91:8507; U.S. Pat. No. 5,916,563 to Young et al., U.S. Pat. No. 5,905,040 to Mazzara et al., U.S. Pat. Nos. 5,882,652, 5,863,541 to Samulski et al.). The antigen may be presented in the parvovirus capsid. Alternatively, the immunogen or antigen may be expressed from a heterologous nucleic acid molecule introduced into a recombinant vector genome. Any immunogen or antigen of interest as described herein and/or as is known in the art can be provided by the virus vector of the present invention.

An immunogenic polypeptide can be any polypeptide, peptide, and/or epitope suitable for eliciting an immune response and/or protecting the subject against an infection and/or disease, including, but not limited to, microbial, bacterial, protozoal, parasitic, fungal and/or viral infections and diseases. For example, the immunogenic polypeptide can be an orthomyxovirus immunogen (e.g., an influenza virus immunogen, such as the influenza virus hemagglutinin (HA) surface protein or the influenza virus nucleoprotein, or an equine influenza virus immunogen) or a lentivirus immunogen (e.g., an equine infectious anemia virus immunogen, a Simian Immunodeficiency Virus (SIV) immunogen, or a Human Immunodeficiency Virus (HIV) immunogen, such as the HIV or SIV envelope GP160 protein, the HIV or SIV matrix/capsid proteins, and the HIV or SIV gag, pol and env genes products). The immunogenic polypeptide can also be an arenavirus immunogen (e.g., Lassa fever virus immunogen, such as the Lassa fever virus nucleocapsid protein and the Lassa fever envelope glycoprotein), a poxvirus immunogen (e.g., a vaccinia virus immunogen, such as the vaccinia L1 or L8 gene products), a flavivirus immunogen (e.g., a yellow fever virus immunogen or a Japanese encephalitis virus immunogen), a filovirus immunogen (e.g., an Ebola virus immunogen, or a Marburg virus immunogen, such as NP and GP gene products), a bunyavirus immunogen (e.g., RVFV, CCHF, and/or SFS virus immunogens), or a coronavirus immunogen (e.g., an infectious human coronavirus immunogen, such as the human coronavirus envelope glycoprotein, or a porcine transmissible gastroenteritis virus immunogen, or an avian infectious bronchitis virus immunogen). The immunogenic polypeptide can further be a polio immunogen, a herpes immunogen (e.g., CMV, EBV, HSV immunogens) a mumps immunogen, a measles immunogen, a rubella immunogen, a diphtheria toxin or other diphtheria immunogen, a pertussis antigen, a hepatitis (e.g., hepatitis A, hepatitis B, hepatitis C, etc.) immunogen, and/or any other vaccine immunogen now known in the art or later identified as an immunogen.

Alternatively, the immunogenic polypeptide can be any tumor or cancer cell antigen. Optionally, the tumor or cancer antigen is expressed on the surface of the cancer cell. Exemplary cancer and tumor cell antigens are described in S.A. Rosenberg (*Immunity* 10:281 (1991)). Other illustrative cancer and tumor antigens include, but are not limited to: BRCA1 gene product, BRCA2 gene product, gp100, tyrosinase, GAGE-1/2, BAGE, RAGE, LAGE, NY-ESO-1, CDK-4, β-catenin, MUM-1, Caspase-8, KIAA0205, HPVE, SART-1, PRAME, p15, melanoma tumor antigens (Kawakami et al. (1994) *Proc. Natl. Acad. Sci. USA* 91:3515; Kawakami et al. (1994) *J. Exp. Med.*, 180:347; Kawakami et al. (1994) *Cancer Res.* 54:3124), MART-1, gp100 MAGE-1, MAGE-2, MAGE-3, CEA, TRP-1, TRP-2, P-15, tyrosinase (Brichard et al. (1993) *J. Exp. Med.* 178: 489); HER-2/neu gene product (U.S. Pat. No. 4,968,603), CA 125, LK26, FB5 (endosialin), TAG 72, AFP, CA19-9, NSE, DU-PAN-2, CA50, SPan-1, CA72-4, HCG, STN (sialyl Tn antigen), c-erbB-2 proteins, PSA, L-CanAg, estrogen receptor, milk fat globulin, p53 tumor suppressor protein (Levine. (1993) *Ann. Rev. Biochem.* 62:623); mucin antigens (International Patent Publication No. WO 90/05142); telomerases; nuclear matrix proteins; prostatic acid phosphatase; papilloma virus antigens; and/or antigens now known or later discovered to be associated with the following cancers: melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified (see, e.g., Rosenberg, (1996) *Ann. Rev. Med.* 47:481-91).

As a further alternative, the heterologous nucleic acid molecule can encode any polypeptide, peptide and/or epitope that is desirably produced in a cell in vitro, ex vivo, or in vivo. For example, the virus vectors may be introduced into cultured cells and the expressed gene product isolated therefrom.

It will be understood by those skilled in the art that the heterologous nucleic acid molecule(s) of interest can be operably associated with appropriate control sequences. For example, the heterologous nucleic acid molecule can be operably associated with expression control elements, such as transcription/translation control signals, origins of replication, polyadenylation signals, internal ribosome entry sites (IRES), promoters, and/or enhancers, and the like.

Further, regulated expression of the heterologous nucleic acid molecule(s) of interest can be achieved at the post-transcriptional level, e.g., by regulating selective splicing of different introns by the presence or absence of an oligonucleotide, small molecule and/or other compound that selectively blocks splicing activity at specific sites (e.g., as described in WO 2006/119137).

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

In embodiments wherein the heterologous nucleic acid sequence(s) is transcribed and then translated in the target cells, specific initiation signals are generally included for efficient translation of inserted protein coding sequences. These exogenous translational control sequences, which may include the ATG initiation codon and adjacent sequences, can be of a variety of origins, both natural and synthetic.

The virus vectors according to the present invention provide a means for delivering heterologous nucleic acid molecules into a broad range of cells, including dividing and non-dividing cells. The virus vectors can be employed to deliver a nucleic acid molecule of interest to a cell in vitro, e.g., to produce a polypeptide in vitro or for ex vivo or in vivo gene therapy. The virus vectors are additionally useful in a method of delivering a nucleic acid to a subject in need thereof, e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors can also be used to produce a polypeptide of interest or functional RNA in cultured cells or in a subject (e.g., using the subject as a bioreactor to produce the polypeptide or to observe the effects of the functional RNA on the subject, for example, in connection with screening methods).

In general, the virus vectors of the present invention can be employed to deliver a heterologous nucleic acid molecule encoding a polypeptide or functional RNA to treat and/or prevent any disorder or disease state for which it is beneficial to deliver a therapeutic polypeptide or functional RNA. Illustrative disease states include, but are not limited to: cystic fibrosis (cystic fibrosis transmembrane regulator protein) and other diseases of the lung, hemophilia A (Factor VIII), hemophilia B (Factor IX), thalassemia (ß-globin), anemia (erythropoietin) and other blood disorders, Alzheimer's disease (GDF; neprilysin), multiple sclerosis (ß-interferon), Parkinson's disease (glial-cell line derived neurotrophic factor [GDNF]), Huntington's disease (RNAi to remove repeats), amyotrophic lateral sclerosis, epilepsy (galanin, neurotrophic factors), and other neurological disorders, cancer (endostatin, angiostatin, TRAIL, FAS-ligand, cytokines including interferons; RNAi including RNAi against VEGF or the multiple drug resistance gene product, mir-26a [e.g., for hepatocellular carcinoma]), diabetes mellitus (insulin), muscular dystrophies including Duchenne (dystrophin, mini-dystrophin, insulin-like growth factor I, a sarcoglycan [e.g., α, β, γ], RNAi against myostatin, myostatin propeptide, follistatin, activin type II soluble receptor, anti-inflammatory polypeptides such as the Ikappa B dominant mutant, sarcospan, utrophin, mini-utrophin, antisense or RNAi against splice junctions in the dystrophin gene to induce exon skipping [see, e.g., WO/2003/095647], antisense against U7 snRNAs to induce exon skipping [see, e.g., WO/2006/021724], and antibodies or antibody fragments against myostatin or myostatin propeptide) and Becker, Gaucher disease (glucocerebrosidase), Hurler's disease (α-L-iduronidase), adenosine deaminase deficiency (adenosine deaminase), glycogen storage diseases (e.g., Fabry disease [α-galactosidase] and Pompe disease [lysosomal acid α-glucosidase]) and other metabolic disorders, congenital emphysema (al-antitrypsin), Lesch-Nyhan Syndrome (hypoxanthine guanine phosphoribosyl transferase), Niemann-Pick disease (sphingomyelinase), Tays Sachs disease (lysosomal hexosaminidase A), Maple Syrup Urine Disease (branched-chain keto acid dehydrogenase), retinal degenerative diseases (and other diseases of the eye and retina; e.g., PDGF for macular degeneration and/or vasohibin or other inhibitors of VEGF or other angiogenesis inhibitors to treat/prevent retinal disorders, e.g., in Type I diabetes), diseases of solid organs such as brain (including Parkinson's Disease [GDNF], astrocytomas [endostatin, angiostatin and/or RNAi against VEGF], glioblastomas [endostatin, angiostatin and/or RNAi against VEGF]), liver, kidney, heart including congestive heart failure or peripheral artery disease (PAD) (e.g., by delivering protein phosphatase inhibitor I (I-1) and fragments thereof (e.g., I1C), serca2a, zinc finger proteins that regulate the phospholamban gene, Barkct, β2-adrenergic receptor, β2-adrenergic receptor kinase (BARK), phosphoinositide-3 kinase (PI3 kinase), S100A1, parvalbumin, adenylyl cyclase type 6, a molecule that effects G-protein coupled receptor kinase type 2 knockdown such as a truncated constitutively active bARKct; calsarcin, RNAi against phospholamban; phospholamban inhibitory or dominant-negative molecules such as phospholamban S16E, etc.), arthritis (insulin-like growth factors), joint disorders (insulin-like growth factor 1 and/or 2), intimal hyperplasia (e.g., by delivering enos, inos), improve survival of heart transplants (superoxide dismutase), AIDS (soluble CD4), muscle wasting (insulin-like growth factor I), kidney deficiency (erythropoietin), anemia (erythropoietin), arthritis (anti-inflammatory factors such as IRAP and TNFα soluble receptor), hepatitis (α-interferon), LDL receptor deficiency (LDL receptor), hyperammonemia (ornithine transcarbamylase), Krabbe's disease (galactocerebrosidase), Batten's disease, spinal cerebral ataxias including SCA1, SCA2 and SCA3, phenylketonuria (phenylalanine hydroxylase), autoimmune diseases, and the like. The invention can further be used following organ transplantation to increase the success of the transplant and/or to reduce the negative side effects of organ transplantation or adjunct therapies (e.g., by administering immunosuppressant agents or inhibitory nucleic acids to block cytokine production). As another example, bone morphogenic proteins (including BNP 2, 7, etc., RANKL and/or VEGF) can be administered with a bone allograft, for example, following a break or surgical removal in a cancer patient.

The invention can also be used to produce induced pluripotent stem cells (iPS). For example, a virus vector of the invention can be used to deliver stem cell associated nucleic acid(s) into a non-pluripotent cell, such as adult fibroblasts, skin cells, liver cells, renal cells, adipose cells, cardiac cells, neural cells, epithelial cells, endothelial cells, and the like. Nucleic acids encoding factors associated with stem cells are known in the art. Nonlimiting examples of such factors associated with stem cells and pluripotency include Oct-3/4, the SOX family (e.g., SOX1, SOX2, SOX3 and/or SOX15), the Klf family (e.g., Klf1, Klf2, Klf4 and/or Klf5), the Myc family (e.g., C-myc, L-myc and/or N-myc), NANOG and/or LIN28.

The invention can also be practiced to treat and/or prevent a metabolic disorder such as diabetes (e.g., insulin), hemophilia (e.g., Factor IX or Factor VIII), a lysosomal storage disorder such as a mucopolysaccharidosis disorder (e.g., Sly syndrome [β-glucuronidase], Hurler Syndrome [α-L-iduronidase], Scheie Syndrome [α-L-iduronidase], Hurler-Scheie Syndrome [α-L-iduronidase], Hunter's Syndrome [iduronate sulfatase], Sanfilippo Syndrome A [heparan sulfamidase], B [N-acetylglucosaminidase], C [acetyl-CoA:α-glucosaminide acetyltransferase], D [N-acetylglucosamine 6-sulfatase], Morquio Syndrome A [galactose-6-sulfate sulfatase], B [β-galactosidase], Maroteaux-Lamy Syndrome [N-acetylgalactosamine-4-sulfatase], etc.), Fabry disease (α-galactosidase), Gaucher's disease (glucocerebrosidase), or a glycogen storage disorder (e.g., Pompe disease; lysosomal acid α-glucosidase).

Gene transfer has substantial potential use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present invention permit the treatment and/or prevention of genetic diseases.

The virus vectors according to the present invention may also be employed to provide a functional RNA to a cell in vitro or in vivo. Expression of the functional RNA in the cell, for example, can diminish expression of a particular target protein by the cell. Accordingly, functional RNA can be administered to decrease expression of a particular protein in a subject in need thereof. Functional RNA can also be administered to cells in vitro to regulate gene expression and/or cell physiology, e.g., to optimize cell or tissue culture systems or in screening methods.

In addition, virus vectors according to the instant invention find use in diagnostic and screening methods, whereby a nucleic acid of interest is transiently or stably expressed in a cell culture system, or alternatively, a transgenic animal model.

The virus vectors of the present invention can also be used for various non-therapeutic purposes, including but not limited to use in protocols to assess gene targeting, clearance, transcription, translation, etc., as would be apparent to one skilled in the art. The virus vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

As a further aspect, the virus vectors of the present invention may be used to produce an immune response in a subject. According to this embodiment, a virus vector comprising a heterologous nucleic acid sequence encoding an immunogenic polypeptide can be administered to a subject, and an active immune response is mounted by the subject against the immunogenic polypeptide. Immunogenic polypeptides are as described hereinabove. In some embodiments, a protective immune response is elicited.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation, in IMMUNOLOGY: BASIC PROCESSES* 117 (Joseph A. Bellanti ed., 1985). Alternatively stated, an active immune response is mounted by the host after exposure to an immunogen by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "protective" immune response or "protective" immunity as used herein indicates that the immune response confers some benefit to the subject in that it prevents or reduces the incidence of disease. Alternatively, a protective immune response or protective immunity may be useful in the treatment and/or prevention of disease, in particular cancer or tumors (e.g., by preventing cancer or tumor formation, by causing regression of a cancer or tumor and/or by preventing metastasis and/or by preventing growth of metastatic nodules). The protective effects may be complete or partial, as long as the benefits of the treatment outweigh any disadvantages thereof.

In particular embodiments, the virus vector or cell comprising the heterologous nucleic acid molecule can be administered in an immunogenically effective amount, as described below.

The virus vectors of the present invention can also be administered for cancer immunotherapy by administration of a virus vector expressing one or more cancer cell antigens (or an immunologically similar molecule) or any other immunogen that produces an immune response against a cancer cell. To illustrate, an immune response can be produced against a cancer cell antigen in a subject by administering a virus vector comprising a heterologous nucleic acid encoding the cancer cell antigen, for example to treat a patient with cancer and/or to prevent cancer from developing in the subject. The virus vector may be administered to a subject in vivo or by using ex vivo methods, as described herein. Alternatively, the cancer antigen can be expressed as part of the virus capsid or be otherwise associated with the virus capsid (e.g., as described above).

As another alternative, any other therapeutic nucleic acid (e.g., RNAi) or polypeptide (e.g., cytokine) known in the art can be administered to treat and/or prevent cancer.

As used herein, the term "cancer" encompasses tumor-forming cancers. Likewise, the term "cancerous tissue" encompasses tumors. A "cancer cell antigen" encompasses tumor antigens.

The term "cancer" has its understood meaning in the art, for example, an uncontrolled growth of tissue that has the potential to spread to distant sites of the body (i.e., metastasize). Exemplary cancers include, but are not limited to melanoma, adenocarcinoma, thymoma, lymphoma (e.g., non-Hodgkin's lymphoma, Hodgkin's lymphoma), sarcoma, lung cancer, liver cancer, colon cancer, leukemia, uterine cancer, breast cancer, prostate cancer, ovarian cancer, cervical cancer, bladder cancer, kidney cancer, pancreatic cancer, brain cancer and any other cancer or malignant condition now known or later identified. In representative embodiments, the invention provides a method of treating and/or preventing tumor-forming cancers.

The term "tumor" is also understood in the art, for example, as an abnormal mass of undifferentiated cells within a multicellular organism. Tumors can be malignant or benign. In representative embodiments, the methods disclosed herein are used to prevent and treat malignant tumors.

By the terms "treating cancer," "treatment of cancer" and equivalent terms it is intended that the severity of the cancer is reduced or at least partially eliminated and/or the progression of the disease is slowed and/or controlled and/or the disease is stabilized. In particular embodiments, these terms indicate that metastasis of the cancer is prevented or reduced or at least partially eliminated and/or that growth of metastatic nodules is prevented or reduced or at least partially eliminated.

By the terms "prevention of cancer" or "preventing cancer" and equivalent terms it is intended that the methods at least partially eliminate or reduce and/or delay the incidence and/or severity of the onset of cancer. Alternatively stated, the onset of cancer in the subject may be reduced in likelihood or probability and/or delayed.

It is known in the art that immune responses may be enhanced by immunomodulatory cytokines (e.g., α-interferon, β-interferon, γ-interferon, ω-interferon, τ-interferon, interleukin-1α, interleukin-1β, interleukin-2, interleukin-3, interleukin-4, interleukin 5, interleukin-6, interleukin-7, interleukin-8, interleukin-9, interleukin-10, interleukin-11, interleukin 12, interleukin-13, interleukin-14, interleukin-18, B cell Growth factor, CD40 Ligand, tumor necrosis factor-α, tumor necrosis factor-β, monocyte chemoattractant protein-1, granulocyte-macrophage colony stimulating factor, and lymphotoxin). Accordingly, immunomodulatory cytokines (preferably, CTL inductive cytokines) may be administered to a subject in conjunction with the virus vector.

Cytokines may be administered by any method known in the art. Exogenous cytokines may be administered to the subject, or alternatively, a nucleic acid encoding a cytokine may be delivered to the subject using a suitable vector, and the cytokine produced in vivo.

Subjects, Pharmaceutical Formulations, and Modes of Administration

Virus vectors and AAV particles according to the present invention find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammal" as used herein includes, but is not limited to, humans, non-human primates, bovines, ovines, caprines, equines, felines, canines, lagomorphs, etc. Human subjects include neonates, infants, juveniles, adults and geriatric subjects.

In representative embodiments, the subject is "in need of" the methods of the invention.

In particular embodiments, the present invention provides a pharmaceutical composition comprising a virus vector and/or capsid and/or AAV particle of the invention in a pharmaceutically acceptable carrier and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form. For administration to a subject or for other pharmaceutical uses, the carrier will be sterile and/or physiologically compatible.

By "pharmaceutically acceptable" it is meant a material that is not toxic or otherwise undesirable, i.e., the material may be administered to a subject without causing any undesirable biological effects.

One aspect of the present invention is a method of transferring a nucleic acid molecule to a cell in vitro. The virus vector may be introduced into the cells at the appropriate multiplicity of infection according to standard transduction methods suitable for the particular target cells. Titers of virus vector to administer can vary, depending upon the target cell type and number, and the particular virus vector, and can be determined by those of skill in the art without undue experimentation. In representative embodiments, at least about $10^3$ infectious units, optionally at least about $10^5$ infectious units are introduced to the cell.

The cell(s) into which the virus vector is introduced can be of any type, including but not limited to neural cells (including cells of the peripheral and central nervous systems, in particular, brain cells such as neurons and oligodendricytes), lung cells, cells of the eye (including retinal cells, retinal pigment epithelium, and corneal cells), epithelial cells (e.g., gut and respiratory epithelial cells), muscle cells (e.g., skeletal muscle cells, cardiac muscle cells, smooth muscle cells and/or diaphragm muscle cells), dendritic cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. In representative embodiments, the cell can be any progenitor cell. As a further possibility, the cell can be a stem cell (e.g., neural stem cell, liver stem cell). As still a further alternative, the cell can be a cancer or tumor cell. Moreover, the cell can be from any species of origin, as indicated above.

The virus vector can be introduced into cells in vitro for the purpose of administering the modified cell to a subject. In particular embodiments, the cells have been removed from a subject, the virus vector is introduced therein, and the cells are then administered back into the subject. Methods of removing cells from subject for manipulation ex vivo, followed by introduction back into the subject are known in the art (see, e.g., U.S. Pat. No. 5,399,346). Alternatively, the recombinant virus vector can be introduced into cells from a donor subject, into cultured cells, or into cells from any other suitable source, and the cells are administered to a subject in need thereof (i.e., a "recipient" subject).

Suitable cells for ex vivo nucleic acid delivery are as described above. Dosages of the cells to administer to a subject will vary upon the age, condition and species of the subject, the type of cell, the nucleic acid being expressed by the cell, the mode of administration, and the like. Typically, at least about $10^2$ to about $10^8$ cells or at least about $10^3$ to about $10^6$ cells will be administered per dose in a pharmaceutically acceptable carrier. In particular embodiments, the cells transduced with the virus vector are administered to the subject in a treatment effective or prevention effective amount in combination with a pharmaceutical carrier.

In some embodiments, the virus vector is introduced into a cell and the cell can be administered to a subject to elicit an immunogenic response against the delivered polypeptide (e.g., expressed as a transgene or in the capsid). Typically, a quantity of cells expressing an immunogenically effective amount of the polypeptide in combination with a pharmaceutically acceptable carrier is administered. An "immunogenically effective amount" is an amount of the expressed polypeptide that is sufficient to evoke an active immune response against the polypeptide in the subject to which the pharmaceutical formulation is administered. In particular embodiments, the dosage is sufficient to produce a protective immune response (as defined above). The degree of protection conferred need not be complete or permanent, as long as the benefits of administering the immunogenic polypeptide outweigh any disadvantages thereof.

A further aspect of the invention is a method of administering the virus vector and/or virus capsid to subjects. Administration of the virus vectors and/or capsids according to the present invention to a human subject or an animal in need thereof can be by any means known in the art. Optionally, the virus vector and/or capsid is delivered in a treatment effective or prevention effective dose in a pharmaceutically acceptable carrier.

The virus vectors and/or capsids of the invention can further be administered to elicit an immunogenic response (e.g., as a vaccine). Typically, immunogenic compositions of the present invention comprise an immunogenically effective amount of virus vector and/or capsid in combination with a pharmaceutically acceptable carrier. Optionally, the dosage is sufficient to produce a protective immune response (as defined above). The degree of protection conferred need not be complete or permanent, as long as the benefits of administering the immunogenic polypeptide outweigh any disadvantages thereof. Subjects and immunogens are as described above.

Dosages of the virus vector and/or capsid to be administered to a subject depend upon the mode of administration, the disease or condition to be treated and/or prevented, the individual subject's condition, the particular virus vector or capsid, and the nucleic acid to be delivered, and the like, and can be determined in a routine manner. Exemplary doses for achieving therapeutic effects are titers of at least about $10^5$, $10^6$, $10^7$, $10^8$, $10^9$, $10^{10}$, $10^{11}$, $10^{12}$, $10^3$, $10^{14}$, $10^{15}$ transducing units, optionally about $10^8$ to about $10^{13}$ transducing units.

In particular embodiments, more than one administration (e.g., two, three, four, five, six, seven, eight, nine, 10, etc., or more administrations) may be employed to achieve the desired level of gene expression over a period of various intervals, e.g., hourly, daily, weekly, monthly, yearly, etc.

Exemplary modes of administration include oral, rectal, transmucosal, intranasal, inhalation (e.g., via an aerosol), buccal (e.g., sublingual), vaginal, intrathecal, intraocular, transdermal, in utero (or in ovo), parenteral (e.g., intravenous, subcutaneous, intradermal, intramuscular [including administration to skeletal, diaphragm and/or cardiac muscle], intradermal, intrapleural, intracerebral, and intraarticular), topical (e.g., to both skin and mucosal surfaces, including airway surfaces, and transdermal administration), intralymphatic, and the like, as well as direct tissue or organ injection (e.g., to liver, skeletal muscle, cardiac muscle, diaphragm muscle or brain). Administration can also be to a tumor (e.g., in or near a tumor or a lymph node). The most suitable route in any given case will depend on the nature and severity of the condition being treated and/or prevented and on the nature of the particular vector that is being used.

The virus vector and/or capsid can be delivered by intravenous administration, intra-arterial administration, intraperitoneal administration, limb perfusion, (optionally, isolated limb perfusion of a leg and/or arm; see, e.g. Arruda et al. (2005) *Blood* 105: 3458-3464), and/or direct intramuscular injection. In particular embodiments, the virus vector and/or capsid is administered to a limb (arm and/or leg) of a subject (e.g., a subject with muscular dystrophy such as DMD) by limb perfusion, optionally isolated limb perfusion (e.g., by intravenous or intra-articular administration). In embodiments of the invention, the virus vectors and/or capsids of the invention can advantageously be administered without employing "hydrodynamic" techniques. Tissue delivery (e.g., to muscle) of prior art vectors is often enhanced by hydrodynamic techniques (e.g., intravenous/intravenous administration in a large volume), which increase pressure in the vasculature and facilitate the ability of the vector to cross the endothelial cell barrier. In particular embodiments, the viral vectors and/or capsids of the invention can be administered in the absence of hydrodynamic techniques such as high volume infusions and/or elevated intravascular pressure (e.g., greater than normal systolic pressure, for example, less than or equal to a 5%, 10%, 15%, 20%, 25% increase in intravascular pressure over normal systolic pressure). Such methods may reduce or avoid the side effects associated with hydrodynamic techniques such as edema, nerve damage and/or compartment syndrome.

The invention can also be practiced to produce antisense RNA, RNAi or other functional RNA (e.g., a ribozyme) for systemic delivery.

Injectables can be prepared in conventional forms, either as liquid solutions or suspensions, solid forms suitable for solution or suspension in liquid prior to injection, or as emulsions. Alternatively, one may administer the virus vector and/or virus capsids of the invention in a local rather than systemic manner, for example, in a depot or sustained-release formulation. Further, the virus vector and/or virus capsid can be delivered adhered to a surgically implantable matrix (e.g., as described in U.S. Patent Publication No. US-2004-0013645-A1).

The virus vectors and virus capsids can be administered to cells of the brain and/or tissues of the CNS and may advantageously result in broader distribution of the virus vector or capsid than would be observed in the absence of the present invention.

In particular embodiments, the delivery vectors of the invention may be administered to treat diseases of the CNS, including genetic disorders, neurodegenerative disorders, psychiatric disorders and tumors. Illustrative diseases of the CNS include, but are not limited to Alzheimer's disease, Parkinson's disease, Huntington's disease, Canavan disease, Leigh's disease, Refsum disease, Tourette syndrome, primary lateral sclerosis, amyotrophic lateral sclerosis, progressive muscular atrophy, Pick's disease, muscular dystrophy, multiple sclerosis, myasthenia gravis, Binswanger's disease, trauma due to spinal cord or head injury, Tay Sachs disease, Lesch-Nyan disease, epilepsy, cerebral infarcts, psychiatric disorders including mood disorders (e.g., depression, bipolar affective disorder, persistent affective disorder, secondary mood disorder), schizophrenia, drug dependency (e.g., alcoholism and other substance dependencies), neuroses (e.g., anxiety, obsessional disorder, somatoform disorder, dissociative disorder, grief, post-partum depression), psychosis (e.g., hallucinations and delusions), dementia, paranoia, attention deficit disorder, psychosexual disorders, sleeping disorders, pain disorders, eating or weight disorders (e.g., obesity, cachexia, anorexia nervosa, and bulemia) and cancers and tumors (e.g., pituitary tumors) of the CNS.

Disorders of the CNS include ophthalmic disorders involving the retina, posterior tract, and optic nerve (e.g., retinitis pigmentosa, diabetic retinopathy and other retinal degenerative diseases, uveitis, age-related macular degeneration, glaucoma).

Most, if not all, ophthalmic diseases and disorders are associated with one or more of three types of indications: (1) angiogenesis, (2) inflammation, and (3) degeneration. The delivery vectors of the present invention can be employed to deliver anti-angiogenic factors; anti-inflammatory factors; factors that retard cell degeneration, promote cell sparing, or promote cell growth and combinations of the foregoing.

Diabetic retinopathy, for example, is characterized by angiogenesis. Diabetic retinopathy can be treated by delivering one or more anti-angiogenic factors either intraocularly (e.g., in the vitreous) or periocularly (e.g., in the sub-Tenon's region). One or more neurotrophic factors may also be co-delivered, either intraocularly (e.g., intravitreally) or periocularly.

Uveitis involves inflammation. One or more anti-inflammatory factors can be administered by intraocular (e.g., vitreous or anterior chamber) administration of a delivery vector of the invention.

Retinitis pigmentosa, by comparison, is characterized by retinal degeneration. In representative embodiments, retinitis pigmentosa can be treated by intraocular (e.g., vitreal administration) of a delivery vector encoding one or more neurotrophic factors.

Age-related macular degeneration involves both angiogenesis and retinal degeneration. This disorder can be treated by administering the inventive deliver vectors encoding one or more neurotrophic factors intraocularly (e.g., vitreous) and/or one or more anti-angiogenic factors intraocularly or periocularly (e.g., in the sub-Tenon's region).

Glaucoma is characterized by increased ocular pressure and loss of retinal ganglion cells. Treatments for glaucoma include administration of one or more neuroprotective agents that protect cells from excitotoxic damage using the inventive delivery vectors. Such agents include N-methyl-D-aspartate (NMDA) antagonists, cytokines, and neurotrophic factors, delivered intraocularly, optionally intravitreally.

In other embodiments, the present invention may be used to treat seizures, e.g., to reduce the onset, incidence or severity of seizures. The efficacy of a therapeutic treatment for seizures can be assessed by behavioral (e.g., shaking, ticks of the eye or mouth) and/or electrographic means (most seizures have signature electrographic abnormalities). Thus, the invention can also be used to treat epilepsy, which is marked by multiple seizures over time.

In one representative embodiment, somatostatin (or an active fragment thereof) is administered to the brain using a delivery vector of the invention to treat a pituitary tumor. According to this embodiment, the delivery vector encoding somatostatin (or an active fragment thereof) is administered by microinfusion into the pituitary. Likewise, such treatment can be used to treat acromegaly (abnormal growth hormone secretion from the pituitary). The nucleic acid (e.g., GenBank Accession No. J00306) and amino acid (e.g., GenBank Accession No. P01166; contains processed active peptides somatostatin-28 and somatostatin-14) sequences of somatostatins are known in the art.

In particular embodiments, the vector can comprise a secretory signal as described in U.S. Pat. No. 7,071,172.

In representative embodiments of the invention, the virus vector and/or virus capsid is delivered to the CNS (e.g., to the brain or to the eye) after systemic administration. The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. The virus vector and/or capsid may also be delivered to different regions of the eye such as the retina, cornea and/or optic nerve after peripheral administration.

The virus vector and/or capsid may be delivered into the cerebrospinal fluid (e.g., by lumbar puncture) for more disperse administration of the delivery vector. The virus vector and/or capsid may further be administered intravascularly to the CNS in situations in which the blood-brain barrier has been perturbed (e.g., brain tumor or cerebral infarct).

The virus vector and/or capsid can be administered to the desired region(s) of the CNS by any route known in the art, including but not limited to, intrathecal, intra-ocular, intracerebral, intraventricular, intravenous (e.g., in the presence of a sugar such as mannitol), intranasal, intra-aural, intraocular (e.g., intra-vitreous, sub-retinal, anterior chamber) and peri-ocular (e.g., sub-Tenon's region) delivery as well as intramuscular delivery with retrograde delivery to motor neurons.

In particular embodiments, the virus vector and/or capsid is administered in a liquid formulation by direct injection (e.g., stereotactic injection) to the desired region or compartment in the CNS. In other embodiments, the virus vector and/or capsid may be provided by topical application to the desired region or by intra-nasal administration of an aerosol formulation. Administration to the eye, may be by topical application of liquid droplets. As a further alternative, the virus vector and/or capsid may be administered as a solid, slow-release formulation (see, e.g., U.S. Pat. No. 7,201,898).

In yet additional embodiments, the virus vector can used for retrograde transport to treat and/or prevent diseases and disorders involving motor neurons (e.g., amyotrophic lateral sclerosis (ALS); spinal muscular atrophy (SMA), etc.). For example, the virus vector can be delivered to muscle tissue from which it can migrate into neurons.

In some embodiments, the present invention provides a method of identifying a BBB-passable peptide that binds to an AAV particle, the method comprising: a) injecting a phage peptide library of peptides into a subject; b) collecting central nervous system (CNS) tissue comprising the phage of the phage peptide library that has passed the BBB; c) amplifying the phage in vitro; d) incubating the phage with AAV particles; e) harvesting the phage bound to the AAV particles; f) repeating steps d)-e) for at least about 3 cycles; and g) sequencing the phage harvested in the final cycle, thereby identifying the BBB-passable peptide that binds to an AAV particle. The phage library may be any known and/or later generated phage library, including, but not limited to, the Ph.D.—12 Phage Display Peptide Library (New England Biolabs). The CNS tissue may be any tissue of the CNS, including but not limited to, the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes. cortex, basal ganglia, hippocampus and portaamygdala), limbic system, neocortex, corpus striatum, cerebrum, and inferior colliculus. In some embodiments, the method comprises collecting brain tissue. Amplification of the phage may be performed with any known technique in the art. Repetitions (e.g., cycles) of incubating the phage in vitro, incubating the phage with an AAV particle, and harvesting the phage bound to the AAV particle (e.g., repeating steps d)-e)) may be performed for, at least, about 2 to about 5 cycles, e.g., about 2, 3, 4, or 5 cycles. In some embodiments, repeating steps d)-e) may be performed for at least about 3 cycles. In some embodiments, repeating steps d)-e) may be performed for at least about 4 cycles. The AAV particles may be any AAV virion of this invention, including but not limited to, AAV8 and/or AAV9. In some embodiments, the method provides for incubating the phage with AAV9 particles (e.g., with a plurality of AAV9 particles).

The invention is further described by any of the following numbered paragraphs:

1. An adeno-associated virus (AAV) particle comprising a surface-bound peptide, wherein the peptide bound to the surface of the AAV particle is selected from the group consisting of:
   a) Angiopep-2;
   b) GSH;
   c) HIV-1 TAT (48-60);
   d) ApoE (159-167)2;
   e) Leptin 30 (61-90);
   f) THR;
   g) PB5-3;
   h) PB5-5;
   i) PB5-14; and
   j) any combination of (a)-(i) above.
2. The AAV particle of paragraph 1, wherein the AAV is of a serotype or any combination of serotypes listed in Table 1.
3. The AAV particle of paragraph 1, wherein the AAV is AAV8, AAV9, AAV2, AAV2i8, AAV9.45 or any variant, mutant, or combination thereof.
4. The AAV particle of any preceding paragraph, wherein the protein bound to the surface of the AAV particle is present on the AAV particle surface in an amount ranging from about 2000 protein molecules per AAV particle to about $4 \times 10^7$ protein molecules per AAV particle.
5. The AAV particle of any preceding paragraph, comprising a heterologous nucleic acid molecule.
6. The AAV particle of any preceding paragraph, wherein said AAV particle comprising the surface-bound peptide has enhanced transduction activity across the blood brain barrier (BBB) relative to an AAV particle lacking the surface-bound protein.
7. The AAV particle of any preceding paragraph, wherein said AAV particle comprising the surface-bound peptides has enhanced transduction activity of cells of the brain and/or central nervous system.
8. A pharmaceutical formulation comprising the AAV particle of any preceding paragraph in a pharmaceutically acceptable carrier.
9. A method of administering a nucleic acid to a cell of the brain and/or central nervous system, comprising contacting the cell with the AAV particle of any of paragraphs 1-7 or the pharmaceutical formulation of paragraph 8.
10. A method of delivering a nucleic acid to a cell of the brain and/or central nervous system of a subject, comprising administering to the subject the AAV particle of any of paragraphs 1-7 or the pharmaceutical formulation of paragraph 8.
11. The method of paragraph 9, wherein the AAV particle is administered systemically.
12. The method of paragraphs 9-11, wherein the subject is a human subject.
13. A modified adeno-associated virus (AAV) capsid protein comprising an insertion of a polypeptide at a position between amino acids corresponding to amino acids 588 and 589 of AAV9, wherein the polypeptide is selected from the group consisting of:
   a) PB5-3;
   b) PB5-5;
   c) PB5-14;
   d) Angiopep-2;
   e) GSH;
   f) HIV-1 TAT (48-60);
   g) ApoE (159-167)2;
   h) Leptin 30 (61-90); and
   i) THR.
14. The modified AAV capsid protein of paragraph 13, wherein the inserted polypeptide further comprises a glycine at the N-terminus, the C-terminus, or both the N- and C-terminus.
15. The modified AAV capsid protein of paragraph 13 or 14, which is of an AAV serotype or any combination of serotypes listed in Table 1.
16. The modified AAV capsid protein of any one of paragraphs 13-15, which is an AAV9 capsid protein.
17. A nucleic acid molecule encoding a modified AAV capsid protein of any one of paragraphs 13-16.
18. The nucleic acid molecule of paragraph 17 that is comprised within a vector.
19. An AAV particle comprising the modified AAV capsid protein of any one of paragraphs 13-16.

20. The AAV particle of paragraph 19, that is an AAV serotype or any combination of serotypes listed in Table 1.
21. The AAV particle of paragraph any one of paragraphs 19-20, wherein the AAV is AAV8, AAV9, AAV2, AAV2i8, AAV9.45 or any variant, mutant, or combination thereof.
22. The AAV particle of any one of paragraphs 19-21, comprising a heterologous nucleic acid molecule.
23. The AAV particle of paragraph 22, wherein the heterologous nucleic acid molecule encodes a therapeutic polypeptide
24. The AAV particle of any one of paragraphs 19-23, that has enhanced transduction activity across the blood brain barrier (BBB) relative to a control AAV particle with a capsid lacking the inserted polypeptide.
25. The AAV particle of any one of paragraphs 19-24, that has enhanced transduction activity of cells of the brain and/or central nervous system relative to a control AAV particle with a capsid lacking the inserted polypeptide.
26. The AAV particle of any one of paragraphs 19-25, that has enhanced transduction to one or more of cortex, striatum, thalamus, cerebellum and spinal cord of a subject.
27. The AAV particle of any one of paragraphs 19-26, that has enhanced transduction to one or more of astrocytes, CC1+ oligodendrocytes, neuronal subtypes including NeuN+ cells throughout the brain, midbrain tyrosine hydroxylase (TH)+ dopaminergic neurons, Calbindin+ cerebellar Purkinje cells, interneuron populations and CD31+ endothelial cells of a subject.
28. A pharmaceutical formulation comprising the AAV particle of any of paragraphs 19-27 or the modified capsid protein of any of paragraphs 13-17, in a pharmaceutically acceptable carrier.
29. A method of administering a nucleic acid to a cell of the brain and/or central nervous system, comprising contacting the cell with the AAV particle of any of paragraphs 19-27 or the pharmaceutical formulation of paragraph 28.
30. A method of delivering a nucleic acid to a cell of the brain and/or central nervous system of a subject, comprising administering to the subject the AAV particle of any of paragraphs 19-27 or the pharmaceutical formulation of paragraph 28.
31. The method of paragraph 30, wherein the AAV particle or pharmaceutical formulation is administered systemically.
32. The method of any of paragraphs 29-31, wherein the subject is a human subject.

Having described the present invention, the same will be explained in greater detail in the following examples, which are included herein for illustration purposes only, and which are not intended to be limiting to the invention.

EXAMPLES

Example 1

Among the non-invasive approaches, BBB shuttle peptides have proved their potential in preclinical research and clinical trials because of their easier obtaining, lower immunogenicity and higher chemical versatility. The BBB shuttle peptides are molecules capable of transporting a variety of cargoes into the brain parenchyma without disrupting the BBB integrity. Several targeted peptides have been identified with the ability to cross the BBB for brain delivery. For example, the versatile BBB shuttle peptide, Angiopep-2, could effectively transport a wide variety of particles across the BBB mediated by low-density lipoprotein receptor-related protein-1.

Cell lines and peptides. HEK293 cells and human Huh7 cells were maintained in Dulbecco's modified Eagle's medium (DMEM) with supplementation of 10% (v/v) heat inactivated fetal bovine serum (FBS), penicillin (100 U/mL), and streptomycin (100 ug/mL). Variant Chinese hamster ovary (CHO)-TRVB cells, which are devoid of endogenous TfR1, were kindly provided by Dr. T. E. McGraw (Weill Cornell Medical College, NY) and were grown in F12 mix medium (Lonza, USA) supplemented with 5% FBS. Human brain endothelial capillary hCMEC/D3 cells (Millipore, USA) were plated in collagen I (Thermo Fisher Scientific, USA)-coated dishes and grown in EBM-2 medium (Lonza, USA) supplemented with 0.025% VEGF, 0.025% LONG® R3 IGF-I, 0.025% hEGF, 0.0025% hBFGF, 0.01% hydrocortisone, penicillin (100 U/mL), streptomycin (100 μg/mL), and 2.5% FBS. All cells were maintained at 37° C. and 5% $CO_2$. All peptides with >95% purity were synthesized by Neo Scientific (MA, USA) and KareBay Biochem, Inc. (NJ, USA). Peptides (stock solution, 10 mM) were dissolved in Dulbecco's phosphate-buffered saline (DPBS) with 10% DMSO. The 5'-FAM labeled THR peptide was synthesized by High-Throughput Peptide Synthesis and Array (HTPSA) Core Facility at the University of North Carolina (UNC) at Chapel Hill.

Plasmid construction. Plasmid mCherry-TFR-20 (Addgene 55144) expressing human TfR1 was purchased from Addgene. The plasmid named mCherry-mTfR-20 was constructed by PCR as follows: mouse TfR1 gene was amplified from the plasmid pAcGP67A-murine TfR (Addgene 12392) with forward primer 5-TATTCTCGAGCGCCACCAT-GATGGATCAAGCCAGATCAG-3 (SEQ ID NO:131) and reverse primer 5-AATAGAATTCTGAAAACTCATTGT-CAATATTCCAAAT-3 (SEQ ID NO:132), and swapped the human TfR1 gene of the plasmid with mCherry-TFR-20.

Virus production. Recombinant AAV8 full particles expressing luciferase, driven by the CBA promoter (AAV8/luc), were produced using triple transfection in HEK293 cells as previously described. Briefly, AAV transgene plasmid pTR/CBA-luc, AAV helper plasmid containing AAV8 Rep and Cap genes, and Ad helper plasmid pXX680 were co-transfected into HEK293 cells. 48 h post-transfection, HEK293 cells were collected and lysed. Supernatant was subjected to CsCl gradient ultra-centrifugation. Fractions containing AAV were collected and viral titer was determined by real-time quantitative PCR (qPCR) using the Light Cycler 480 instrument with SYBR green (Roche, USA) and a pair of primers that were designed to bind to a homologous sequence on the Inverted Terminal Repeats (ITR) region.

MTT assay, The 3-(4, 5-dimethyl-2-thiazolyl)-2, 5-diphenyl-2H-tetrazolium bromide (MTT) assay was performed to measure the cytotoxicity of peptides to the cells with the Vybrant® MTT cell proliferation assay kit (Thermo Fisher Scientific, USA) according to the manufacture's instruction. Cells grown in a 48-well plate were transduced with the complex of AAV8/luc and peptides. After 48 h, medium was removed and replaced with fresh culture medium. 10 μl MTT was added into the cells and incubated for 4 h at 37° C., and then 100 μl of the SDS-HCl solution was added into the wells and further incubated for 4 h at 37° C. before absorption was measured at 570 nm by the Victor instrument (Perkin-Elmer, MA).

In vitro transduction assay. At least 4-5 h prior to AAV transduction, cells were seeded in 48-well plates with a density of 1E+05 cells each well. Cells were infected with 1E+04 vector genomes (vg) of AAV8/luc virus per cell and harvested after 48 h. Luciferase activity was measured following manufacturer's instruction (Promega, Madison, WI).

Neutralization assay. Huh7 or HEK293 cells were seeded in 48-well plates with a density of 5E+04 cells each well. The complex of AAV8/luc and different concentrations of THR was incubated at 4° C. for 2 h, then, two-fold dilutions of the mouse AAV8 sera were incubated with 1E+04vg of AAV8/luc virus or the complex of AAV8/luc and THR per cell for 1 h at 37° C. The final mixture was added into cells and incubated at 37° C. for 48 h. Cells were lysed with passive lysis buffer (Promega, Madison, WI) and luciferase activity was measured. Nab titers were defined as the highest dilution for which luciferase activity was 50% lower than serum-free controls.

AAV8 binding assay. The complex of AAV8/luc and THR or human apo-transferrin protein (Sigma, 616395, USA) was incubated at 4° C. for 2 h, 10000 vg AAV8/luc virus alone or the complex was added into Huh7 cells at a cell density of 4E+05 per well for 1 h at 4° C., and then washed with DPBS 3 times. Finally, genome DNA (gDNA) was extracted from the cells with the DNeasy blood & tissue kit (Qiagen, USA) and was quantified by qPCR with luciferase primers and reference GAPDH primers.

Transcytosis assay on the hCMEC/D3 cell line. hCMEC/D3 cells were seeded into Transwell®-COL collagen-coated membrane inserts (24 Well Permeable Support with 0.4 μm Pore Polycarbonate Membrane and 6.5 mm Inserts, Sigma, USA) at a density of 5E+04 cells per well in EBM-2 cultured medium. The medium was changed every 2-3 days. After about 2 weeks, cells were washed with DPBS and cultured in serum-free EBM-2 medium and treated with AAV8 or the complex of virus and peptide. The medium in the basal chamber was collected at the indicated different time points. Viral titers were calculated by qPCR according to established procedures, and primers were designed against the ITR region.

Permeability assay in vitro. The permeability assay was performed using dextran conjugated with FITC (FITC-dextran) according to the manufacturer's instructions. Briefly, at the indicated time points, FITC-dextran was added to the cells seeded on the collagen-coated cell inserts and incubated at room temperature (RT) for 30 min. Following incubation, inserts were removed and the medium remaining in the basal chamber was collected and analyzed for fluorescence intensity of FITC-dextran using a microplate reader (Biotek Instruments) with excitation and emission wavelengths of 485 and 530 nm, respectively. All treatments were performed in triplicate.

Western blot assay. The expression of ZO-1 protein in hCMEC/D3 cells was determined. Cells were harvested in RIPA lysis buffer (Sigma, USA) supplemented with a protease inhibitor cocktail (Sigma, USA). Samples were run on 4-15% (vol/vol) TGX™ precast protein gel (Bio-Rad, USA) and transferred to nitrocellulose membranes. Membranes were blocked with 5% (wt/vol) nonfat milk followed by incubation with a specific ZO-1 monoclonal antibody (Thermo Fisher Scientific, 33-9100, USA) and extensive washing in DPBS containing 0.05% Tween-20 (PBST), and then incubated with horseradish peroxidase-conjugated goat anti-mouse IgG (Thermo Fisher Scientific, USA) for 1 h at RT. Membranes were extensively washed in PBST, and immunoblots were visualized by enhanced chemiluminescence detection (ECL, Thermo, USA).

Immunofluorescence. Plasmids mCherry-TFR-20 and mCherry-mTfR-20 were separately transfected into the 50-70% confluent CHO-TRVB cells grown on glass coverslips using lipofectamine 3000 reagent (Invitrogen, USA). After 48 h post-transfection, the coverslips were washed and incubated with 1 nM 5-FAM-THR at 37° C. for 1 h, then cells were acid-washed with 0.2 M glycine/HCl, pH 2.2, and fixed in 4% paraformaldehyde for 30 min at 4° C. Finally, DAPI was used at a 1:5,000 dilution for 5 min at RT. Coverslips were mounted and imaged on the Olympus IX-83 fluorescence microscope.

AAV8 competitive binding assay. For THR competitive binding analysis, 10 ul of Protein G resin (Thermo, USA) per system was incubated with 1 ug of human transferrin antibody or goat IgG antibody control at 4° C. overnight. The next day, 1E+10 vg AAV8/luc were firstly incubated with human serum albumin (HSA) of physiological concentration, THR or PEPXT-1 control peptide at different dilutions or PBS on ice for 2 h, and then added the human transferrin at a 1:100 dilution of physiological concentration into the complex and incubated on ice for another 2 h. After that, the mixture was added to the complex of protein G resin and transferrin antibody and incubated at 4° C. overnight. Finally, the complex was stringently washed three times with cold DPBS. DNA from the complex was extracted and applied for qPCR to determine AAV genome copy number per cell using luc specific primers.

Animal study. C57BL/6 female mice, at 5-6 weeks of age, were originally purchased from Jackson Laboratory (Bar Harbor, ME). All mice were maintained in a specific pathogen-free facility at the UNC-Chapel Hill, All procedures were approved by the UNC Institutional Animal Care and Use Committee. Mice were administered with AAV8/Luc incubated with peptides via retro-orbital injection. Luciferase expression was imaged at the indicated time points using a Xenogen IVIS Lumina (Caliper Lifesciences, Waltham, MA) following intraperitoneal injection of D-luciferin substrate (Nanolight Pinetop, AZ). Bioluminescent images were analyzed using Living Image (PerkinElmer, Waltham, MA). At various time points after injection, blood was collected from the retro-orbital plexus, and the viral titers were tested by qPCR.

Quantitation of luciferase expression in tissues. Animals utilized for imaging studies were sacrificed after one-week post imaging work, and the tissues of the heart, liver, spleen, skeletal muscle and brain were collected, and were minced and homogenized in passive lysis buffer. Then the lysates were centrifuged at 10,000 rpm for 5 minutes to remove cellular debris. Supernatant was transferred to 96-well plates for luciferase activity analysis as described above. Total protein concentration in tissue lysates was measured using the Bradford assay (Bio-Rad Laboratories, Philadelphia, PA).

Measurement of AAV genome copy number in tissue. Total gDNA from different minced tissues was isolated with the DNeasy blood & tissue kit (Qiagen, USA). Luciferase gene was measured by qPCR assay. Mouse-lamin gene served as an internal control.

Histological processing and immunohistochemistry. Mice were anesthetized 4 weeks post-injection and transcardially perfused with 25 ml of DPBS followed by 15 ml of ice-cold 4% paraformaldehyde (PFA) in DPBS. The brains were extracted and post-fixed in 4% PFA overnight at 4° C. Brains were then dehydrated in 30% sucrose in DPBS overnight at 4° C. Serial 40 m free-floating sections of the entire brain were cut with a Cryostat (Leica Biosystems, USA). Immunohistochemistry (IHC) was performed on floating sections with primary and secondary antibodies. In brief, free-floating brain sections were permeated in Tris-buffered saline (TBS) containing 0.5% Triton X-100 (Sigma, St. Louis, MO) (TBST) for 30 min at RT, and then blocked in 0.05% TBST containing 3% donkey serum (Sigma, D9663, St. Louis, MO) for 1 h at RT. Sections were incubated at 4° C. overnight with primary antibodies diluted in blocking buffer. The following day, tissue sections were washed in 0.05% TBST and incubated with the appropriate secondary antibodies in blocking buffer for 2 h at RT. Finally, the sections were washed and were mounted onto slides with DAPI (Sigma, St. Louis, MO). The whole brain was examined under an Olympus epifluorescence microscope for general GFP expression. Z-stack confocal imaging was acquired for the region with the most abundant GFP expression. All images were captured on a Zeiss LSM 710 Spectral Confocal Laser Scanning Microscope using a 20-objective. The primary and second antibodies used in this study were as follows: rabbit anti-GFP (Abcam, Cambridge, MA, ab6556), goat anti-CD31 (Abcam), mouse anti-NeuN (Millipore, MAB377, Billerica, MA), rat anti-GFAP (Thermo Fisher Scientific, 13-0300, USA). Alexa Fluor 488-conjugated donkey anti-rabbit (Invitrogen A21206), Alexa Fluor 594-conjugated donkey anti-goat (Invitrogen A11058), Alexa Fluor 594-conjugated donkey anti-mouse (Invitrogen A21203), and Alexa Fluor 594-conjugated donkey anti-rat (Invitrogen A21209).

Statistical analysis. All quantitative data are presented as mean±standard deviation (SD). Only p≤0.05 was considered a statistically significant difference. Graphs are representative of data sets from at least three independent assays.

Figure 1B:
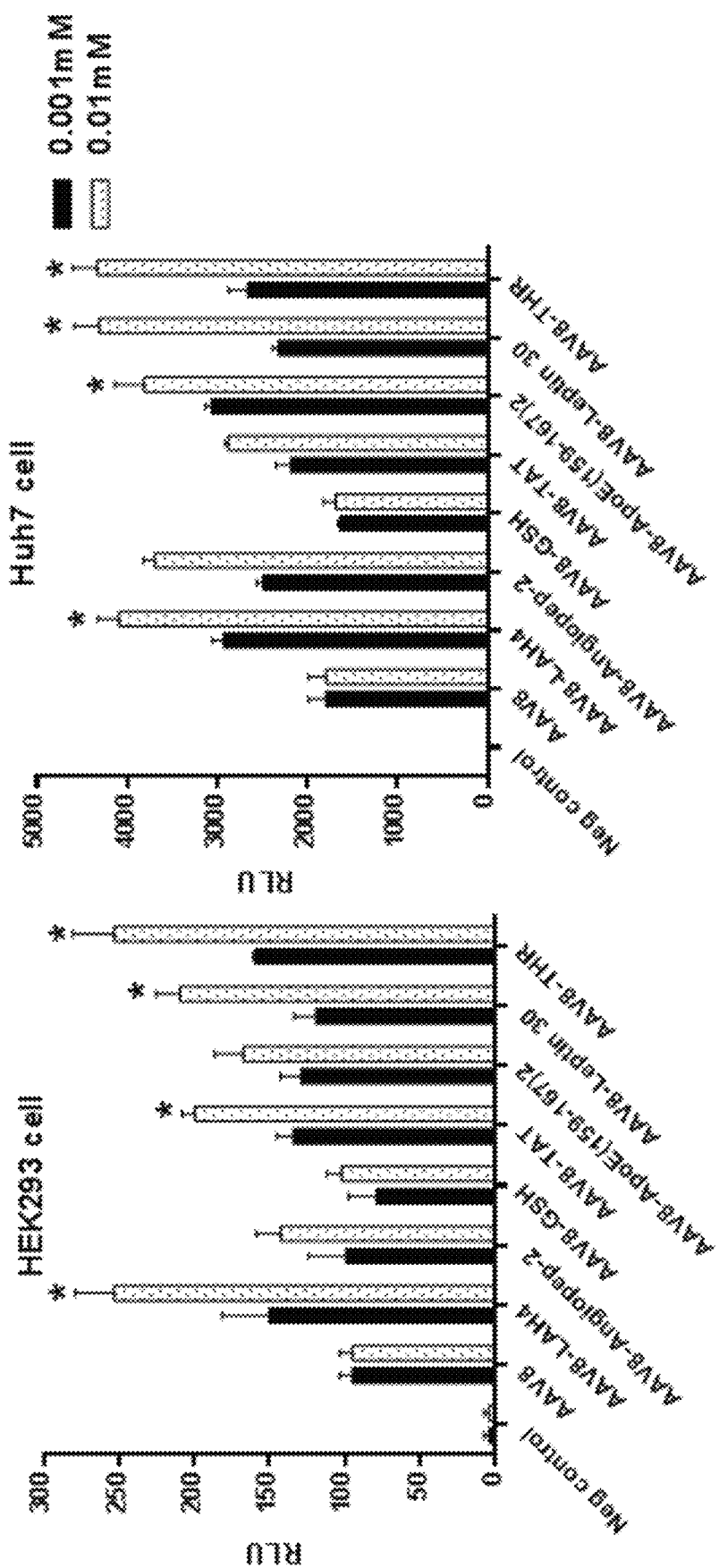

The complex of AAV8 and peptides influences AAV8 transduction in vitro and in vivo. To identify the potential and functional peptides that enhanced AAV8 transduction, we screened several reported peptides as shown in Table 5 and Table 6. First, we tested the cytotoxicity of peptides at different concentrations on cells. When peptide at 0.001 mM or 0.01 mM was added to HEK293 or Huh7 cells for 48 h, cytotoxicity was measured by MTT assay, and no cytotoxicity was observed in cells treated with peptides (FIG. 1A). After that, we performed the transduction assay in vitro. We incubated the 10000 vg AAV8/luc and peptides for 2 h at 4° C., and then applied the mixture to HEK293 cells or Huh7 cells. After 48 h, the cell lysate was collected for luciferase analysis. The results showed that several peptides, such as LAH4, HIV-1 TAT (48-60), leptin 30 (61-90) and THR, significantly enhanced AAV8 transduction to a different degree in both cell lines (FIG. 1B, p<0.05). THR peptide endowed the most significant increase of AAV8 transduction compared to the AAV8 only group in both cell lines.

Figure 2A:
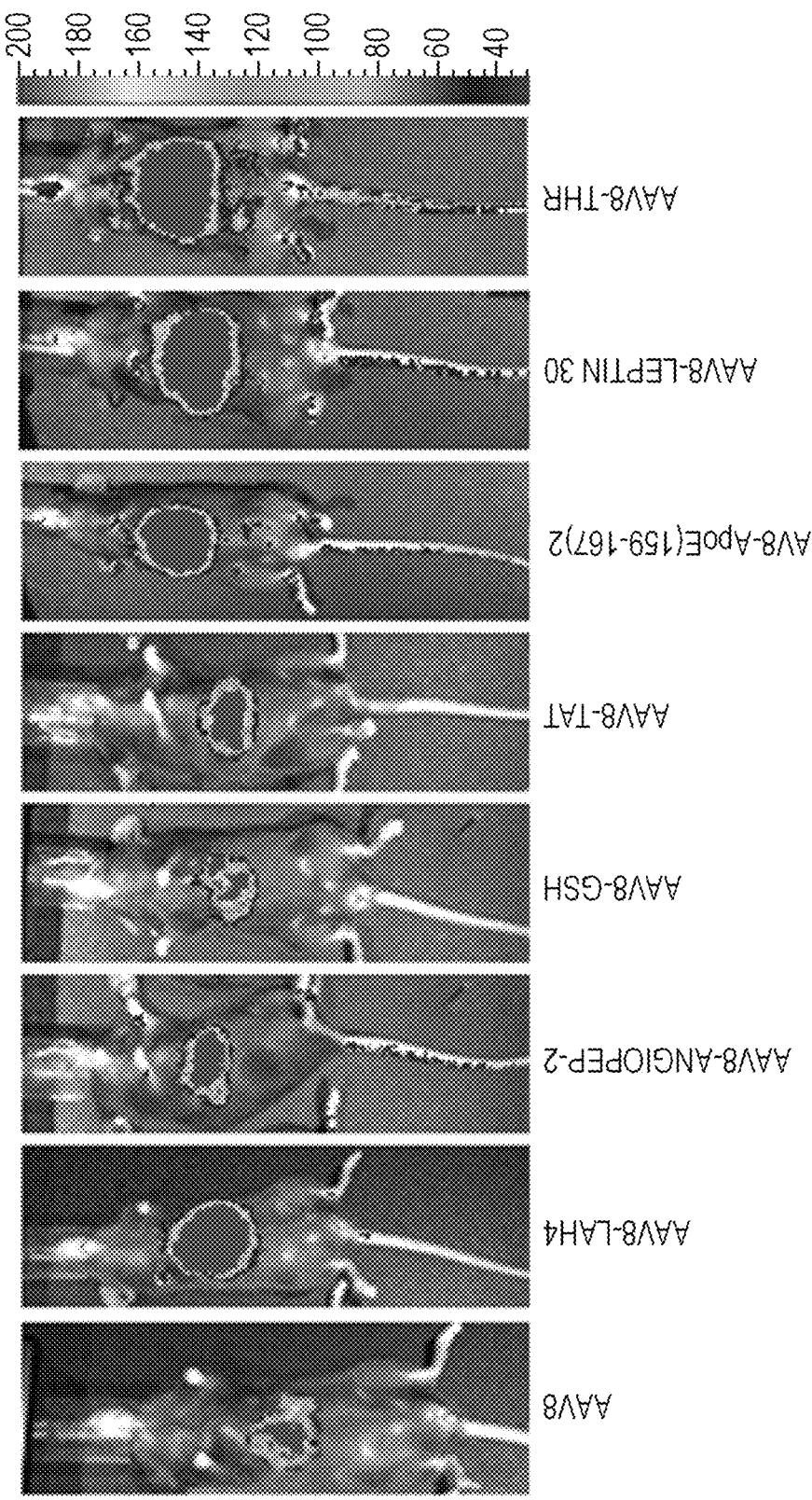
FIGS. 2A-2D show THR peptide significantly enhances AAV8 transduction in vivo, especially in the brain. 5E+10 vg of AAV8-Luc alone or the complex of AAV8 and 0.1 mM peptides were administered via intravenous injection. At one-week post-injection, the in vivo luminescence imaging (FIG. 2A) and the photon signal (FIG. 2B) was measured and calculated. At three weeks post-injection, mice were euthanized and the tissues were harvested for DNA extraction. Relative luciferase expression level (FIG. 2C) and vector copy numbers (FIG. 2D) of different tissue lysates were determined separately. The data represents the average and standard deviation from 5 mice. * $p<0.001$,  $p<0.01$, and $*p<0.05$ when compared to control mice with AAV8 treatment only.
Figure 2B:
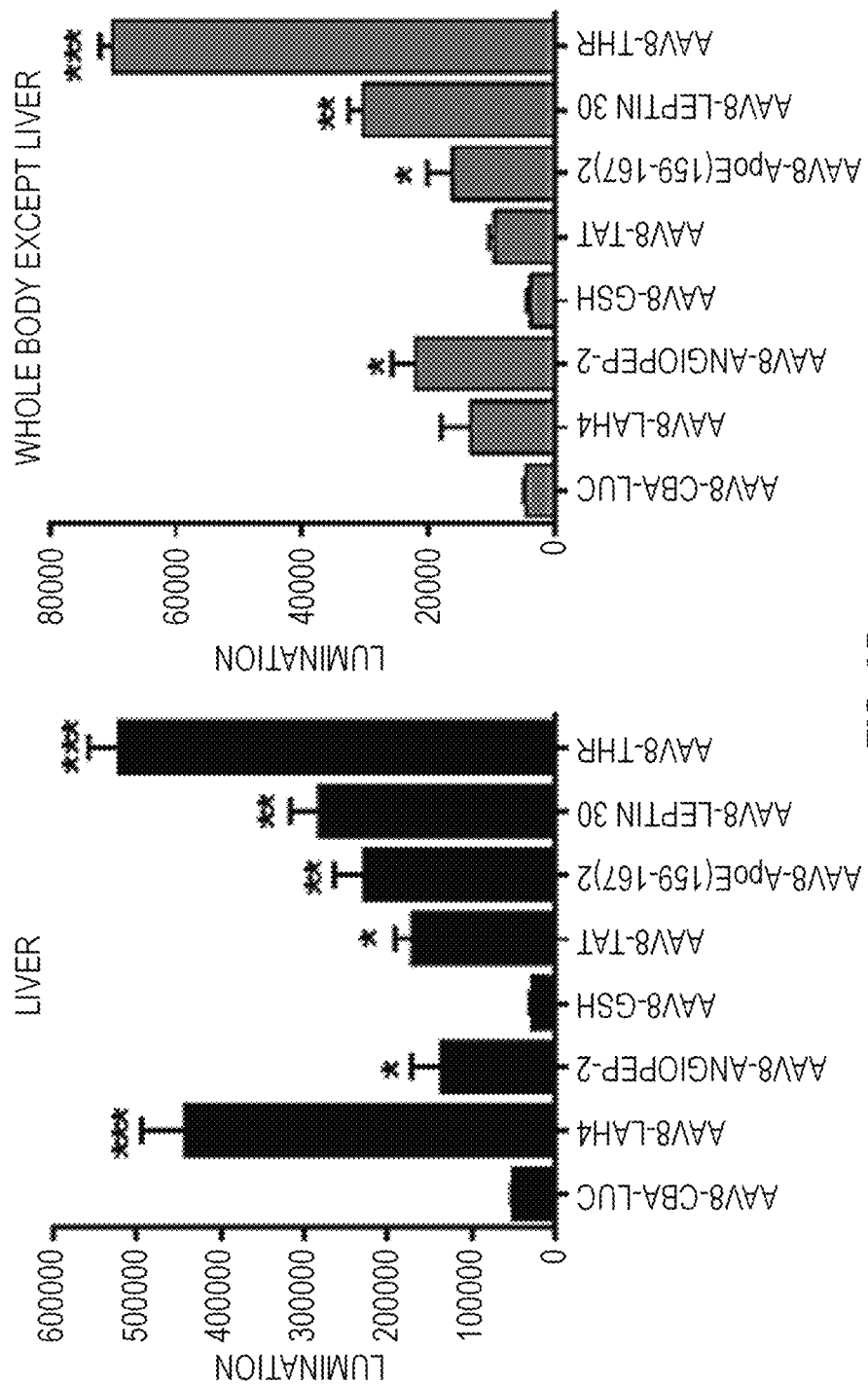

We performed an immunofluorescence assay on CHO-TRVB cells, and showed that THR could interact with mouse TfR1. To further study the effect of peptides on AAV transduction in vivo, the complexes of 0.1 mM peptides and 5E+10 vg of AAV8/luc vector were incubated and injected into C57BL/6 mice via the retro-orbital vein and imaging was carried out on the 7th day. As shown in FIGS. 2A and 2B, transgene expression in the liver was higher in AAV8 vectors treated with peptides LAH4, Angiopep-2, TAT, ApoE(159-167)2, leptin30 (61-90) and THR. More importantly, consistent with the assay in vitro, THR peptide significantly increased AAV8 transduction overall, in the whole body compared with other groups, especially in brain (FIG. 2B).

Figure 2C:
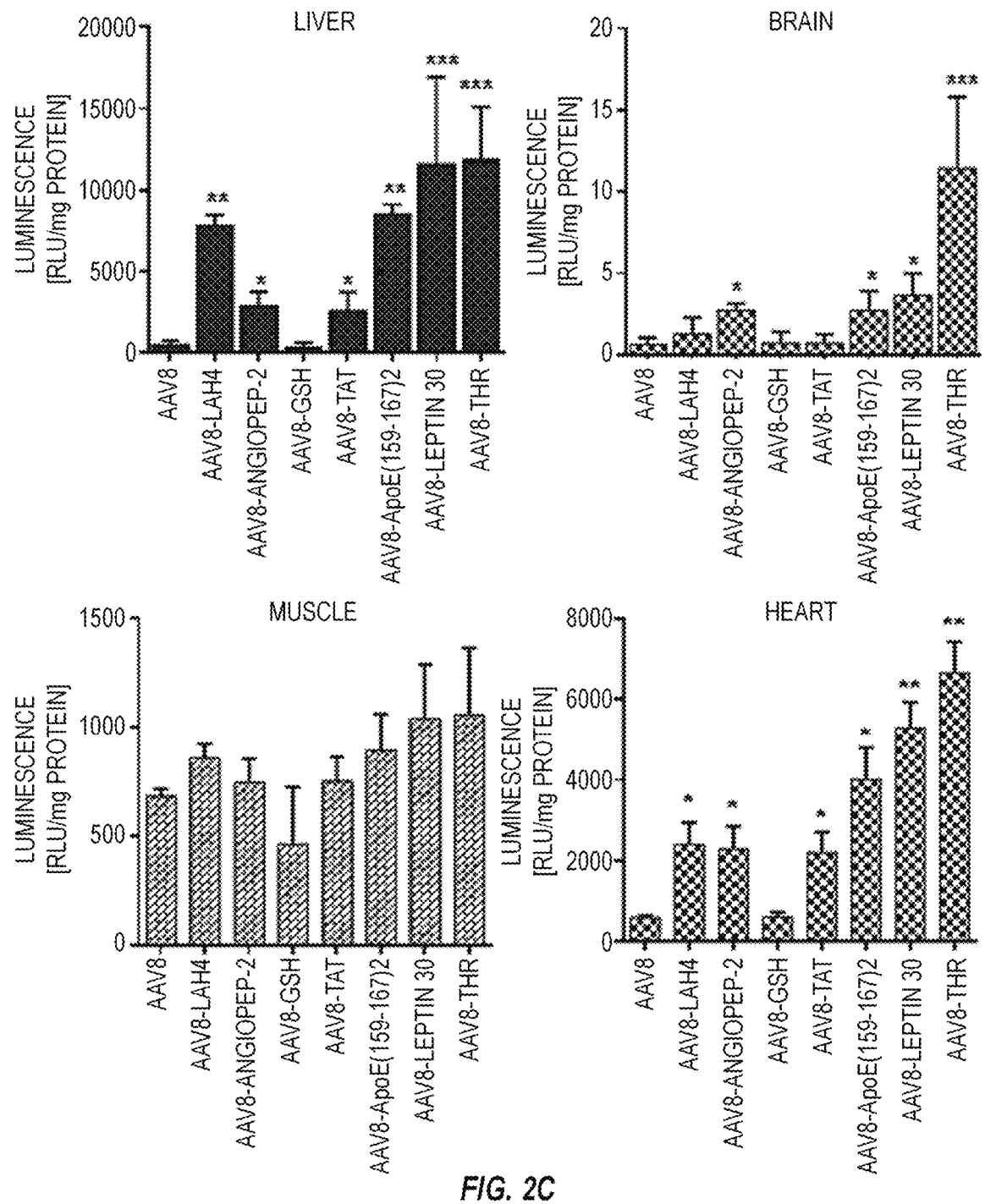
Figure 2D:
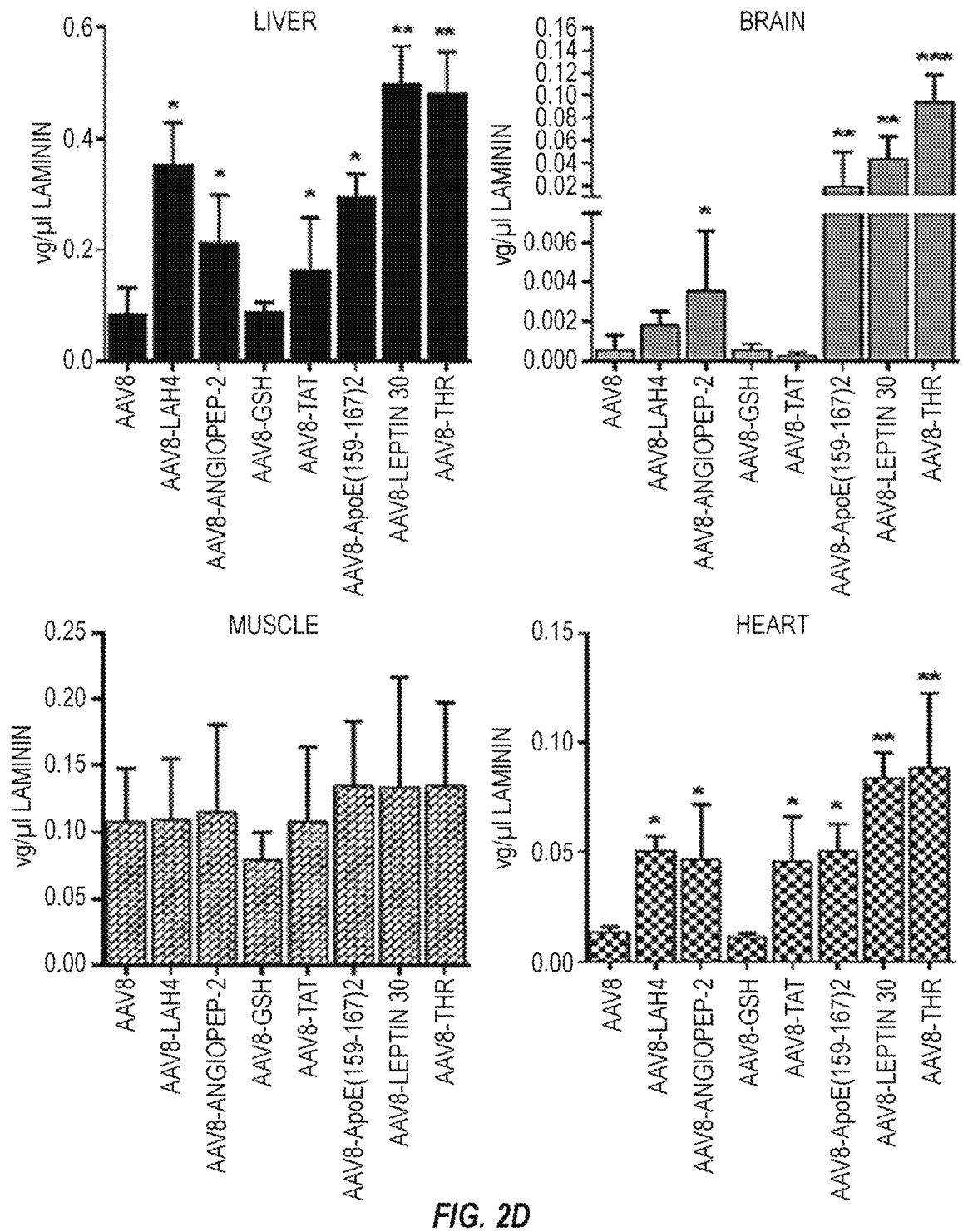

The results implicate that the THR has the potential function for the enhancing AAV8's ability to cross the BBB. Meanwhile, we evaluated the luc gene expression and viral genome number by qPCR with collected heart, liver, muscle, and brain tissues. The bio-distribution analysis showed that much higher AAV genome copy number was detected in the brain of mice receiving AAV8 vectors treated with peptides Angiopep-2, ApoE (159-167)2, leptin30 (61-90) and THR. Although LAH4 and HIV-1 TAT (48-60) increased AAV8 liver transduction, there was no effect on brain transduction (FIGS. 2C and 2D). These results indicate that BBB shuttle peptides are able to increase the amount of AAV8 vector that can cross the BBB and enhance the brain transduction. Consistent with the imaging results, incubation of peptides Angiopep-2, ApoE(159-167)2, leptin30 (61-90) and THR increased AAV8 transduction in the brain (FIGS. 2C and 2D). However, it is interesting that we could not measure the enhanced AAV8 transduction in muscle in different groups.

Figure 3A:
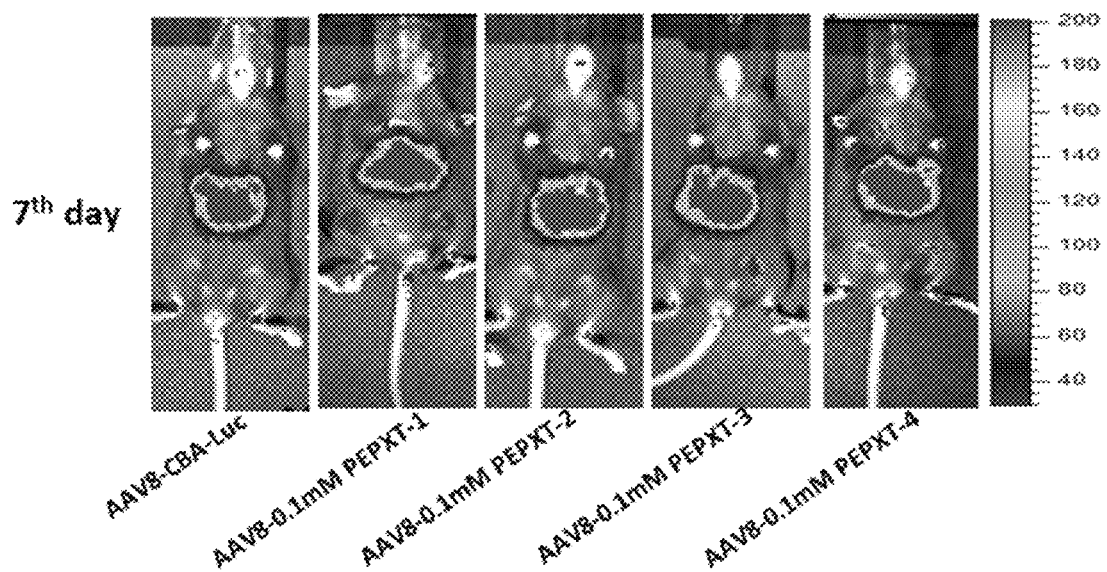
FIGS. 3A-3D show no significant effect of peptide polarity on AAV8 transduction.
Figure 3B:
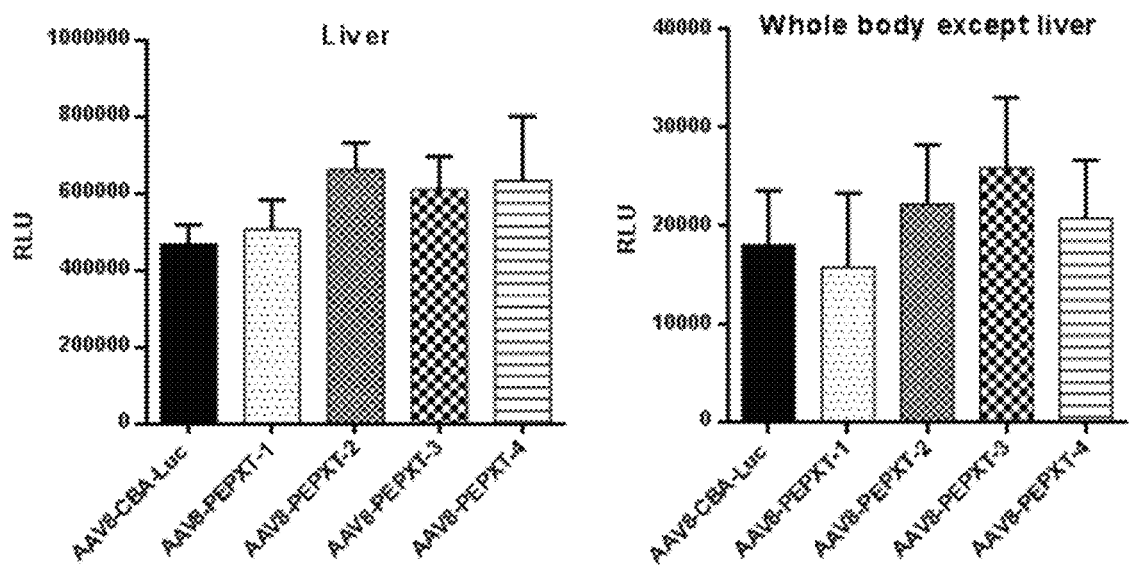
Figure 3C:
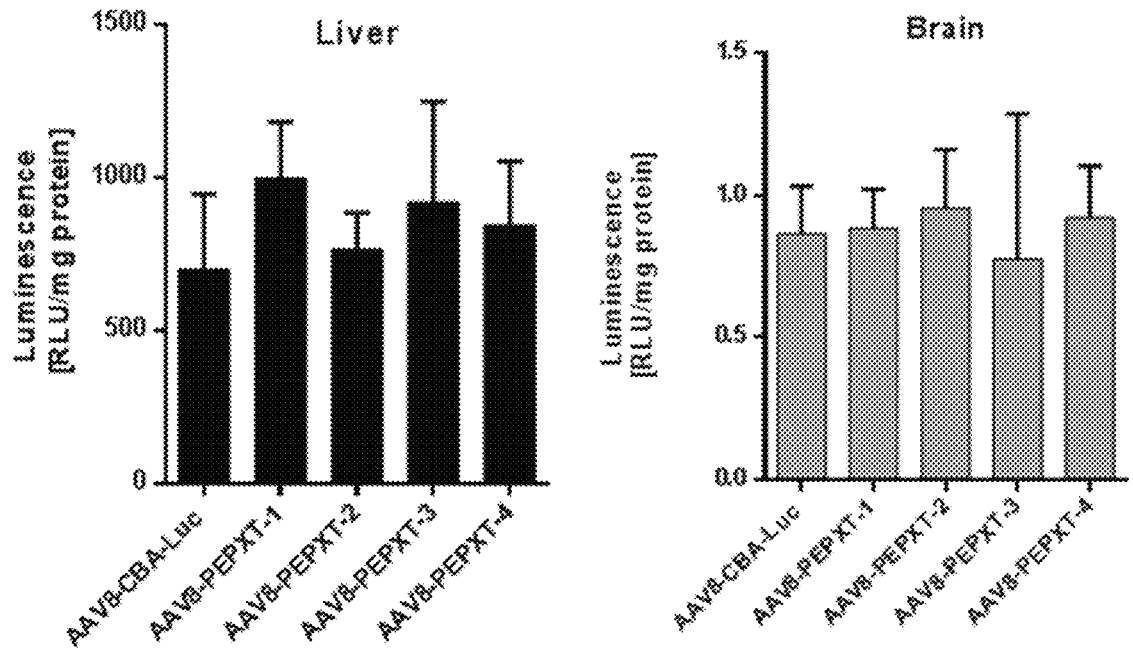
Figure 3D:
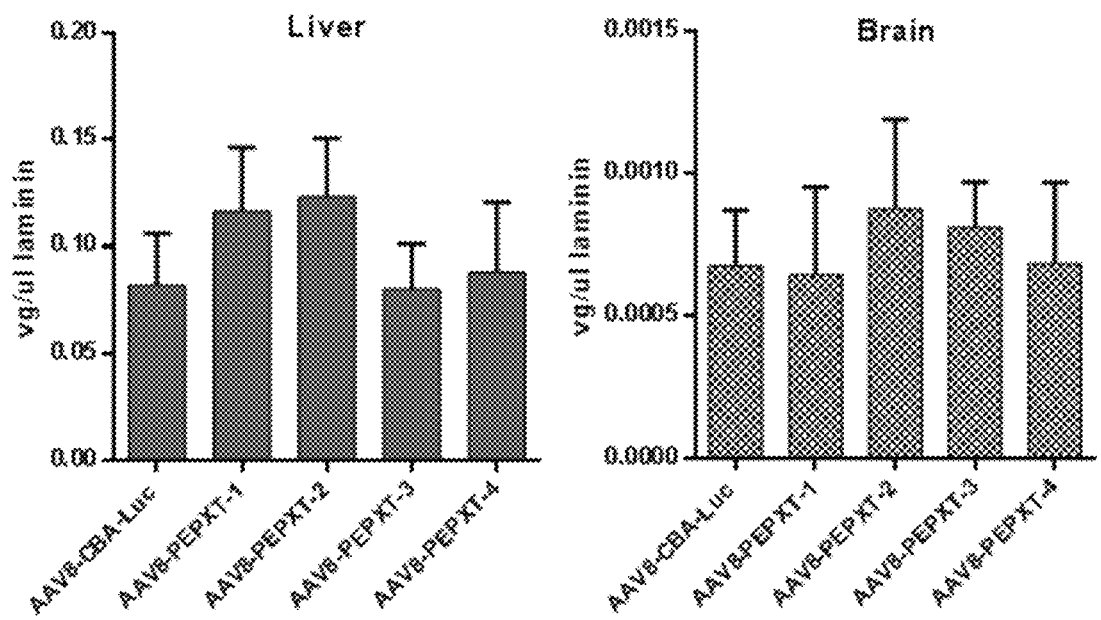

The polarity of peptides does not significantly affect AAV8 transduction. It is well known that polarity plays an important role for the function of the peptide. To rule out the non-specificity of the peptides' interaction with AAV8 virions for increasing AAV's ability to cross the BBB and enhance the brain transduction, we have designed four control peptides with different polarities (Table 5). The complex of peptides and AAV8/luc was incubated and injected into the C57BL/6 mice. At day 7 post AAV8 administration, imaging was taken. No enhancement of transgene expression in the liver and the brain was achieved (FIGS. 3A-3D). Neither the viral expression nor the viral copy genome had a significant change (FIGS. 3C and 3D). Combined with the result from peptide LAH4 and HIV-1 TAT (48-60), The BBB shuttle peptides do specifically interact with AAV8 virions to increase AAV8's ability to cross the BBB and enhance the brain transduction.

Figure 4A:
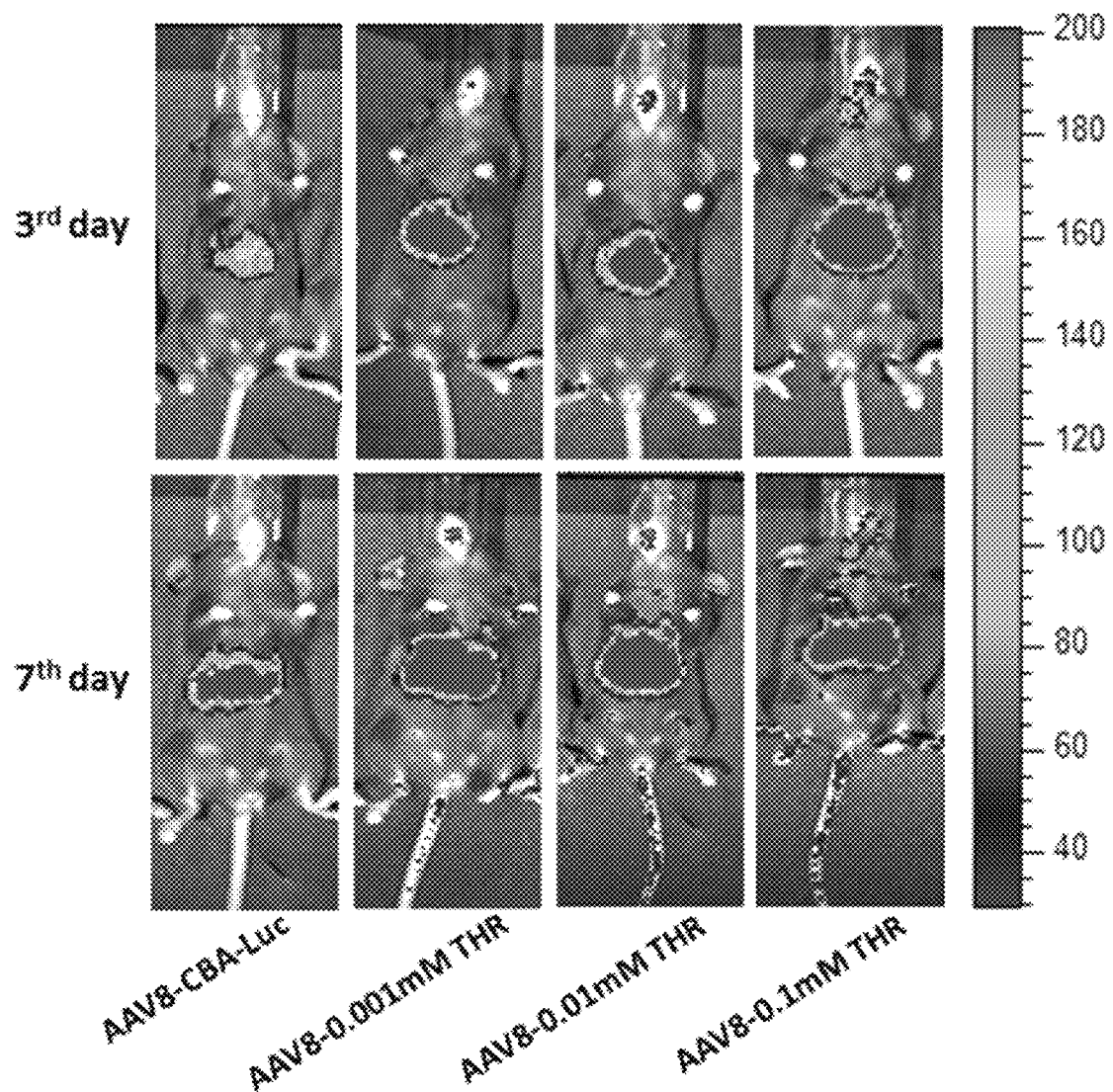
FIGS. 4A-4C show THR enhances the AAV8 transduction in vivo in a dose-dependent manner, especially in the brain.
Figures 4B, 4C:
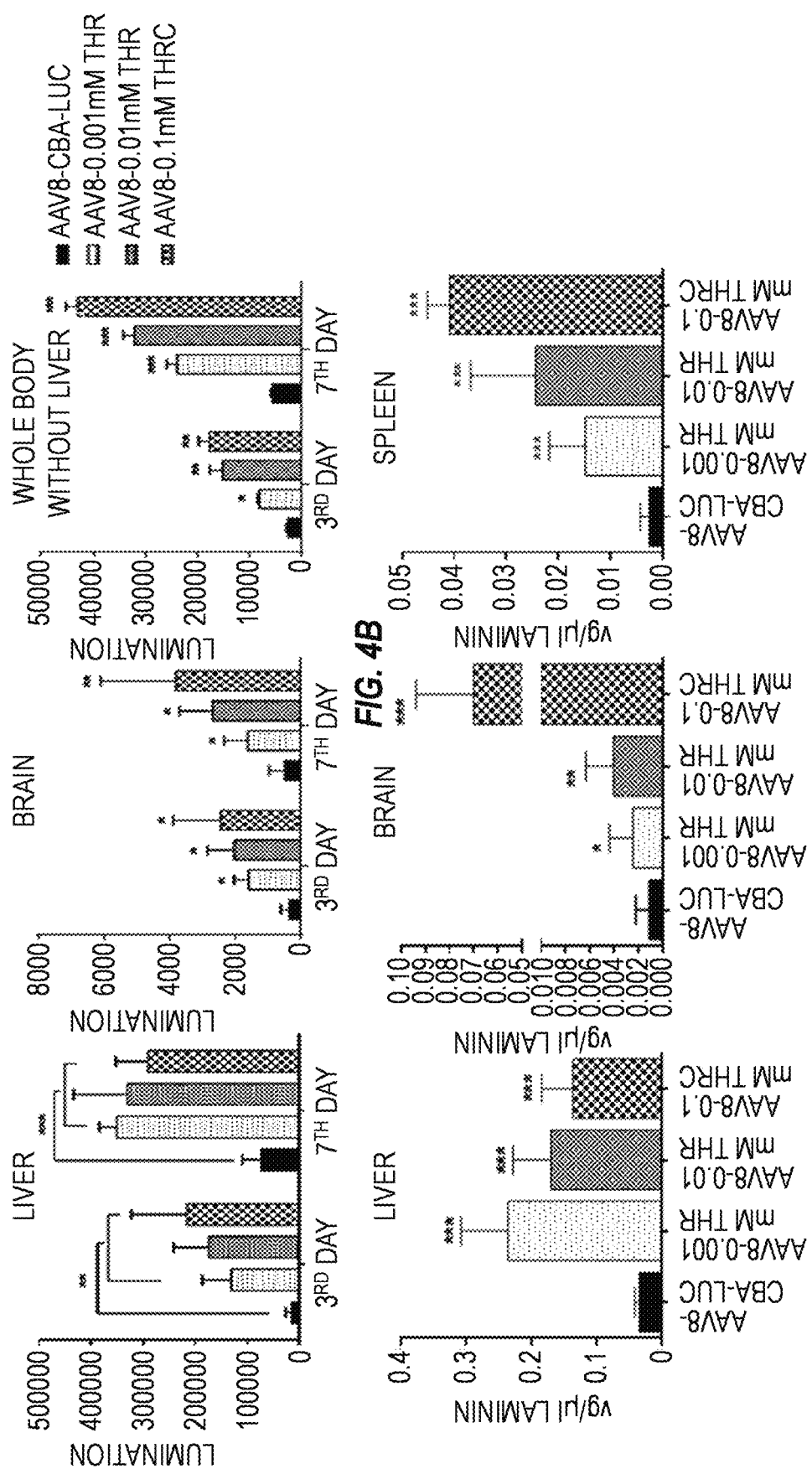

THR enhanced AAV8 transduction dose-dependently in different tissues in vivo. Based on the above results, the THR peptide executed the best function, so the THR peptide was chosen for the following experiments. To further verify the effects of THR peptide observed in vitro and in vivo, five or six-week old female C57BL/6 mice were administered with different concentrations of THR peptide, combined with 5E+10 particles of AAV8/luc via retro-orbital injection. Luciferase expression was imaged at the indicated time points. As shown in FIGS. 4A and 4B, THR of increased concentration endowed stronger imaging signals. At the same time, to quantify the transduction efficiency of a complex of AAV8/luc and peptides, we measured viral genome number in the liver, brain and spleen, and results showed that the gene copy number in the three groups with THR had significantly higher enhancement than the control group (FIG. 4C). Higher amount of THR resulted in more vector genome copy number in the brain.

Figure 5A:
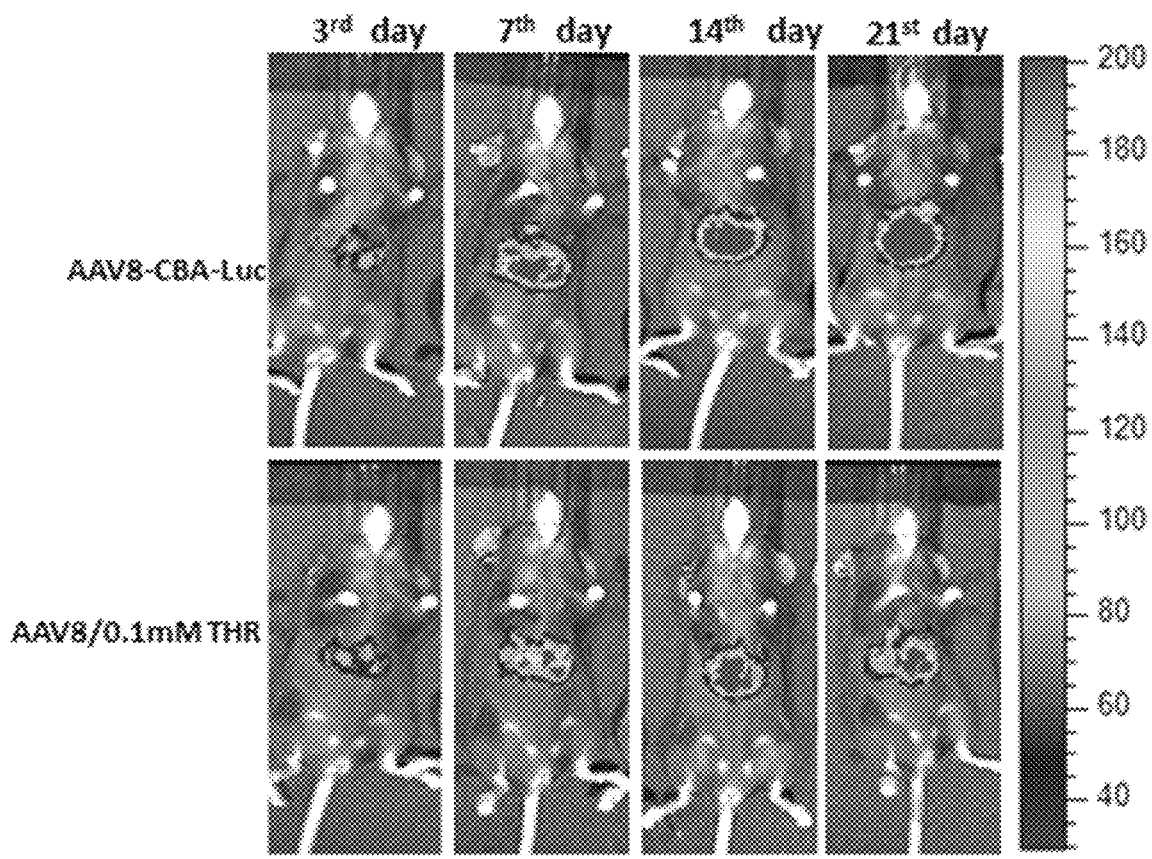
FIGS. 5A-5D show the THR binding with AAV8 is necessary for the enhanced transduction.
Figure 5B:
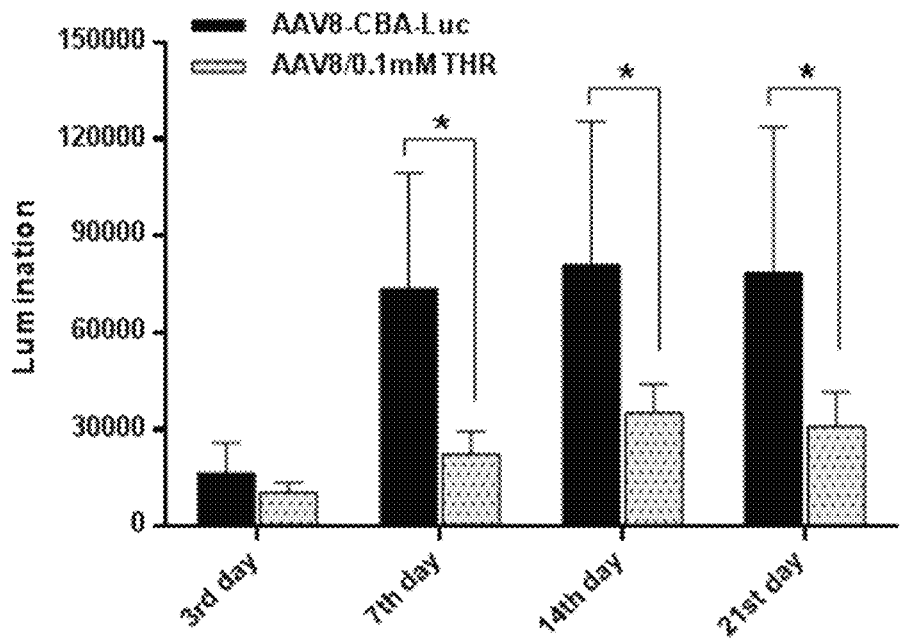
Figure 5C:
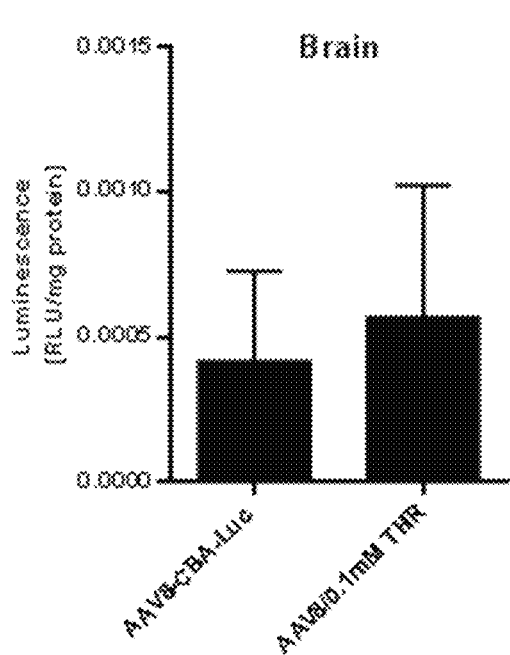
Figure 5D:
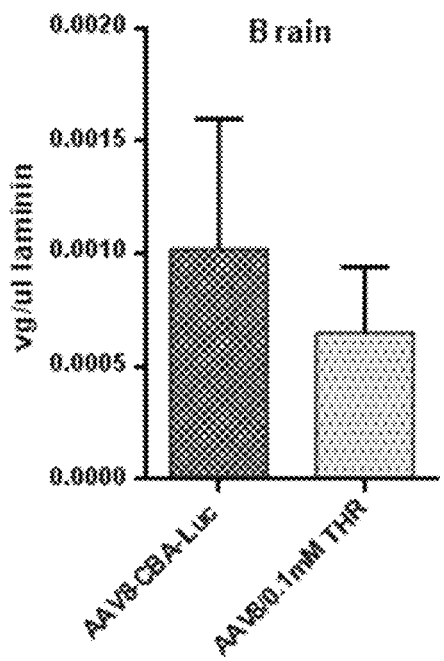

Direct interaction of THR with AAV8 is necessary for the enhanced transduction. The above results just showed that the THR could enhance the AAV8 transduction. However, it is unclear that whether the effect of THR on AAV8 ability to cross the BBB and enhance brain transduction requires direct interaction of THR with the AAV8 virions. For this end, we mixed THR peptide with AAV8/luc vector (AAV8/ 0.1 mM THR) just before AAV8 injection. After systemic administration of the mixture of AAV8 and THR peptide, imaging was performed at different time points. Transgene expression in the liver region was calculated. Application of THR blocked AAV8 liver transduction (FIGS. 5A and 5B). We also did not observe a significant difference between the two groups based on luciferase expression and virus distribution in the brain (FIG. 5C). This result indicates that increased AAV8 ability to cross the BBB needs the direct interaction of virus and THR peptide.

Figure 6A:
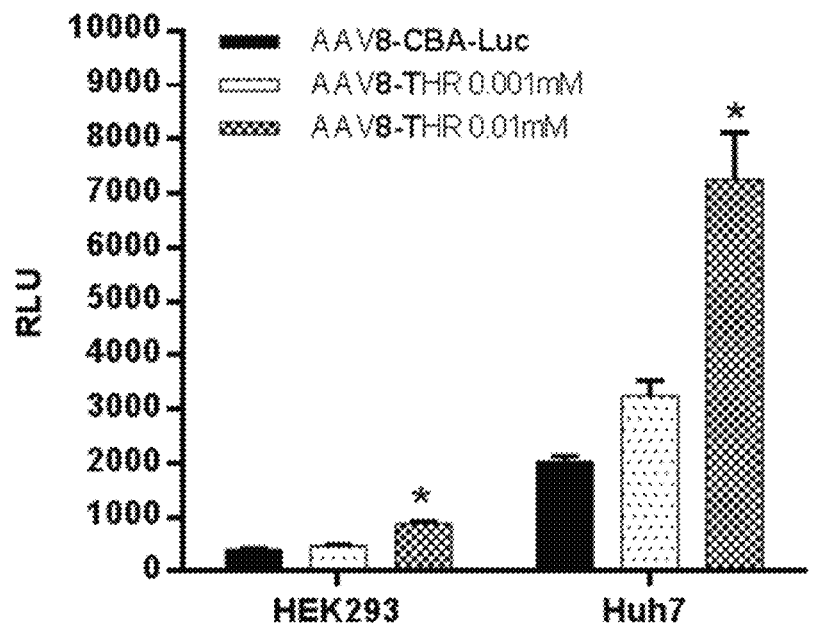
FIGS. 6A and 6B show THR does not interfere with the AAV8 biology.
Figure 6B:
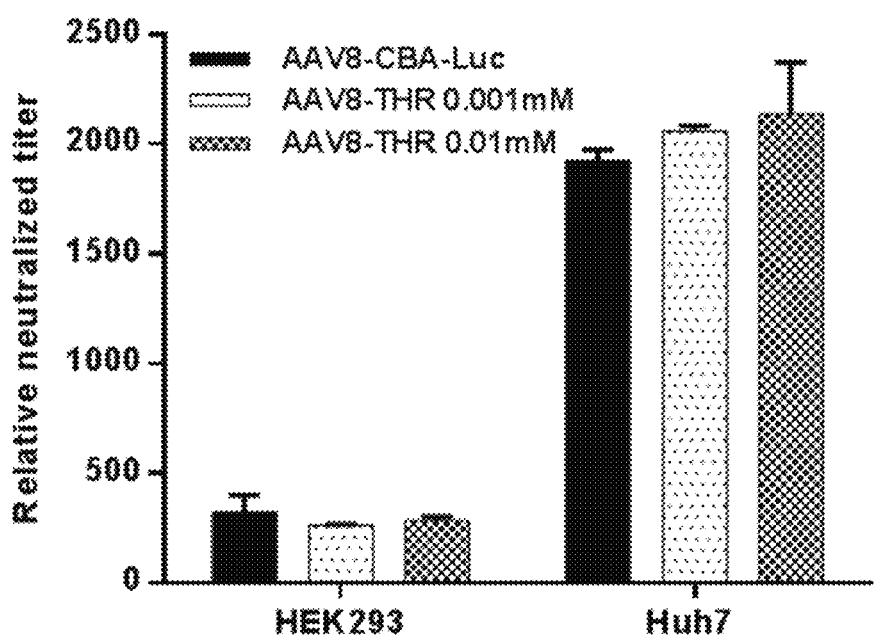

THR did not affect the AAV8 biology. To determine whether the THR could interfere with the AAV8 biology, we performed a neutralization assay in vitro. As shown in FIG. 6B, THR at different concentrations did not interfere with the AAV8/luc neutralization titer under the condition of increased AAV8/luc transduction (FIG. 6A).

Figure 7A:
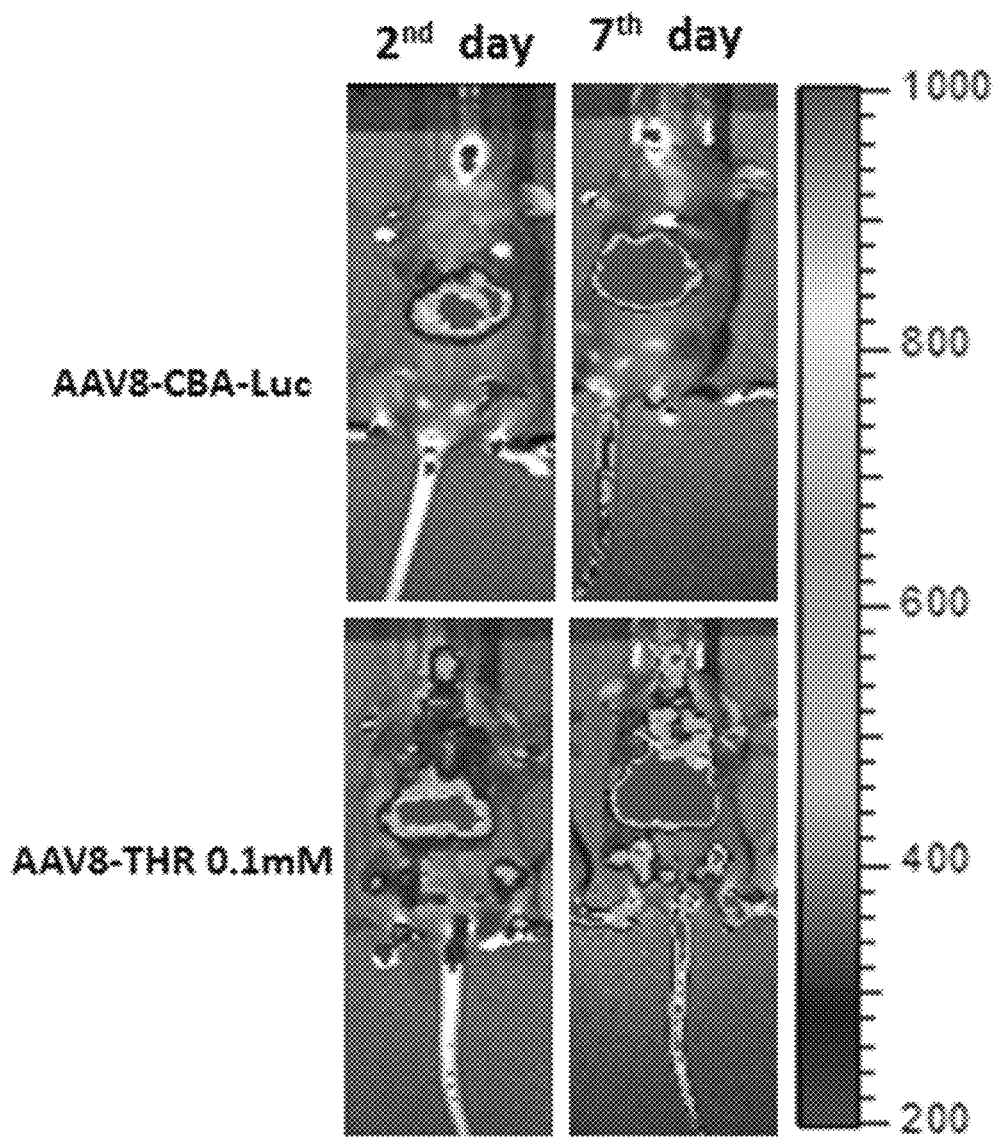
FIGS. 7A-7C show THR enhanced the AAV8 transduction by decreasing the AAV8 clearance in the blood.
Figure 7B:
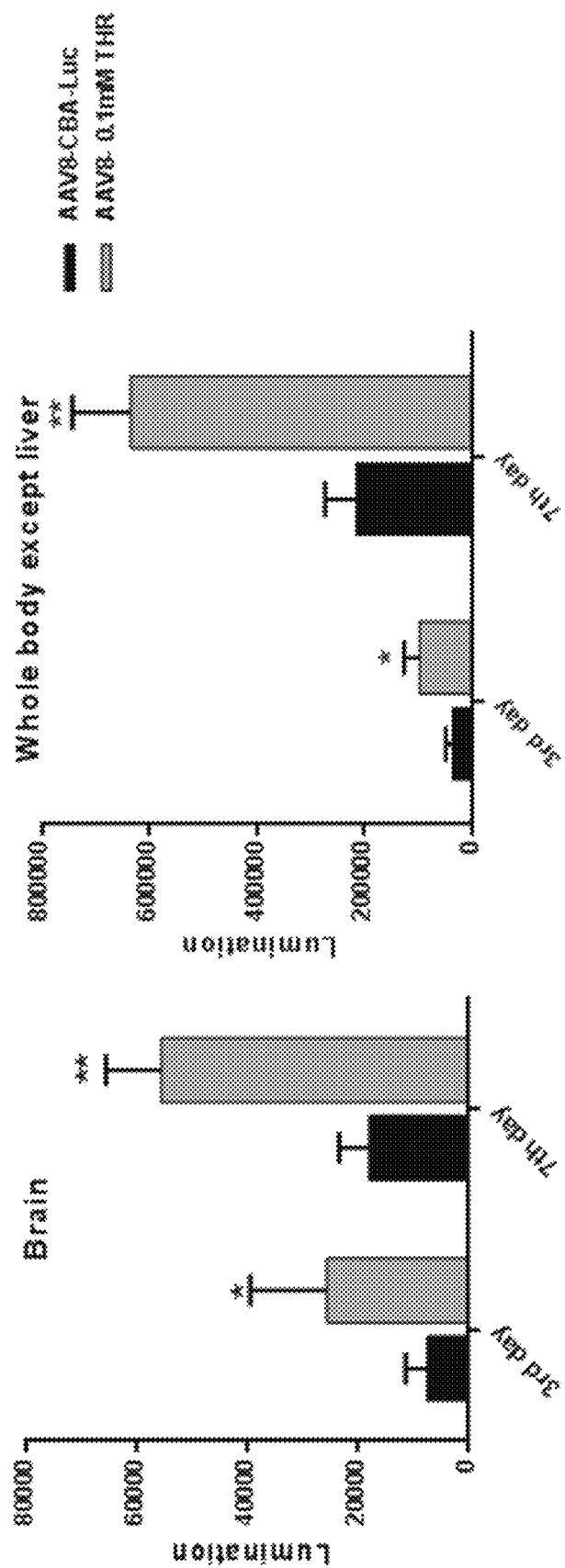
Figure 7C:
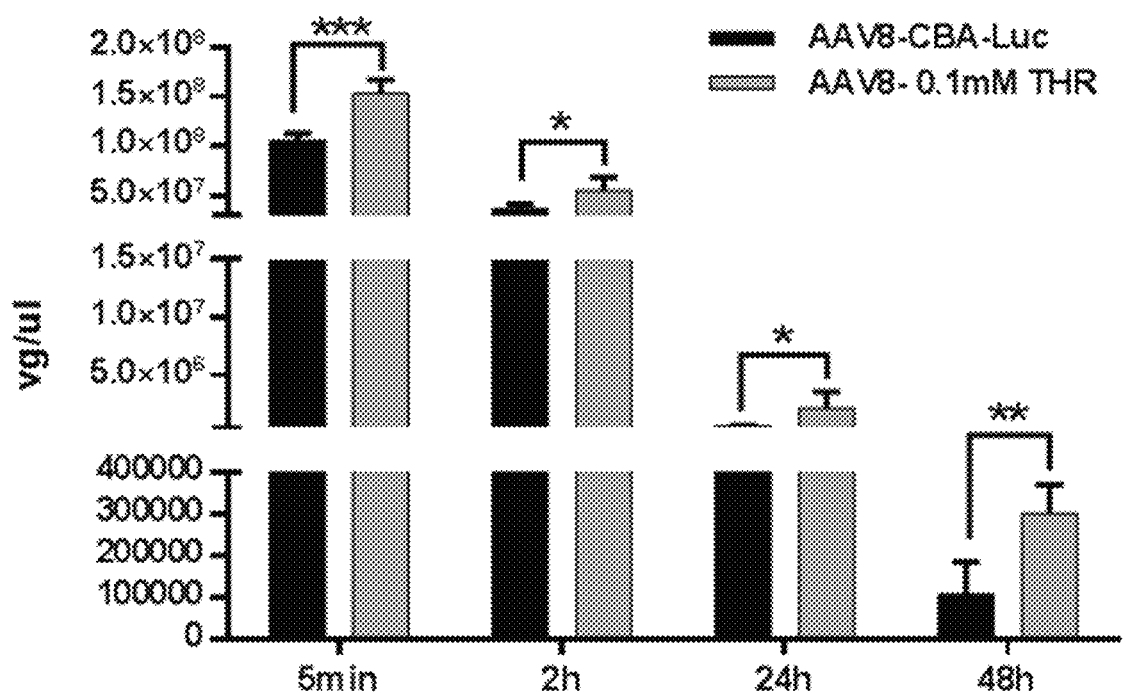

THR significantly enhanced AAV8 transduction by decreasing AAV8 clearance in blood. To understand extracellular factors in THR-mediated enhanced AAV8 transduction in vivo following systemic administration, we exploited the role of THR for the blood clearance rate following intravenous administration of high dose (1E+11 vg each mouse) of AAV8/luc or the incubated complex of virus and THR (AAV8-0.1 mM THR) into C57BL/6 mice separately. Consistent with previous findings, THR enhanced the AAV8 transduction in both the whole body and the brain (FIGS. 7A and 7B). More importantly, as shown in FIG. 7C, the group with AAV8-0.1 mM THR injection consistently exhibited substantially delayed blood clearance than the other one at both early (5 min) and late time points (48 h), which suggested that it might be accountable for the enhanced AAV8 transduction.

Figure 8A:
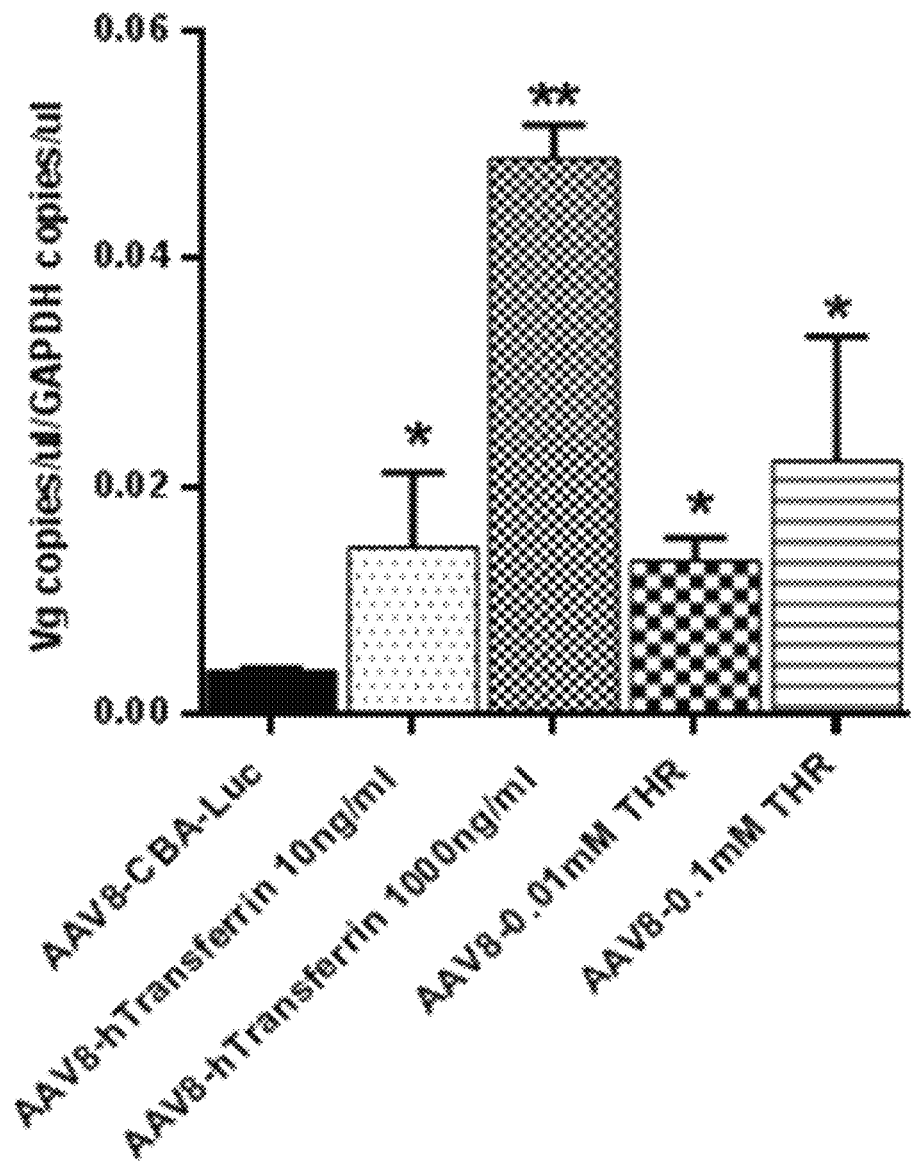
FIGS. 8A and 8B show THR enhanced the binding ability of AAV8 dose dependently and transcytosis in hCMEC/D3 cells time dependently under baseline activation after AAV8 and THR complex exposure.
Figure 8B:
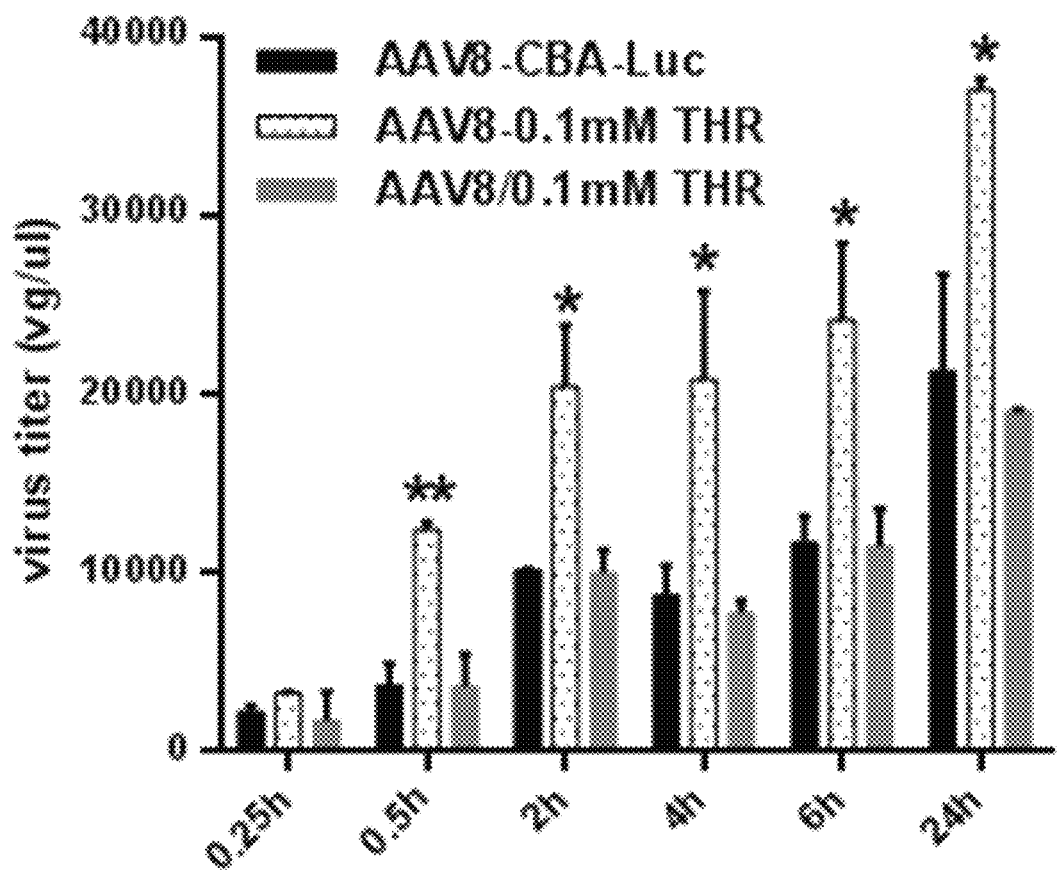
Figure 10A:
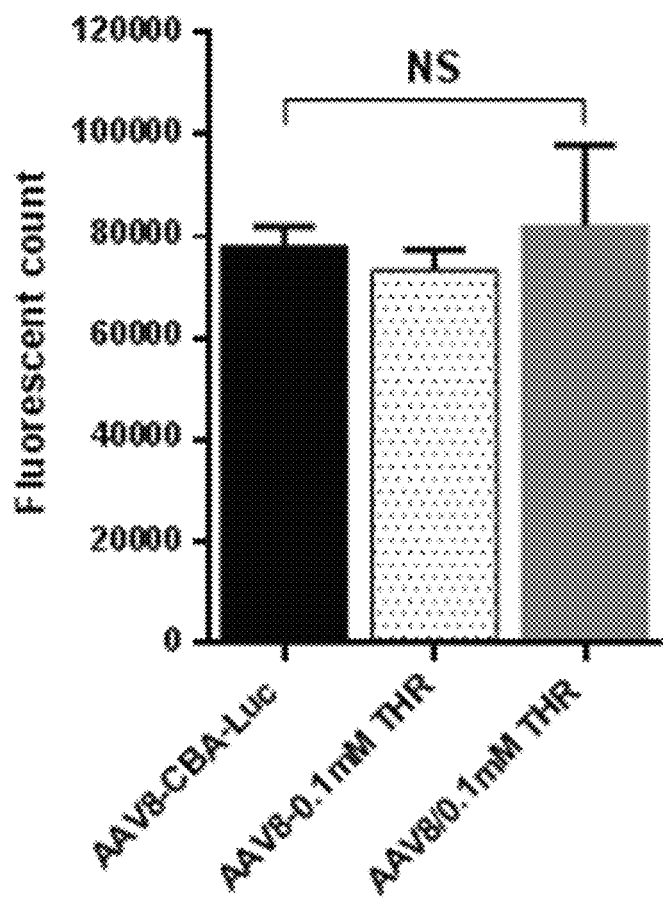
FIGS. 10A and 10B show hCMEC/D3 cells maintain baseline activation after AAV8 and THR complex exposure.
Figure 10B:
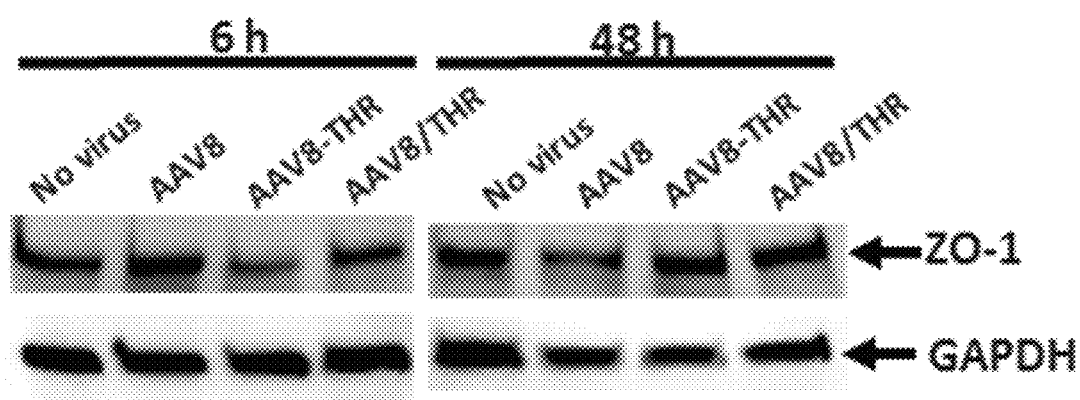

THR enhanced AAV8 binding to cells and endothelial cell permeability. We then chose to investigate the underlying mechanism of the THR enhancing transduction. We performed the binding assay in Huh7 cells. Incubation of THR with AAV8 dramatically increased AAV8 virions binding to the Huh7 cells surface, similar with the results from human transferrin (hTf) as the positive control (FIG. 8A). On the other hand, to elucidate how THR mediates AAV8 crossing the BBB, we did an in vitro endothelial cell permeability analysis in a well-defined system using BBB hCMEC/D3 endothelial cells. We designed three groups: AAV8 vector incubated with DPBS (AAV8/luc cohort), addition of THR to culture medium just before application of AAV8 vector incubated with PBS (AAV8/0.1 mM THR cohort), and AAV8 vector incubated with THR (AAV8-0.1 mM THR cohort). For the endothelial cell permeability assay, it is a prerequisite that the integrity of the apical cell monolayer is determined. Therefore, we firstly analyzed the BBB membrane's integrity by measuring fluorescence intensity of FITC-dextran and major junction protein ZO-1 expression by Western blot analysis. The results just showed that there was no difference for FITC permeability and ZO-1 protein expression in different groups (FIGS. 10A and 10B). Significant increase of AAV8 permeability was observed when AAV8 vector was pre-incubated with THR peptide (AAV8-0.1 mM THR cohort) at every time point except for 15 min after application of AAV8 vector (FIG. 8B), however, no marked difference between the cohorts of AAV8/0.1 mM THR and AAV8 was shown, which further implicates that the THR binding with AAV8 is necessary for the enhanced transduction. These observations demonstrated that the direct interaction of AAV8 with THR peptide increased AAV virions binding to the cell surface, and then enhanced the ability to cross the BBB.

Figure 9:
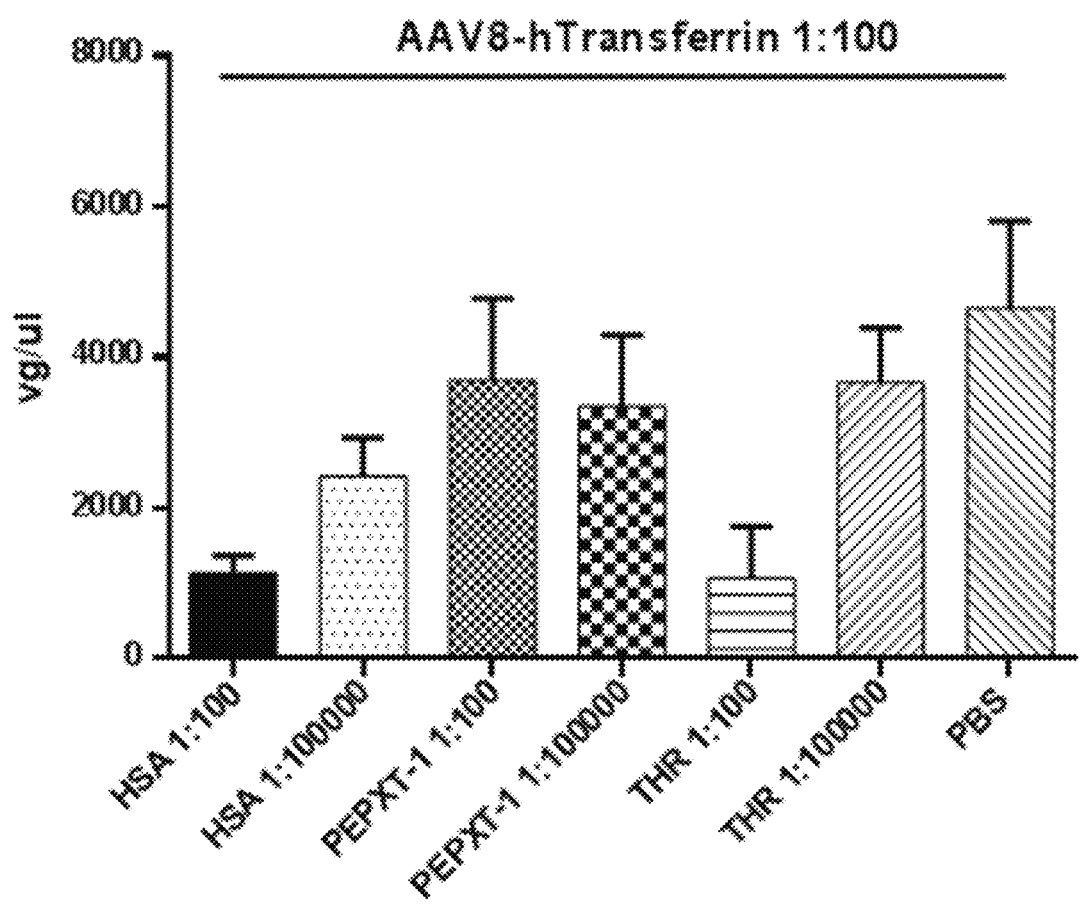
FIG. 9 shows that THR peptide competes with human transferrin binding to AAV8. Diluted HSA (1:100 and 1:100000 of physiological concentration), peptide control (1:100 and 1:100000 dilution), THR (1:100 and 1:100000 dilution), and PBS control were used to block AAV8 capsid on Huh7 cells in vitro. Then, human transferrin (1:100 of physiological concentration) was added into the mixture separately, and the transferrin antibody was used for pull down and the gene copy number of AAV8 was measured by qPCR.

THR competed with the human transferrin binding to AAV8 virions. Our previous study demonstrated that several serum proteins (transferrin, albumin, and ApoB) are able to directly interact with AAV8 and enhance AAV8 liver transduction in vitro and in vivo. Further study shows that these proteins competitively bind to the same locations of AAV8 virions. To investigate whether THR also binds to the same location of AAV8 virions as human serum proteins, we performed a competitive assay. AAV8 was firstly incubated with human serum albumin (HSA), control peptide PEPXT-1 or THR at different dilutions for 2 h at 4° C., then human transferrin was added to the mixture for another 1 h. The transferrin antibody was used to pull down transferrin bound AAV8 virions and AAV8 gene copy number was measured by qPCR. As shown in FIG. 9, consistent to our previous report, HSA blocked transferrin binding to AAV8, and there was no effect of control peptide PEPXT-1 on inhibition of transferrin binding to AAV8. When high concentration of THR peptide was used, there was a similar effect of blocked transferrin binding to AAV8 virions as HSA. Thus, BBB shuttle peptides execute the function to increase AAV8's ability to cross the BBB by binding to the same location of AAV virions as human serum proteins.

Figure 11A:
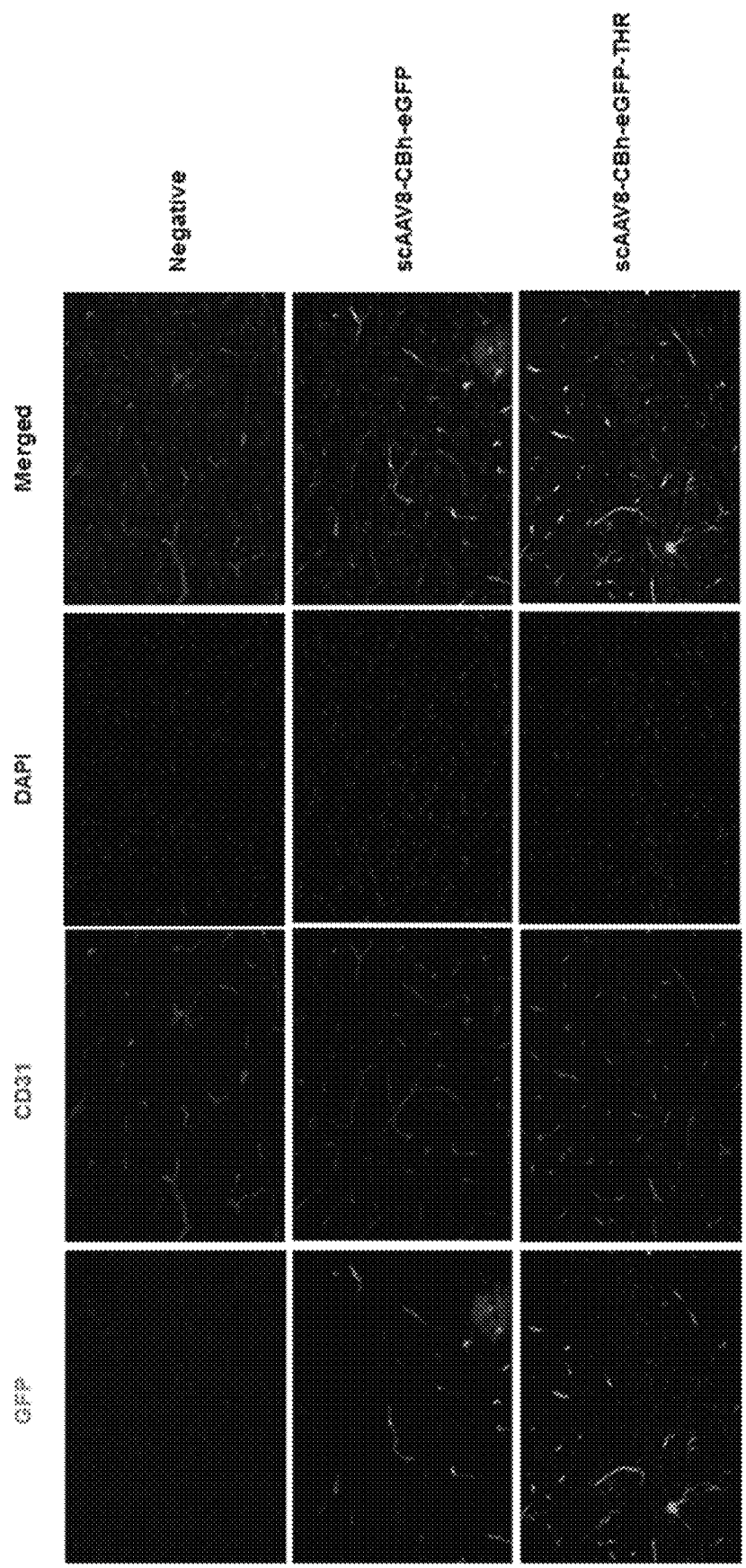
FIGS. 11A-11C show intravenous injection of the THR and scAAV8-CBh-eGFP complex leading to neuron cell transduction in the brain. $2\times10^{11}$ vg of either scAAV8-CBh-eGFP or scAAV8-eGFP-0.4 mM THR was retro-orbitally injected into the mice (n=3). Representative images of the EGFP expression (green) of AAV8 was colocalized with CD31 (red, endothelial marker) in the cortex (FIG. 11A), GFAP (red, astrocyte marker) in the cortex (FIG. 11B), and NeuN (red, neuronal marker) in the hippocampal CA1 region (FIG. 11C) in the mice brain, and were merged with DAPI (blue), were captured and assessed after 4 weeks. Scale bars, 50 μm (Objective 20× optical axis).
Figure 11B:
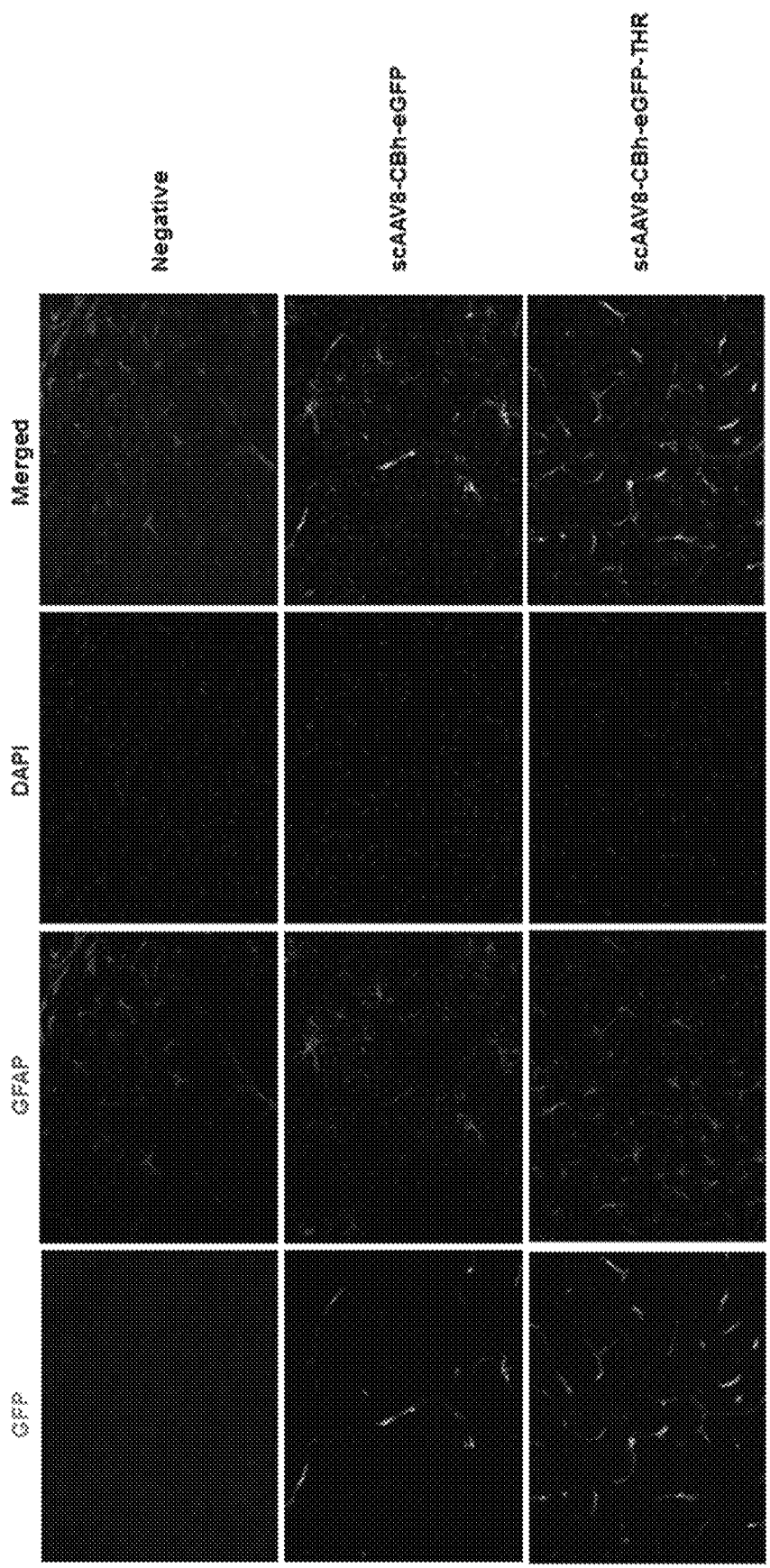
Figure 11C:
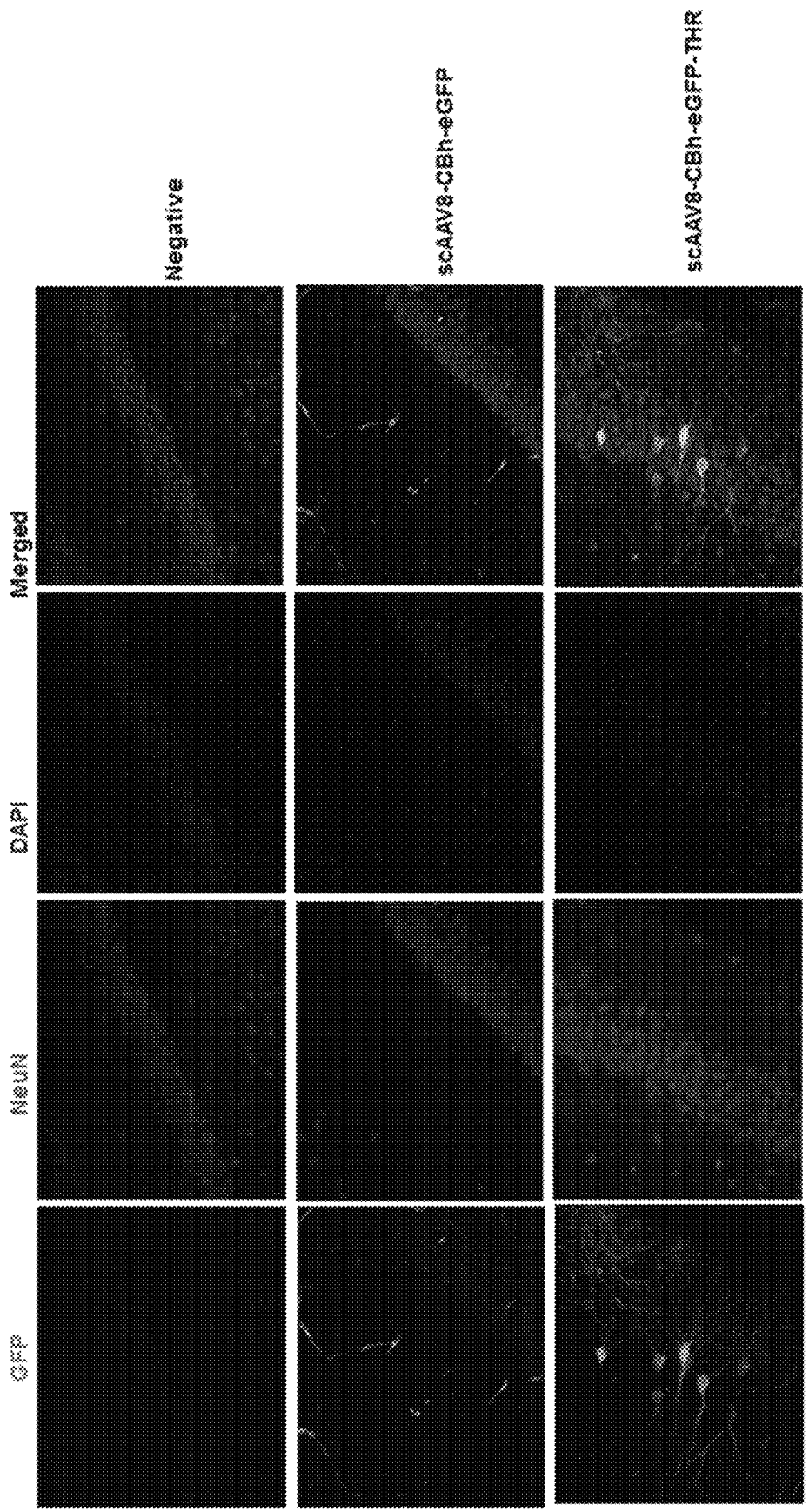

THR promotes AAV8 crossing the BBB and targeting neuron cells in the brain. Bas V8/luc vectors pre-incubated with THR induced high transduction in the brain. Luciferase analysis results were unable to differentiate whether the high transduction levels were from either the endothelial or brain parenchymal cells. Therefore, we assessed transgene expression in different cells of the brain 4 weeks after intravenous injection of $2\times10^{11}$ vg of scAAV8-CBh-eGFP pre-incubated with 0.4 mM of THR (scAAV8-eGFP-THR) for 2 h at 4° C. An efficient transduction of brain endothelial cells was observed in the mice treated with either the scAAV8-CBh-eGFP viruses or scAAV8-CBh-eGFP-THR (FIG. 11A). Higher neuron transduction was observed in mice receiving scAAV8-eGFP-THR than was observed in mice treated with scAAV8-CBh-eGFP (FIG. 11C). No astrocyte transduction was observed in the mice treated with either scAAV8-CBh-eGFP orscAAV8-eGFP-THR (FIG. 11B). These results confirm the notion that THR has the potential to increase the ability of AAV8 to cross the BBB and enhance brain transduction, especially in neuronal cells.

The objective of our present study is to explore the possibility of applying the BBB shuttle peptides to enhance AAV vector's ability to cross the BBB and brain transduction. Herein, we found that several peptides with different mechanisms increased the AAV8 brain transduction after systemic administration, with THR peptide being the best. We further demonstrated that the THR was able to directly bind to AAV8 virions and increase AAV8 BBB permeability via the TfR1 receptor-mediated mechanism.

Taken together, the data presented here clearly demonstrated for the first time that BBB shuttle peptides could bind to AAV8 directly and further enhance AAV8 transduction into the brain. These results strongly support the feasibility of BBB shuttle peptides promoting AAV transduction. This finding is of utmost importance for clinical trials in patients with CNS disorders and those requiring systemic administration of AAV vector. ed on transgene expression and AAV genome copy number, systemic administration of AA Example 2

In Example 1, we demonstrated that several BBB peptides (especially the THR peptide) are able to directly interact with AAV8 virions and increase AAV8 ability to cross the BBB. Compared to AAV8, AAV9 vector induces much higher brain transduction after systemic administration, and AAV9 has been broadly proposed for neurological disorders in clinical trials. However, the THR peptide did not increase AAV9 ability to cross the BBB and failed to enhance AAV9 brain transduction after systemic administration. In the following study, we successfully isolated a peptide, PB5-3, from the Ph.D-12 mer library and demonstrated that the peptide PB5-3 specifically enhanced AAV9 ability to cross the BBB and increase brain transduction after systemic administration in mice.

Figure 12A:
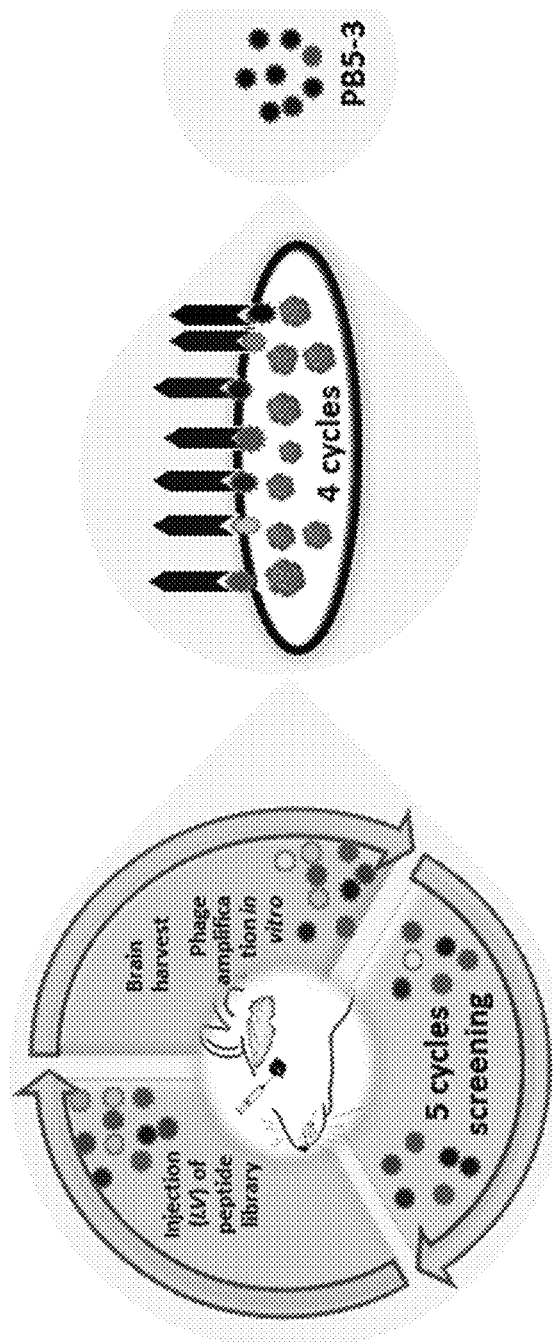
FIGS. 12A-12B show a schematic of identified PB5-3 peptide by phage display screening in vivo and in vitro. $1\times10^{11}$ of the Ph.D-12 mer library were injected into C57BL mice. Two hours later, the brain was harvested and phages were isolated for next round of expansion in mice. Expansion was repeated for a total of 5 cycles. After the last cycle, phages with brain tropism were isolated and applied to $1\times10^{10}$ particles of AAV9-coated plates. After washing, AAV9 binding phages were harvested and amplified for next round of isolation (FIG. 12A). After 4 rounds of selection, AAV9-binding phages were sequenced, the amino acid sequence of the identified PB5-3 (SEQ ID NO:133), PB5-5 (SEQ ID NO:134), PB5-14 (SEQ ID NO:135), are shown (FIG. 12B).
Figure 12B:
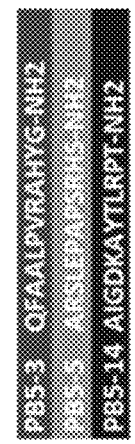
Figure 12B:
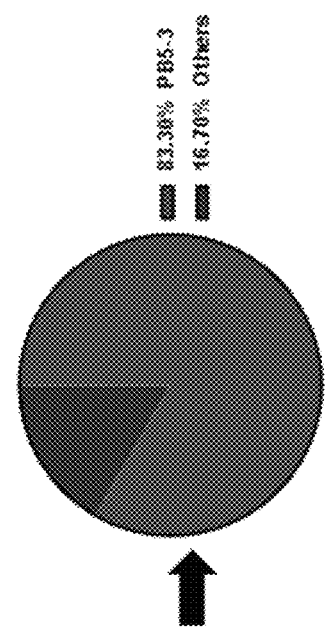
Figure 12B:
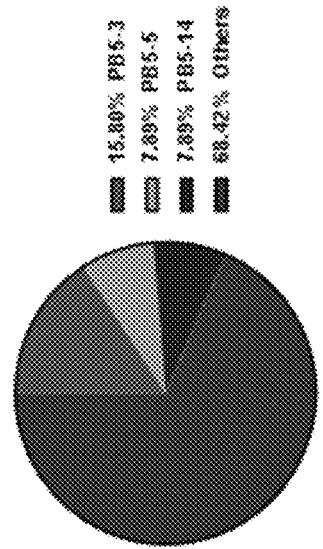

Peptides with the ability to cross the BBB and to bind to AAV9. To isolate peptides with the ability to cross the BBB and bind to AAV9, we first injected the Ph.D-12 mer phage library into C57BL mice via the retro-orbital vein. Two hrs later, mice were perfused with PBS and the brains were harvested for phage isolation and amplification. The phage library from the first round selection in the brain was injected into mice for further rounds of selection. After 5 rounds, the phage library was negatively selected by binding to a 48 well plate and then incubated with an AAV9 virion-coated plate. After washing, AAV9-binding phages were harvested and amplified for the next cycle of selection. Such selection was repeated for four cycles (FIG. 12A). After the last cycle of phage selection, 40 individual phages were sequenced. Results from 38 clones were available (FIG. 12B). The peptide PB5-3 was detected in 6 phages, PB5-5 in 3 phages and PB5-14 in another 3 phages. These peptides have different sequences (FIG. 12B and Table 7).

Figure 13A:
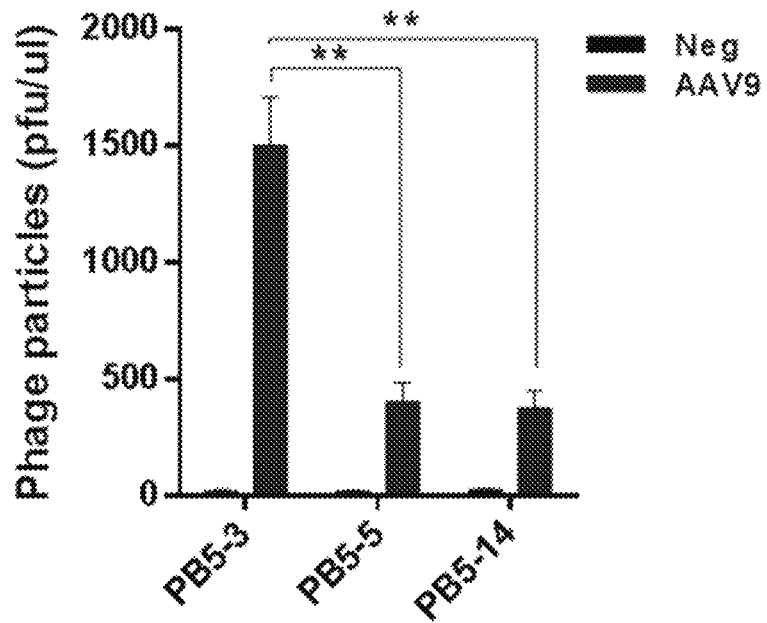
FIGS. 13A-13B show binding specificity of PB5-3 peptide to AAV9. After coating with $1\times10^{10}$ particles of AAV9, different phages at a dose of $1\times10^{11}$ were added to a 96 well plate and incubated. After washing, the number of bound phages was detected (FIG. 13A). A 96 well-plate was coated with $1\times10^{10}$ particles of AAV vectors/well from serotypes 6, 8 and 9 overnight. After washing, $1\times10^{11}$ of PB5-3 phages were added and incubated at room temperature for 2 hrs. After washing, the phage particles were detected (FIG. 13B).
Figure 13B:
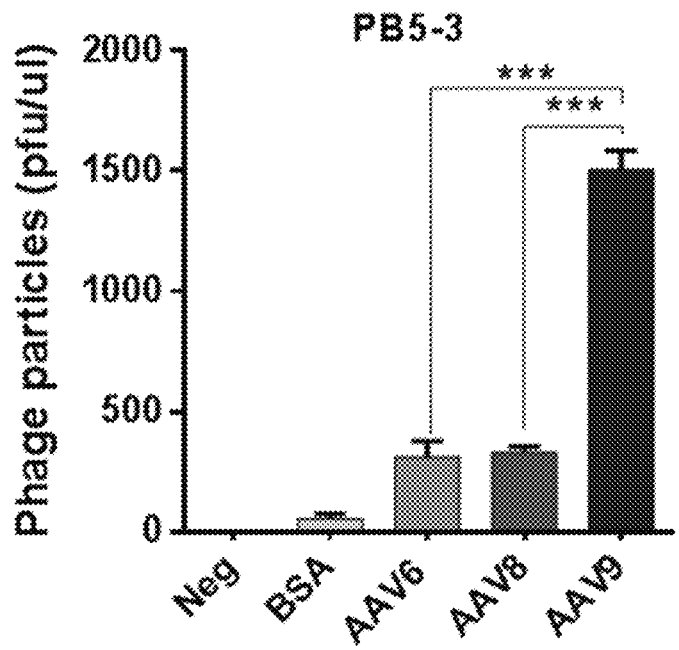

PB5-3 demonstrated high specific binding affinity to AAV9. To study the AAV9 virion binding affinity of the peptides isolated from phage, first we compared the affinity of the different peptides to AAV9 virions. After incubation of an AAV9-coated plate with different phages and several washings, much more PB5-3 phages were detected to bind to AAV9 than PB5-5 and PB5-14 phages (FIG. 13A). Next, we studied whether the phages isolated from in vitro and in vivo selections showed specific binding affinity to AAV9. We coated the plate with AAV virions from different serotypes. After incubation with PB5-3 phages, the number of phages on the AAV9-coated plate was much higher than that with AAV6 and AAV8 (FIG. 13B). This result indicates that serotype specific peptides can be isolated from in vitro and in vivo selection.

Figure 14A:
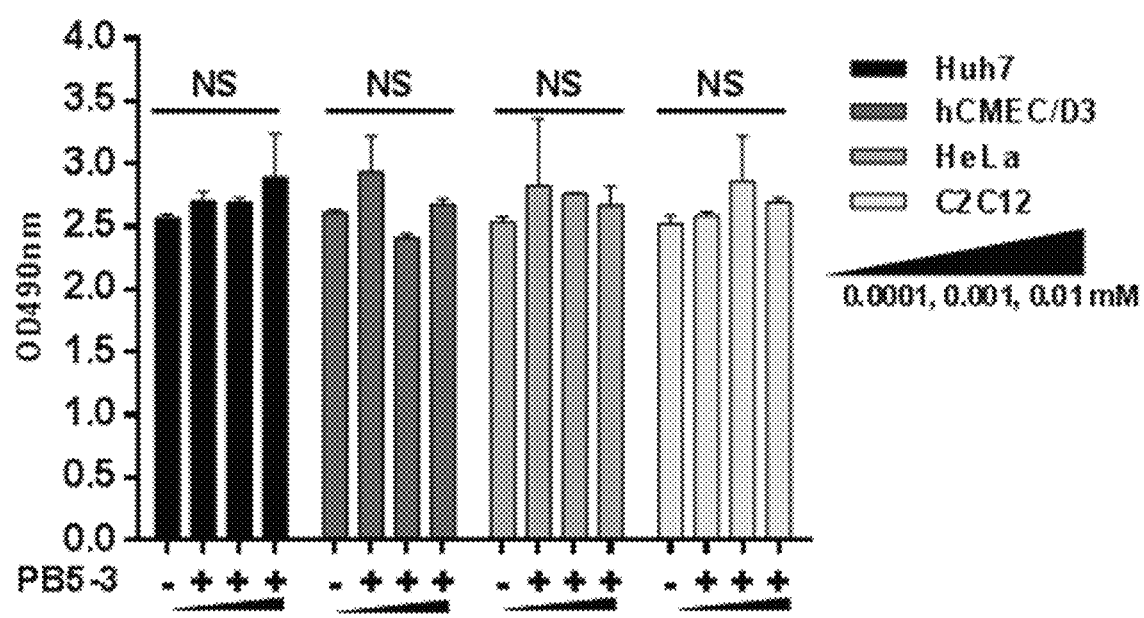
FIGS. 14A-14C show PB5-3 specifically enhances AAV9 transduction in vitro. $1\times10^{4}$ cells were incubated with PB5-3 peptide at different concentrations for 48 hrs. Cell proliferation was analyzed with MTT assay (FIG. 14A). AAV9/luc vectors at a dose of $1\times10^{9}$ particles were incubated with PB5-3 peptide for 2 hrs at 4° C., then the mixture was applied to different cells and incubated for 2 days. Luciferase expression from cell lysate was detected (FIG. 14B). For comparison, PB5-3 was added to cells just before infection of AAV9 (FIG. 14C).
Figure 14B:
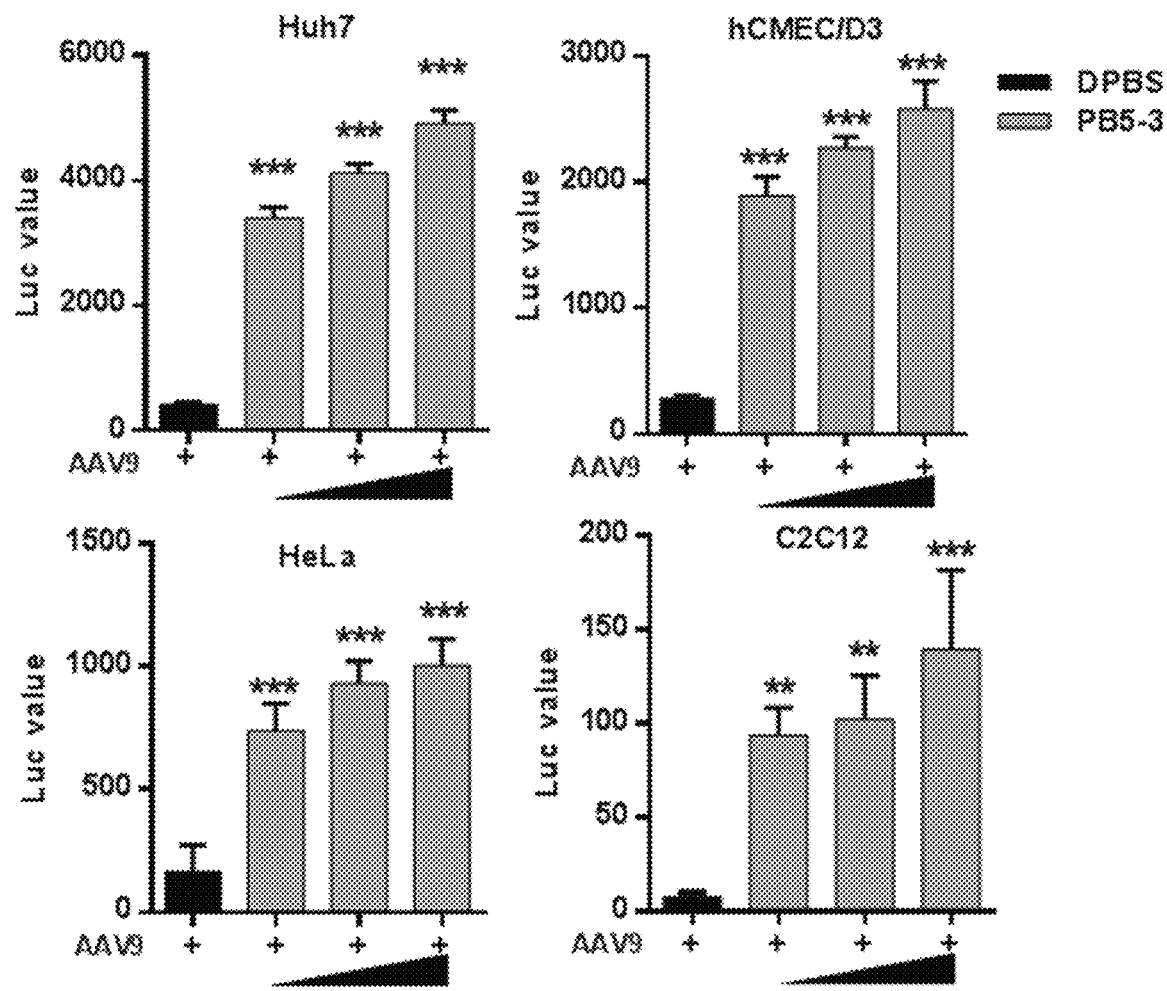
Figure 14C:
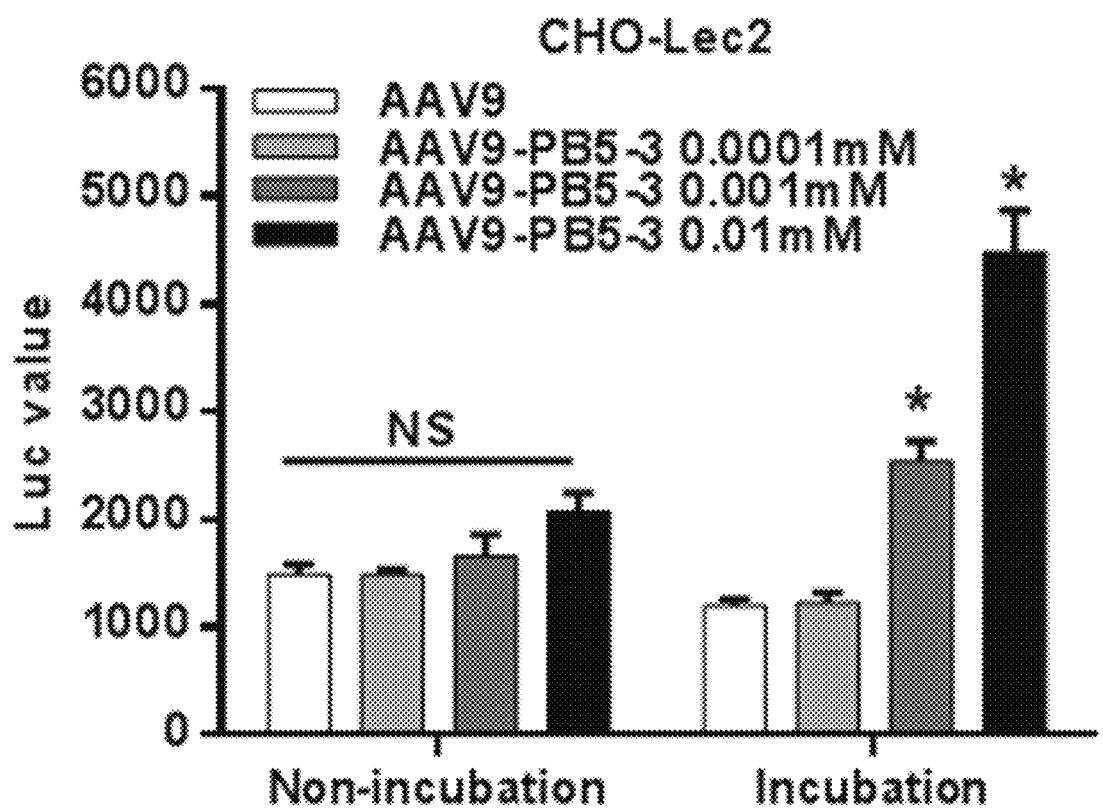

PB5-3 peptide specifically enhances AAV9 transduction in cell lines. Next, we examined the effect of PB5-3 on AAV9 transduction in vitro. We found that PB5-3 peptide had no toxicities on different cell types based on a MTT assay (FIG. 14A). When incubating PB5-3 with AAV9 virions, enhanced transduction was observed in different cell lines including Huh7, Hela, C2C12 and hCMEC/D3 (FIG. 14B). Without incubation, PB5-3 failed to increase AAV9 transduction (FIG. 14C). Consistent with previous studies, the direct interaction of peptide and AAV virions is required to enhance AAV9 transduction.

Figure 15A:
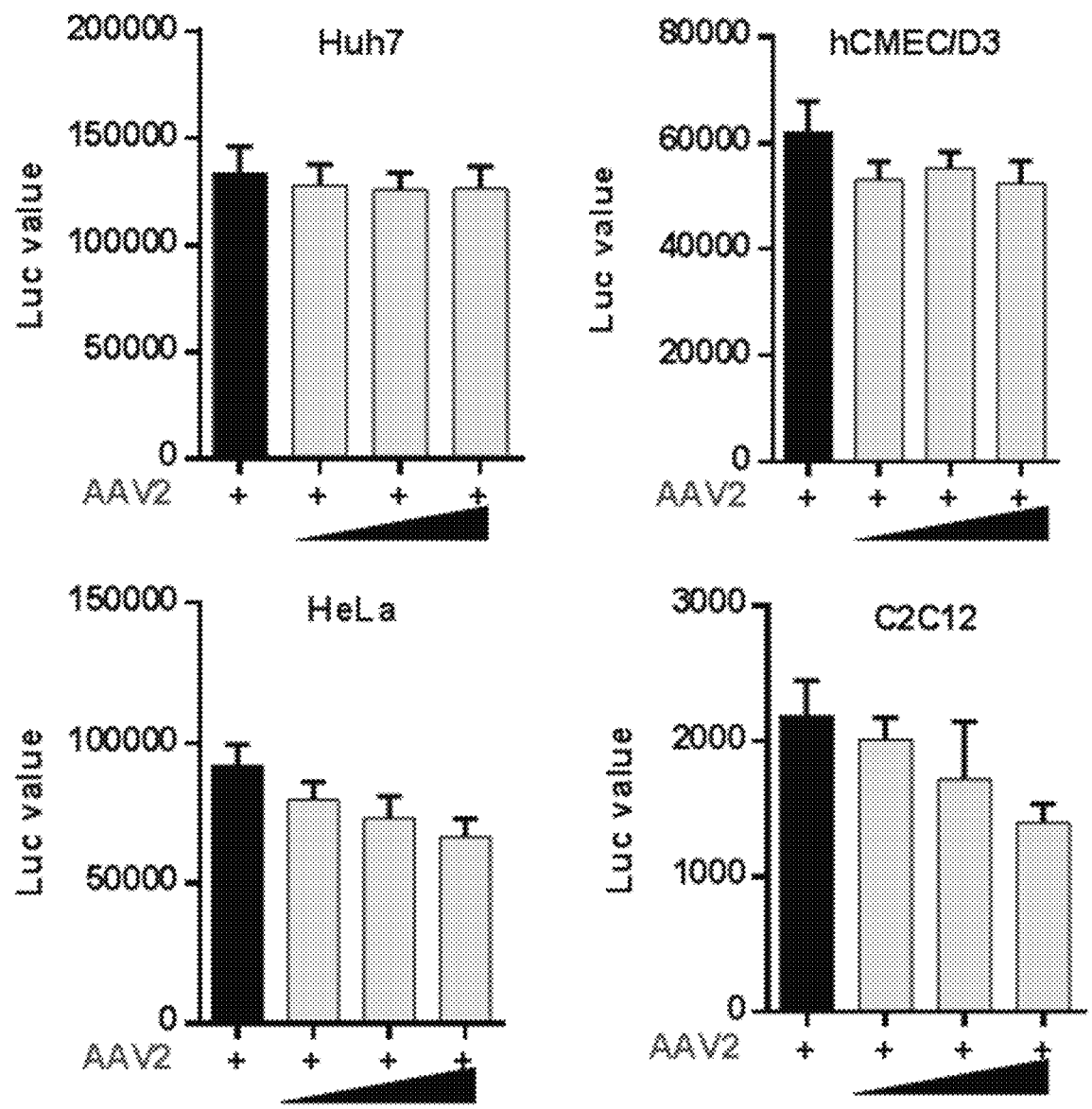
FIGS. 15A-15C show no enhancement of PB5-3 on AAV vectors from other serotypes. $1\times10^{9}$ particles of AAV/luc vectors from serotype 2 (FIG. 15A), 6 (FIG. 15B), and 8 (FIG. 15C) were incubated with PB5-3 peptide for 2 hr at 4° C. The complex of AAV vector and peptide was applied to Huh7 or hCMEC/D3 cells. Two days later, the lysate from these cells was harvested for luciferase analysis.
Figure 15B:
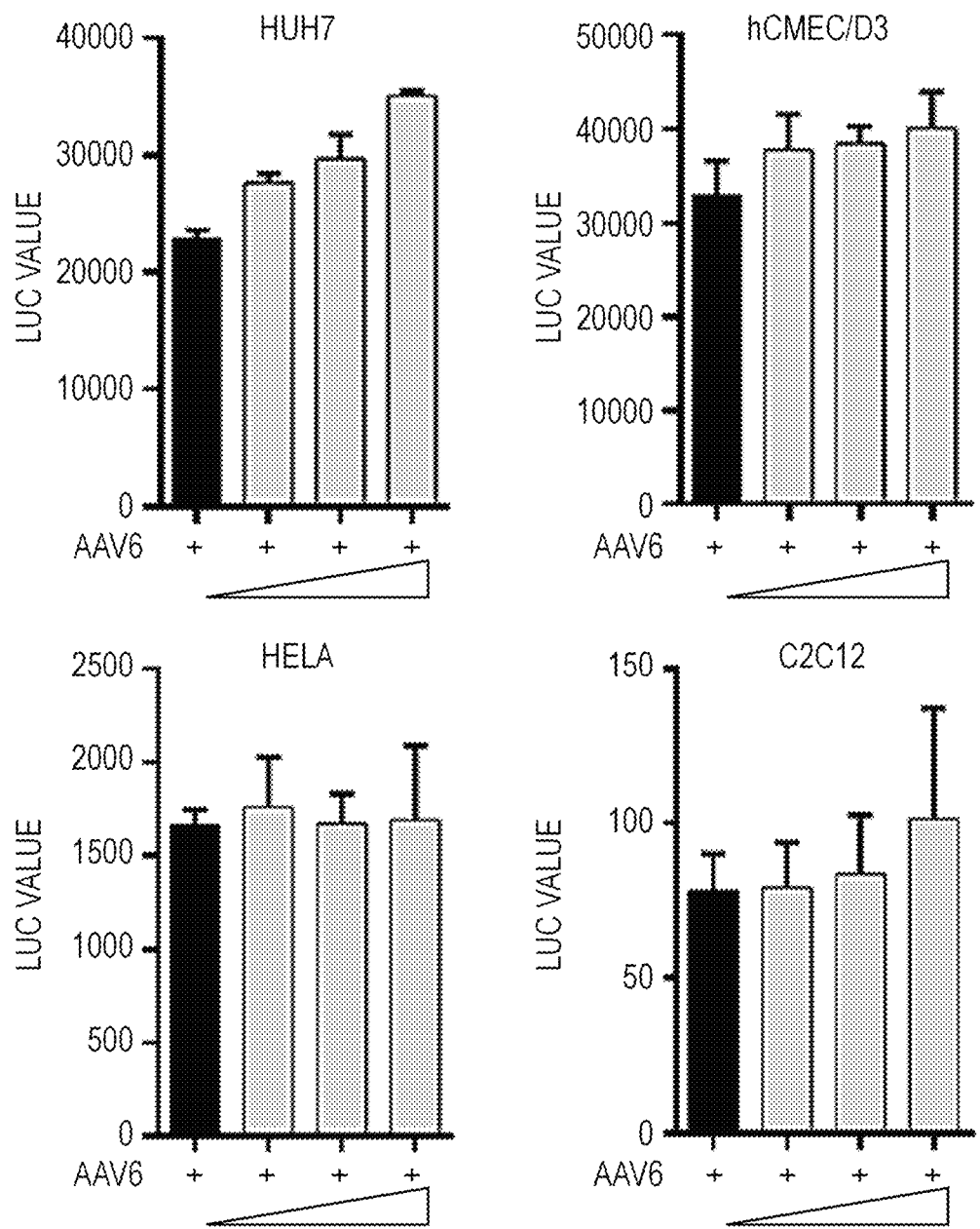
Figure 15C:
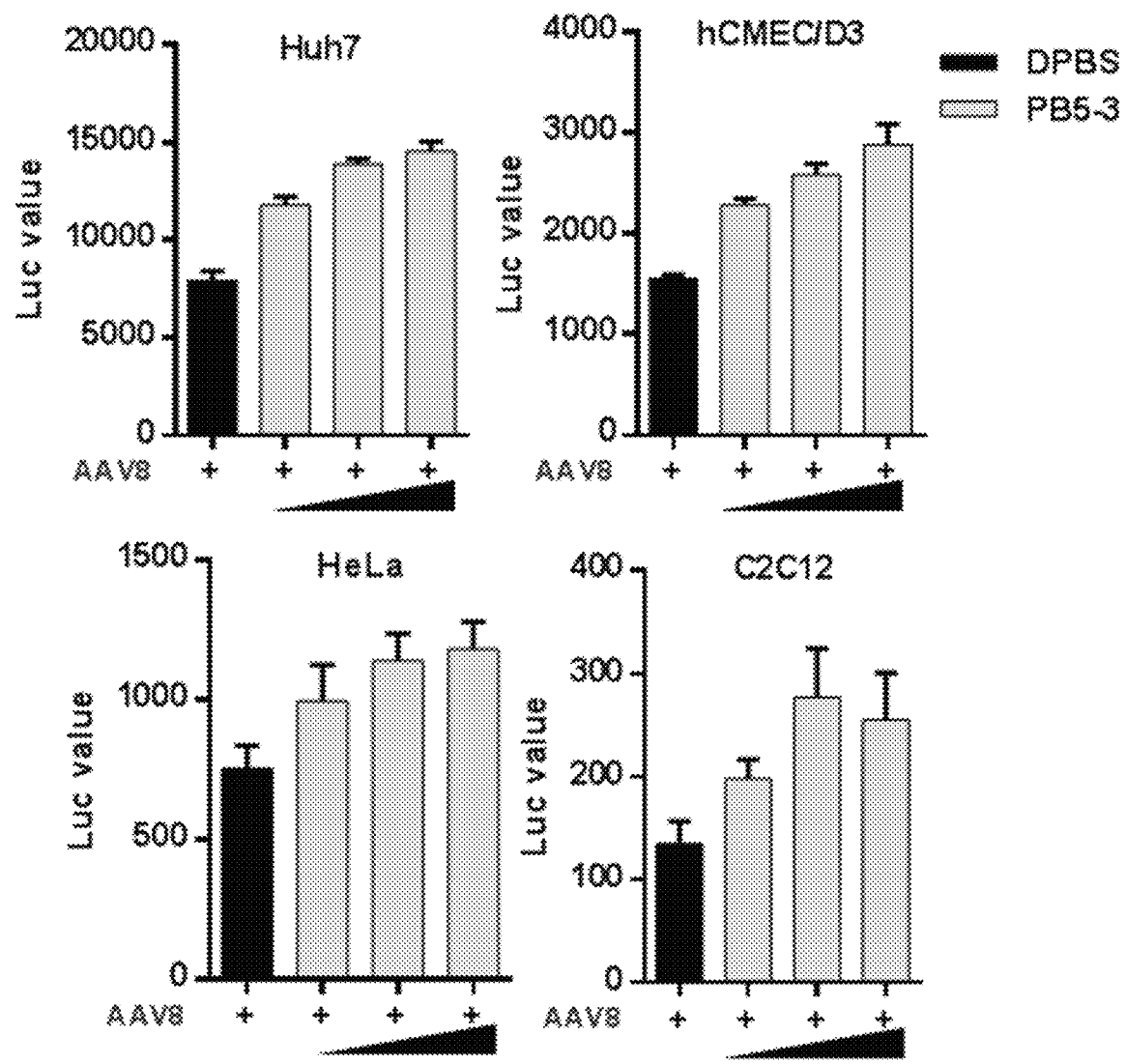

Analysis of enhancement of AAV transduction from other serotypes with PB5-3 peptide in vitro. To further investigate the specific effect of PB5-3 on AAV9, we tested the effect of PB5-3 on AAV transduction from other serotypes. AAV vectors from serotypes 2, 6, and 8 were incubated with PB5-3 and then the mixture was applied to Huh7 or hCMEC/D3 cells. The transduction was detected two days later after AAV infection. No enhanced transduction was observed in either cell line with AAV2, 6, or 8 (FIGS. 15A-C).

Figure 16A:
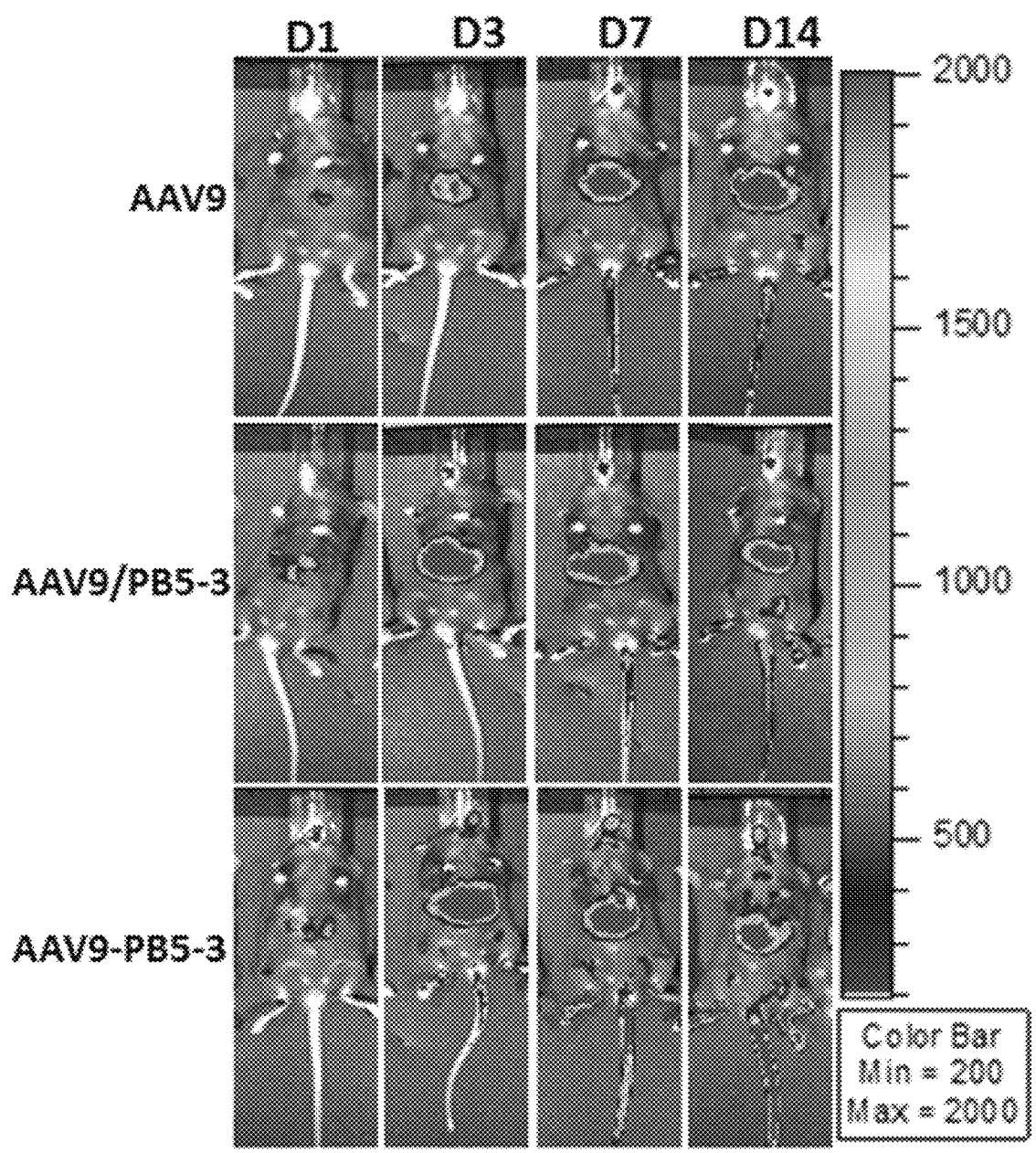
FIGS. 16A-16C show enhanced brain transduction in mice after systemic administration of AAV9/PB5-3 complex. $1\times10^{10}$ particles of AAV9/luc vectors were incubated with PB5-3 for 2 hr at 4° C. The complex was injected into C57BL mice via the retro-orbital vein. At indicated time points, mouse imaging was performed.
Figure 16B:
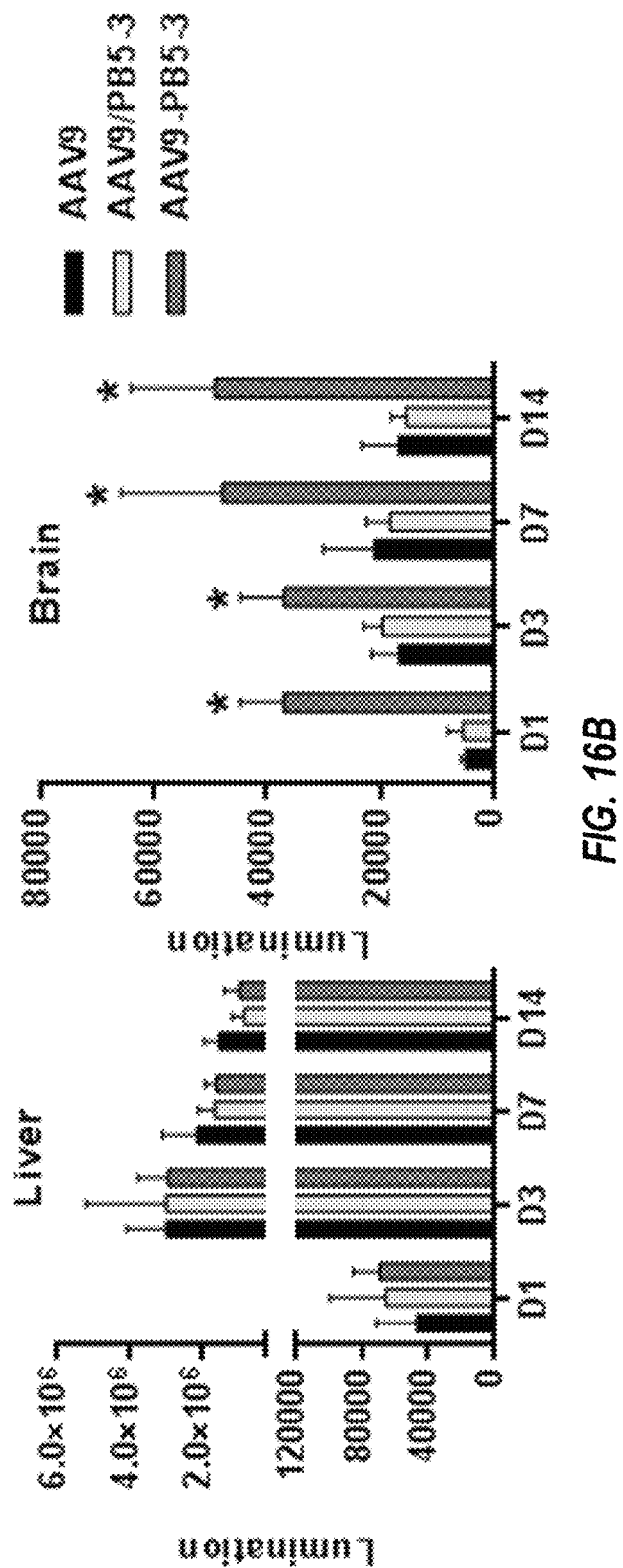
Figure 16C:
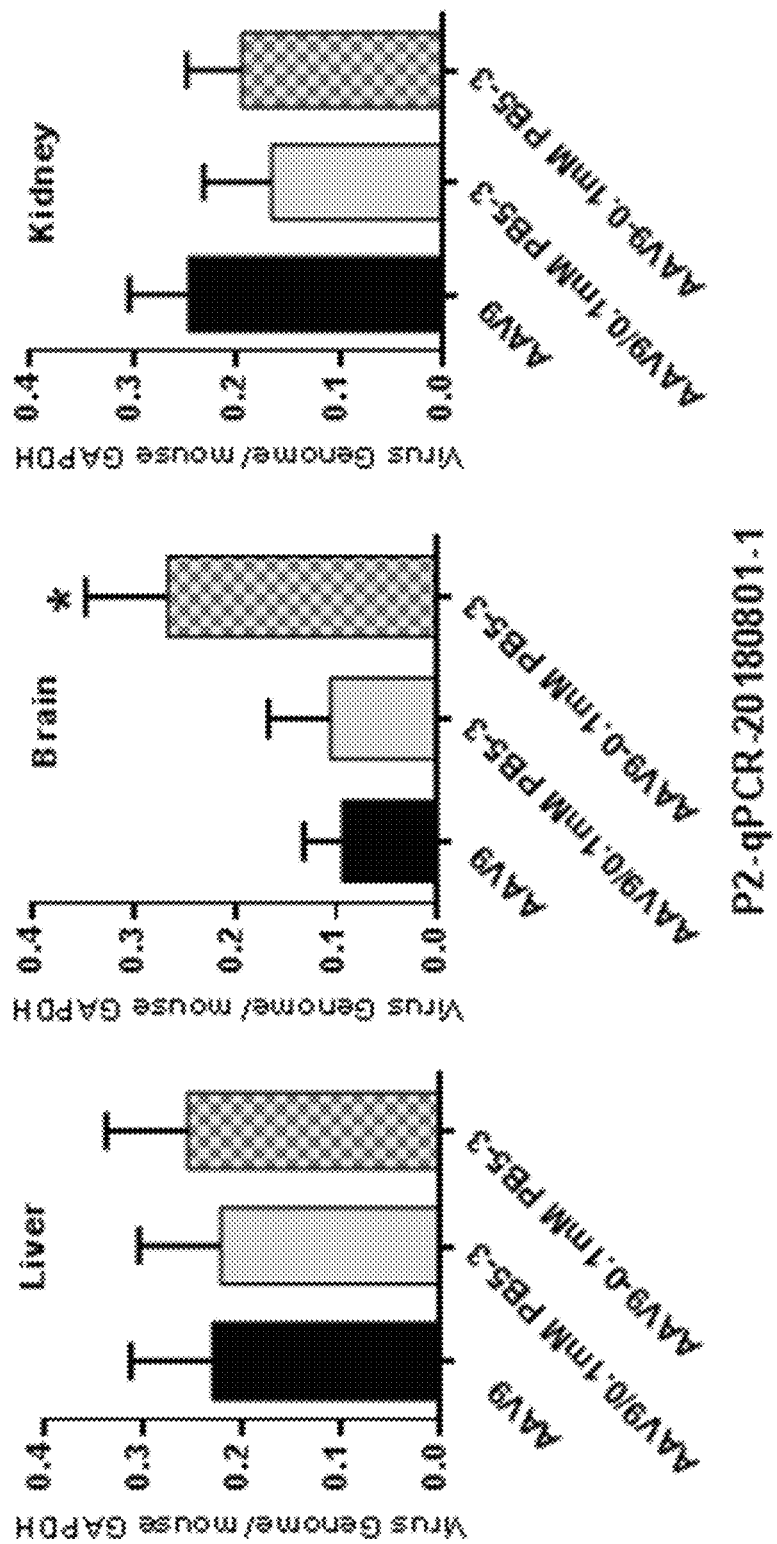
Figure 17:
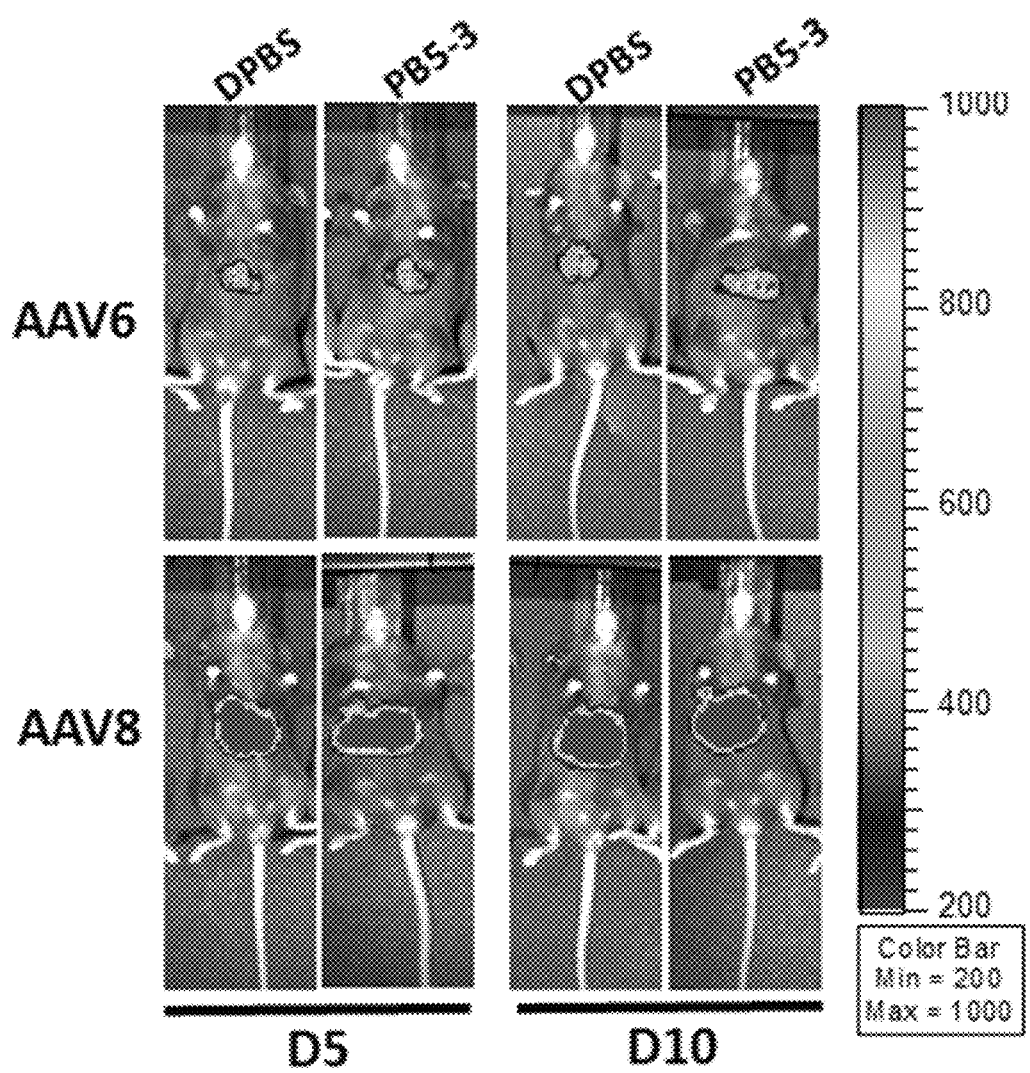
FIG. 17 shows there is no effect of PB5-3 on brain transduction from other AAV serotypes in mice after systemic administration. AAV/luc vectors from serotypes 6 or 8 at a dose of $5\times10^{10}$ or $1\times10^{10}$ particles, respectively, were incubated with PB5-3 for 2 hrs at 4° C. The complex was injected into C57BL mice via retro-orbital vein. At day 5 and 10 post AAV injection, mouse imaging was carried out. Representative imaging is shown from five mice.
Figure 18:
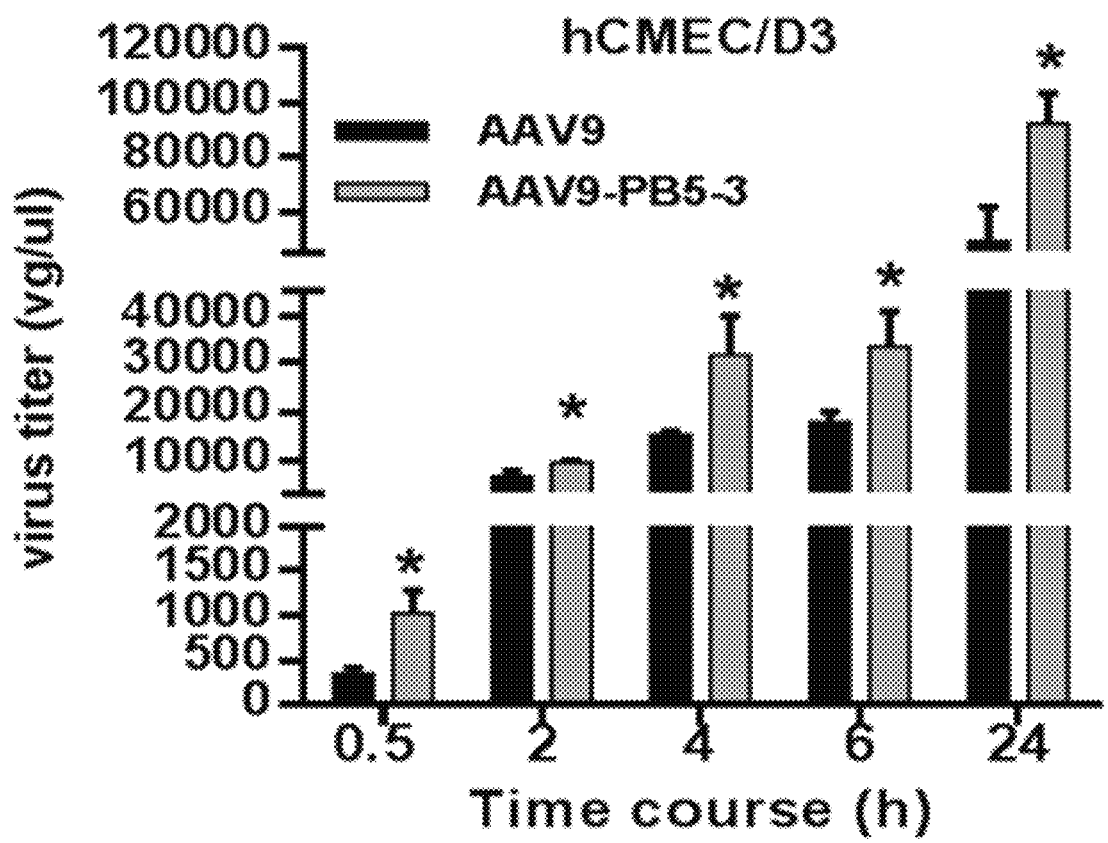
FIG. 18 shows that PB5-3 increases AAV9 permeability. hCMEC/D3 cells were cultured to form a monolayer in a transwell and incubated with AAV9 only, or the incubated AAV9-0.1 mM THR complex. Media in the basal chamber was collected at indicated time points and viral genome copy number was analyzed by qPCR. All treatments were performed in triplicate. *$p<0.05$ when compared to cells with the AAV9 only.

PB5-3 peptide enhances AAV9 transduction in the brain after systemic administration. To study the effect of PB5-3 peptide on AAV9 transduction in mice, we injected AAV9 vectors pre-incubated with PB5-3 peptide into C57BL mice via the retro-orbital vein. At days 1, 3, 7, and 14 post AAV administration, mouse imaging was taken. As shown in FIGS. 16A-16C, high transduction in brain tissues was observed when mice were treated with AAV9 pre-incubated with PB5-3 peptide. FIG. 16A shows representative imaging. Transduction in the liver was similar regardless of AAV9 pre-incubation with PB5-3 peptide (FIG. 16B). Consistent to tissue transgene expression, AAV genome copy number in the brain but not in other tissues was higher in mice receiving the complex of AAV9 and PB5-3 (FIG. 16C). This result suggests that interaction of PB5-3 with AAV9 is able to increase AAV9 potential to cross the BBB and enhance the brain transduction.

No effect of PB5-3 peptide on AAV brain transduction from other serotypes after systemic administration. To confirm the result in vitro that PB5-3 peptide could not efficiently bind to other AAV serotypes except for AAV9, we administered AAV6 and AAV8 vectors pre-incubated with PB5-3 in C57BL mice via retro-orbital injection. At days 5 and 10 post AAV application, mouse imaging was carried out. No brain transduction enhancement from AAV6 and AAV8 pre-incubated with PB5-3 was observed after systemic administration (FIG. 17). This result further implicates the specificity of PB5-3 for AAV9.

PB5-3 peptide enhances AAV9 permeability in vitro. To study whether PB5-3 affects the ability of AAV9 to cross the endothelial cell layer, we performed an in vitro endothelial cell permeability analysis in a well-defined system using BBB hCMEC/D3 endothelial cells. Two groups were designed: an AAV9 vector incubated with DPBS (AAV9 cohort); and an AAV9 vector incubated with PB5-3 (AAV9-PB5-3 cohort). A significant increase in the endothelial cell permeability was observed when the AAV9 vector was pre-incubated with the PB5-3 peptide at indicated time points (FIG. 18). These observations indicate that the interaction of AAV9 with the PB5-3 peptide increased the ability of AAV9 to cross the BBB.

Based on results from this study, we are able to isolate AAV serotype specific peptides which have the potential to interact with AAV vectors, increase AAV ability to cross the BBB, and enhance AAV brain transduction for clinical applications.

Example 3

Generation of the AAV9 Vector Constructs AAV9-PB5-3, AAV9-PB5-5, and AAV9-PB5-14 for the Delivery to the Central Nervous System (CNS)

An alternative to having the peptides described herein surface-bound to the AAV particle is to have them expressed in the context of the capsid protein of the AAV particle. Specifically, the peptides can be expressed in the capsid adjacent the threefold spike capsid domain (e.g., between amino acids 588 and 589 (the VP1 position) of the AAV capsid.

As described herein, recombinant adeno-associated virus 9 vectors (rAAV9s) will be generated carrying the peptide sequences of PB5-3, PB5-5, and PB5-14 inserted into their capsid protein for the delivery to the central nervous system (CNS) using the vector rAAV-Cap-in-cis-lox. It is expected that the peptides PB5-3, PB5-5 and PB-14 will enhance the ability of the AAV9 vector to cross the blood brain barrier (BBB) and that they can be used for efficient and specific long-term CNS-directed transgene expression.

Generation of AAV9-PB5-3, AAV9-PB5-5, and AAV9-PB5-14 vector constructs. As described herein, an AAV vector construct will be generated carrying PB5-3, PB5-5, and PB5-14 for the delivery to the central nervous system (CNS). The rAAV vectors AAV9-PB5-3, AAV9-PB5-5, and AAV9-PB5-14 by inserting the amino acids (AA) of the peptide sequences of PB5-3; PB5-5 and PB5-14 between AA588-589 (VP1 position) of the AAV9 capsid of the rAAV-Cap-in-cis-lox (Deverman et al. Nature Biotech 34, p. 204-209 (2016)). The following peptide sequences will be inserted: PB5-3: QFAALPVRAHYG-NH2 (SEQ ID NO:133), PB5-5: ARSLEPAPSRHS-NH2 (SEQ ID NO:134) and PB5-14: AIGDKAYTLRPT-NH2 (SEQ ID NO:135). If necessary, an amino acid such as Glycine will be added to the N-terminus, the C-terminus, or both, of the peptide sequences to provide flexibility at the junctions of the peptide insertions into the AAV capsid. This will ensure any structure is necessary for these peptides to function at enhancing transduction activity of the vector.

Cloning of the peptides PB5-3, PB5-5, and PB5-14 into the rAAV-Cap-in-cis-lox vector. The rAAV-Cap-in-cis-lox plasmid contains a full-length AAV Cap gene, controlled by regulatory elements from the AAV Rep gene, with a Cre-invertible switch. The rAAV-Cap-in-cis-lox plasmid contains three main elements flanked by AAV2 ITRs: (i) an mCherry expression cassette, which is comprised of a 398 bp fragment of the human UBC gene upstream of the mCherry cDNA followed by a synthetic polyadenylation sequence; (ii) the AAV9 capsid gene and regulatory sequences, which comprise a AAV5 p41 promoter sequence (1680-1974 of GenBank AF085716.1) and splicing sequences from the AAV2 rep gene; and (iii) a Cre-dependent switch, which comprises a SV40 polyadenylation sequence (pA) flanked by inverted lox71 and lox66 sites. The rAAV-Cap-in-cis-lox plasmids also contain two unique restriction sites, XbaI and AgeI, within the capsid sequence. Because the rAAV-Cap-in-cis-lox vectors lack a functional Rep gene, Rep must be provided in trans for virus production. The rAAV-Cap-in-cis-lox together with a Rep-AAP AAV plasmid can efficiently generate rAAV.

The rAAV vectors AAV9-PB5-3, AAV9-PB5-5, and AAV9-PB5-14 will be generated by inserting 12 amino acids (AA) of the peptide sequences of PB5-3; PB5-5 and PB5-14 between AA588-589 (VP1 position) of the AAV9 capsid of the rAAV-Cap-in-cis-lox. Ultramer oligonucleotides (IDT Integrated DNA Technologies) encoding the peptides QFAALPVRAHYG-NH2 (PB5-3 (SEQ ID NO:133)), ARSLEPAPSRHS-NH2 (PB5-5 (SEQ ID NO:134)) and AIGDKAYTLRPT-NH2 (PB5-14 (SEQ ID NO:135)) including a 15-bp overlap on each side of the sequence with homology to the insertion site on the AAV plasmid will be synthesized by in vitro gene synthesis and cloned into the rAAV-Cap-in-cis-lox capsid using an in-fusion cloning procedure (Takarabio, Cat. #638911, In-Fusion HD Cloning Plus), which allows for the joining of the DNA fragments in a single, isothermal reaction. Based on Michelfelder et al., ((2011) Peptide Ligands Incorporated into the Threefold Spike Capsid Domain to Re-Direct Gene Transduction of AAV8 and AAV9 in vivo. PLoS ONE 6(8)) the peptides PB5-3, PB5-5, and PB5-14 will be positioned within the threefold spike region on the capsid surface allowing for efficient transduction. The peptides may also be inserted into the analogous site in capsid proteins of other AAV serotypes (e.g., AAV2, AAV8) or hybrid serotypes, for example by the methods disclosed in Michelfelder et al. ((2011) Peptide Ligands Incorporated into the Threefold Spike Capsid Domain to Re-Direct Gene Transduction of AAV8 and AAV9 in vivo. *PLoS ONE* 6(8).)

In-fusion HD cloning. In-Fusion HD Cloning are designed for fast, directional cloning of one or more fragments of DNA into any vector. The In-Fusion Enzyme fuses DNA fragments (e.g., PCR-generated inserts and linearized vectors) efficiently and precisely by recognizing 15-bp overlaps at their ends. Ultramer oligonucleotides (IDT Integrated DNA Technologies) encoding the peptides QFAALPVRAHYG-NH2 (PB5-3 (SEQ ID NO:133)), ARSLEPAPSRHS-NH2 (PB5-5 (SEQ ID NO: 134)) and AIGDKAYTLRPT-NH2 (PB5-14 (SEQ ID NO:135)) including a 15-bp overlap on each side of the sequence with homology to the insertion site on the rAAV-Cap-in-cis-lox plasmid will be synthesized, the rAAV-Cap-in-cis-lox vector will be linearized using the unique restriction site XbaI and the in-fusion cloning reaction will be performed. The reaction products will then be treated with Plasmid Safe (PS) DNase (Epicentre; E3105K) to digest any unassembled fragments and purified using a QIAquick PCR Purification Kit (Qiagen). This reaction will yield over 100 ng of assembled plasmid (as defined by the amount of DNA remaining after the PS DNase digestion step). Competent cells will be transformed with the assembled AAV9-PB5-3, AAV9-PB5-5, and AAV9-PB5-14 vectors.

Delivery of the PB5-3, PB5-5 and PB-14 vectors to the Central Nervous system (CNS). The effects on transduction efficiency of the AAV9-PB5-3, AAV9-PB5-5, and AAV9-PB5-14 vector constructs will be examined in vivo and compared to unmodified AAV9 vectors. AAV9-PB5-3, AAV9-PB5-5, and AAV9-PB5-14 and unmodified AAV9 vectors will be used to package a single-stranded (ss) GFP reporter vector driven by the ubiquitous CAG promoter (ssAAV-CAG-GFP). It is expected that AAV9-PB5-3, AAV9-PB5-5, and AAV9-PB5-14 and AAV9 vectors will produce virus with similar efficiencies. $1 \times 10^{12}$ vector genomes (vg) of either vector will be administered to six-week-old mice by intravenous injection and the transduction by GFP expression will be assessed three weeks later.

In order to assess the transduction efficiency of the vectors to the CNS, GFP immunohistochemistry (IHC) and/or native eGFP fluorescence of several brain regions, the spinal cord and retina will be performed. It is expected that the AAV9-PB5-3, AAV9-PB5-5, and AAV9-PB5-14 vectors will transduce the entire adult CNS with high efficiency. Further, PARS-based CLARITY for whole body tissue clearing will be performed and the native eGFP fluorescence through cleared sections of tissue from the spinal cord, cortex and striatum. It is to be expected that the cellular level tropism of the AAV9-PB5-3, AAV9-PB5-5, and AAV9-PB5-14 and AAV9 in most organs (liver, heart, skeletal muscle and kidneys) will be similar compared to unmodified AAV9 vectors.

In order to quantify the efficiency of gene transfer to the CNS by the AAV9-PB5-3, AAV9-PB5-5, and AAV9-PB5-14 vectors compared with unmodified but otherwise identical AAV9 vectors, the number of viral genomes present in several brain regions will be measured 25 days post-injection. It is expected that AAV9-PB5-3, AAV9-PB5-5, and AAV9-PB5-14 vectors will provide an enhanced gene transfer efficiency compared to AAV9 to one or more of the following CNS regions: cortex, striatum, thalamus, cerebellum and spinal cord.

In order to examine the cell types transduced by AAV9-PB5-3, AAV9-PB5-5, and AAV9-PB5-14 vectors, the co-localization of GFP with several cell-type markers will be analyzed. It is expected that AAV9-PB5-3, AAV9-PB5-5, and AAV9-PB5-14 vectors will transduce one or more of astrocytes, CC1+ oligodendrocytes, neuronal subtypes including NeuN+ cells throughout the brain, midbrain tyrosine hydroxylase (TH)+ dopaminergic neurons, Calbindin+ cerebellar Purkinje cells, interneuron populations and CD31+ endothelial cells. Native GFP expression will be followed throughout the brain over a year after administration of AAV9-PB5-3, AAV9-PB5-5, and AAV9-PB5-14. It is expected that AAV9-PB5-3, AAV9-PB5-5, and AAV9-PB5-14 will provide an efficient, specific and long-term, CNS-directed transgene expression.

In order to quantify the fraction of several cell types transduced by AAV9-PB5-3, AAV9-PB5-5, and AAV9-PB5-

14 vectors as compared to unmodified AAV9 vectors and to facilitate reliable individual cell counting, a vector expressing a nuclear-localized GFP (NLS-GFP) under the control of the CAG promoter, ssAAV-CAG-NLS-GFP will be constructed. It is expected that adult intravenous administration of AAV9-PB5-3, AAV9-PB5-5, and AAV9-PB5-14 will efficiently target one or more of neuronal and glial cell types in the adult mouse such as the majority of Aldh1L1+ astrocytes, NeuN+ neurons, Olig2+ oligodendrocyte lineage cells across all brain regions, Chat+ motor neurons throughout the spinal cord, TH+ midbrain dopaminergic neurons and Calbindin+ Purkinje cells.

Transduction efficiency of the AAV9-PB5-3, AAV9-PB5-5, and AAV9-PB5-14 vectors to human neural cells. In order to determine the transduction efficiency of AAV9-PB5-3, AAV9-PB5-5, and AAV9-PB5-14 to human neural cells, the vectors will be tested on cortical neurons and astrocytes derived from human induced pluripotent stem cells (hiPSCs) using a 3D differentiation method. HiPSC lines from individuals will be differentiated into 3D cerebral cortex-like structures (cortical spheroids), and maintained in vitro for up to 200 days. Aged cortical spheroids contain superficial and deep layer cortical excitatory neurons and up to 20% astrocytes. It is expected that AAV9-PB5-3, AAV9-PB5-5, and AAV9-PB5-14 will transduce one or more of GFAP-expressing astrocytes, MAP2-expressing neurons and intact 3D cortical spheroids more efficiently in comparison with the unmodified AAV9 vectors.

The generated AAV9-PB5-3, AAV9-PB5-5, and AAV9-PB5-14 vectors will enable efficient widespread gene transfer to the CNS. Another important advantage of this system is that it introduces selective pressure for capsids that mediate efficient intracellular trafficking and conversion of the single-stranded viral genome to persistent double-stranded DNA (dsDNA) forms necessary for long-term transduction (only the dsDNA genomes should serve as substrates for Cre).

Plasmids. The rAAV-Cap-in-cis-lox genome plasmid contains three main elements flanked by AAV2 ITRs: (i) an mCherry expression cassette, which is comprised of a 398 bp fragment of the human UBC gene upstream of the mCherry cDNA followed by a synthetic polyadenylation sequence40; (ii) the AAV9 capsid gene and regulatory sequences, which are comprised of the AAV5 p41 promoter sequence (1680-1974 of GenBank AF085716.1) and splicing sequences taken from the AAV2 rep gene; and (iii) a Cre-dependent switch, which is comprised of the SV40 polyadenylation sequence (pA) flanked by inverted lox71 and lox66 sites43. The rAAV-Cap-in-cis-lox genome plasmid also contains two unique restriction sites, XbaI and AgeI, within the capsid sequence.

Virus production and purification. Recombinant AAVs will be generated by triple transfection of 293T cells (ATCC) using polyethylenimine (PEI). Viral particles will be harvested from the media at 72 hrs post transfection and from the cells and media at 120 hrs. Cell pellets will be resuspended in 10 mM Tris with 2 mM MgCl2, pH 8, freeze-thawed three times, and treated with 100 U/mL Benzonase (Epicentre) at 37° C. for at least 1 hr. Viral media will be concentrated by precipitation with 8% polyethylene glycol 8000 (Sigma-Aldrich) with 500 mM sodium chloride, resuspended in Tris-MgCl2, and then added to the lysates. The combined stocks will be then adjusted to 500 mM NaCl, incubated at 37° C. for 30 minutes, and clarified by centrifugation at 2000×g. The clarified stocks will be then purified over iodixanol (Optiprep, Sigma; D1556) step gradients (15%, 25%, 40% and 60%).

Viruses will be concentrated and formulated in phosphate buffered saline (PBS). AAV stability, yield and infectivity will be tested as done in Grieger et al., (Clinical Vector. Mol Ther. 24 (2016); P. 287-297) and Francois A. et al. (Mol Ther Methods Clin Dev. 10 (2018); P. 223-236).

Virus Titers. Virus titers will be determined by measuring the number of DNaseI-resistant virus genomes using qPCR with linearized genome plasmid as a standard. Infectivity of the AAV particles will be assessed by titration of the infectious AAV particles by qPCR as described in and Francois A. et al. (2018).

Animals. GFAP-Cre mice expressing Cre under the control of the mouse GFAP promoter (012886)23 and C57Bl/6J mice (000664) will be purchased from the Jackson Laboratory (JAX). Intravenous administration of rAAV vectors will be performed by injecting the virus into the retro-orbital sinus. Mice will be randomly assigned to groups of predetermined sample size. No mice will be excluded from these analyses. Experimenters will be blinded to sample groups.

Vector biodistribution. Six-week-old mice female C57Bl/6 mice will be injected intravenously with $1\times10^{11}$ vg of the ssAAV-CAG-GFP vector packaged into the indicated AAV capsid (AAV9-PB5-3, AAV9-PB5-5, and AAV9-PB5-14). Animals will be randomly assigned to groups. 25 days after injection, the mice will be euthanized and tissues and indicated brain regions will be collected and frozen at −80° C. DNA will be isolated from the tissue samples using Qiagen DNeasy Blood and Tissue kit. Vector genomes will be detected using PCR primers that bind to the WPRE element and will be normalized to mouse genomes using primers specific to the mouse glucagon gene. Absolute quantification will be performed using serial dilutions of linearized plasmid standards of known concentration.

Tissue preparation, immunohistochemistry and imaging. Mice will be anesthetized with Nembutal and transcardially perfused with 0.1 M phosphate buffer (PB) at room temperature (RT) at pH 7.4 and then with freshly prepared, ice-cold 4% paraformaldehyde (PFA) in PB. Brains will be post-fixed in 4% PFA overnight and then sectioned by vibratome or cryoprotected and sectioned by cryostat. IHC will be performed on floating sections with primary and secondary antibodies in PBS containing 10% goat or donkey serum and 0.5% Triton X-100 (no detergent will be used for GAD67 staining). Primary antibodies used will be mouse anti-AAV capsid (1:20; American Research Products, 03-65158, clone B1), rabbit anti-GFP (1:1000; Invitrogen, A11122), chicken anti-GFP (1:1000; Abcam, ab13970), mouse anti-CC1 (1:200; Calbiochem, OP80), rabbit anti-GFAP (1:1000; Dako, Z0334), mouse anti-NeuN (1:500; Millipore, MAB377), rabbit anti-Iba1 (1:500; Biocare Medical, CP290), mouse anti-Calbindin D28K (1:200; Sigma, CB-955), rabbit anti-Calretinin (1:1000; Chemicon, AB5054), mouse anti-GAD67 (1:1000; Millipore, MAB5406), guinea pig anti-MAP2 (1:1000; Synaptic Systems, 188004), mouse anti-Parvalbumin (1:1000; Sigma), Tyrosine Hydroxlyase (1:1000, Aves) and rabbit anti-CD31 (1:50; Abcam, ab28364).

Quantification of cell type-specific transduction. Six-week-old female mice will be randomly assigned to groups and injected intravenously with $2\times10^{12}$ vg of ssAAV-CAG-NLS-GFP packaged into the AAV9-PB5-3, AAV9-PB5-5, AAV9-PB5-14 and unmodified AAV9 capsids. Three weeks later, the mice will be perfused and the brains will be processed and immunostained for the indicated antigen as described above. Confocal single-plane images of the cell type-specific immunostaining and native NLS-GFP fluorescence will be taken. Cell counting will be performed by first counting and marking each cell stained by the cell-specific antigen by viewing the IHC channel. Next those marked IHC+ cells that will be positive for native GFP fluorescence will be counted. Due to the stark transduction efficiency differences between capsids, the counting will be not blinded by group.

Tissue clearing. Mice will be perfused with 60-80 mL of ice-cold 4% PFA in PBS at a flow rate of 14 mL per minute. The flow rate will be then reduced to 2-3 mL/min and continued for 2 hrs at RT. The mice will be then placed in individual custom-built chambers and perfused with 200 mL of recycling RT 4% acrylamide in PB at 2-3 mL/min overnight followed by a 2-hr perfusion flush with PB to remove residual polymers/monomers from the vasculature. The polymerization process will be initiated by placing the chambers in a 42° C. water bath and delivering, by perfusion (2-3 mL/min), of 200 mL of recycling, degassed PB containing 0.25% VA-044 initiator for 2-4 hrs. The mice will be then perfused with 8% SDS in PBS, pH 7.5 for 7 days. The SDS containing solution will be refreshed two times during the 7 days and then flushed out by perfusion of 2 L of non-recirculating PB overnight. Cleared tissue samples will be mounted in RIMS solution (refractive index of 1.46) for imaging.

Generation of cortical spheroids from human iPSC lines. Human cortical spheroids will be generated from iPSC lines. Briefly, iPSC lines derived from two healthy control individuals will be grown on inactivated mouse embryonic fibroblast feeders in the following medium: DMEM/F12, Knockout Serum 20%, 1 mM non-essential amino acids (1:100), GlutaMax (1:200), β-mercaptoethanol (0.1 mM), penicillin and streptomycin (1:100) (Life Technologies). Cultures will be regularly tested and maintained mycoplasma free. Colonies of iPSCs will be detached intact with dispase (0.35 mg/ml, Invitrogen) and transferred into low-attachment plates in iPSC medium supplemented with dorsomorphin (5 µM, Sigma) and SB-431542 (10 µM, Tocris), and the medium will be changed daily. On day six of in vitro differentiation, neural spheroids will be transferred to NPC medium (Neurobasal A, B27 without vitamin A, GlutaMax (1:100), penicillin and streptomycin; Life Technologies), which will be supplemented with EGF (20 ng/ml) and FGF2 (20 ng/ml) until day 24, and then supplemented with BDNF (20 ng/ml) and NT3 (20 ng/ml) from day 25 to 42. From day 43 onwards, cortical spheroids will be maintained in NPC medium, which will be changed every 4 days.

Dissociation and viral infection of cortical spheroids. For enzymatic dissociation and culture in monolayer, cortical spheroids at day 170-200 of in vitro differentiation (two independent neural differentiations of one iPSC line from one individual and one differentiation of an iPSC line from another individual) will be incubated with Accutase (Innovative Cell Technologies) for 25 min at 37° C., will be washed three times with NPC media and gently triturated with a P-200 pipette. Cells will be plated on poly-ornithine and laminin coated glass coverslip (15 mm) at ~300,000 cells/well and maintained in NPC media supplemented with BDNF (20 ng/ml) and NT3 (20 ng/ml) for the first 24 hrs, and then maintained in NPC media without growth factors.

Cultures grown on coverslips will be infected with each of the viruses at a titer of $1\times10^9$ vg/well and fixed 5 days later with 4% paraformaldehyde (PFA) for 10 min. For immunocytochemistry, cells will be permeabilized with 0.2% Triton X-100 for 10 min and blocked with 10% goat serum in PBS for 1 hr. Coverslips will be then incubated with antibodies diluted in blocking solution for 2 hr. Nuclei will be visualized with Hoechst 33258 (Life Technologies, 1:10,000). Cells will be imaged with a Zeiss M1 Axioscope using a 40× objective. The proportion of GFP+ cells co-labeled with either GFAP or MAP2 will be quantified in images of 10 random fields per coverslip for each experimental condition. Results presented are the average of two separate dissociation and infection experiments.

To infect intact 3D cultures with the AAV9-PB5-3, AAV9-PB5-5, AAV9-PB5-14 and unmodified AAV9 vectors, single human cortical spheroids at day 197 days of in vitro differentiation will be transferred overnight into 1.5 ml Eppendorf tubes containing $6\times10^9$ vg/400 µl in NPC media, and will be fixed 7 days later in 4% PFA overnight. Fixed spheroids will be then transferred into 30% sucrose for 24 hrs, embedded in O.C.T. (Fisher Scientific) and cut at 14 µm sections. For immunohistochemistry, sections will be blocked with 10% goat serum in PBS containing 0.3% Triton-X100 for 1 hr. Images will be collected with a Leica TCS SP8 confocal microscope.

Further description of these methods can be found in Michelfelder et al., ((2011) PLoS ONE 6(8)), Deverman et al. (2016) Nat Biotechnol. 2016 February; 34(2): 204-209), Grieger et al. (2016) "Production of Recombinant Adeno-associated Virus Vectors Using Suspension HEK293 Cells and Continuous Harvest of Vector from the Culture Media for GMP FIX and FLT1 Clinical Vector" Mol Ther. 2016 February; 24(2):287-297 and Francois A., (2018) "Molecular Therapy: Methods & Clinical Development" Mol Ther Methods Clin Dev. 2018 Jul. 27; 10:223-236.

Although the present invention has been described with reference to specific details of certain embodiments thereof, it is not intended that such details should be regarded as limitations upon the scope of the invention except as and to the extent that they are included in the accompanying claims.

Throughout this application, various patents, patent publications, and non-patent publications are referenced. The disclosures of these patents and publications in their entireties are incorporated by reference into this application in order to more fully describe the state of the art to which this invention pertains.

TABLE 1

|  | GenBank Accession Number |  | GenBank Accession Number |  | GenBank Accession Number |
|---|---|---|---|---|---|
| Complete Genomes |  | Hu S17 | AY695376 | Hu66 | AY530626 |
| Adeno-associated virus 1 | NC_002077, AF063497 | Hu T88 | AY695375 | Hu42 | AY530605 |
| Adeno-associated virus 2 | NC_001401 | Hu T71 | AY695374 | Hu67 | AY530627 |
| Adeno-associated virus 3 | NC_001729 | Hu T70 | AY695373 | Hu40 | AY530603 |
| Adeno-associated virus 3B | NC_001863 | Hu T40 | AY695372 | Hu41 | AY530604 |
| Adeno-associated virus 4 | NC_001829 | Hu T32 | AY695371 | Hu37 | AY530600 |
| Adeno-associated virus 5 | Y18065, AF085716 | Hu T17 | AY695370 | Rh40 | AY530559 |
| Adeno-associated virus 6 | NC_001862 | Hu LG15 | AY695377 | Rh2 | AY243007 |

TABLE 1-continued

| | GenBank Accession Number | | GenBank Accession Number | | GenBank Accession Number |
|---|---|---|---|---|---|
| Avian AAV ATCC VR-865 | AY186198, AY629583, NC_004828 | Clade C | | Bb1 | AY243023 |
| Avian AAV strain DA-1 | NC_006263, AY629583 | Hu9 | AY530629 | Bb2 | AY243022 |
| Bovine AAV | NC 005889, AY388617, AAR26465 | Hu10 | AY530576 | | |
| AAV11 | AAT46339, AY631966 | Hu11 | AY530577 | Rh10 | AY243015 |
| AAV12 | ABI16639, DQ813647 | | | Hu17 | AY530582 |
| Clade A | | Hu53 | AY530615 | Hu6 | AY530621 |
| AAV1 | NC_002077, AF063497 | Hu55 | AY530617 | Rh25 | AY530557 |
| AAV6 | NC_001862 | Hu54 | AY530616 | Pi2 | AY530554 |
| Hu.48 | AY530611 | Hu7 | AY530628 | Pi1 | AY530553 |
| Hu 43 | AY530606 | Hu18 | AY530583 | Pi3 | AY530555 |
| Hu 44 | AY530607 | Hu15 | AY530580 | Rh57 | AY530569 |
| Hu 46 | AY530609 | Hu16 | AY530581 | Rh50 | AY530563 |
| Clade B | | Hu25 | AY530591 | Rh49 | AY530562 |
| Hu. 19 | AY530584 | Hu60 | AY530622 | Hu39 | AY530601 |
| Hu. 20 | AY530586 | Ch5 | AY243021 | Rh58 | AY530570 |
| Hu 23 | AY530589 | Hu3 | AY530595 | Rh61 | AY530572 |
| Hu22 | AY530588 | Hu1 | AY530575 | Rh52 | AY530565 |
| Hu24 | AY530590 | Hu4 | AY530602 | Rh53 | AY530566 |
| Hu21 | AY530587 | Hu2 | AY530585 | Rh51 | AY530564 |
| Hu27 | AY530592 | Hu61 | AY530623 | Rh64 | AY530574 |
| Hu28 | AY530593 | Clade D | | Rh43 | AY530560 |
| Hu 29 | AY530594 | Rh62 | AY530573 | AAV8 | AF513852 |
| Hu63 | AY530624 | Rh48 | AY530561 | Rh8 | AY242997 |
| Hu64 | AY530625 | Rh54 | AY530567 | Rh1 | AY530556 |
| Hu13 | AY530578 | Rh55 | AY530568 | Clade F | |
| Hu56 | AY530618 | Cy2 | AY243020 | Hu14 (AAV9) | AY530579 |
| Hu57 | AY530619 | AAV7 | AF513851 | Hu31 | AY530596 |
| Hu49 | AY530612 | Rh35 | AY243000 | Hu32 | AY530597 |
| Hu58 | AY530620 | Rh37 | AY242998 | Clonal Isolate | |
| Hu34 | AY530598 | Rh36 | AY242999 | AAV5 | Y18065, AF085716 |
| Hu35 | AY530599 | Cy6 | AY243016 | AAV 3 | NC_001729 |
| AAV2 | NC_001401 | Cy4 | AY243018 | AAV 3B | NC_001863 |
| Hu45 | AY530608 | Cy3 | AY243019 | AAV4 | NC_001829 |
| Hu47 | AY530610 | Cy5 | AY243017 | Rh34 | AY243001 |
| Hu51 | AY530613 | Rh13 | AY243013 | Rh33 | AY243002 |
| Hu52 | AY530614 | Clade E | | Rh32 | AY243003 |
| Hu T41 | AY695378 | Rh38 | AY530558 | | |

TABLE 2

Amino acid residues and abbreviations.

| | Abbreviation | |
|---|---|---|
| Amino Acid Residue | Three-Letter Code | One-Letter Code |
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

TABLE 3

| TABLE 3Serotype | Position 1 | Position 2 |
|---|---|---|
| AAV1 | A263X | T265X |
| AAV2 | Q263X | -265X |
| AAV3a | Q263X | -265X |
| AAV3b | Q263X | -265X |
| AAV4 | S257X | -259X |
| AAV5 | G253X | V255X |
| AAV6 | A263X | T265X |
| AAV7 | E264X | A266X |
| AAV8 | G264X | S266X |
| AAV9 | S263X | S265X |

Where, (X) → mutation to any amino acid
(-) → insertion of any amino acid
Note:
Position 2 inserts are indicated by the site of insertion

TABLE 4

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |

TABLE 4-continued

| Modified Amino Acid Residue | Abbreviation |
|---|---|
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,2'-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methylisoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-Cl) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

TABLE 5

Sequences and Polarity of Peptides Used in the Study

| Peptides | Sequences (SEQ ID NO.) | Polarity | Proposed transporter |
|---|---|---|---|
| LAH4 | KKALLALALHHLAHLALALKKAC (SEQ ID NO: 180) | Basic | N/A |
| Angiopep-2 | TFFYGGSRGKRNNFKTEEY-OH (SEQ ID NO: 181) | Basic | LRP1 |
| GSH | r-g-L-glutamyl-CG-OH | | GSH transporter |
| HIV-1 TAT(48-60) | GRKKRRQRRRPPQ (SEQ ID NO: 182) | Basic | AMT |
| ApoE (159-167)2 | (LRKLRKRLL)2 (SEQ ID NO: 138) | Basic | LRP1, LRP2, LDLR |
| Leptin 30 (61-90) | YQQILTSMPSRNVIQISNDLENLRDLLHVL (SEQ ID NO: 141) | Neutral | Leptin receptor |
| THR | THRPPMWSPVWP-NH2 (SEQ ID NO: 139) | Basic | TfR1 |
| PEPXT-1 | FILMVWAPFI (SEQ ID NO: 183) | Neutral | N/A |
| PEPXT-2 | STNQSTNQST (SEQ ID NO: 184) | Neutral | N/A |
| PEPXT-3 | DEDEDEDEDE (SEQ ID NO: 185) | Acid | N/A |
| PEPXT-4 | RKHRKHRKHR (SEQ ID NO: 186) | Basic | N/A |

TABLE 6

BBB Shuttle Peptides

| Peptide | Sequence (SEQ ID NO.) |
|---|---|
| Angiopep-2 | TFFYGGSRGKRNNFKTEEY-OH (SEQ ID NO: 136) |
| ApoB (3371-3409) | SSVIDALQYKLEGTTRLTRKRGLKLATALSLSNKFVEGS (SEQ ID NO: 137) |

TABLE 6-continued

| BBB Shuttle Peptides | |
|---|---|
| Peptide | Sequence (SEQ ID NO.) |
| ApoE (159-167)2 | (LRKLRKRLL)2 (SEQ ID NO: 138) |
| Peptide-22 | Ac-C(&)MPRLRGC(&)-NH2 |
| THR | THRPPMWSPVWP-NH2 (SEQ ID NO: 139) |
| THR retro-enantio | pwvpswmpprht-NH2 (SEQ ID NO: 140) |
| CRT | C(&)RTIGPSVC(&) |
| Leptin30 | YQQILTSMPSRNVIQISNDLENLRDLLHVL (SEQ ID NO: 141) |
| RVG29 | YTIWMPENPRPGTPCDIFTNSRGKRASNG-OH (SEQ ID NO: 142) |
| D-CDX | GreirtGraerwsekf-OH (SEQ ID NO: 143) |
| Apamine | C(&1)NC(&2)KAPETALC(&1)-ARRC(&2)QQH-NH2 |
| MiniAp-4 | [Dap](&)KAPETALD(&) |
| GSH | g-L-glutamyl-CG-OH |
| G23 | HLNILSTLWKYRC (SEQ ID NO: 144) |
| g7 | GFtGFLS(O-b-Glc)-NH2 |
| TGN | TGNYKALHPHNG (SEQ ID NO: 145) |
| TAT (47-57) | YGRKKRRQRRR-NH2 (SEQ ID NO: 146) |
| SynB1 | RGGRLSYSRRRFSTSTGR (SEQ ID NO: 147) |
| Diketopiperazines | &(N-MePhe)-(N-MePhe)Diketopiperazines |
| PhPro | (Phenylproline)4-NH2 (SEQ ID NO: 179) |
| PepH3 | AGILKRW (SEQ ID NO: 148) |
| gH625 | Ac-HGLASTLTRWAHYNALIRAFGGG-COOH (SEQ ID NO: 149) |
| SGV | SGVYKVAYDWQH (SEQ ID NO: 150) |
| B6 | G-GHKAKGPRK-LGS (SEQ ID NO: 151) |
| HAI | HAIYPRH (SEQ ID NO: 152) |
| -SxTSSTx- | AC-SYTSSTM-CGGGS (SEQ ID NO: 153) |
| CRT | CRTIGPSVC (SEQ ID NO: 154) |
| GLA | GLAHSFSDFARDFVA (SEQ ID NO: 155) |
| GYR | GYRPVHNIRGHWAPG (SEQ ID NO: 156) |

TABLE 6-continued

| BBB Shuttle Peptides | |
|---|---|
| Peptide | Sequence (SEQ ID NO.) |
| LNP | KKRTLRKNDRKKRC (SEQ ID NO: 157) |
| T7 | HAIYPRH (SEQ ID NO: 158) |
| RVG | YTIWMPENPRPGTPCDIFTNSRGKRASNG (SEQ ID NO: 159) |
| #2077 | RLSSVDSDLSGC (SEQ ID NO: 160) |
| TP10 | AGYLLGKINLKALAALAKKIL (SEQ ID NO: 161) |
| TP10-2 | AGYLLGKINLKPLAALAKKIL (SEQ ID NO: 162) |
| pVEC | LLIILRRRIRKQAHAHSK (SEQ ID NO: 163) |
| SynB3 | RRLSYSRRRF (SEQ ID NO: 164) |
| ANP | SLRRSSCFGGRMDRIGAQSGLGCNSFRY (SEQ ID NO: 165) |
| BNP | SPKMVQGSGCFGRKMDRISSSSGLGCKVLRRH (SEQ ID NO: 166) |
| PHP.B | AQ-TLAVPFK (SEQ ID NO: 167) |
| PHP.B2 | SVSKPEL (SEQ ID NO: 168) |
| PHP.B3 | FTLTTPK (SEQ ID NO: 169) |
| PHP.A | YTLSQGW (SEQ ID NO: 170) |
| G2A15 | LAKERLS (SEQ ID NO: 171) |
| PHP.eB | DG-TLAVPFK (SEQ ID NO: 172) |
| PHP.S (G2A12) | QAVRTSL (SEQ ID NO: 173) |
| BR1 | NRGTEWD (SEQ ID NO: 174) |
| BR2 | ADGVQWT (SEQ ID NO: 175) |
| BR3 | DDGVSWK (SEQ ID NO: 176) |
| BR4 | SDGLTWS (SEQ ID NO: 177) |
| BR5 | SDGLAWV (SEQ ID NO: 178) |

TABLE 7

PB5 peptide sequences

| PB5-3 | QFAALPVRAHYG-NH2 (SEQ ID NO: 133) |
| PB5-5 | ARSLEPAPSRHS-NH2 (SEQ ID NO: 134) |
| PB5-14 | AIGDKAYTLRPT-NH2 (SEQ ID NO: 135) |

---

What is claimed is:

1. An adeno-associated virus (AAV) particle comprising a surface-bound peptide, wherein the peptide bound to the surface of the AAV particle is selected from the group consisting of:
   a) PB5-3 (SEQ ID NO:133);
   b) PB5-5 (SEQ ID NO: 134);
   c) PB5-14 (SEQ ID NO:135); and
   d) any combination of (a)-(c) above.

2. The AAV particle of claim 1, wherein the AAV is of a serotype or any combination of serotypes selected from the group consisting of AAV1, AAV2, AAV3, AAV3B, AAV4, AAV5, AAV6, AAV7, AAV8, AAV9, Avian AAV, Avian AAV strain DA-1, Bovine AAV, AAV11, AAV12, Clade A, Hu.48, Hu 43, Hu 44, Hu 46, Clade B, Hu. 19, Hu. 20, Hu 23, Hu22, Hu24, Hu21, Hu27, Hu28, Hu 29, Hu63, Hu64, Hu13, Hu56, Hu57, Hu49, Hu58, Hu34, Hu35, Hu45, Hu47, Hu51, Hu52, Hu T41, Hu S17, Hu T88, Hu T71, Hu T70, Hu T40, Hu T32, Hu T17, Hu LG15, Clade C, Hu9, Hu10, Hu11, Hu53, Hu55, Hu54, Hu7, Hu18, Hu15, Hu16, Hu25, Hu60, Ch5, Hu3, Hu1, Hu4, Hu2, Hu61, Clade D, Rh62, Rh48, Rh54, Rh55, Cy2, Rh35, Rh37, Rh36, Cy6, Cy4, Cy3, Cy5, Rh13, Clade E, Rh38, Hu66, Hu42, Hu67, Hu40, Hu41, Hu37, Rh40, Rh2, Bb1, Bb2, Rh10, Hu17, Hu6, Rh25, Pi2, Pi1, Pi3, Rh57, Rh50, Rh49, Hu39, Rh58, Rh61, Rh52, Rh53, Rh51, Rh64, Rh43, AAV8, Rh8, Rh1, Clade F, Hu14, Hu31, Hu32, Rh34, Rh33, and Rh32.

3. The AAV particle of claim 1, wherein the AAV is AAV8, AAV9, AAV2, AAV2i8, AAV9.45 or any variant, mutant, or combination thereof.

4. The AAV particle of claim 1, wherein the peptide bound to the surface of the AAV particle is present on the AAV particle surface in an amount ranging from about 2000 protein molecules per AAV particle to about $4 \times 10^7$ protein molecules per AAV particle.

5. The AAV particle of claim 1, comprising a heterologous nucleic acid molecule.

6. The AAV particle of claim 1, wherein said AAV particle comprising the surface-bound peptide has enhanced transduction activity across the blood brain barrier (BBB) relative to an AAV particle lacking the surface-bound peptide.

7. The AAV particle of claim 1, wherein said AAV particle comprising the surface-bound peptides has enhanced transduction activity of cells of the brain and/or central nervous system.

8. The AAV particle of claim 1 that is comprised within a pharmaceutically acceptable carrier.

9. A method of administering a nucleic acid to a cell of the brain and/or central nervous system, comprising contacting the cell with the AAV particle of claim 1.

10. The method of claim 9, wherein the AAV particle is administered systemically.

11. The method of claim 10, wherein the subject is a human subject.

* * * * *

UNITED STATES PATENT AND TRADEMARK OFFICE
CERTIFICATE OF CORRECTION

PATENT NO. : 12,281,335 B2
APPLICATION NO. : 18/518000
DATED : April 22, 2025
INVENTOR(S) : Li et al.

It is certified that error appears in the above-identified patent and that said Letters Patent is hereby corrected as shown below:

In the Specification

Column 8, Lines 28-29: Please correct "NC 001729, NC 001863, NC_001829, NC 001862," to read --NC_001729, NC_001863, NC_001829, NC_001862,--

Column 8, Line 32: Please correct "NC 001358," to read --NC_001358,--

Column 29, Line 56: Please correct "E4K" to read --E→K--

Column 36, Line 21: Please correct "factora" to read --factorα--

Column 40, Line 47: Please correct "(al-antitrypsin)" to read --(α1-antitrypsin)--

Column 54, Line 65: Please correct "40 m" to read --40 μm--

Column 55, Line 60: Please correct "ApoE(159-167)2" to read --ApoE(159-167)$_2$--

Column 56, Line 5: Please correct "ApoE (159-167)2" to read --ApoE (159-167)$_2$--

Column 56, Line 12: Please correct "ApoE(159-167)2" to read --ApoE(159-167)$_2$--

Column 63, Line 67 – Column 64, Line 1: Please remove the paragraph break between "60%)." and "Viruses"

Signed and Sealed this
Nineteenth Day of August, 2025

Coke Morgan Stewart
*Acting Director of the United States Patent and Trademark Office*

SEQUENCE LISTING

```
Sequence total quantity: 186
SEQ ID NO: 1            moltype = AA  length = 6
FEATURE                 Location/Qualifiers
REGION                  1..6
                        note = peptide
source                  1..6
                        mol_type = protein
                        organism = synthetic construct
SEQUENCE: 1
RGNRQA                                                                       6

SEQ ID NO: 2            moltype = AA  length = 5
FEATURE                 Location/Qualifiers
REGION                  1..5
                        note = peptide
source                  1..5
                        mol_type = protein
                        organism = synthetic construct
SEQUENCE: 2
FVFLP                                                                        5

SEQ ID NO: 3            moltype =   length =
SEQUENCE: 3
000

SEQ ID NO: 4            moltype = AA  length = 4
FEATURE                 Location/Qualifiers
REGION                  1..4
                        note = peptide
source                  1..4
                        mol_type = protein
                        organism = synthetic construct
SEQUENCE: 4
RGNR                                                                         4

SEQ ID NO: 5            moltype = AA  length = 7
FEATURE                 Location/Qualifiers
VARIANT                 7
                        note = MISC_FEATURE - where Xaa is G or S
source                  1..7
                        mol_type = protein
                        organism = synthetic construct
SEQUENCE: 5
NSVRDLX                                                                      7

SEQ ID NO: 6            moltype = AA  length = 7
FEATURE                 Location/Qualifiers
REGION                  1..7
                        note = peptide
source                  1..7
                        mol_type = protein
                        organism = synthetic construct
SEQUENCE: 6
PRSVTVP                                                                      7

SEQ ID NO: 7            moltype = AA  length = 7
FEATURE                 Location/Qualifiers
VARIANT                 6
                        note = MISC_FEATURE - Xaa is any naturally occurring amino
                         acid
VARIANT                 7
                        note = MISC_FEATURE - Xaa is S or A
```

```
source                         1..7
                               mol_type = protein
                               organism = synthetic construct
SEQUENCE: 7
NSVSSXX                                                              7

SEQ ID NO: 8                   moltype = AA  length = 6
FEATURE                        Location/Qualifiers
REGION                         1..6
                               note = peptide
source                         1..6
                               mol_type = protein
                               organism = synthetic construct
SEQUENCE: 8
NGRAHA                                                               6

SEQ ID NO: 9                   moltype = AA  length = 7
FEATURE                        Location/Qualifiers
REGION                         1..7
                               note = peptide
source                         1..7
                               mol_type = protein
                               organism = synthetic construct
SEQUENCE: 9
QPEHSST                                                              7

SEQ ID NO: 10                  moltype = AA  length = 7
FEATURE                        Location/Qualifiers
REGION                         1..7
                               note = peptide
source                         1..7
                               mol_type = protein
                               organism = synthetic construct
SEQUENCE: 10
VNTANST                                                              7

SEQ ID NO: 11                  moltype = AA  length = 7
FEATURE                        Location/Qualifiers
REGION                         1..7
                               note = peptide
source                         1..7
                               mol_type = protein
                               organism = synthetic construct
SEQUENCE: 11
HGPMQKS                                                              7

SEQ ID NO: 12                  moltype = AA  length = 7
FEATURE                        Location/Qualifiers
REGION                         1..7
                               note = peptide
source                         1..7
                               mol_type = protein
                               organism = synthetic construct
SEQUENCE: 12
PHKPPLA                                                              7

SEQ ID NO: 13                  moltype = AA  length = 7
FEATURE                        Location/Qualifiers
REGION                         1..7
                               note = peptide
source                         1..7
                               mol_type = protein
                               organism = synthetic construct
SEQUENCE: 13
IKNNEMW                                                              7

SEQ ID NO: 14                  moltype = AA  length = 7
FEATURE                        Location/Qualifiers
REGION                         1..7
                               note = peptide
source                         1..7
                               mol_type = protein
                               organism = synthetic construct
SEQUENCE: 14
RNLDTPM                                                              7

SEQ ID NO: 15                  moltype = AA  length = 7
FEATURE                        Location/Qualifiers
REGION                         1..7
```

```
                         note = peptide
source                   1..7
                         mol_type = protein
                         organism = synthetic construct
SEQUENCE: 15
VDSHRQS                                                                         7

SEQ ID NO: 16            moltype = AA   length = 7
FEATURE                  Location/Qualifiers
REGION                   1..7
                         note = peptide
source                   1..7
                         mol_type = protein
                         organism = synthetic construct
SEQUENCE: 16
YDSKTKT                                                                         7

SEQ ID NO: 17            moltype = AA   length = 7
FEATURE                  Location/Qualifiers
REGION                   1..7
                         note = peptide
source                   1..7
                         mol_type = protein
                         organism = synthetic construct
SEQUENCE: 17
SQLPHQK                                                                         7

SEQ ID NO: 18            moltype = AA   length = 7
FEATURE                  Location/Qualifiers
REGION                   1..7
                         note = peptide
source                   1..7
                         mol_type = protein
                         organism = synthetic construct
SEQUENCE: 18
STMQQNT                                                                         7

SEQ ID NO: 19            moltype = AA   length = 7
FEATURE                  Location/Qualifiers
REGION                   1..7
                         note = peptide
source                   1..7
                         mol_type = protein
                         organism = synthetic construct
SEQUENCE: 19
TERYMTQ                                                                         7

SEQ ID NO: 20            moltype = AA   length = 7
FEATURE                  Location/Qualifiers
REGION                   1..7
                         note = peptide
source                   1..7
                         mol_type = protein
                         organism = synthetic construct
SEQUENCE: 20
QPEHSST                                                                         7

SEQ ID NO: 21            moltype = AA   length = 7
FEATURE                  Location/Qualifiers
REGION                   1..7
                         note = peptide
source                   1..7
                         mol_type = protein
                         organism = synthetic construct
SEQUENCE: 21
DASLSTS                                                                         7

SEQ ID NO: 22            moltype = AA   length = 7
FEATURE                  Location/Qualifiers
REGION                   1..7
                         note = peptide
source                   1..7
                         mol_type = protein
                         organism = synthetic construct
SEQUENCE: 22
DLPNKKT                                                                         7

SEQ ID NO: 23            moltype = AA   length = 7
FEATURE                  Location/Qualifiers
```

```
REGION                      1..7
                            note = peptide
source                      1..7
                            mol_type = protein
                            organism = synthetic construct
SEQUENCE: 23
DLTAARL                                                                  7

SEQ ID NO: 24               moltype = AA  length = 7
FEATURE                     Location/Qualifiers
REGION                      1..7
                            note = peptide
source                      1..7
                            mol_type = protein
                            organism = synthetic construct
SEQUENCE: 24
EPHQFNY                                                                  7

SEQ ID NO: 25               moltype = AA  length = 7
FEATURE                     Location/Qualifiers
REGION                      1..7
                            note = peptide
source                      1..7
                            mol_type = protein
                            organism = synthetic construct
SEQUENCE: 25
EPQSNHT                                                                  7

SEQ ID NO: 26               moltype = AA  length = 7
FEATURE                     Location/Qualifiers
REGION                      1..7
                            note = peptide
source                      1..7
                            mol_type = protein
                            organism = synthetic construct
SEQUENCE: 26
MSSWPSQ                                                                  7

SEQ ID NO: 27               moltype = AA  length = 7
FEATURE                     Location/Qualifiers
REGION                      1..7
                            note = peptide
source                      1..7
                            mol_type = protein
                            organism = synthetic construct
SEQUENCE: 27
NPKHNAT                                                                  7

SEQ ID NO: 28               moltype = AA  length = 7
FEATURE                     Location/Qualifiers
REGION                      1..7
                            note = peptide
source                      1..7
                            mol_type = protein
                            organism = synthetic construct
SEQUENCE: 28
PDGMRTT                                                                  7

SEQ ID NO: 29               moltype = AA  length = 7
FEATURE                     Location/Qualifiers
REGION                      1..7
                            note = peptide
source                      1..7
                            mol_type = protein
                            organism = synthetic construct
SEQUENCE: 29
PNNNKTT                                                                  7

SEQ ID NO: 30               moltype = AA  length = 7
FEATURE                     Location/Qualifiers
REGION                      1..7
                            note = peptide
source                      1..7
                            mol_type = protein
                            organism = synthetic construct
SEQUENCE: 30
QSTTHDS                                                                  7

SEQ ID NO: 31               moltype = AA  length = 7
```

-continued

```
FEATURE              Location/Qualifiers
REGION               1..7
                     note = peptide
source               1..7
                     mol_type = protein
                     organism = synthetic construct
SEQUENCE: 31
TGSKQKQ                                                                          7

SEQ ID NO: 32        moltype = AA  length = 7
FEATURE              Location/Qualifiers
REGION               1..7
                     note = peptide
source               1..7
                     mol_type = protein
                     organism = synthetic construct
SEQUENCE: 32
SLKHQAL                                                                          7

SEQ ID NO: 33        moltype = AA  length = 7
FEATURE              Location/Qualifiers
REGION               1..7
                     note = peptide
source               1..7
                     mol_type = protein
                     organism = synthetic construct
SEQUENCE: 33
SPIDGEQ                                                                          7

SEQ ID NO: 34        moltype = AA  length = 8
FEATURE              Location/Qualifiers
REGION               1..8
                     note = peptide
source               1..8
                     mol_type = protein
                     organism = synthetic construct
SEQUENCE: 34
WIFPWIQL                                                                         8

SEQ ID NO: 35        moltype = AA  length = 9
FEATURE              Location/Qualifiers
REGION               1..9
                     note = peptide
source               1..9
                     mol_type = protein
                     organism = synthetic construct
SEQUENCE: 35
CDCRGDCFC                                                                        9

SEQ ID NO: 36        moltype = AA  length = 5
FEATURE              Location/Qualifiers
REGION               1..5
                     note = peptide
source               1..5
                     mol_type = protein
                     organism = synthetic construct
SEQUENCE: 36
CNGRC                                                                            5

SEQ ID NO: 37        moltype = AA  length = 7
FEATURE              Location/Qualifiers
REGION               1..7
                     note = peptide
source               1..7
                     mol_type = protein
                     organism = synthetic construct
SEQUENCE: 37
CPRECES                                                                          7

SEQ ID NO: 38        moltype = AA  length = 10
FEATURE              Location/Qualifiers
REGION               1..10
                     note = peptide
source               1..10
                     mol_type = protein
                     organism = synthetic construct
SEQUENCE: 38
CTTHWGFTLC                                                                      10
```

```
SEQ ID NO: 39            moltype = AA   length = 9
FEATURE                  Location/Qualifiers
REGION                   1..9
                         note = peptide
source                   1..9
                         mol_type = protein
                         organism = synthetic construct
SEQUENCE: 39
CGRRAGGSC                                                                 9

SEQ ID NO: 40            moltype = AA   length = 9
FEATURE                  Location/Qualifiers
REGION                   1..9
                         note = peptide
source                   1..9
                         mol_type = protein
                         organism = synthetic construct
SEQUENCE: 40
CKGGRAKDC                                                                 9

SEQ ID NO: 41            moltype = AA   length = 9
FEATURE                  Location/Qualifiers
REGION                   1..9
                         note = peptide
source                   1..9
                         mol_type = protein
                         organism = synthetic construct
SEQUENCE: 41
CVPELGHEC                                                                 9

SEQ ID NO: 42            moltype = AA   length = 9
FEATURE                  Location/Qualifiers
REGION                   1..9
                         note = peptide
source                   1..9
                         mol_type = protein
                         organism = synthetic construct
SEQUENCE: 42
CRRETAWAK                                                                 9

SEQ ID NO: 43            moltype = AA   length = 14
FEATURE                  Location/Qualifiers
REGION                   1..14
                         note = peptide
source                   1..14
                         mol_type = protein
                         organism = synthetic construct
SEQUENCE: 43
VSWFSHRYSP FAVS                                                          14

SEQ ID NO: 44            moltype = AA   length = 13
FEATURE                  Location/Qualifiers
REGION                   1..13
                         note = peptide
source                   1..13
                         mol_type = protein
                         organism = synthetic construct
SEQUENCE: 44
GYRDGYAGPI LYN                                                           13

SEQ ID NO: 45            moltype =     length =
SEQUENCE: 45
000

SEQ ID NO: 46            moltype =     length =
SEQUENCE: 46
000

SEQ ID NO: 47            moltype = AA   length = 7
FEATURE                  Location/Qualifiers
REGION                   1..7
                         note = peptide
source                   1..7
                         mol_type = protein
                         organism = synthetic construct
SEQUENCE: 47
RPLPPLP                                                                   7

SEQ ID NO: 48            moltype = AA   length = 7
```

```
FEATURE                     Location/Qualifiers
REGION                      1..7
                            note = peptide
source                      1..7
                            mol_type = protein
                            organism = synthetic construct
SEQUENCE: 48
APPLPPR                                                                      7

SEQ ID NO: 49               moltype = AA  length = 12
FEATURE                     Location/Qualifiers
REGION                      1..12
                            note = peptide
source                      1..12
                            mol_type = protein
                            organism = synthetic construct
SEQUENCE: 49
DVFYPYPYAS GS                                                               12

SEQ ID NO: 50               moltype = AA  length = 6
FEATURE                     Location/Qualifiers
REGION                      1..6
                            note = peptide
source                      1..6
                            mol_type = protein
                            organism = synthetic construct
SEQUENCE: 50
MYWYPY                                                                       6

SEQ ID NO: 51               moltype = AA  length = 12
FEATURE                     Location/Qualifiers
REGION                      1..12
                            note = peptide
source                      1..12
                            mol_type = protein
                            organism = synthetic construct
SEQUENCE: 51
DITWDQLWDL MK                                                               12

SEQ ID NO: 52               moltype = AA  length = 8
FEATURE                     Location/Qualifiers
VARIANT                     5
                            note = MISC_FEATURE - Xaa is G or L
source                      1..8
                            mol_type = protein
                            organism = synthetic construct
SEQUENCE: 52
CWDDXWLC                                                                     8

SEQ ID NO: 53               moltype = AA  length = 14
FEATURE                     Location/Qualifiers
REGION                      1..14
                            note = peptide
source                      1..14
                            mol_type = protein
                            organism = synthetic construct
SEQUENCE: 53
EWCEYLGGYL RCYA                                                             14

SEQ ID NO: 54               moltype = AA  length = 14
FEATURE                     Location/Qualifiers
VARIANT                     2
                            note = MISC_FEATURE - Xaa can be any naturally occurring
                             amino acid
VARIANT                     4..5
                            note = MISC_FEATURE - Xaa can be any naturally occurring
                             amino acid
VARIANT                     8
                            note = MISC_FEATURE - Xaa can be any naturally occurring
                             amino acid
VARIANT                     11
                            note = MISC_FEATURE - Xaa can be any naturally occurring
                             amino acid
VARIANT                     13
                            note = MISC_FEATURE - Xaa can be any naturally occurring
                             amino acid
source                      1..14
                            mol_type = protein
                            organism = synthetic construct
```

```
SEQUENCE: 54
YXCXXGPXTW XCXP                                                    14

SEQ ID NO: 55          moltype = AA   length = 14
FEATURE                Location/Qualifiers
REGION                 1..14
                       note = peptide
source                 1..14
                       mol_type = protein
                       organism = synthetic construct
SEQUENCE: 55
IEGPTLRQWL AARA                                                    14

SEQ ID NO: 56          moltype =     length =
SEQUENCE: 56
000

SEQ ID NO: 57          moltype = AA   length = 7
FEATURE                Location/Qualifiers
VARIANT                1
                       note = MISC_FEATURE - Xaa can be any naturally occurring
                        amino acid
VARIANT                3..4
                       note = MISC_FEATURE - Xaa can be any naturally occurring
                        amino acid
source                 1..7
                       mol_type = protein
                       organism = synthetic construct
SEQUENCE: 57
XFXXYLW                                                             7

SEQ ID NO: 58          moltype = AA   length = 13
FEATURE                Location/Qualifiers
REGION                 1..13
                       note = peptide
source                 1..13
                       mol_type = protein
                       organism = synthetic construct
SEQUENCE: 58
SSIISHFRWG LCD                                                     13

SEQ ID NO: 59          moltype = AA   length = 13
FEATURE                Location/Qualifiers
REGION                 1..13
                       note = peptide
source                 1..13
                       mol_type = protein
                       organism = synthetic construct
SEQUENCE: 59
MSRPACPPND KYE                                                     13

SEQ ID NO: 60          moltype = AA   length = 8
FEATURE                Location/Qualifiers
REGION                 1..8
                       note = peptide
source                 1..8
                       mol_type = protein
                       organism = synthetic construct
SEQUENCE: 60
CLRSGRGC                                                            8

SEQ ID NO: 61          moltype = AA   length = 9
FEATURE                Location/Qualifiers
REGION                 1..9
                       note = peptide
source                 1..9
                       mol_type = protein
                       organism = synthetic construct
SEQUENCE: 61
CHWMFSPWC                                                           9

SEQ ID NO: 62          moltype =     length =
SEQUENCE: 62
000

SEQ ID NO: 63          moltype = AA   length = 8
FEATURE                Location/Qualifiers
REGION                 1..8
                       note = peptide
```

```
source                          1..8
                                mol_type = protein
                                organism = synthetic construct
SEQUENCE: 63
CSSRLDAC                                                                       8

SEQ ID NO: 64                   moltype = AA   length = 7
FEATURE                         Location/Qualifiers
REGION                          1..7
                                note = peptide
source                          1..7
                                mol_type = protein
                                organism = synthetic construct
SEQUENCE: 64
CLPVASC                                                                        7

SEQ ID NO: 65                   moltype = AA   length = 13
FEATURE                         Location/Qualifiers
REGION                          1..13
                                note = peptide
source                          1..13
                                mol_type = protein
                                organism = synthetic construct
SEQUENCE: 65
CGFECVRQCP ERC                                                                13

SEQ ID NO: 66                   moltype = AA   length = 13
FEATURE                         Location/Qualifiers
REGION                          1..13
                                note = peptide
source                          1..13
                                mol_type = protein
                                organism = synthetic construct
SEQUENCE: 66
CVALCREACG EGC                                                                13

SEQ ID NO: 67                   moltype = AA   length = 9
FEATURE                         Location/Qualifiers
REGION                          1..9
                                note = peptide
source                          1..9
                                mol_type = protein
                                organism = synthetic construct
SEQUENCE: 67
SWCEPGWCR                                                                      9

SEQ ID NO: 68                   moltype = AA   length = 7
FEATURE                         Location/Qualifiers
REGION                          1..7
                                note = peptide
source                          1..7
                                mol_type = protein
                                organism = synthetic construct
SEQUENCE: 68
YSGKWGW                                                                        7

SEQ ID NO: 69                   moltype = AA   length = 7
FEATURE                         Location/Qualifiers
REGION                          1..7
                                note = peptide
source                          1..7
                                mol_type = protein
                                organism = synthetic construct
SEQUENCE: 69
GLSGGRS                                                                        7

SEQ ID NO: 70                   moltype = AA   length = 7
FEATURE                         Location/Qualifiers
REGION                          1..7
                                note = peptide
source                          1..7
                                mol_type = protein
                                organism = synthetic construct
SEQUENCE: 70
LMLPRAD                                                                        7

SEQ ID NO: 71                   moltype = AA   length = 9
FEATURE                         Location/Qualifiers
REGION                          1..9
```

```
                            note = peptide
source                      1..9
                            mol_type = protein
                            organism = synthetic construct
SEQUENCE: 71
CSCFRDVCC                                                                      9

SEQ ID NO: 72               moltype = AA  length = 9
FEATURE                     Location/Qualifiers
REGION                      1..9
                            note = peptide
source                      1..9
                            mol_type = protein
                            organism = synthetic construct
SEQUENCE: 72
CRDVVSVIC                                                                      9

SEQ ID NO: 73               moltype = AA  length = 5
FEATURE                     Location/Qualifiers
REGION                      1..5
                            note = peptide
source                      1..5
                            mol_type = protein
                            organism = synthetic construct
SEQUENCE: 73
CNGRC                                                                          5

SEQ ID NO: 74               moltype = AA  length = 6
FEATURE                     Location/Qualifiers
REGION                      1..6
                            note = peptide
source                      1..6
                            mol_type = protein
                            organism = synthetic construct
SEQUENCE: 74
MARSGL                                                                         6

SEQ ID NO: 75               moltype = AA  length = 6
FEATURE                     Location/Qualifiers
REGION                      1..6
                            note = peptide
source                      1..6
                            mol_type = protein
                            organism = synthetic construct
SEQUENCE: 75
MARAKE                                                                         6

SEQ ID NO: 76               moltype = AA  length = 6
FEATURE                     Location/Qualifiers
REGION                      1..6
                            note = peptide
source                      1..6
                            mol_type = protein
                            organism = synthetic construct
SEQUENCE: 76
MSRTMS                                                                         6

SEQ ID NO: 77               moltype = AA  length = 6
FEATURE                     Location/Qualifiers
REGION                      1..6
                            note = peptide
source                      1..6
                            mol_type = protein
                            organism = synthetic construct
SEQUENCE: 77
KCCYSL                                                                         6

SEQ ID NO: 78               moltype = AA  length = 14
FEATURE                     Location/Qualifiers
REGION                      1..14
                            note = peptide
source                      1..14
                            mol_type = protein
                            organism = synthetic construct
SEQUENCE: 78
MYWGDSHWLQ YWYE                                                               14

SEQ ID NO: 79               moltype = AA  length = 7
FEATURE                     Location/Qualifiers
```

```
REGION                      1..7
                            note = peptide
source                      1..7
                            mol_type = protein
                            organism = synthetic construct
SEQUENCE: 79
MQLPLAT                                                                  7

SEQ ID NO: 80               moltype = AA  length = 4
FEATURE                     Location/Qualifiers
REGION                      1..4
                            note = peptide
source                      1..4
                            mol_type = protein
                            organism = synthetic construct
SEQUENCE: 80
EWLS                                                                     4

SEQ ID NO: 81               moltype = AA  length = 4
FEATURE                     Location/Qualifiers
REGION                      1..4
                            note = peptide
source                      1..4
                            mol_type = protein
                            organism = synthetic construct
SEQUENCE: 81
SNEW                                                                     4

SEQ ID NO: 82               moltype = AA  length = 4
FEATURE                     Location/Qualifiers
REGION                      1..4
                            note = peptide
source                      1..4
                            mol_type = protein
                            organism = synthetic construct
SEQUENCE: 82
TNYL                                                                     4

SEQ ID NO: 83               moltype = AA  length = 8
FEATURE                     Location/Qualifiers
REGION                      1..8
                            note = peptide
source                      1..8
                            mol_type = protein
                            organism = synthetic construct
SEQUENCE: 83
WIFPWIQL                                                                 8

SEQ ID NO: 84               moltype = AA  length = 12
FEATURE                     Location/Qualifiers
REGION                      1..12
                            note = peptide
source                      1..12
                            mol_type = protein
                            organism = synthetic construct
SEQUENCE: 84
WDLAWMFRLP VG                                                           12

SEQ ID NO: 85               moltype = AA  length = 13
FEATURE                     Location/Qualifiers
REGION                      1..13
                            note = peptide
source                      1..13
                            mol_type = protein
                            organism = synthetic construct
SEQUENCE: 85
CTVALPGGYV RVC                                                          13

SEQ ID NO: 86               moltype = AA  length = 13
FEATURE                     Location/Qualifiers
REGION                      1..13
                            note = peptide
source                      1..13
                            mol_type = protein
                            organism = synthetic construct
SEQUENCE: 86
CVAYCIEHHC WTC                                                          13

SEQ ID NO: 87               moltype = AA  length = 12
```

```
FEATURE                 Location/Qualifiers
REGION                  1..12
                        note = peptide
source                  1..12
                        mol_type = protein
                        organism = synthetic construct
SEQUENCE: 87
CVFAHNYDYL VC                                                          12

SEQ ID NO: 88           moltype = AA  length = 10
FEATURE                 Location/Qualifiers
REGION                  1..10
                        note = peptide
source                  1..10
                        mol_type = protein
                        organism = synthetic construct
SEQUENCE: 88
CVFTSNYAFC                                                             10

SEQ ID NO: 89           moltype = AA  length = 7
FEATURE                 Location/Qualifiers
REGION                  1..7
                        note = peptide
source                  1..7
                        mol_type = protein
                        organism = synthetic construct
SEQUENCE: 89
VHSPNKK                                                                7

SEQ ID NO: 90           moltype = AA  length = 7
FEATURE                 Location/Qualifiers
REGION                  1..7
                        note = peptide
source                  1..7
                        mol_type = protein
                        organism = synthetic construct
SEQUENCE: 90
CRGDGWC                                                                7

SEQ ID NO: 91           moltype = AA  length = 6
FEATURE                 Location/Qualifiers
VARIANT                 1
                        note = MISC_FEATURE - Xaa can be any naturally occurring
                         amino acid
VARIANT                 6
                        note = MISC_FEATURE - Xaa can be any naturally occurring
                         amino acid
source                  1..6
                        mol_type = protein
                        organism = synthetic construct
SEQUENCE: 91
XRGCDX                                                                 6

SEQ ID NO: 92           moltype =   length =
SEQUENCE: 92
000

SEQ ID NO: 93           moltype = AA  length = 11
FEATURE                 Location/Qualifiers
REGION                  1..11
                        note = peptide
source                  1..11
                        mol_type = protein
                        organism = synthetic construct
SEQUENCE: 93
SGKGPRQITA L                                                           11

SEQ ID NO: 94           moltype = AA  length = 15
FEATURE                 Location/Qualifiers
VARIANT                 10
                        note = MISC_FEATURE - Xaa is A or Q
VARIANT                 11
                        note = MISC_FEATURE - Xaa is N or A
VARIANT                 12
                        note = MISC_FEATURE - Xaa is L or Y
VARIANT                 14
                        note = MISC_FEATURE - Xaa is N, M or R
VARIANT                 15
                        note = MISC_FEATURE - Xaa is R or K
```

```
source                     1..15
                           mol_type = protein
                           organism = synthetic construct
SEQUENCE: 94
AAAAAAAAAX XXTXX                                                           15

SEQ ID NO: 95              moltype = AA  length = 6
FEATURE                    Location/Qualifiers
REGION                     1..6
                           note = peptide
source                     1..6
                           mol_type = protein
                           organism = synthetic construct
SEQUENCE: 95
VYMSPF                                                                      6

SEQ ID NO: 96              moltype = AA  length = 7
FEATURE                    Location/Qualifiers
REGION                     1..7
                           note = peptide
source                     1..7
                           mol_type = protein
                           organism = synthetic construct
SEQUENCE: 96
ATWLPPR                                                                     7

SEQ ID NO: 97              moltype = AA  length = 12
FEATURE                    Location/Qualifiers
REGION                     1..12
                           note = peptide
source                     1..12
                           mol_type = protein
                           organism = synthetic construct
SEQUENCE: 97
HTMYYHHYQH HL                                                              12

SEQ ID NO: 98              moltype = AA  length = 19
FEATURE                    Location/Qualifiers
REGION                     1..19
                           note = peptide
source                     1..19
                           mol_type = protein
                           organism = synthetic construct
SEQUENCE: 98
SEVGCRAGPL QWLCEKYFG                                                       19

SEQ ID NO: 99              moltype = AA  length = 18
FEATURE                    Location/Qualifiers
REGION                     1..18
                           note = peptide
source                     1..18
                           mol_type = protein
                           organism = synthetic construct
SEQUENCE: 99
CGLLPVGRPD RNVWRWLC                                                        18

SEQ ID NO: 100             moltype = AA  length = 15
FEATURE                    Location/Qualifiers
REGION                     1..15
                           note = peptide
source                     1..15
                           mol_type = protein
                           organism = synthetic construct
SEQUENCE: 100
CKGQCDRFKG LPWEC                                                           15

SEQ ID NO: 101             moltype = AA  length = 5
FEATURE                    Location/Qualifiers
REGION                     1..5
                           note = peptide
source                     1..5
                           mol_type = protein
                           organism = synthetic construct
SEQUENCE: 101
SGRSA                                                                       5

SEQ ID NO: 102             moltype = AA  length = 4
FEATURE                    Location/Qualifiers
REGION                     1..4
```

```
                    note = peptide
source              1..4
                    mol_type = protein
                    organism = synthetic construct
SEQUENCE: 102
WGFP                                                                    4

SEQ ID NO: 103      moltype =   length =
SEQUENCE: 103
000

SEQ ID NO: 104      moltype = AA  length = 17
FEATURE             Location/Qualifiers
REGION              1..17
                    note = peptide
source              1..17
                    mol_type = protein
                    organism = synthetic construct
SEQUENCE: 104
AEPMPHSLNF SQYLWYT                                                     17

SEQ ID NO: 105      moltype = AA  length = 6
FEATURE             Location/Qualifiers
VARIANT             4
                    note = MISC_FEATURE - Xaa is W or F
source              1..6
                    mol_type = protein
                    organism = synthetic construct
SEQUENCE: 105
WAYXSP                                                                  6

SEQ ID NO: 106      moltype = AA  length = 7
FEATURE             Location/Qualifiers
REGION              1..7
                    note = peptide
source              1..7
                    mol_type = protein
                    organism = synthetic construct
SEQUENCE: 106
IELLQAR                                                                 7

SEQ ID NO: 107      moltype = AA  length = 16
FEATURE             Location/Qualifiers
REGION              1..16
                    note = peptide
source              1..16
                    mol_type = protein
                    organism = synthetic construct
SEQUENCE: 107
AYTKCSRQWR TCMTTH                                                      16

SEQ ID NO: 108      moltype = AA  length = 15
FEATURE             Location/Qualifiers
REGION              1..15
                    note = peptide
source              1..15
                    mol_type = protein
                    organism = synthetic construct
SEQUENCE: 108
PQNSKIPGPT FLDPH                                                       15

SEQ ID NO: 109      moltype = AA  length = 15
FEATURE             Location/Qualifiers
REGION              1..15
                    note = peptide
source              1..15
                    mol_type = protein
                    organism = synthetic construct
SEQUENCE: 109
SMEPALPDWW KMFK                                                        15

SEQ ID NO: 110      moltype = AA  length = 16
FEATURE             Location/Qualifiers
REGION              1..16
                    note = peptide
source              1..16
                    mol_type = protein
                    organism = synthetic construct
SEQUENCE: 110
```

```
ANTPCGPYTH DCPVKR                                                         16

SEQ ID NO: 111          moltype = AA  length = 12
FEATURE                 Location/Qualifiers
REGION                  1..12
                        note = peptide
source                  1..12
                        mol_type = protein
                        organism = synthetic construct
SEQUENCE: 111
TACHQHVRMV RP                                                             12

SEQ ID NO: 112          moltype = AA  length = 12
FEATURE                 Location/Qualifiers
REGION                  1..12
                        note = peptide
source                  1..12
                        mol_type = protein
                        organism = synthetic construct
SEQUENCE: 112
VPWMEPAYQR FL                                                             12

SEQ ID NO: 113          moltype = AA  length = 8
FEATURE                 Location/Qualifiers
REGION                  1..8
                        note = peptide
source                  1..8
                        mol_type = protein
                        organism = synthetic construct
SEQUENCE: 113
DPRATPGS                                                                   8

SEQ ID NO: 114          moltype = AA  length = 12
FEATURE                 Location/Qualifiers
REGION                  1..12
                        note = peptide
source                  1..12
                        mol_type = protein
                        organism = synthetic construct
SEQUENCE: 114
FRPNRAQDYN TN                                                             12

SEQ ID NO: 115          moltype = AA  length = 9
FEATURE                 Location/Qualifiers
REGION                  1..9
                        note = peptide
source                  1..9
                        mol_type = protein
                        organism = synthetic construct
SEQUENCE: 115
CTKNSYLMC                                                                  9

SEQ ID NO: 116          moltype = AA  length = 11
FEATURE                 Location/Qualifiers
VARIANT                 2
                        note = MISC_FEATURE - Xaa is R or Q
VARIANT                 3
                        note = MISC_FEATURE - Xaa is L or R
VARIANT                 5
                        note = MISC_FEATURE - Xaa is G or N
VARIANT                 6..7
                        note = MISC_FEATURE - Xaa can be any naturally occurring
                         amino acid
VARIANT                 9
                        note = MISC_FEATURE - Xaa is A or N
source                  1..11
                        mol_type = protein
                        organism = synthetic construct
SEQUENCE: 116
CXXTXXXGXG C                                                              11

SEQ ID NO: 117          moltype = AA  length = 9
FEATURE                 Location/Qualifiers
REGION                  1..9
                        note = peptide
source                  1..9
                        mol_type = protein
                        organism = synthetic construct
SEQUENCE: 117
```

```
CPIEDRPMC                                                                        9

SEQ ID NO: 118         moltype = AA  length = 12
FEATURE                Location/Qualifiers
REGION                 1..12
                       note = peptide
source                 1..12
                       mol_type = protein
                       organism = synthetic construct
SEQUENCE: 118
HEWSYLAPYP WF                                                                   12

SEQ ID NO: 119         moltype = AA  length = 9
FEATURE                Location/Qualifiers
REGION                 1..9
                       note = peptide
source                 1..9
                       mol_type = protein
                       organism = synthetic construct
SEQUENCE: 119
MCPKHPLGC                                                                        9

SEQ ID NO: 120         moltype = AA  length = 15
FEATURE                Location/Qualifiers
REGION                 1..15
                       note = peptide
source                 1..15
                       mol_type = protein
                       organism = synthetic construct
SEQUENCE: 120
RMWPSSTVNL SAGRR                                                                15

SEQ ID NO: 121         moltype = AA  length = 20
FEATURE                Location/Qualifiers
REGION                 1..20
                       note = peptide
source                 1..20
                       mol_type = protein
                       organism = synthetic construct
SEQUENCE: 121
SAKTAVSQRV WLPSHRGGEP                                                           20

SEQ ID NO: 122         moltype = AA  length = 20
FEATURE                Location/Qualifiers
REGION                 1..20
                       note = peptide
source                 1..20
                       mol_type = protein
                       organism = synthetic construct
SEQUENCE: 122
KSREHVNNSA CPSKRITAAL                                                           20

SEQ ID NO: 123         moltype = AA  length = 4
FEATURE                Location/Qualifiers
REGION                 1..4
                       note = peptide
source                 1..4
                       mol_type = protein
                       organism = synthetic construct
SEQUENCE: 123
EGFR                                                                             4

SEQ ID NO: 124         moltype = AA  length = 6
FEATURE                Location/Qualifiers
REGION                 1..6
                       note = peptide
source                 1..6
                       mol_type = protein
                       organism = synthetic construct
SEQUENCE: 124
AGLGVR                                                                           6

SEQ ID NO: 125         moltype = AA  length = 15
FEATURE                Location/Qualifiers
REGION                 1..15
                       note = peptide
source                 1..15
                       mol_type = protein
                       organism = synthetic construct
```

```
SEQUENCE: 125
GTRQGHTMRL GVSDG                                                        15

SEQ ID NO: 126          moltype = AA   length = 15
FEATURE                 Location/Qualifiers
REGION                  1..15
                        note = peptide
source                  1..15
                        mol_type = protein
                        organism = synthetic construct
SEQUENCE: 126
IAGLATPGWS HWLAL                                                        15

SEQ ID NO: 127          moltype = AA   length = 7
FEATURE                 Location/Qualifiers
REGION                  1..7
                        note = peptide
source                  1..7
                        mol_type = protein
                        organism = synthetic construct
SEQUENCE: 127
SMSIARL                                                                 7

SEQ ID NO: 128          moltype = AA   length = 7
FEATURE                 Location/Qualifiers
REGION                  1..7
                        note = peptide
source                  1..7
                        mol_type = protein
                        organism = synthetic construct
SEQUENCE: 128
HTFEPGV                                                                 7

SEQ ID NO: 129          moltype = AA   length = 15
FEATURE                 Location/Qualifiers
REGION                  1..15
                        note = peptide
source                  1..15
                        mol_type = protein
                        organism = synthetic construct
SEQUENCE: 129
NTSLKRISNK RIRRK                                                        15

SEQ ID NO: 130          moltype = AA   length = 15
FEATURE                 Location/Qualifiers
REGION                  1..15
                        note = peptide
source                  1..15
                        mol_type = protein
                        organism = synthetic construct
SEQUENCE: 130
LRIKRKRRKR KKTRK                                                        15

SEQ ID NO: 131          moltype = DNA   length = 39
FEATURE                 Location/Qualifiers
misc_feature            1..39
                        note = primer
source                  1..39
                        mol_type = other DNA
                        organism = synthetic construct
SEQUENCE: 131
tattctcgag cgccaccatg atggatcaag ccagatcag                              39

SEQ ID NO: 132          moltype = DNA   length = 37
FEATURE                 Location/Qualifiers
misc_feature            1..37
                        note = primer
source                  1..37
                        mol_type = other DNA
                        organism = synthetic construct
SEQUENCE: 132
aatagaattc tgaaaactca ttgtcaatat tccaaat                                37

SEQ ID NO: 133          moltype = AA   length = 12
FEATURE                 Location/Qualifiers
REGION                  1..12
                        note = peptide
source                  1..12
                        mol_type = protein
```

```
                        organism = synthetic construct
SEQUENCE: 133
QFAALPVRAH YG                                                                12

SEQ ID NO: 134          moltype = AA   length = 12
FEATURE                 Location/Qualifiers
REGION                  1..12
                        note = peptide
source                  1..12
                        mol_type = protein
                        organism = synthetic construct
SEQUENCE: 134
ARSLEPAPSR HS                                                                12

SEQ ID NO: 135          moltype = AA   length = 12
FEATURE                 Location/Qualifiers
REGION                  1..12
                        note = peptide
source                  1..12
                        mol_type = protein
                        organism = synthetic construct
SEQUENCE: 135
AIGDKAYTLR PT                                                                12

SEQ ID NO: 136          moltype = AA   length = 19
FEATURE                 Location/Qualifiers
REGION                  1..19
                        note = peptide
source                  1..19
                        mol_type = protein
                        organism = synthetic construct
SEQUENCE: 136
TFFYGGSRGK RNNFKTEEY                                                         19

SEQ ID NO: 137          moltype = AA   length = 39
FEATURE                 Location/Qualifiers
REGION                  1..39
                        note = peptide
source                  1..39
                        mol_type = protein
                        organism = synthetic construct
SEQUENCE: 137
SSVIDALQYK LEGTTRLTRK RGLKLATALS LSNKFVEGS                                   39

SEQ ID NO: 138          moltype = AA   length = 18
FEATURE                 Location/Qualifiers
REGION                  1..18
                        note = peptide
source                  1..18
                        mol_type = protein
                        organism = synthetic construct
SEQUENCE: 138
LRKLRKRLLL RKLRKRLL                                                          18

SEQ ID NO: 139          moltype = AA   length = 12
FEATURE                 Location/Qualifiers
REGION                  1..12
                        note = peptide
source                  1..12
                        mol_type = protein
                        organism = synthetic construct
SEQUENCE: 139
THRPPMWSPV WP                                                                12

SEQ ID NO: 140          moltype = AA   length = 12
FEATURE                 Location/Qualifiers
REGION                  1..12
                        note = peptide
source                  1..12
                        mol_type = protein
                        organism = synthetic construct
SEQUENCE: 140
PWVPSWMPPR HT                                                                12

SEQ ID NO: 141          moltype = AA   length = 30
FEATURE                 Location/Qualifiers
REGION                  1..30
                        note = peptide
source                  1..30
```

```
                        mol_type = protein
                        organism = synthetic construct
SEQUENCE: 141
YQQILTSMPS RNVIQISNDL ENLRDLLHVL                                         30

SEQ ID NO: 142          moltype = AA   length = 29
FEATURE                 Location/Qualifiers
REGION                  1..29
                        note = peptide
source                  1..29
                        mol_type = protein
                        organism = synthetic construct
SEQUENCE: 142
YTIWMPENPR PGTPCDIFTN SRGKRASNG                                          29

SEQ ID NO: 143          moltype = AA   length = 16
FEATURE                 Location/Qualifiers
REGION                  1..16
                        note = peptide
source                  1..16
                        mol_type = protein
                        organism = synthetic construct
SEQUENCE: 143
GREIRTGRAE RWSEKF                                                        16

SEQ ID NO: 144          moltype = AA   length = 13
FEATURE                 Location/Qualifiers
REGION                  1..13
                        note = peptide
source                  1..13
                        mol_type = protein
                        organism = synthetic construct
SEQUENCE: 144
HLNILSTLWK YRC                                                           13

SEQ ID NO: 145          moltype = AA   length = 12
FEATURE                 Location/Qualifiers
REGION                  1..12
                        note = peptide
source                  1..12
                        mol_type = protein
                        organism = synthetic construct
SEQUENCE: 145
TGNYKALHPH NG                                                            12

SEQ ID NO: 146          moltype = AA   length = 11
FEATURE                 Location/Qualifiers
REGION                  1..11
                        note = peptide
source                  1..11
                        mol_type = protein
                        organism = synthetic construct
SEQUENCE: 146
YGRKKRRQRR R                                                             11

SEQ ID NO: 147          moltype = AA   length = 18
FEATURE                 Location/Qualifiers
REGION                  1..18
                        note = peptide
source                  1..18
                        mol_type = protein
                        organism = synthetic construct
SEQUENCE: 147
RGGRLSYSRR RFSTSTGR                                                      18

SEQ ID NO: 148          moltype = AA   length = 7
FEATURE                 Location/Qualifiers
REGION                  1..7
                        note = peptide
source                  1..7
                        mol_type = protein
                        organism = synthetic construct
SEQUENCE: 148
AGILKRW                                                                   7

SEQ ID NO: 149          moltype = AA   length = 23
FEATURE                 Location/Qualifiers
REGION                  1..23
                        note = peptide
```

```
SITE                       1
                           note = MISC_FEATURE - contains acetyl group as an end cap
source                     1..23
                           mol_type = protein
                           organism = synthetic construct
SEQUENCE: 149
HGLASTLTRW AHYNALIRAF GGG                                              23

SEQ ID NO: 150             moltype = AA  length = 12
FEATURE                    Location/Qualifiers
REGION                     1..12
                           note = peptide
source                     1..12
                           mol_type = protein
                           organism = synthetic construct
SEQUENCE: 150
SGVYKVAYDW QH                                                          12

SEQ ID NO: 151             moltype = AA  length = 13
FEATURE                    Location/Qualifiers
REGION                     1..13
                           note = peptide
source                     1..13
                           mol_type = protein
                           organism = synthetic construct
SEQUENCE: 151
GGHKAKGPRK LGS                                                         13

SEQ ID NO: 152             moltype = AA  length = 7
FEATURE                    Location/Qualifiers
REGION                     1..7
                           note = peptide
source                     1..7
                           mol_type = protein
                           organism = synthetic construct
SEQUENCE: 152
HAIYPRH                                                                7

SEQ ID NO: 153             moltype = AA  length = 14
FEATURE                    Location/Qualifiers
REGION                     1..14
                           note = peptide
source                     1..14
                           mol_type = protein
                           organism = synthetic construct
SEQUENCE: 153
ACSYTSSTMC GGGS                                                        14

SEQ ID NO: 154             moltype = AA  length = 9
FEATURE                    Location/Qualifiers
REGION                     1..9
                           note = peptide
source                     1..9
                           mol_type = protein
                           organism = synthetic construct
SEQUENCE: 154
CRTIGPSVC                                                              9

SEQ ID NO: 155             moltype = AA  length = 15
FEATURE                    Location/Qualifiers
REGION                     1..15
                           note = peptide
source                     1..15
                           mol_type = protein
                           organism = synthetic construct
SEQUENCE: 155
GLAHSFSDFA RDFVA                                                       15

SEQ ID NO: 156             moltype = AA  length = 15
FEATURE                    Location/Qualifiers
REGION                     1..15
                           note = peptide
source                     1..15
                           mol_type = protein
                           organism = synthetic construct
SEQUENCE: 156
GYRPVHNIRG HWAPG                                                       15

SEQ ID NO: 157             moltype = AA  length = 14
```

```
FEATURE                 Location/Qualifiers
REGION                  1..14
                        note = peptide
source                  1..14
                        mol_type = protein
                        organism = synthetic construct
SEQUENCE: 157
KKRTLRKNDR KKRC                                                         14

SEQ ID NO: 158          moltype = AA  length = 7
FEATURE                 Location/Qualifiers
REGION                  1..7
                        note = peptide
source                  1..7
                        mol_type = protein
                        organism = synthetic construct
SEQUENCE: 158
HAIYPRH                                                                 7

SEQ ID NO: 159          moltype = AA  length = 29
FEATURE                 Location/Qualifiers
REGION                  1..29
                        note = peptide
source                  1..29
                        mol_type = protein
                        organism = synthetic construct
SEQUENCE: 159
YTIWMPENPR PGTPCDIFTN SRGKRASNG                                         29

SEQ ID NO: 160          moltype = AA  length = 12
FEATURE                 Location/Qualifiers
REGION                  1..12
                        note = peptide
source                  1..12
                        mol_type = protein
                        organism = synthetic construct
SEQUENCE: 160
RLSSVDSDLS GC                                                           12

SEQ ID NO: 161          moltype = AA  length = 21
FEATURE                 Location/Qualifiers
REGION                  1..21
                        note = peptide
source                  1..21
                        mol_type = protein
                        organism = synthetic construct
SEQUENCE: 161
AGYLLGKINL KALAALAKKI L                                                 21

SEQ ID NO: 162          moltype = AA  length = 21
FEATURE                 Location/Qualifiers
REGION                  1..21
                        note = peptide
source                  1..21
                        mol_type = protein
                        organism = synthetic construct
SEQUENCE: 162
AGYLLGKINL KPLAALAKKI L                                                 21

SEQ ID NO: 163          moltype = AA  length = 18
FEATURE                 Location/Qualifiers
REGION                  1..18
                        note = peptide
source                  1..18
                        mol_type = protein
                        organism = synthetic construct
SEQUENCE: 163
LLIILRRRIR KQAHAHSK                                                     18

SEQ ID NO: 164          moltype = AA  length = 10
FEATURE                 Location/Qualifiers
REGION                  1..10
                        note = peptide
source                  1..10
                        mol_type = protein
                        organism = synthetic construct
SEQUENCE: 164
RRLSYSRRRF                                                              10
```

-continued

```
SEQ ID NO: 165            moltype = AA   length = 28
FEATURE                   Location/Qualifiers
REGION                    1..28
                          note = peptide
source                    1..28
                          mol_type = protein
                          organism = synthetic construct
SEQUENCE: 165
SLRRSSCFGG RMDRIGAQSG LGCNSFRY                                           28

SEQ ID NO: 166            moltype = AA   length = 32
FEATURE                   Location/Qualifiers
REGION                    1..32
                          note = peptide
source                    1..32
                          mol_type = protein
                          organism = synthetic construct
SEQUENCE: 166
SPKMVQGSGC FGRKMDRISS SSGLGCKVLR RH                                      32

SEQ ID NO: 167            moltype = AA   length = 9
FEATURE                   Location/Qualifiers
REGION                    1..9
                          note = peptide
source                    1..9
                          mol_type = protein
                          organism = synthetic construct
SEQUENCE: 167
AQTLAVPFK                                                                 9

SEQ ID NO: 168            moltype = AA   length = 7
FEATURE                   Location/Qualifiers
REGION                    1..7
                          note = peptide
source                    1..7
                          mol_type = protein
                          organism = synthetic construct
SEQUENCE: 168
SVSKPEL                                                                   7

SEQ ID NO: 169            moltype = AA   length = 7
FEATURE                   Location/Qualifiers
REGION                    1..7
                          note = peptide
source                    1..7
                          mol_type = protein
                          organism = synthetic construct
SEQUENCE: 169
FTLTTPK                                                                   7

SEQ ID NO: 170            moltype = AA   length = 7
FEATURE                   Location/Qualifiers
REGION                    1..7
                          note = peptide
source                    1..7
                          mol_type = protein
                          organism = synthetic construct
SEQUENCE: 170
YTLSQGW                                                                   7

SEQ ID NO: 171            moltype = AA   length = 7
FEATURE                   Location/Qualifiers
REGION                    1..7
                          note = peptide
source                    1..7
                          mol_type = protein
                          organism = synthetic construct
SEQUENCE: 171
LAKERLS                                                                   7

SEQ ID NO: 172            moltype = AA   length = 9
FEATURE                   Location/Qualifiers
REGION                    1..9
                          note = peptide
source                    1..9
                          mol_type = protein
                          organism = synthetic construct
SEQUENCE: 172
DGTLAVPFK                                                                 9
```

```
SEQ ID NO: 173          moltype = AA  length = 7
FEATURE                 Location/Qualifiers
REGION                  1..7
                        note = peptide
source                  1..7
                        mol_type = protein
                        organism = synthetic construct
SEQUENCE: 173
QAVRTSL                                                                  7

SEQ ID NO: 174          moltype = AA  length = 7
FEATURE                 Location/Qualifiers
REGION                  1..7
                        note = peptide
source                  1..7
                        mol_type = protein
                        organism = synthetic construct
SEQUENCE: 174
NRGTEWD                                                                  7

SEQ ID NO: 175          moltype = AA  length = 7
FEATURE                 Location/Qualifiers
REGION                  1..7
                        note = peptide
source                  1..7
                        mol_type = protein
                        organism = synthetic construct
SEQUENCE: 175
ADGVQWT                                                                  7

SEQ ID NO: 176          moltype = AA  length = 7
FEATURE                 Location/Qualifiers
REGION                  1..7
                        note = peptide
source                  1..7
                        mol_type = protein
                        organism = synthetic construct
SEQUENCE: 176
DDGVSWK                                                                  7

SEQ ID NO: 177          moltype = AA  length = 7
FEATURE                 Location/Qualifiers
REGION                  1..7
                        note = peptide
source                  1..7
                        mol_type = protein
                        organism = synthetic construct
SEQUENCE: 177
SDGLTWS                                                                  7

SEQ ID NO: 178          moltype = AA  length = 7
FEATURE                 Location/Qualifiers
REGION                  1..7
                        note = peptide
source                  1..7
                        mol_type = protein
                        organism = synthetic construct
SEQUENCE: 178
SDGLAWV                                                                  7

SEQ ID NO: 179          moltype = AA  length = 4
FEATURE                 Location/Qualifiers
REGION                  1..4
                        note = peptide
REGION                  1..4
                        note = misc - phenyl substittuted
source                  1..4
                        mol_type = protein
                        organism = synthetic construct
SEQUENCE: 179
PPPP                                                                     4

SEQ ID NO: 180          moltype = AA  length = 23
FEATURE                 Location/Qualifiers
REGION                  1..23
                        note = peptide
source                  1..23
                        mol_type = protein
```

```
                         organism = synthetic construct
SEQUENCE: 180
KKALLALALH HLAHLALALK KAC                                         23

SEQ ID NO: 181           moltype = AA   length = 19
FEATURE                  Location/Qualifiers
REGION                   1..19
                         note = peptide
source                   1..19
                         mol_type = protein
                         organism = synthetic construct
SEQUENCE: 181
TFFYGGSRGK RNNFKTEEY                                              19

SEQ ID NO: 182           moltype = AA   length = 13
FEATURE                  Location/Qualifiers
REGION                   1..13
                         note = peptide
source                   1..13
                         mol_type = protein
                         organism = synthetic construct
SEQUENCE: 182
GRKKRRQRRR PPQ                                                    13

SEQ ID NO: 183           moltype = AA   length = 10
FEATURE                  Location/Qualifiers
REGION                   1..10
                         note = protein
source                   1..10
                         mol_type = protein
                         organism = synthetic construct
SEQUENCE: 183
FILMVWAPFI                                                        10

SEQ ID NO: 184           moltype = AA   length = 10
FEATURE                  Location/Qualifiers
REGION                   1..10
                         note = peptide
source                   1..10
                         mol_type = protein
                         organism = synthetic construct
SEQUENCE: 184
STNQSTNQST                                                        10

SEQ ID NO: 185           moltype = AA   length = 10
FEATURE                  Location/Qualifiers
REGION                   1..10
                         note = peptride
source                   1..10
                         mol_type = protein
                         organism = synthetic construct
SEQUENCE: 185
DEDEDEDEDE                                                        10

SEQ ID NO: 186           moltype = AA   length = 10
FEATURE                  Location/Qualifiers
REGION                   1..10
                         note = peptide
source                   1..10
                         mol_type = protein
                         organism = synthetic construct
SEQUENCE: 186
RKHRKHRKHR                                                        10
```